US012419700B2

US 12,419,700 B2
Sep. 23, 2025

(12) United States Patent
Girijavallabhan et al.

(10) Patent No.: US 12,419,700 B2
(45) Date of Patent: Sep. 23, 2025

(54) METHODS AND APPLICATIONS FOR PROVIDING EDUCATIONAL GUIDANCE FOR PERIPHERAL IV THERAPY

(71) Applicant: Becton, Dickinson and Company, Franklin Lakes, NJ (US)

(72) Inventors: Reshma C. Girijavallabhan, Whippany, NJ (US); Michael S. Ferrara, Wyckoff, NJ (US); Judith A. LaJoie, Freehold, NJ (US); Shannon Hillyer, Old Saybrook, CT (US); Susan Fleming, Toronto (CA); Ajoy C. Mahtab, Devon, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 50 days.

(21) Appl. No.: 18/214,797

(22) Filed: Jun. 27, 2023

(65) Prior Publication Data

US 2023/0346488 A1  Nov. 2, 2023

Related U.S. Application Data

(63) Continuation of application No. 16/143,089, filed on Sep. 26, 2018, now abandoned.

(Continued)

(51) Int. Cl.
*A61B 34/00* (2016.01)
*A61B 5/00* (2006.01)
(Continued)

(52) U.S. Cl.
CPC ............ *A61B 34/25* (2016.02); *A61B 5/489* (2013.01); *A61B 90/37* (2016.02); *A61M 5/427* (2013.01);
(Continued)

(58) Field of Classification Search
None
See application file for complete search history.

(56) References Cited

U.S. PATENT DOCUMENTS

| 6,012,034 A | * | 1/2000 | Hamparian | G16H 70/20 |
| | | | | 604/95.01 |
| 2009/0070140 A1 | | 3/2009 | Morsch et al. | |

(Continued)

FOREIGN PATENT DOCUMENTS

WO  WO-2016028821 A1 * 2/2016 ............ G09B 23/30

*Primary Examiner* — Patricia J Park
(74) *Attorney, Agent, or Firm* — The Webb Law Firm

(57) ABSTRACT

Computer-implemented methods and applications for providing a user with educational guidance for peripheral IV therapy are described. In one example, a computer-implemented method for providing educational guidance for peripheral IV therapy includes displaying, on a display of a machine, a main menu including a plurality of person profiles; machine-prompting the user to select one person profile of the plurality of person profiles; machine-prompting the user to select an insertion site from a plurality of insertion sites on a person's appendage based on the selected person profile; machine-prompting the user to select a first product category from a plurality of product categories; and machine-prompting the user to select a first product of a plurality of products within the first product category, the first product being a most appropriate product of the plurality of products based at least in part on the selected person profile.

12 Claims, 126 Drawing Sheets

Related U.S. Application Data

(60) Provisional application No. 62/672,990, filed on May 17, 2018, provisional application No. 62/564,863, filed on Sep. 28, 2017, provisional application No. 62/564,857, filed on Sep. 28, 2017.

(51) Int. Cl.
  *A61B 90/00* (2016.01)
  *A61M 5/42* (2006.01)
  *A61B 34/10* (2016.01)

(52) U.S. Cl.
  CPC ... *A61B 2034/107* (2016.02); *A61B 2034/252* (2016.02)

(56) References Cited

U.S. PATENT DOCUMENTS

| | | | |
|---|---|---|---|
| 2009/0142740 A1* | 6/2009 | Liang | A61B 34/10 434/262 |
| 2009/0317781 A1 | 12/2009 | Oosthuizen | |
| 2011/0263980 A1 | 10/2011 | Mills et al. | |
| 2012/0190981 A1* | 7/2012 | Harris | A61B 5/14 604/95.01 |
| 2014/0099616 A1 | 4/2014 | Hussam | |
| 2014/0236019 A1* | 8/2014 | Rahum | A61B 5/0075 600/473 |
| 2015/0087969 A1 | 3/2015 | Shekhar et al. | |
| 2015/0209113 A1 | 7/2015 | Burkholz et al. | |
| 2018/0140347 A1* | 5/2018 | Chen | A61N 1/06 |
| 2020/0398039 A1* | 12/2020 | Helm | A61M 25/02 |

\* cited by examiner

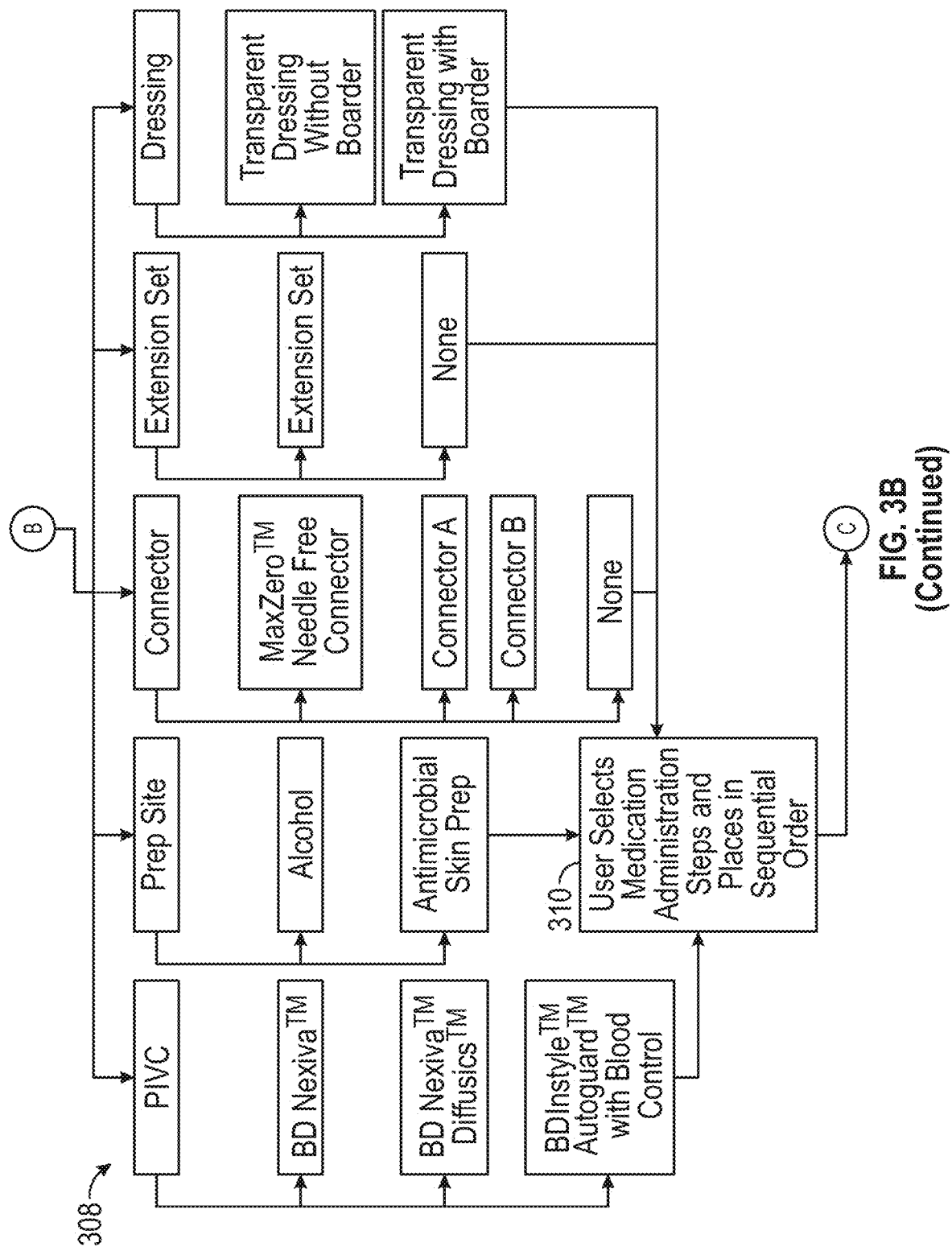

Welcome to the BD App...

The Objective of this App is to Provide a High-Level Understanding of the Following:

- Context and Importance of Peripheral IV Therapy
- Importance of Proper Site Selection and the Impact it has on Complications and Intended Therapy
- Considerations for Proper IV Catheter Selection
- Key Points Relative to Proper Insertion, Access and Maintenance of an IV Catheter.

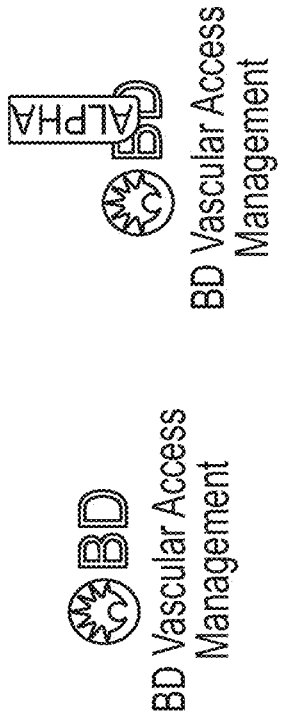

FIG. 4

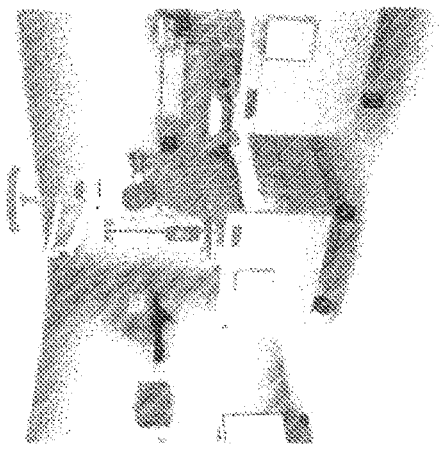

V.O. and/or Text

- Peripheral IV catheter placement is the most common invasive hospital procedure and required by up to 90% of hospitalized patients. (2) (Heim, J Infus Nurs. 2015)(pg 189/col 2/P 1)
- Clinical standards suggest removing IVs when clinically indicated (3) Infusion Nurses Society, 2016) (pg 591/Section 44/col 1/P 2).
- Up to 50% are removed earlier than intended due to complications. (2)(Heim, J Infus Nurs. 2015)(pg 189/col 2/P 1)
- IV complications are a burden to healthcare systems. (1)(Keogh, Trials. 2016)(pg 2/Section Background/col 1/P1)
- Let's learn more about these complications.(no citation required)

Skip >

1) Keogh S, et al. Varied flushing frequency and volume to prevent peripheral intravenous catheter failure: a pilot factorial randomized controlled trial in adult medical-surgical hospital patients. Trials. 2016;17:348.
2) Helm RE, Klausner JD, Klemperer JD, Flint LM, Huang E. Accepted but unacceptable: peripheral IV catheter failure. J Infus Nurs. 2015 May-Jun;38(3):189-203.
3) Infusion Nurses Society. Infusion Nurses Standards of Practice. J Infus Nurs. 2016 Jan-Feb;39(1 Suppl) S1-159

FIG. 5

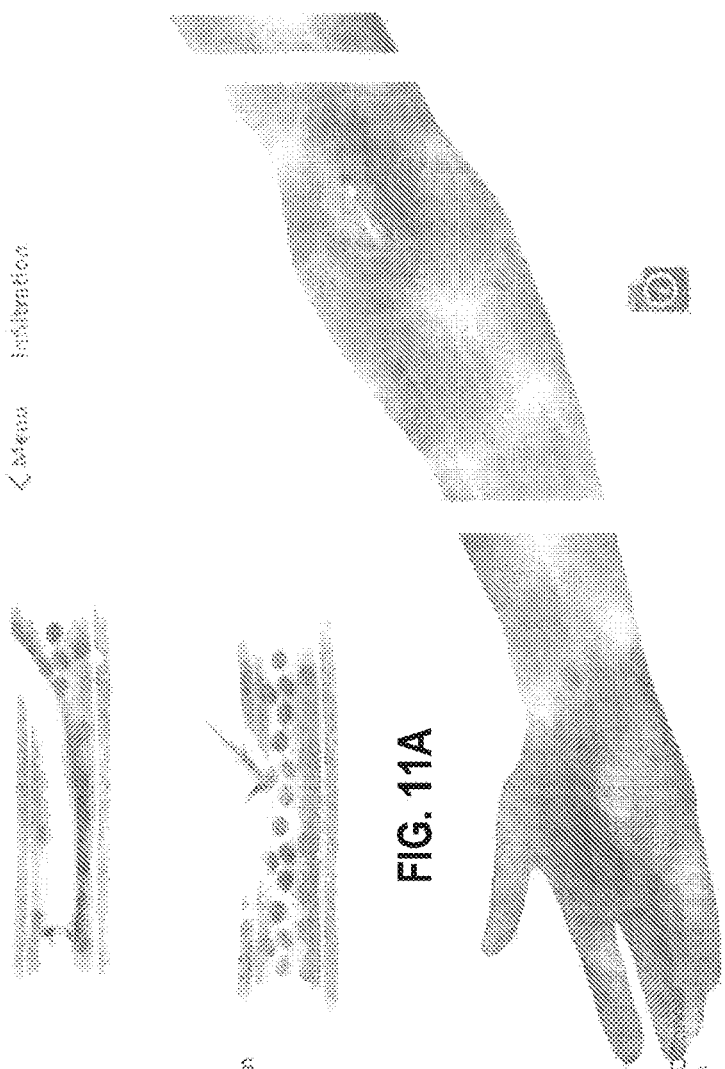
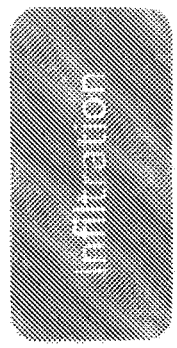
FIG. 11A
FIG. 11

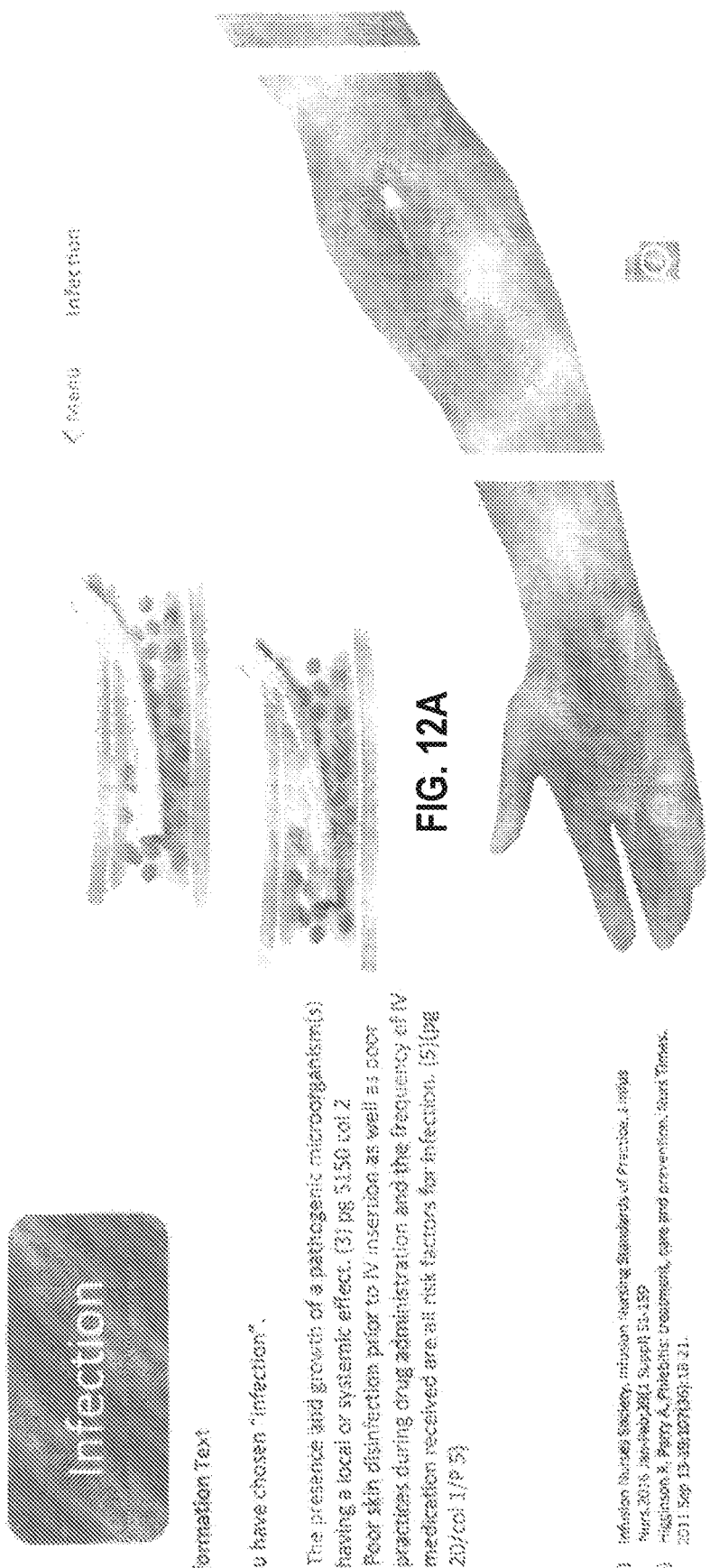

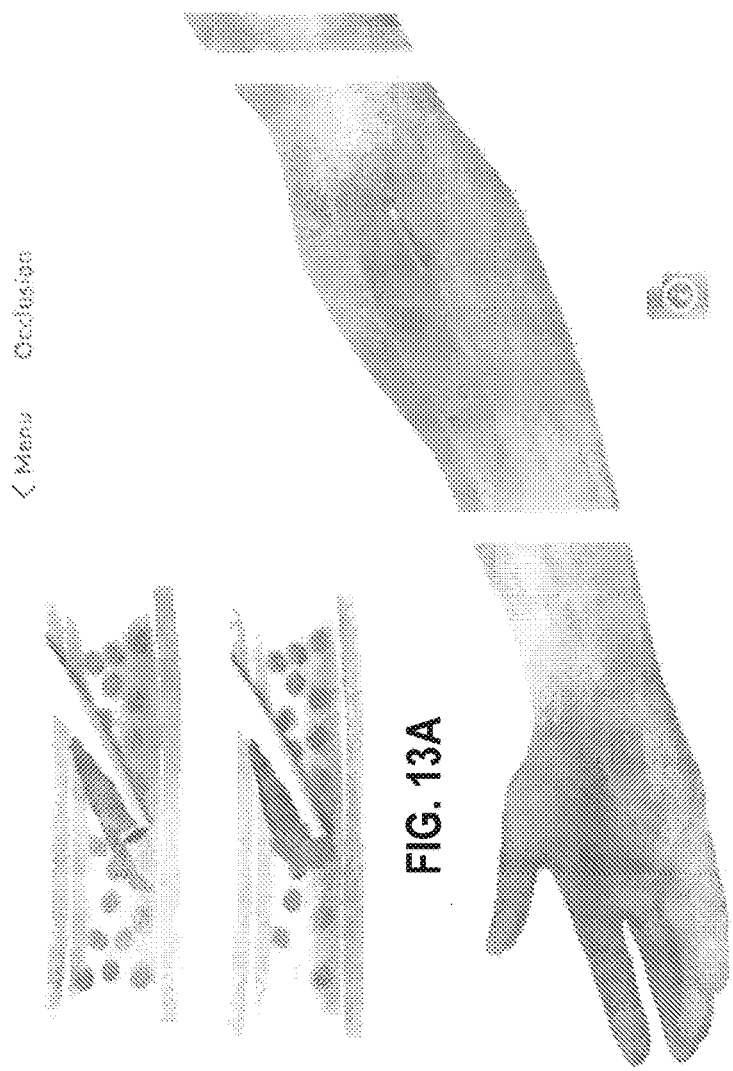
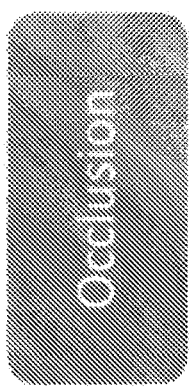
FIG. 13A
FIG. 13

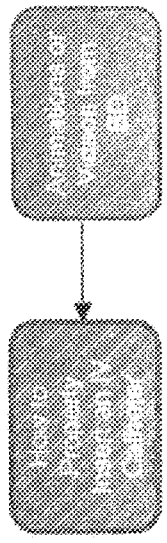

Information Text

- Perform skin antisepsis. The most recent INS Standards of Practice recommend using the skin antiseptic agent of >0.5% chlorhexidine in alcohol solution. (3)(pgS65/col 1/P 3)
  - If there is a contraindication to alcoholic chlorhexidine solution, tincture of iodine, an iodophor (povidone-iodine), or 70% alcohol may also be used. (3)(pg S65/col 1/P 3)
- Allow the antiseptic agent to fully dry before insertion. (3)(pg S65/col 1/P 3)
- Use a new pair of disposable gloves along with a "no-touch" technique for peripheral IV insertion, meaning that the insertion site is not palpated after skin antisepsis. (3)(pg S65/col 1/P 5)
- Some additional considerations:
  - Use vascular visualization technology to increase success for patients with the difficult vascular access. (3)(Section 26/pg S51/col 2/P 2)
  - Select the smallest-gauge peripheral catheter that will accommodate the prescribed therapy and patient need. (3)(Section 26/pg S51/col 2/P 4)
  - Do not use peripheral catheters for continuous vesicant therapy, parenteral nutrition, or infusates with an osmolarity greater than 900 mOsm/L. (3)(Section 26/pg S51/col 2/P 3)

3) Infusion Nurses Society. Infusion Nursing Standards of Practice. J Infus Nurs. 2016 Jan-Feb;39(1 Suppl) S1-159

FIG. 22

Best Practices to Insert a Peripheral IV Catheter

| Section | Timing | Script | Notes |
|---|---|---|---|
| Introduction | 0:00-0:13 | • Best Practices to Insert, Access, and Maintain a Peripheral IV Catheter<br>• First Access the Patient<br>• Then Select the Proper Insertion Site and Gather Supplies | |
| Skin Prep | 0:13-0:20 | • Then Wash Hands, Apply Gloves, and Apply Skin Antiseptic to the Insertion Site | • Remove Clock<br>• Remove Hand w/CloraPrep<br>• Remove BD CloraPrep Brand Name |
| Insert and Stabilize IV Catheter | 0:20-0:30 | • After Preparation, Insert & Stabilize the Peripheral IV Catheter, Apply Dressing, Attach Needless Connector and Label Appropriately<br>• Use PFS to Confirm IV Placement and Assess Patency | • Remove Brand Names for BD Nexiva, DB CloraSheild, and BD MaxZero |
| Confirm Proper Placement | 0:37-0:39 | • Flush to Clear the Line | • Start Right after the Big Spinning Syringe (0:37)<br>• Stop before the Blood Comes Back into the Line (0:39) |

FIG. 23

| Best Practices to Access and Maintain a Peripheral IV Catheter | | |
|---|---|---|
| Access and Maintain | 1.21 – 2.04 | • To access the device, disinfect the connector in accordance with your hospital's policy<br>• Remember each time the site is accessed it should be disinfected<br>• Flush with a prefilled saline syringe to access patency and clean any residual fluid or medication<br>• Next disinfect the connector again in accordance with your hospital's policy<br>• Afterward administer the medication<br>• Disinfect the connector again after the medication has been delivered<br>• Flush with a final prefilled saline flush syringe to clear the medication and lock the catheter during periods of non-use<br>• Repeat this process every time a medication is delivered | • Pick up at (1.21) and end at (2.04).<br>• Note: throughout this portion you see reference / symbols for 'GAS' at 1.32, 1.44 and 1.51 – please delete them throughout |

FIG. 25

Storyboard References

1) Keogh S, Flynn J, Marsh N, Mihala G, Davies K, Rickard C. Varied flushing frequency and volume to prevent peripheral intravenous catheter failure: a pilot, factorial randomized controlled trial in adult medical-surgical hospital patients. Trials. 2016;26(1):348.

2) Palm RE, Klausner JD, Klemperer JD, Flint LM, Huang E. Acceptable but unacceptable: peripheral IV catheter failure. J Infus Nurs. 2015;38(3):189-203.

3) Infusion Nurses Society. Infusion Nursing Standards of Practice. J Infus Nurs. 2016;39(1 Suppl):S1-159.

4) Riley DC, Garcia S. Emergency department ultrasonography guided long-axis antecubital intravenous cannulation: How to do it. Critical Ultrasound Journal. 2012;4(1):3

5) Higginson R, Parry A. Phlebitis: treatment, care and prevention. Nurs Times. 2011;107(36):18-21.

6) Doellman D, Hadaway L, Bowe-Geddes LA, Franklin M, LeDonne J, Papke-O'Donnell L, Schulmeister L, Petti J. Infiltration and extravasation: update on prevention and management. J Infus Nurs. 2009;32(4):203-11.

7) Wallis MC, McGrail M, Webster J, Marsh N, Gowardman J, Playford EG, Rickard CM. Risk factors for peripheral intravenous catheter failure: a multivariate analysis of data from a randomized controlled trial. Infect Control Hosp Epidemiol. 2014;35(1):63-8.

METHODS AND APPLICATIONS FOR PROVIDING EDUCATIONAL GUIDANCE FOR PERIPHERAL IV THERAPY

CROSS-REFERENCE TO RELATED APPLICATIONS

This application is a continuation of U.S. patent application Ser. No. 16/143,089, filed Sep. 26, 2018, which claims priority to U.S. Provisional Application Ser. Nos. 62/672,990, filed May 17, 2018; 62/564,857, filed Sep. 28, 2017; and 62/564,863, filed Sep. 28, 2017, each of which is incorporated herein by reference in its entirety.

TECHNICAL FIELD

The present application relates generally to systems, methods, and applications for proper placement of peripheral IV catheters and applications for proper placement, access, care and maintenance of peripheral IV catheters, as required for treatment of hospital patients. More specifically, the present application relates to a system, methods, and applications for providing educational guidance for the proper placement of peripheral IV catheters required for treatment of hospital patients.

BACKGROUND

Peripheral IV catheter placement is the most common invasive hospital procedure and required by up to 90% of hospitalized patients. Clinical standards suggest removing IVs when clinically indicated; however, up to 50% of placed IV catheters are removed earlier than intended due to complications associated with the placement of the IV catheter. These IV complications are a heavy burden to the healthcare system, and it would be beneficial to provide systems and methods for preventing and avoiding such complications.

BRIEF SUMMARY OF SOME EXAMPLE EMBODIMENTS

The present disclosure addresses certain of those foregoing problems and burdens. In one aspect, a computer-implemented method for providing educational guidance for peripheral IV therapy includes displaying, on a display of a machine, a main menu including a plurality of person profiles. The machine prompts a user to select one person profile of the plurality of person profiles. The machine prompts the user to select an insertion site from a plurality of insertion sites on a person's appendage for inserting an IV catheter based on the selected person profile. The machine instructs the user to position a sticker operatively coupled to the machine at the selected insertion site on the person's appendage. A user interface is displayed on the display indicating placement of the sticker at the selected insertion site. In certain embodiments, the machine is programmed to know the preferred insertion site of the plurality of insertion sites. In alternative embodiments, the machine determines whether the selected insertion site is a preferred insertion site or a non-preferred insertion site.

In another aspect, a computer-implemented method for providing a user with educational guidance for peripheral IV therapy includes receiving, by a machine, a request from a user for initiating a learning program and displaying, on a display of the machine, a main menu including a plurality of person profiles. The machine prompts the user to select a first person profile of the plurality of person profiles. Based on the first person profile, a plurality of insertion sites on a person's appendage for inserting an IV are displayed on the display, wherein the plurality of insertion sites includes a preferred insertion site and a non-preferred insertion site. The machine prompts the user to select a first insertion site from a plurality of insertion sites on a person's appendage for inserting the IV catheter. The machine instructs the user to position a sticker operatively coupled to the machine on the person's appendage corresponding to the selected insertion site. In certain embodiments, the machine is programmed to know the preferred insertion site and the non-preferred insertion sites of the plurality of insertion sites. In alternative embodiments, the machine determines that the selected insertion site is a non-preferred insertion site.

In yet another aspect, a computer-implemented method for providing a user with educational guidance for peripheral IV therapy includes receiving, by the machine, a request from a user for initiating a learning program. A plurality of insertion sites on a person's appendage for inserting an IV are displayed on a display of the machine, wherein the plurality of insertion sites includes a preferred insertion site and a non-preferred insertion site. The machine prompts the user to select a first insertion site from the plurality of insertion sites. The machine instructs the user to position a sticker operatively coupled to the machine on the person's appendage corresponding to the selected insertion site. In certain embodiments, the machine is programmed to know the preferred insertion site and the non-preferred insertion sites of the plurality of insertion sites. In alternative embodiments, the machine determines that the selected insertion site is a non-preferred insertion site. The machine then displays, on the display, information regarding the selected insertion site.

In another aspect, a computer-implemented method for providing educational guidance for peripheral IV therapy, includes displaying, on a display of a machine, a main menu including a plurality of person profiles. The machine prompts the user to select one person profile of the plurality of person profiles. The machine then prompts the user to select an insertion site from a plurality of insertion sites on a person's appendage based on the selected person profile. The user is prompted by the machine to select a first product category from a plurality of product categories. The machine prompts the user to select a first product of a plurality of products within the first product category, the first product being a most appropriate product of the plurality of products based at least in part on the selected person profile.

In another aspect, a system for providing educational guidance on vascular access management, includes a sticker and a machine operatively coupled to the sticker. The machine includes a camera device, wherein with the sticker adhered to a patient's appendage at an insertion site and the machine aligned with the sticker, the camera device is configured to generate an image of the sticker. A processor is operatively coupled to the camera device. The processor is configured to determine whether the sticker is positioned at a preferred insertion site or a non-preferred insertion site on the patient's appendage and generate a graphical representation of the patient's appendage at the insertion site that is displayed on a display of the machine to initiate an educational guidance mode of the machine.

In another aspect, a computer-implemented method for initiating an educational guidance mode on a machine, includes instructing, by the machine, a user to place a sticker at a first insertion site of a plurality of potential insertion sites on a patient's appendage and interacting, via the machine, with the sticker to initiate an educational guidance mode on the computing device. In one embodiment, the machine generates a representative image of the patient's appendage and displays, on a display of the machine, the representative image. In one embodiment, during the educational guidance mode, the machine determines whether the first insertion site is a preferred insertion site or a non-preferred insertion site. The machine then prompts the user to learn more about potential complications and risk factors associated with the selected insertion site.

In another aspect, a method for initiating an educational guidance mode on a machine includes receiving, by the machine, a request from a user to initiate a consequence-based learning program; presenting to the user, via a display of the machine, a plurality of patient profiles; querying the user, by the machine, to select a first patient profile of the plurality of patient profiles presented on the display; upon selection of the first patient profile by the user, prompting the user, by the machine, to select an insertion site from a plurality of potential insertion sites on a patient's appendage for inserting an IV catheter; and instructing the user, by the machine, to select one or more appropriate products required for properly inserting the IV catheter in the patient's appendage at the first insertion site, based at least in part on the first patient profile.

In another aspect, computer-implemented method for providing educational guidance for peripheral IV therapy includes displaying, on a display of a machine, a main menu including a plurality of patient profiles; prompting, by the machine, the user to select one patient profile of the plurality of patient profiles; prompting, by the machine, the user to select an insertion site from a plurality of insertion sites on a patient's appendage for inserting an IV catheter based on the selected patient profile; instructing, by the machine, the user to position a sticker operatively coupled to the machine at the selected insertion site on the patient's appendage; displaying on the display, a user interface indicating placement of the sticker at the selected insertion site; and determining, by the machine, whether the selected insertion site is a preferred insertion site or a non-preferred insertion site. In such a method, if the selected insertion site is the non-preferred insertion site, the method may further include: rendering, by a processing device of the machine, a first graphical image of the selected insertion site; displaying on the display the first graphical image; and displaying on the display one or more complications associated with the selected insertion site. That method may further include prompting the user to select one complication of the one or more complications for further information regarding the selected complication and rendering, by the processing device of the machine, a second graphical image of the patient's arm indicating the selected complication. Such method may further include displaying on the display the second graphical image on a user interface, wherein the user interface includes informational text indicating a definition of the selected complication and an indication of risks associated with the selected complication. In the method, the user interface may further include an additional graphical image illustrating one or more effects of the selected complication. In the above-referenced method, if the selected insertion site is the preferred insertion site, the method may further include rendering, by the processing device of the machine, a graphical image of the selected insertion site and displaying, on the display, the graphical image on a user interface indicating that the user correctly selected the preferred insertion site. In that method, the user interface may also include informational text indicating to the user reasons the selected insertion site is the preferred insertion site for a peripheral IV catheter. Such method may further include displaying, on the display, a user interface indicating the placement of the sticker at the preferred insertion site, and—with the sticker properly positioned at the preferred insertion site—querying the user, by the machine, whether the user is interested in learning more about proper peripheral IV therapy. That method may further include querying the user, by the machine, whether the user is interested in learning more about proper peripheral IV therapy; with an indication that the user is interested in learning more about proper peripheral IV therapy, prompting, by the machine, the user to select one learning topic of a plurality of learning topics displayed on the display; and providing, on the display, information regarding the selected learning topic. Such method may also include that the one or more learning topics comprise considerations for proper IV catheter selection, instructional information for properly inserting an IV catheter, and instructional information for properly accessing and maintaining an IV catheter, and may include providing (e.g., on the display) information regarding the selected learning topic comprises displaying on the display a video illustrating best practices related to a selected learning topic of the one or more learning topics.

In another aspect, a computer-implemented method for providing a user with educational guidance for peripheral IV therapy may include receiving, by a machine, a request from a user for initiating a learning program; displaying, on a display of the machine, a main menu including a plurality of patient profiles; prompting the user to select a first patient profile of the plurality of patient profiles; based on the first patient profile, displaying, on the display, a plurality of insertion sites on a patient's appendage for inserting an IV, wherein the plurality of insertion sites includes a preferred insertion site and a non-preferred insertion site; prompting, by the machine, the user to select a first insertion site from a plurality of insertion sites on a patient's appendage for inserting the IV catheter; instructing, by the machine, the user to position a sticker operatively coupled to the machine on the patient's appendage corresponding to the selected insertion site; and determining, by the machine, that the selected insertion site is a non-preferred insertion site. That method may further include rendering, by a processing device of the machine, a first graphical image of the selected insertion site; displaying, on the display, a user interface including the first graphical image indicating placement of the sticker at the selected insertion site; and displaying, on the display, one or more complications associated with the selected insertion site. Such method may further include having the user interface provide informational text indicating a definition of the at least one complication and an indication of risks associated with the at least one complication, and/or an additional graphical image illustrating one or more effects of the at least one complication.

In another aspect, a computer-implemented method for providing a user with educational guidance for peripheral IV therapy may include receiving, by the machine, a request from a user for initiating a learning program; displaying, on a display of a machine, a plurality of insertion sites on a patient's appendage for inserting an IV, wherein the plurality of insertion sites includes a preferred insertion site and a non-preferred insertion site; prompting, by the machine, the user to select a first insertion site from the plurality of insertion sites; instructing, by the machine, the user to position a sticker operatively coupled to the machine on the patient's appendage corresponding to the selected insertion site; determining, by the machine, that the selected insertion site is a non-preferred insertion site; and displaying, on the display, information regarding the selected insertion site. Such a method may also include rendering, by a processing device of the machine, a first graphical image of the selected insertion site; displaying on the display the first graphical image; and displaying on the display one or more complications associated with the selected non-preferred insertion site. That method may also include prompting the user to select one complication of the one or more complications for further information regarding the selected complication; and rendering, by the processing device of the machine, a second graphical image of the patient's arm indicating the selected complication. That method may further include displaying on the display the second graphical image on a user interface, wherein the user interface includes informational text indicating a definition of the selected complication and an indication of risks associated with the selected complication. The user interface may also include an additional graphical image illustrating one or more effects of the selected complication The above-described method may additionally include steps where before displaying, on a display of a machine, a plurality of insertion sites on a patient's appendage for inserting an IV, displaying, on the display, a main menu including a plurality of patient profiles; prompting the user to select a first patient profile of the plurality of patient profiles; and based on the first patient profile, displaying, on the display, the plurality of insertion sites on a patient's appendage for inserting an IV. The above-described method may additionally include steps of querying the user, by the machine, whether the user is interested in learning more about proper peripheral IV therapy; determining, by the machine, that the user is interested in learning more about proper peripheral IV therapy; prompting, by the machine, the user to select one learning topic of a plurality of learning topics displayed on the display; and providing, on the display, information regarding the selected learning topic.

In another aspect, a system for providing educational guidance on vascular access management may include a sticker; and a machine operatively coupled to the sticker, the machine comprising: a camera device, wherein with the sticker adhered to a patient's appendage at an insertion site and the machine aligned with the sticker, the camera device is configured to generate an image of the sticker; and a processor operatively coupled to the camera device, the processor configured to determine whether the sticker is positioned at a preferred insertion site or a non-preferred insertion site on the patient's appendage and generate a graphical representation of the patient's appendage at the insertion site to display on a display of the machine to initiate an educational guidance mode of the machine. The sticker of that system may include a first surface and an opposing second surface, the first surface comprising a key centrally located on the first surface, one or more indicia on the first surface located at or near a respective corner of the sticker, and an arrow on the first surface positioned along a bottom edge of the sticker. The sticker of that system may include an image of a patient's arm indicating a plurality of insertion sites for an IV catheter. The machine of that system may include rendering circuitry configured to render one or more images of a digital insertion site by rendering one or more graphical images corresponding to data items associated with the insertion site. The machine may comprise a mobile device.

In another aspect, a computer-implemented method for initiating an educational guidance mode on a machine may include: instructing, by the machine, a user to place a sticker at a first insertion site of a plurality of potential insertion sites on a patient's appendage; and interacting, via the machine, with the sticker to initiate an educational guidance mode on the computing device. In that method, with the user holding the machine over the sticker, the method may further include generating, by the machine, a representative image of the patient's appendage and displaying, on a display of the machine, the representative image. The method may also include during the educational guidance mode, determining, by the machine, whether the first insertion site is a preferred insertion site or a non-preferred insertion site. Such method may further include prompting (via the machine) the user to learn more about potential complications and risk factors associated with the selected insertion site.

In another aspect, a method for initiating an educational guidance mode on a machine may include receiving, by the machine, a request from a user to initiate a consequence-based learning program; presenting to the user, via a display of the machine, a plurality of patient profiles; querying the user, by the machine, to select a first patient profile of the plurality of patient profiles presented on the display; upon selection of the first patient profile by the user, prompting the user, by the machine, to select an insertion site from a plurality of potential insertion sites on a patient's appendage for inserting an IV catheter; and instructing the user, by the machine, to select one or more appropriate products required for properly inserting the IV catheter in the patient's appendage at the first insertion site, based at least in part on the first patient profile. In the method, instructing the user (by the machine) to select one or more appropriate products required for properly inserting the IV catheter in the patient's appendage at the first insertion site may also include displaying, on the display, available products; and instructing the user to select one or more appropriate products of the available products to be used in a correct sequence. In the method, instructing the user to select one or more appropriate products of the available products to be used in a correct sequence may include: prompting the user, by the machine, to select from a plurality of catheters an appropriate catheter for the first patient profile; prompting the user, by the machine, to select an appropriate process for preparing the first insertion site for insertion of the catheter; prompting the user, by the machine, to select an appropriate connector from a plurality of connectors; prompting the user, by the machine, to select an appropriate dressing from a plurality of dressing choices; and prompting the user, by the machine, to determine whether an extension set is required; where such method may further include prompting the user, by the machine, to continue with a line access process, wherein, during the line access process, the machine prompts the user to place a plurality of process steps in a numbered process step location, and may still further include prompting the user, by the machine, to build the catheter with the one or more appropriate products selected, scrub the hub, flush the IV catheter, and administer an example medicine; and displaying on the display results of a plurality of selections made by the user. Where, if each selection of the plurality of selections is correct, that method may include displaying on the display a congratulatory response for positive reinforcement, but if one or more selections of the plurality of selections are incorrect, the method may include instructing the user, by the machine, to position a sticker operatively coupled to the machine at the selected insertion site; and prompting the user, by the machine, to place the machine over the sticker to view on the display one or more complications associated with an improper selection of the insertion site. Then, if one or more selections were incorrect, the method may additionally include prompting the user, by the machine, to continue the educational guidance mode; and prompting the user, by the machine, to re-select at least one of the following: a product incorrectly selected or a position of a non-sequential step of the line access process. And, the method may also include determining, by the machine, that the user selected correct products and correctly positioned the line access process steps sequentially; determining, by the machine, that the user is interested in learning more about peripheral IV therapy; and providing the user, by the machine, with a link to a site to learn more about peripheral IV therapy.

In another aspect, a method for providing an educational guidance mode on a machine may include prompting a user, by the machine, to select an insertion site from a plurality of potential insertion sites on a patient's appendage for inserting an IV catheter; instructing the user, by the machine, to select a first product category from a plurality of product categories required for properly inserting the IV catheter in the patient's appendage at the insertion site; instructing the user, by the machine, to select a correct product from the first product category, based at least in part on a profile of the patient; and displaying, on a display of the machine, the selected product. That method may further include instructing the user, by the machine, to select a second product category from a plurality of product categories required for properly inserting the IV catheter in the patient's appendage at the insertion site; instructing the user, by the machine, to select a second correct product from the second product category, based at least in part on a profile of the patient; and displaying, on a display of the machine, the second selected product. Alternatively, the method may include determining, by the machine, that the selected product is not the correct product; and displaying, on the display, one or more complications associated with an improper selection of the correct product.

BRIEF DESCRIPTION OF THE DRAWINGS

The detailed description is described with reference to non-limiting and non-exhaustive embodiments illustrated in the accompanying figures. The same reference numerals in different figures refer to similar or identical items.

FIG. 4 is an example user interface displayed on the example machine during the method of FIG. 3D, according to various embodiments;

FIG. 5 is another example user interface, according to various embodiments;

FIG. 1 OA is another example user interface, according to various embodiments;

FIG. 11 is another example user interface, according to various embodiments;

FIG. 11A is another example user interface, according to various embodiments;

FIG. 12 is another example user interface, according to various embodiments;

FIG. 12A is another example user interface, according to various embodiments;

FIG. 13 is another example user interface, according to various embodiments;

FIG. 13A is another example user interface, according to various embodiments;

FIG. 15A is another example user interface, according to various embodiments;

FIG. 22 is another example user interface, according to various embodiments;

FIG. 23 is another example user interface, according to various embodiments;

FIG. 25 is another example user interface, according to various embodiments;

FIG. 26 is another example user interface, according to various embodiments;

Figure 65:
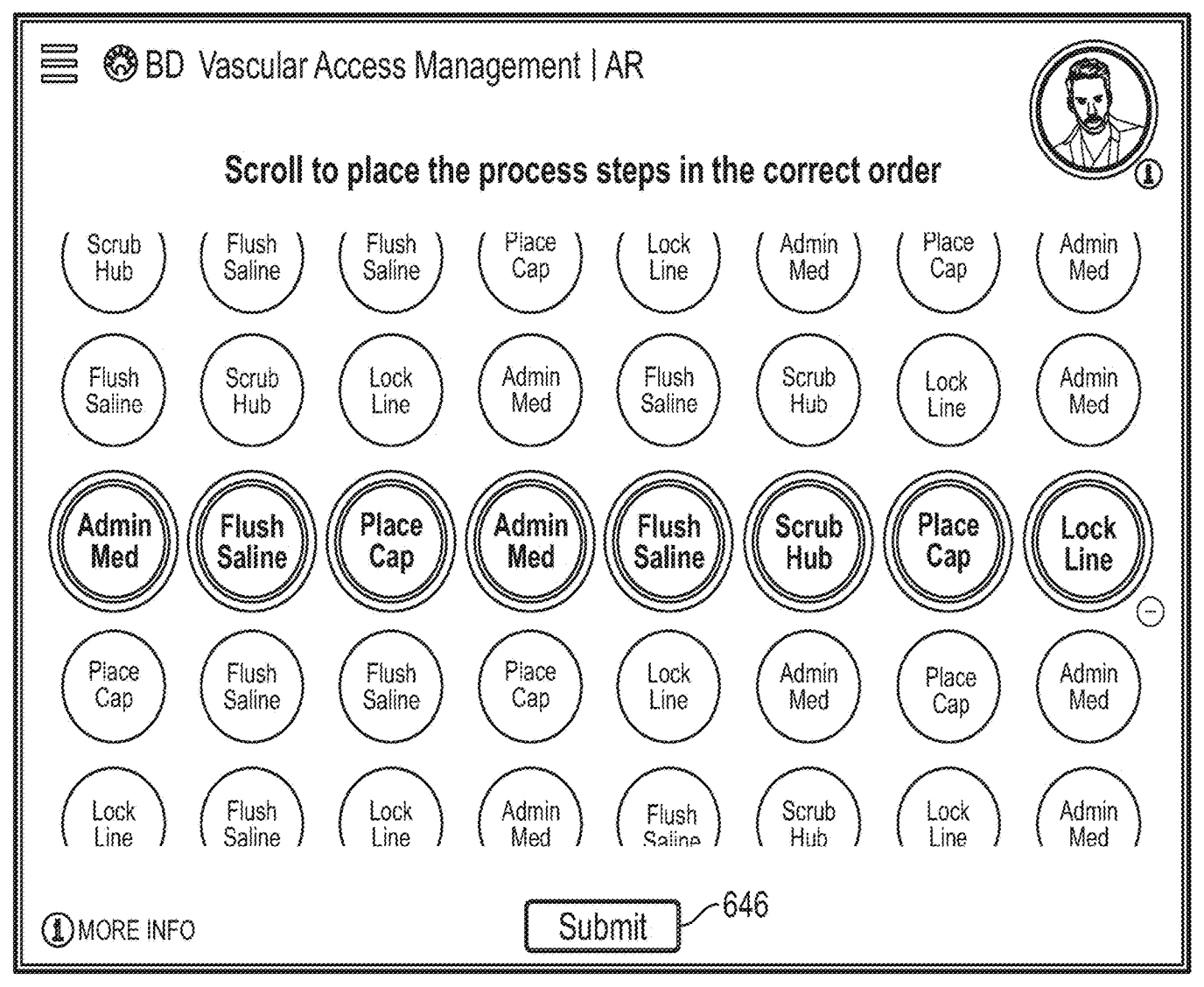

FIG. 65 is another example user interface, according to various embodiments;

FIG. 110 is another example user interface, according to various embodiments;

FIG. 111 is another example user interface, according to various embodiments;

FIG. 112 is another example user interface, according to various embodiments;

FIG. 113 is another example user interface, according to various embodiments;

FIG. 114 is another example user interface, according to various embodiments;

FIG. 115 is another example user interface, according to various embodiments;

FIG. 116 is another example user interface, according to various embodiments;

FIG. 117 is another example user interface, according to various embodiments;

FIG. 118 is another example user interface, according to various embodiments;

FIG. 119 is another example user interface, according to various embodiments; and FIG. 120 is an example machine for use with the system, methods, and applications, according to various embodiments.

DETAILED DESCRIPTION

Figure 1:
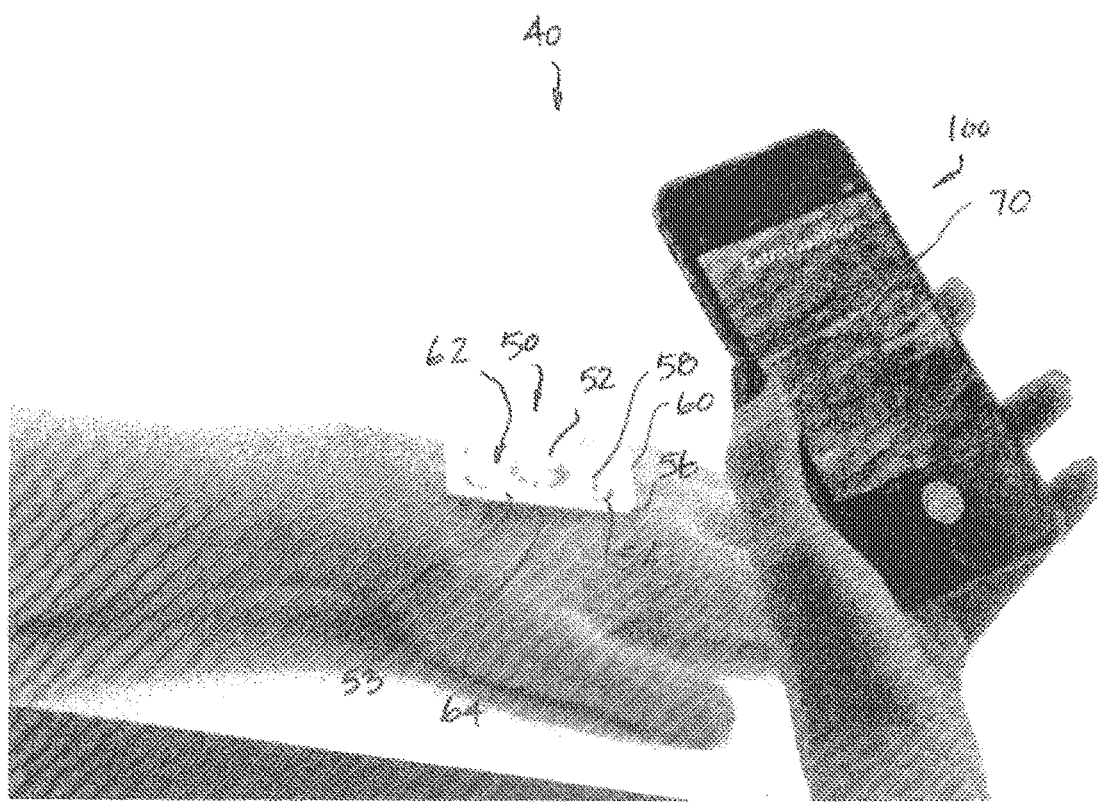
FIG. 1 is a perspective view of an example system for providing educational guidance for peripheral IV therapy using a consequence-based learning (CBL) program, according to various embodiments.

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. Reference herein to any industry standards (e.g., *ASTM, ANSI, IEEE* standards) is defined as complying with the currently published standards as of the original filing date of this disclosure concerning the units, measurements, and testing criteria communicated by those standards unless expressly otherwise defined herein. The terms "proximal" and "distal" are used herein in the common usage sense where they refer respectively to a handle/doctor-end of a device or related object and a tool/patient-end of a device or related object. The terms "about," "substantially," "generally," and other terms of degree, when used with reference to any volume, dimension, proportion, or other quantitative or qualitative value, are intended to communicate a definite and identifiable value within the standard parameters that would be understood by one of skill in the art (equivalent to a medical device engineer with experience in this field), and should be interpreted to include at least any legal equivalents, minor but functionally-insignificant variants, standard manufacturing tolerances, and including at least mathematically significant figures (although not required to be as broad as the largest range thereof).

In example embodiments described herein, a computing device provides consequence-based learning (CBL) applications to provide users with educational guidance for proper peripheral IV therapy. With CBL applications, the user is prompted to select from a list including one or more optimal, correct, or most appropriate responses or choices and one or more sub-optimal, incorrect, or inappropriate responses or choices. Once the learning program is complete, the user is advised of consequences resulting from either proper or improper selections made during the learning program. In certain embodiments, the user is allowed to select a path for optimal and/or suboptimal selections throughout the learning program without knowledge of the optimal path until the results are displayed to the user. The results will allow the user to view best practices information and complications based on augmented reality, mixed reality, and/or virtual reality applications. Further, the learning application provides training on important aspects of proper peripheral IV therapy, such as the importance of properly selecting the insertion site and the impact on complications and intended therapy of improperly selecting the insertion site, considerations for proper IV catheter selection, and key points relevant to proper insertion, access, and maintenance of the IV catheter.

In example embodiments, a method for providing an educational guidance mode on a machine includes prompting a user, by a machine, to select an insertion site from a plurality of potential insertion sites on a person's appendage for inserting an IV catheter, instructing the user, by the machine, to select a first product category from a plurality of product categories required for properly inserting the IV catheter in the person's appendage at the insertion site, instructing the user, by the machine, to select a most appropriate product from the first product category, based at least in part on a profile of the person, and displaying, on a display of the machine, the selected product. The method may further include, without limitation, instructing the user, by the machine, to select a second product category from a plurality of product categories required to ensure adequate skin antisepsis, to enable access to the IV catheter line, for properly inserting the IV catheter in the person's appendage at the insertion site, and/or for properly maintaining the IV catheter in the person's appendage. The method may also include, for example, instructing the user, by the machine, to select a second most appropriate product from the second product category, based at least in part on a profile of the person, and displaying, on a display of the machine, the second selected product. The method may also include determining, by the machine, that the selected product is not the most appropriate product and displaying, on the display, one or more complications associated with an improper selection of the product.

Referring now to the figures, FIG. 1 schematically illustrates a system 40 for vascular access management that includes a sticker 50, such as an augmented reality (AR) sticker or a virtual reality (VR) sticker, and a machine 100, such as an electronic device or a computing device, e.g., a mobile phone or any suitable mobile device, operatively coupled to sticker 50, as described herein. In example embodiments, with sticker 50 adhered to a person's arm in a selected insertion site, as described herein, and machine 100 aligned with sticker 50, e.g., positioned over sticker 50 such that a camera device of machine 100 is positioned to capture or generate an image of sticker 50, system 40 is configured to superimpose a computer-generated image on a display of machine 100, e.g., on the display of a user's mobile phone; thus, providing a composite view. In alternative example embodiments, system 40 is configured to display on machine 100 a computer-generated simulation of a three dimensional image or environment that can be interacted with in a seemingly real or physical way by a person using machine 100 and/or other electronic components operatively coupled to machine 100.

As shown in FIG. 1, sticker 50 includes a key 52 centrally located on a first or outer surface 53 of sticker 50, one or more indicia 54 located at or near a respective corner 56 of sticker 50, and an arrow 58 positioned along a first or bottom edge 60 of sticker 50. Sticker 50 further includes an image 62 of a person's arm indicating potential insertion sites for an IV catheter. For example, sticker 50 may indicate a hand insertion site, a wrist insertion site, and an antecubital insertion site. System 40 may include one or more additional stickers 50, such as an additional sticker 50 not shown in FIG. 1, having the same or similar key 52, indicia 54, and/or image 62 of the person's arm; however, the additional sticker 50 indicates a potential insertion site for an IV catheter different than the potential insertion sites of sticker 50 shown in FIG. 1. For example, the additional sticker 50 may indicate a forearm insertion site. A second or bottom surface 64 of sticker 50 opposite outer surface 53 includes a suitable adhesive to adhere sticker 50 to a surface, such as a person's skin. During the methods described herein, sticker 50 is positioned and, in certain embodiments, adhered to the person's skin at the insertion site selected by the user, with arrow 58 aligned in a distal direction along the person's arm, i.e., in a direction toward the person's fingers. More specifically, a person, e.g., a user, selects an insertion site and places sticker 50 on the person's arm at the selected insertion sites where the user believes the IV catheter should be inserted.

With sticker 50 placed at one of the insertion sites, machine 100 interacts with sticker 50 to initiate an educational guidance mode or application on machine 100. The user selects the corresponding insertion site from a display 70 on machine 100 during an augmented reality application. When the user holds machine 100 over sticker 50, a representative image of the person's arm is displayed on display 70. In example embodiments, during the educational guidance mode or application, such as described herein, machine 100 is configured or programmed to know the preferred insertion site and the non-preferred insertion sites. Further, the user is prompted to learn more about potential complications and risk factors associated with the selected insertion site, whether the insertion site is a preferred insertion site or a non-preferred insertion site. The noninvasive, yet visceral, learning experience provides information about the importance of proper insertion, access, and maintenance of IV catheters. The system, methods, and applications as described herein provide an augmented reality application that allows the user to visualize these complications to educate the user regarding the impact of these complications on clinical outcomes and, in certain embodiments, economic outcomes.

Figure 2:
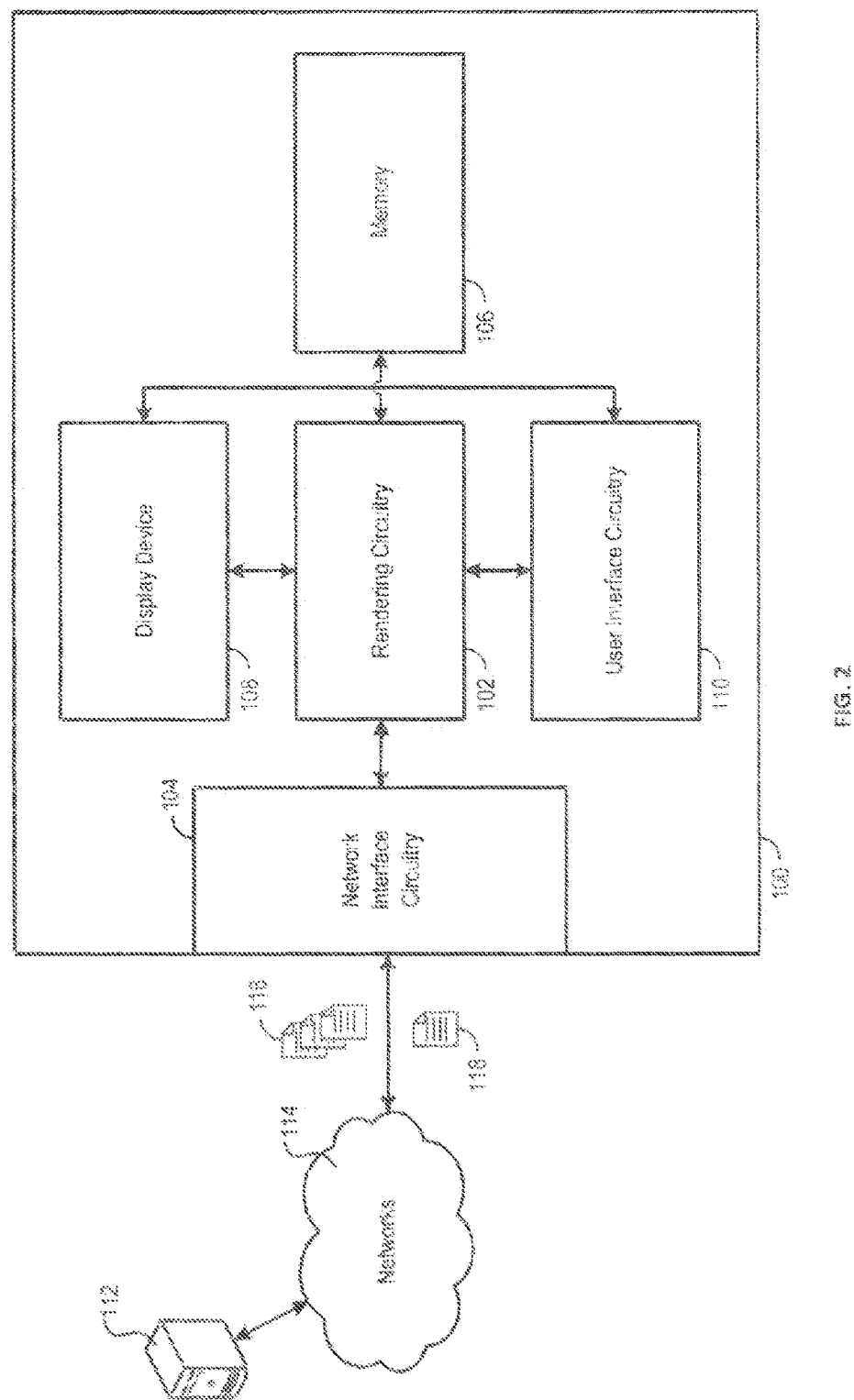
FIG. 2 shows select components of an example machine, according to various embodiments.

FIG. 2 shows at least a portion of example machine 100 (e.g., an electronic device or a computing device, such as the user's mobile phone or other suitable mobile device) configured in accordance with various embodiments for initiating the educational guidance mode or application. In various embodiments, machine 100 includes rendering circuitry 102, network interface circuitry 104, a memory device 106, a display device 108, and user interface circuitry 110. Machine 100 may also include one or more processing devices, such as one or more processors 702 shown in FIG. 120, that, together with instructions stored within memory device 106 or instructions received via network interface circuitry 104, implement portions of the various circuitry elements (e.g., rendering circuitry 102, network interface circuitry 104, and user interface circuitry 110). Rendering circuitry 102 may be communicatively coupled to network interface circuitry 104, memory device 106, display device 108, and user interface circuitry 110 to receive and send data and instructions to and from the various components. Display device 108 may also be communicatively coupled to user interface circuitry 110 to provide visual aspects of a user interface.

In certain example embodiments, network interface circuitry 104 communicates with external devices such as a server 112, via a network 114 such as the Internet. User interface circuitry 110 may include various input components and output components to enable a user to interface with machine 100 to control a display of a person's arm at or near the insertion site. Display device 108 may be integrated with machine 100 or may be otherwise connected to machine 100. Display device 108 may include any suitable type of display, such as display 70, including, for example, a liquid crystal display (LCD), a light emitting diode (LED) display, an electrowetting display (EWD), or another suitable or common display type. Display device 108 provides rendered images of an insertion site in accordance with various embodiments.

Rendering circuitry 102 may render images of a digital insertion site by rendering one or more graphical images corresponding to data items within or associated with the selected insertion site. The data items may correspond to multiple different aspects or elements within an insertion site. For example, the data items within an insertion site may include biological aspects of the insertion site, such as skeletal or musculature aspects, e.g., bones, ligaments, muscles, and/or tendons, as well as vasculature aspects, including, for example, blood vessels, such as arteries, veins, and/or capillaries. The data items may also include other aspects, such as scars, appearing on the person's skin, for example. In example embodiments, the machine includes a suitable actuator, such as one or more slider buttons, configured to provide and manipulate the augmented reality aspects of the disclosed embodiments. For example, in certain embodiments, the machine is configured to provide data items such as varying skin tones, e.g., indicating irritation, inflammation, and/or infection, a varying depth of the person's vasculature, and/or a time-lapse image of the complications arising and progressing as the slider buttons are manipulated by the user.

The data items may also include textual and categorical items applicable to individual points at or near the insertion site, structures or areas at or near the insertion site, or an entire area surrounding the insertion site. Textual and categorical items may include labels, titles, points of interest, borders, boundaries, and the like. Each type of data item discussed above may represent a different data category or data type within the insertion site. For example, a different data category or data type may exist for the skeletal, musculature, and vascular aspects surrounding and/or within the insertion site. According to various embodiments, varying levels of detail can be presented with regard to these different data categories individually or combined together within a view of the insertion site.

The data for the individual aspects of the insertion site may be stored on server 112 and may be received by machine 100 via network 114 such as the Internet using, for example, hypertext transfer protocol (HTTP). Alternatively, the data for individual aspects of the insertion site may exist on a computer readable medium, such as memory 106 or another computer readable medium that can be coupled to (e.g., directly coupled to) and read by machine 100 (e.g., a flash drive, an SD card, a micro SD card, a compact flash card, a compact disc, etc.). Different aspects may exist for different zoom levels for a given insertion site. For example, at a lowest zoom level (e.g., a zoom level 1), the entire person's arm may be shown. However, at the next zoom level (e.g., a zoom level 2), a larger image of an area of the person's arm surrounding the insertion site is shown. With each zoom level, different and/or additional data may be shown in the image. For example, additional detail data may be added to each image as the zoom level increases. Many variations of data are possible and an amount of data and a type of data stored for each insertion site at various zoom levels can be varied as is appropriate in different application settings.

Rendering circuitry 102 may request individual aspects associated with the insertion site selected by the user displayed on display device 108. For example, rendering circuitry 102 may request data associated with a selected insertion site for displaying an image of the insertion site on display device 108. Rendering circuitry 102 may request, via network interface circuitry 104, particular aspects by name or identification, or may communicate the borders of a view of the insertion site and request all aspects therein. Network interface circuitry 104 may subsequently receive the data via network 114 and may provide the data to rendering circuitry 102 or directly to memory device 106. Rendering circuitry 102 may also store the received aspects in memory device 106. Alternatively, the data may be stored or otherwise provided to machine 100 on a computer readable medium that is coupled to machine 100 (e.g., an SD card or flash drive).

In certain embodiments, the user can interface with the insertion site image through user interface circuitry 110. For example, a user may change a location of the displayed insertion site and/or may zoom in or zoom out of the displayed insertion site using user interface circuitry 110. For example, if user interface circuitry 110 includes a touchscreen interface, a user may initiate changes in the displayed insertion site by touching and dragging the insertion site to change the area displayed, or using a two-finger pinch or two-finger expansion to zoom in and zoom out. Such interactions with the insertion site image via user interface circuitry 110 may cause rendering circuitry 102 to re-render all or a portion of the insertion site image to render new insertion site image data according to the same display schema or a different display schema.

Turning to FIG. 2, user interface circuitry 110 may provide an interface to receive commands or instructions from a user to control aspects of the displayed insertion site. In one embodiment, user interface circuitry 110 may provide a graphical user interface (GUI) input to enable a user to select different operations with respect to the insertion site.

In an alternative example embodiment, the GUI input may not actually be displayed on the display device; however, user interface circuitry 110 may be responsive to movement of a pointer, a touchpad, a touchscreen, or another input device in the directions indicated by the GUI input. For example, a user may right click on a mouse and move a pointer in the associated directions to cause changes to the display of the insertion site (e.g., up and down to change the zoom level, right and left to change the level of detail). Further still, user interface circuitry 110 may be responsive to tilting, rotating, or moving the device, which may be interpreted as commands or instructions to alter the view of the map, particularly to change the level of detail displayed. Further still, interface circuitry 110 may be responsive to voice commands, which may be interpreted as commands or instructions to alter the view of the insertion site. In other approaches, interface circuitry 110 may include a camera or light sensor and may be responsive to visual gestures (such as hand gestures, head gestures), facial expressions, or eye movement of a user.

In another embodiment, user interface circuitry 110 receives gestures (e.g., via a touchscreen or a touchpad or by video monitoring of the user) to control the display of the insertion site. For example, a first gesture may control the zoom of the insertion site, while a second gesture may control the level of detail shown within the insertion site. In one example, the first gesture (e.g., to control the zoom of the insertion site) may include a two-finger pinch/spread gesture (one indicates a zoom in, while the other indicates a zoom out). The second gesture (e.g., to control the level of detail provided in the image) may be different from the first gesture and may include a three-finger pinch/spread gesture (one indicates an increase in the level of detail, while the other indicates a decrease in the level detail). Other gestures are possible to control the level of detail of the insertion site, including a two-finger or three-finger rotation gesture or a two-finger or three-finger swipe gesture. Many variations for input gestures and input commands are possible.

Rendering circuitry 102 renders graphical images of an insertion site to include graphical representations of the data items within a visible area of the insertion site at various zoom level. Display device 108 displays the graphical images of the insertion site on display 70.

Figure 3A:
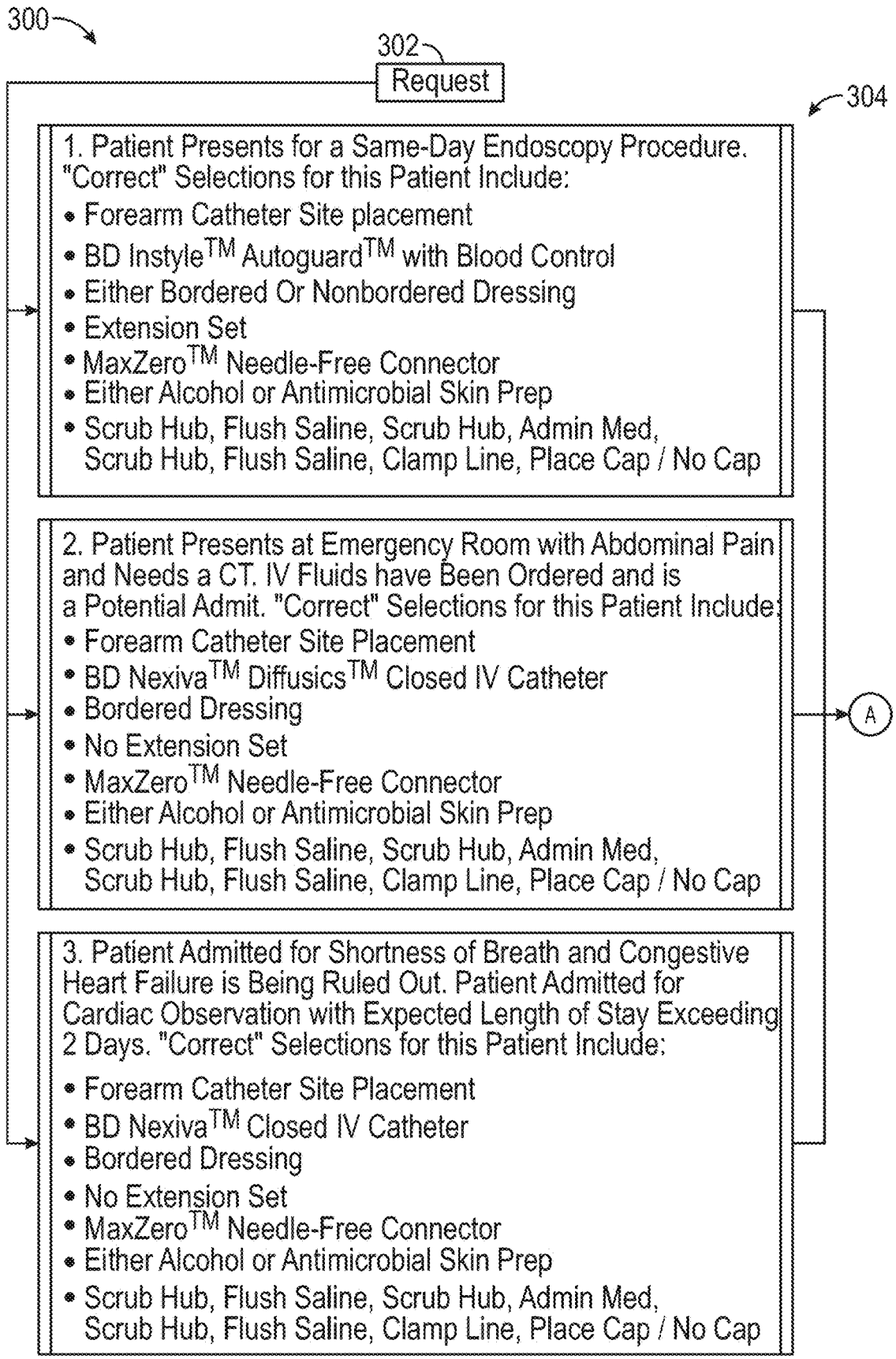
FIG. 3A shows an example method for providing educational guidance for peripheral IV therapy using a consequence-based learning (CBL) program, according to various embodiments.
Figure 3B:
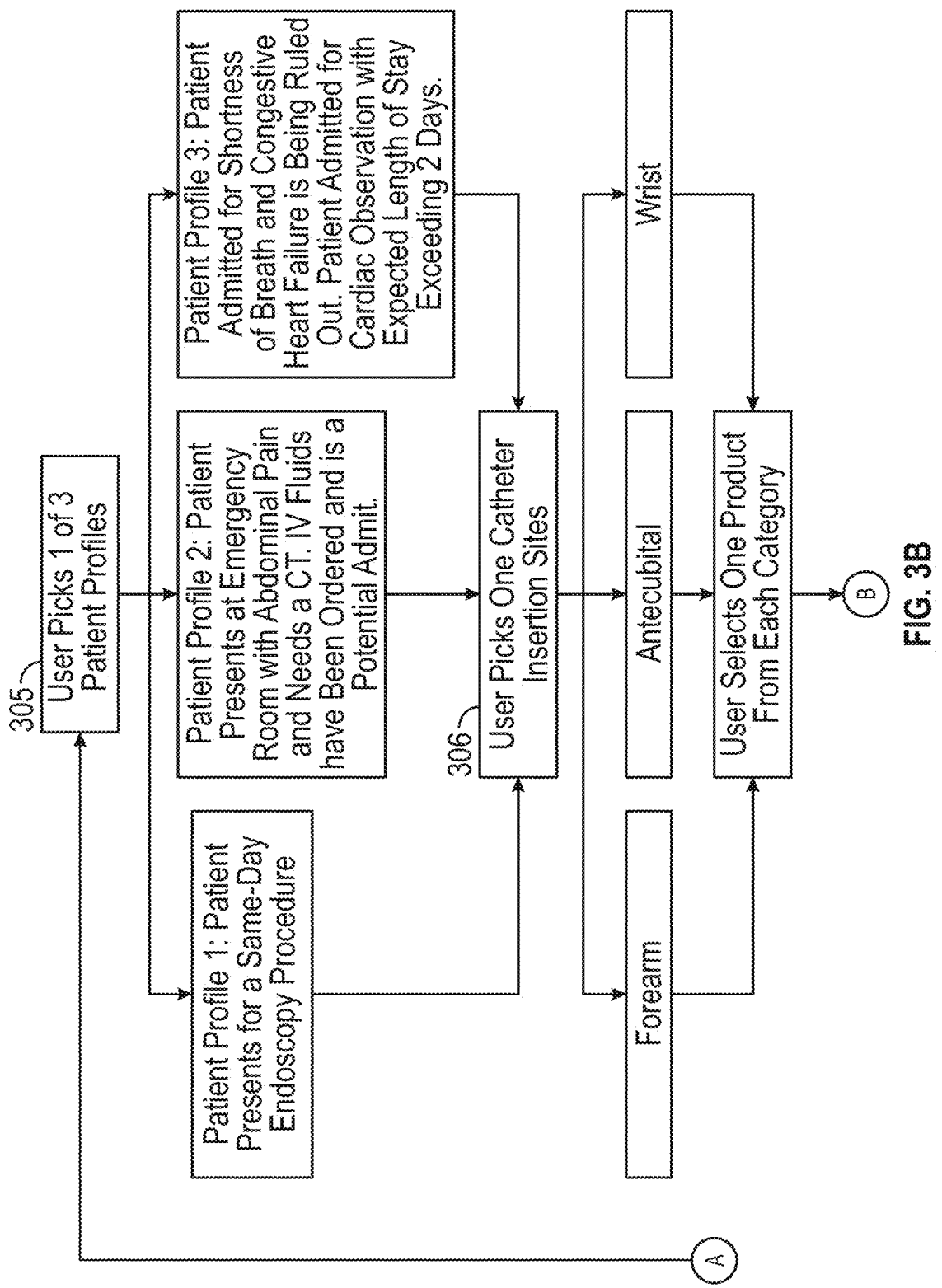
FIG. 3B shows another example method for providing educational guidance for peripheral IV therapy using a consequence-based learning (CBL) program, according to various embodiments.
Figure 3C:
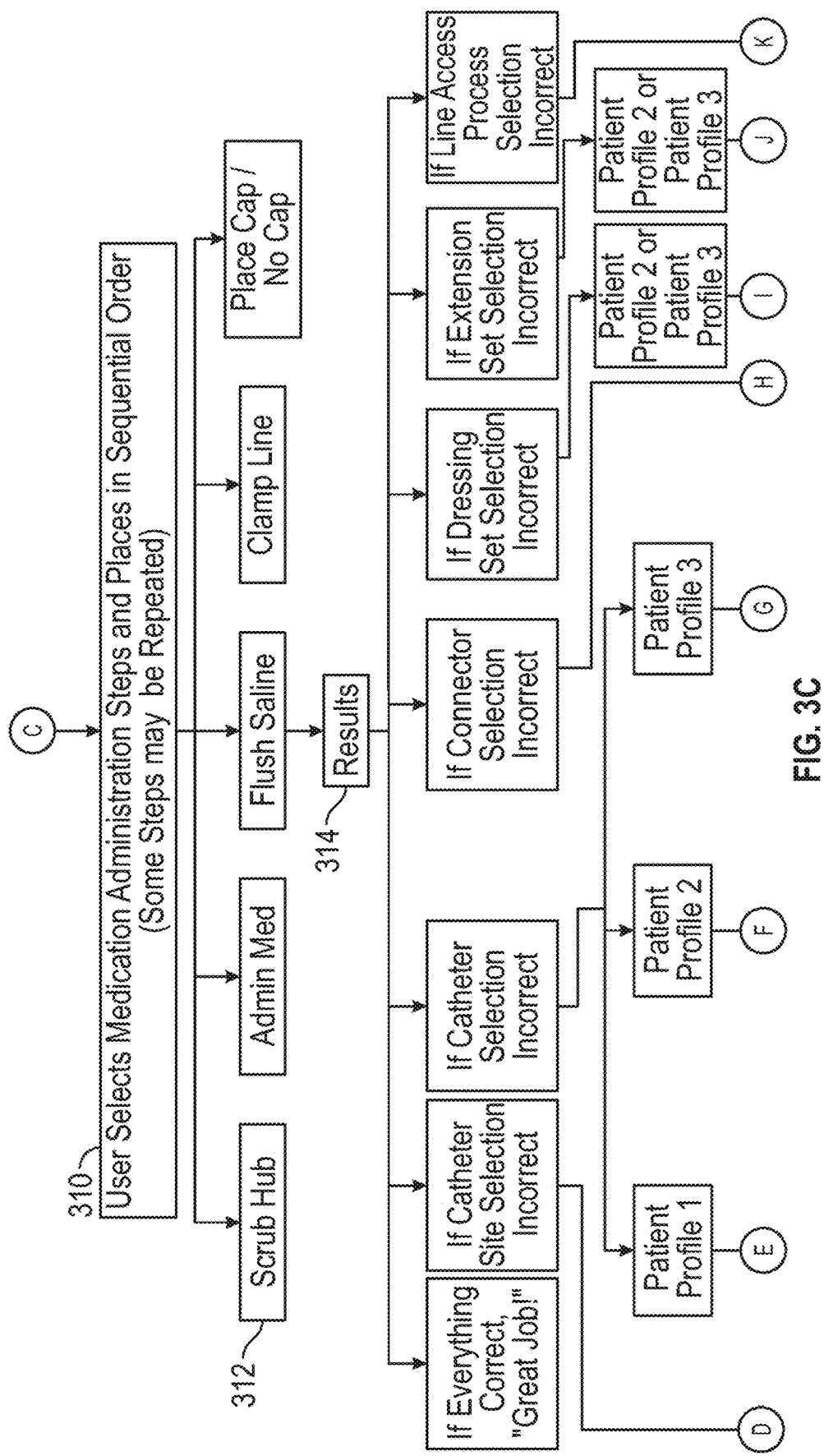
FIG. 3C shows another example method for providing educational guidance for peripheral IV therapy using a consequence-based learning (CBL) program, according to various embodiments.
Figure 3C:
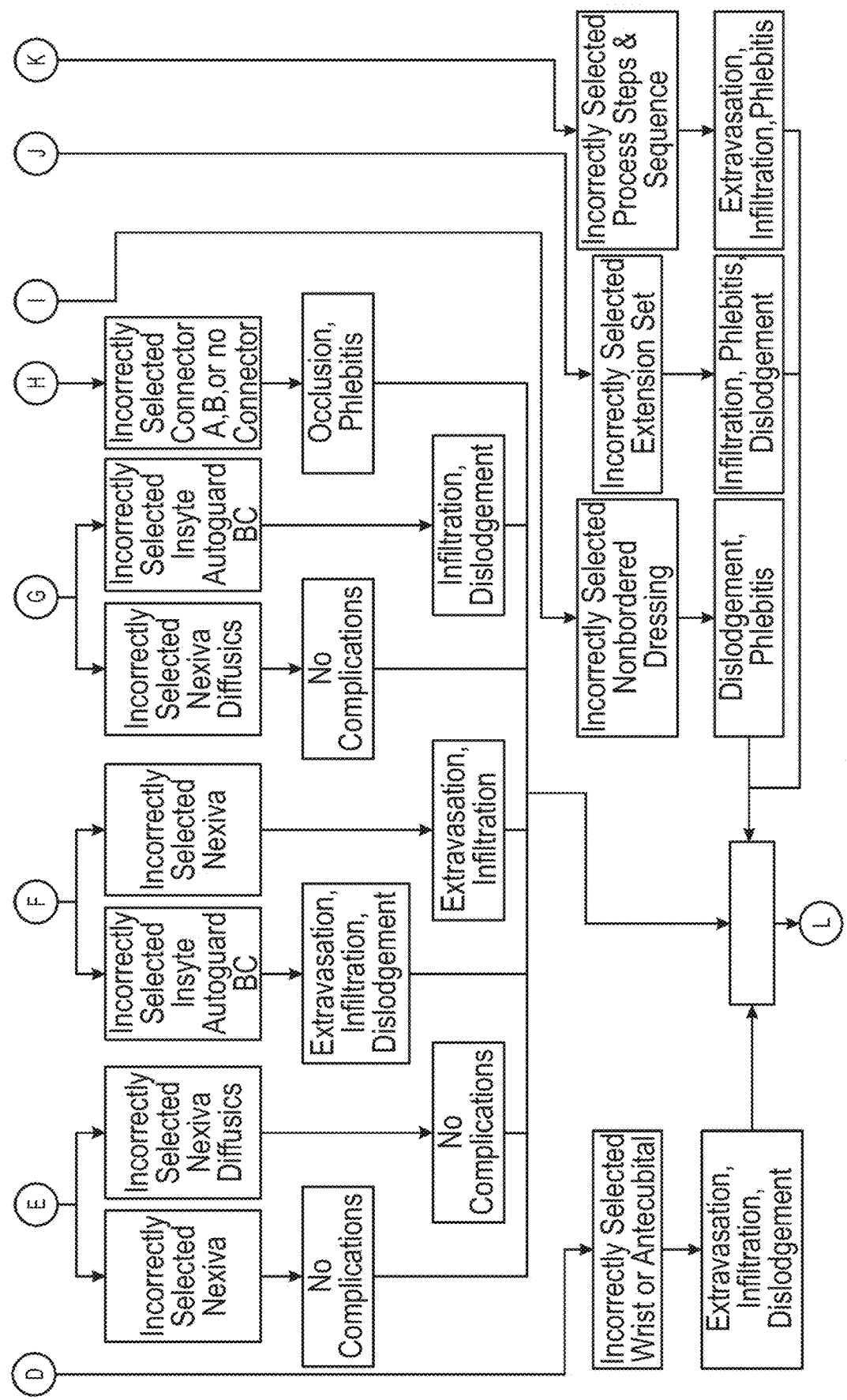
Figure 3C:
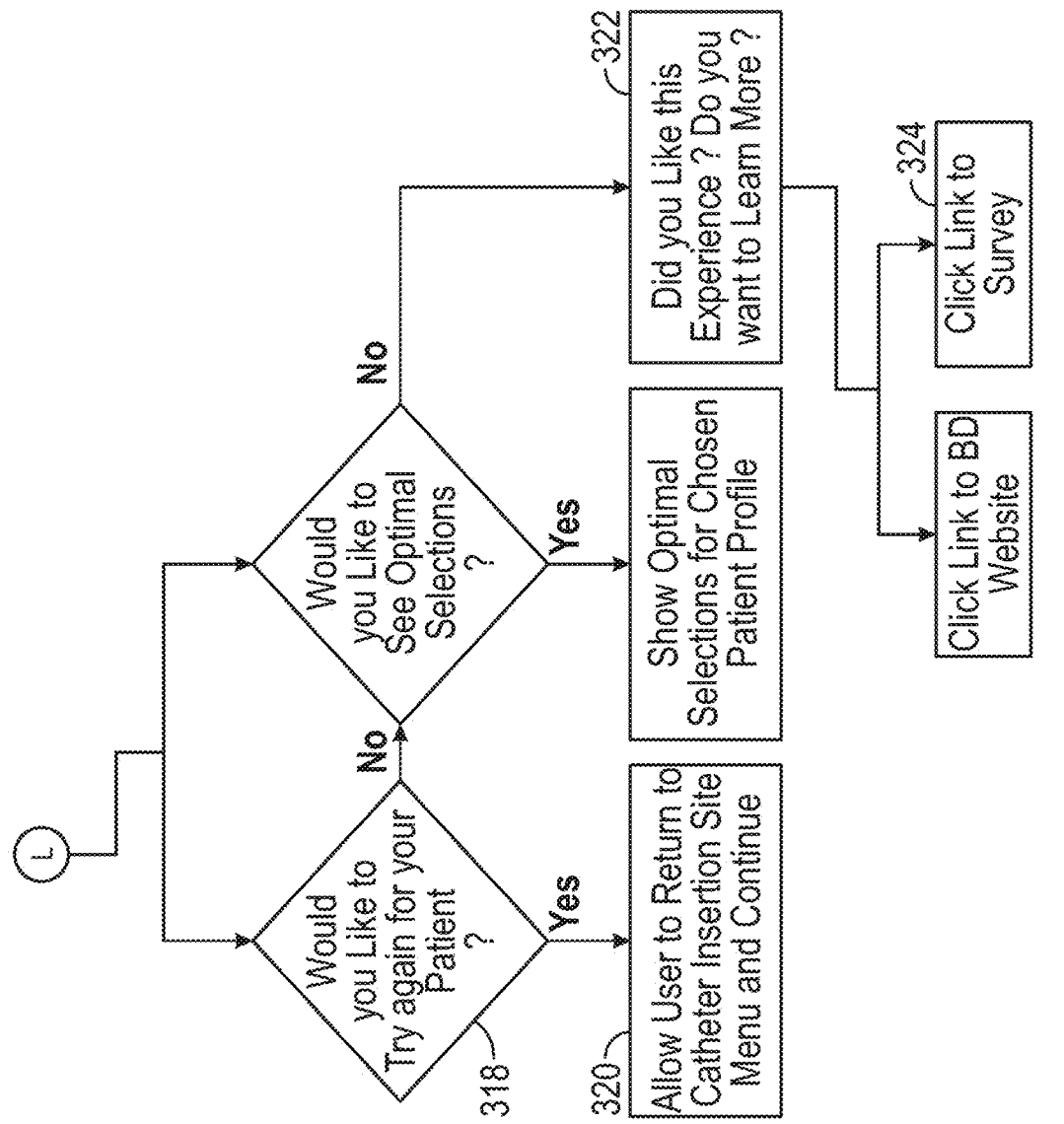

FIGS. 3A-3C show a flow diagram of logic 300 that machine 100 may implement, once the educational guidance mode or application is activated using system 40, as part of a method for providing educational guidance for peripheral IV therapy using suitable learning programs or techniques, such as a consequence-based learning (CBL) program or technique. For example, various circuitry elements discussed above and/or various components of machine 100 machine, such as the one or more processing devices, may be configured to implement some or all of logic 300 shown in FIGS. 3A-3C.

At step 302, machine 100 receives, via a network 114, a request for initiating a CBL program from a user and, in response to the request, machine 100 presents 304 the user with a plurality of example person profiles from which to choose. In example embodiments, the example person profiles are displayed on display 70 of machine 100 or a display operatively coupled to machine 100. For example, machine 100 may present a first person profile indicating a person presenting for a same-day endoscopy procedure. A second person profile is presented indicating a person presenting at an emergency room with an abdominal pain and needing a computed tomography (CT) procedure. In this person profile, a nurse or hospital personnel has ordered IV fluids and the person will potentially be admitted to the hospital. A third person profile is presented indicating a person admitted for shortness of breath and congestive heart failure is being ruled out. The person is admitted for cardiac observation with an expected length of hospital stay exceeding 2 days. Additional or alternative person profiles may be presented 304 by machine 100. Each of these person profiles may require a different set of "correct" or "appropriate" procedures and/or products for IV therapy, although machine 100 does not display the correct or most appropriate procedures and/or products to the user at this time in the CBL program.

For example, the first person profile might require a first catheter, an extension set or no extension set, a suitable skin preparation such as skin antisepsis or 70% isopropyl alcohol, a suitable connector, and a dressing choice of either film with a border or film without a border. The second person profile might require a second catheter, a suitable skin preparation, a suitable connector, and a transparent film with a border; however, this person profile may not require an extension set. The third person profile might require a third catheter, a suitable skin preparation, a suitable connector, and a transparent film with a border; however, this person profile does not require an extension set.

Machine 100 queries the user 305 to select one of the person profiles presented on display 70. Once the user selects one of the person profiles presented to the user, machine 100 prompts 306 the user to select an insertion site on a person's appendage (e.g., a person's arm) for inserting an IV catheter. For example, machine 100 displays various options for selection of an insertion site including an antecubital insertion site, a forearm insertion site, a wrist insertion site, and a hand insertion site.

At step 308, machine 100 instructs the user to select the appropriate products and/or procedures for properly inserting the IV catheter in the person's arm at the selected insertion site, based on the person profile selected by the user. In an example embodiment, machine 100 may display available products on a tray and instruct the user to select, e.g., click and drag, the appropriate products to be used in a most appropriate sequence. In these embodiments, by selecting what the user believes to be the appropriate products for the procedure, the user is required to connect the appropriate products and practice.

For example, in a particular embodiment, a proper procedure may include, in sequence, selecting the most appropriate peripheral IV catheter, preparing the insertion site for insertion of the catheter, providing and coupling a connector to the IV catheter, providing appropriate dressing at or around the insertion sire, providing an extension set, if required, and then proceeding with a line access process. In example embodiments, the user first selects the appropriate catheter for the selected person profile to initiate the educational guidance mode or application. A plurality of catheters, such as a first catheter, a second catheter, and a third catheter, may be displayed on display 70 from which the user is prompted to select the most appropriate catheter for the procedure. The user then selects the appropriate process for preparing the site for insertion. A plurality of possible preparation steps may be displayed on display 70, such as whether to prepare the insertion site with chlorhexidine in alcohol solution or whether to prepare the insertion site with only alcohol. The user selects the appropriate connector, if necessary, to couple to the selected catheter. For example, machine 100 may display a plurality of choices for a connector, such as a first connector, a second connector, a third connector, or no connector. The user selects what the user believes is the appropriate connector choice for the person profile. Once the connector option is selected, machine 100 prompts the user to select the appropriate dressing from a plurality of dressing choices. For example, machine 100 may display on display 70 several choices including a transparent film dressing and a transparent film dressing with a border. The user determines whether an extension set is required. For example, machine 100 may display an option for using an extension set and an option for not using an extension set. Once the products are selected based on the selected person profile, machine 100 prompts the user to continue with a line access process.

During the line access process, the user to places 310 a plurality of process steps in a most appropriate sequential order by clicking, dragging, and dropping each process step in an appropriate numbered process step location. For example, referring to FIG. 3A, machine 100 may display the various steps of the line access process including scrub, flush, cap, administer medicine, in a non-sequential listing on display 70. The user is then required to properly place the process steps in sequential order within the numbered process step locations displayed on display 70. In example embodiments, one or more of the process steps may be required more than once during an appropriate line access process.

Figure 7:
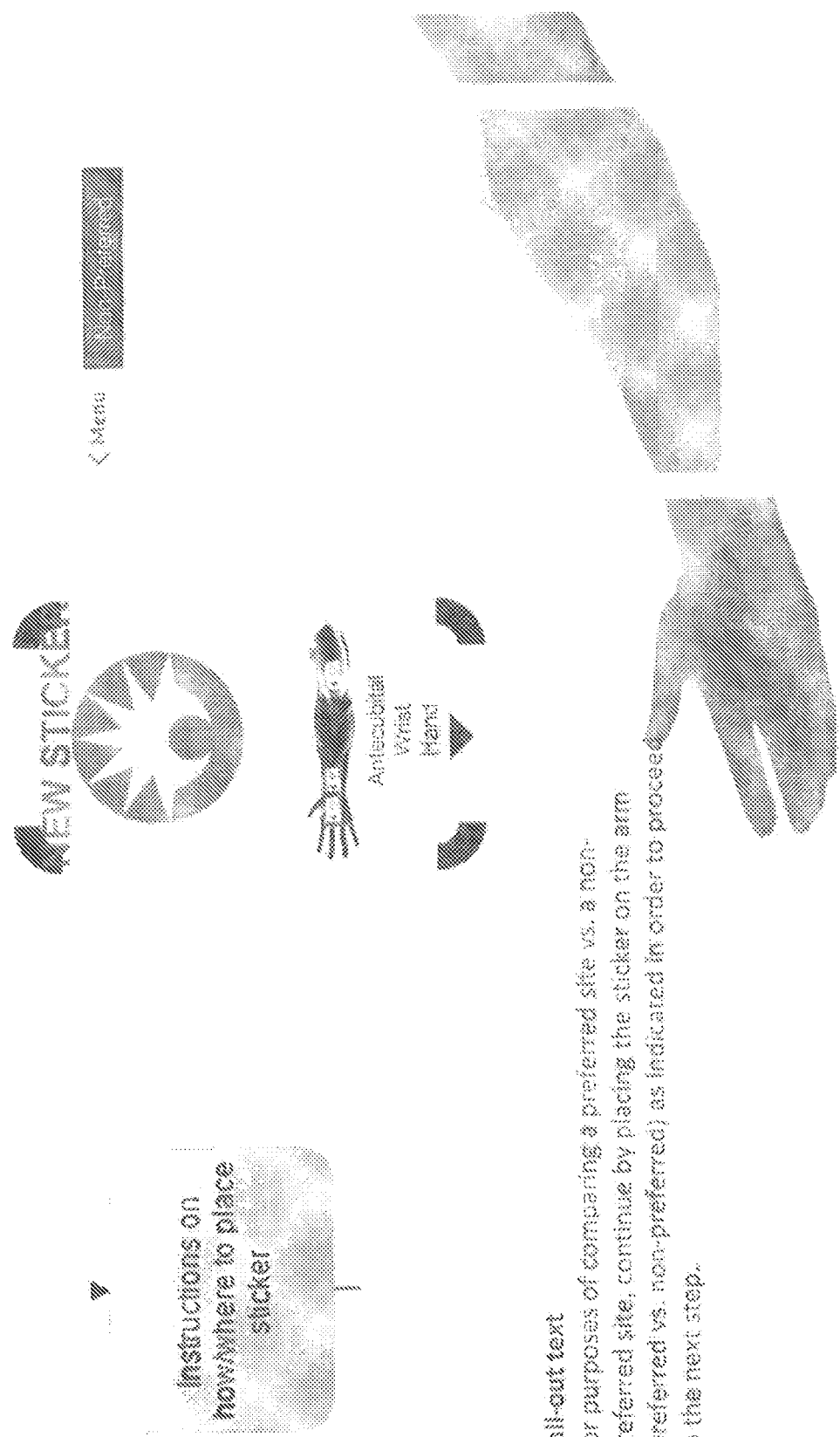
FIG. 7 is another example user interface, according to various embodiments.

At step 312, once the user places the line access process steps in what the user believes is the most appropriate sequential order, machine 100 instructs the user to position sticker 50 at the selected insertion site (e.g., the antecubital insertion site, the forearm insertion site, the wrist insertion site, or the hand insertion site) on the chosen arm (i.e., the right arm or the left arm) in order to proceed to the next step. As shown in FIG. 7, machine 100 displays a user interface indicating placement of sticker 50 at the selected insertion site. The user interface may also indicate the proper alignment and orientation of sticker 50, e.g., an arrow displayed on sticker 50 pointing toward the person's wrist on the chosen arm.

At step 314, machine 100 displays on display 70 (or another suitable display operatively coupled to machine 100) the results of the user's catheter build and listing of the line access process steps. If every user selection is most appropriate, i.e., the catheter was properly built and the listing of the line access process steps were in the most appropriate sequential order, machine 100 displays on display 70 a congratulatory response for positive reinforcement, such as "Great Job!" If, however, one or more selections or process steps were not the most appropriate, machine 100 displays on display 70 complications, if any, associated with the improper selection.

For example, if the user incorrectly selected the catheter based on the selected person profile, machine 100 instructs the user to place machine 100 over sticker 50 to learn of potential results of and/or complications associated with the user's product and/or practice selection for the corresponding person profile. For example, according to certain embodiments, if the user selected person profile 1, the recommended or most appropriate selection for the catheter is the third catheter. If the user selected an incorrect catheter under the circumstances, e.g., the first catheter or the second catheter, machine 100 displays on display 70 potential complications as a consequence of the incorrect catheter selection. In this instance, there is no potential complication as a consequence of incorrectly selecting either the first catheter or the second catheter. Similarly, if the user selected person profile 2, the recommended or most appropriate choice for the catheter is the second catheter. If the user selected an incorrect catheter under the circumstances, e.g., the third catheter or the first catheter, machine 100 displays on display 70 potential complications as a consequence of the incorrect catheter selection. In this instance, if the user incorrectly selected the third catheter, machine 100 displays potential complications associated with this incorrect catheter selection, including, for example, extravasation, infiltration, and/or dislodgement. If the user incorrectly selected the first catheter, machine 100 displays potential complications associated with this incorrect catheter selection, including, for example, extravasation and/or infiltration. Similarly, if the user selected person profile 3, the recommended or most appropriate selection for the catheter is a first catheter. If the user selected an incorrect catheter under the circumstances, e.g., the second catheter or the third catheter, machine 100 displays potential complications as a consequence of the incorrect catheter selection. In this instance, if the user incorrectly selected the second catheter, machine 100 displays that there are no potential complications associated with this incorrect catheter selection. If the user incorrectly selected the third catheter, machine 100 displays potential complications associated with this incorrect catheter selection, including, for example, infiltration and/or dislodgement.

If the user incorrectly selected the connector based on the selected person profile, machine 100 instructs the user to place machine 100 over sticker 50 to learn of potential results of and/or complications associated with the user's product and/or practice selection for the corresponding person profile. For example, according to certain embodiments, if the user selected an incorrect connector, machine 100 displays potential complications as a consequence of the incorrect connector selection, including, for example, phlebitis and/or occlusion.

If the user incorrectly selected the dressing based on the selected person profile, machine 100 instructs the user to place machine 100 over sticker 50 to learn of potential results of and/or complications associated with the user's product and/or practice selection for the corresponding person profile. For example, according to certain embodiments, if the user selected an incorrect dressing, machine 100 displays potential complications as a consequence of the incorrect dressing selection, including, for example, phlebitis and/or dislodgement.

If the user incorrectly selected whether to use an extension set based on the selected person profile, machine 100 instructs the user to place machine 100 over sticker 50 to learn of potential results and/or complications associated with the user's product and/or practice selection for the corresponding person profile. For example, according to certain embodiments, if the user selected to incorrectly use or not use an extension set, machine 100 displays potential complications as a consequence of the incorrect selection, including, for example, a potential result of infiltration, phlebitis and/or dislodgement.

If the user incorrectly selected one or more of the line access process step, machine 100 instructs the user to place machine 100 over sticker 50 to learn of potential results and/or complications associated with the user's product and/or practice selection. For example, according to certain embodiments, if the user incorrectly selected one or more of the line access process step, machine 100 displays potential complications as a consequence of the incorrect selection, including, for example, a potential result of infiltration, dislodgement, phlebitis, and/or other potential complications that may occur. In example embodiments, the machine includes a suitable actuator, such as one or more slider buttons, configured to provide and manipulate the augmented reality aspects of the disclosed embodiments. For example, in certain embodiments, the machine is configured to provide data items such as varying skin tones, e.g., indicating irritation, inflammation, and/or infection, a varying depth of the person's vasculature, and/or a time-lapse image of the complications arising and progressing as the slider buttons are manipulated by the user.

Once machine 100 displays to the user the incorrect selections and the complications and/or potential risks resulting from the incorrect selection or selections, machine 100 prompts 316 the user to decide whether the user would like to achieve a better result for the person. Once prompted, the user may decide to continue with an educational guidance mode or an application to achieve a better result for the person. In a particular embodiment, if a product, e.g., the catheter, the connector, the dressing, the extension set, and/or the line access process selection is incorrect, machine 100 prompts the user to skip to the relevant selection step in order to re-select the appropriate product or re-position the steps of the line access process sequentially. For example, if the user incorrectly selects the catheter, machine 100 directs the user to the prompt for selecting the catheter so that the user is able to select a different catheter. In a particular embodiment, if the user selects a sub-optimal or inappropriate catheter again, machine 100 provides information regarding the most appropriate catheter. A similar process is available to choose other products, e.g., the connector, the dressing, and/or the extension set, and/or line access process steps, if the user initially selected the incorrect, i.e., not the most appropriate, product or step. Once the user selects the most appropriate products and positions the line access process steps in the most appropriate order, machine 100 queries the user 322 whether the user would like to learn more about peripheral IV therapy. If the user is not interested in learning more, the educational guidance mode or application is closed. In one embodiment, machine 100 provides the user 324 with a link to a suitable site, for example, a microsite that provides the results of the application evaluation and/or directs the user to a proper site or a microsite providing a survey for the user to complete.

Figure 3D:
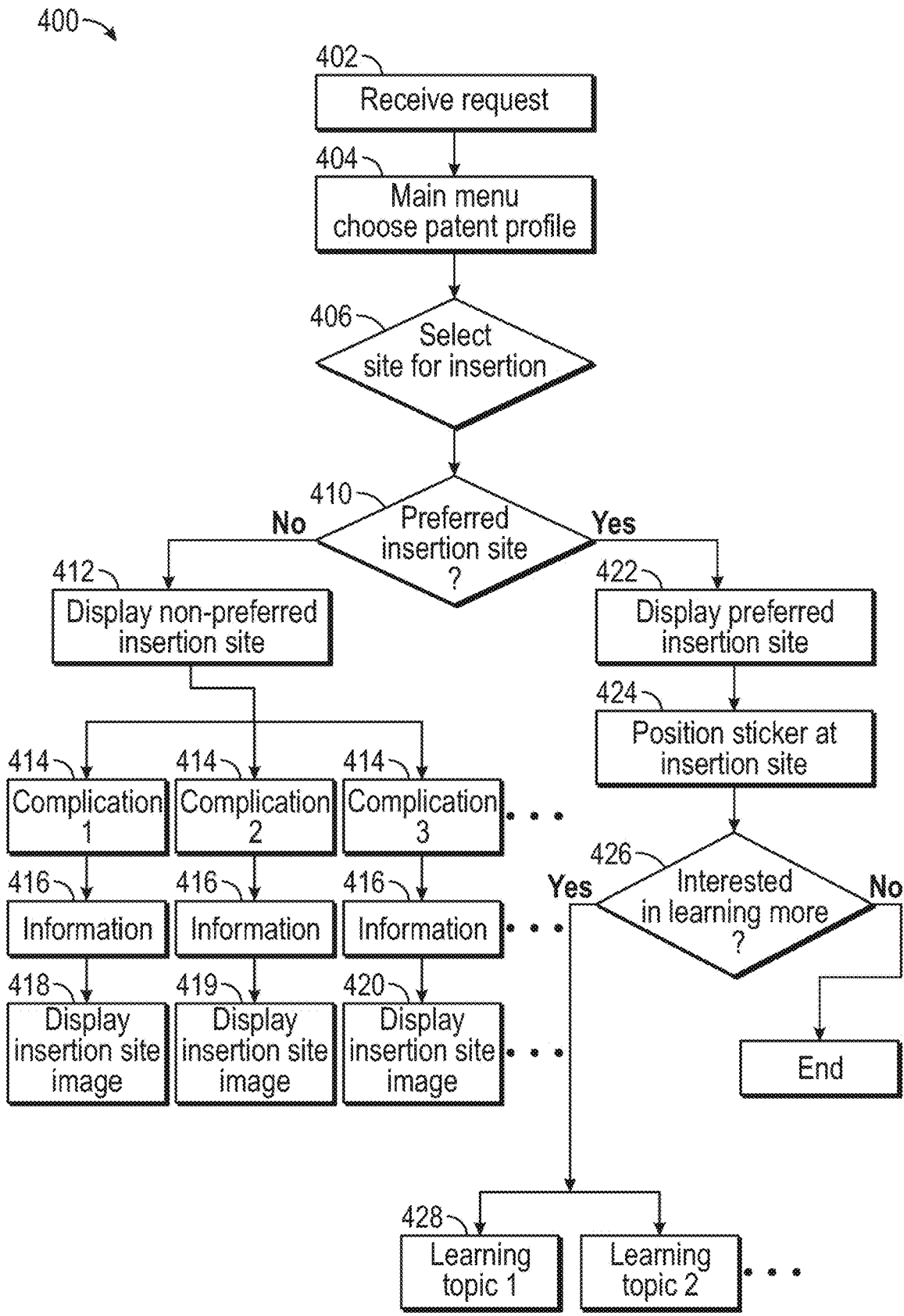
FIG. 3D is an example method for providing educational guidance for peripheral IV therapy using a consequence-based learning (CBL) program, according to various embodiments.

Referring now to FIGS. 3D-25 and 120, in example embodiments, machine 100 may be implemented as part of a method for providing educational guidance for peripheral IV therapy using suitable learning programs such as a consequence-based learning (CBL) program or application. Machine 100 may implement logic, similar to or different from the logic shown in the flow diagram of FIG. 3A-3C, as part of a method in accordance with various embodiments. For instance, various circuitry elements discussed above and/or various components of machine 100, such as one or more processing devices, may be configured to implement some or all of the logic implemented by machine 100 during the CBL program or application. FIG. 3D shows a flow diagram of logic 400 that machine 100 may implement as part of a method in accordance with various embodiments. FIGS. 4-26 illustrate example user interfaces associated with various steps of logic 400 and displayed on display 70 of machine 100 during the CBL program or application.

At step 402, machine 100 receives, via a network 114, a request for initiating a CBL program from a user and, in response to the request, machine 100 presents 404 the user with a main menu including a plurality of example person profiles from which to choose. For example, machine 100 may present a first person profile indicating a 35 year old healthy, right-handed male who presents to the hospital for a routine procedure (preferred insertion site for IV is in the left, non-dominant forearm); a second person profile indicating an 85 year old diabetic, right handed female with fragile veins who presents to the hospital with ischemic right lower extremity (preferred insertion site for IV is in the left non-dominant forearm); and a third person profile indicating a 50 year old hemodialysis left handed male who presents to the hospital with occluded right forearm loop arteriovenous graft (preferred insertion site for IV is in the graft-free, left forearm. Additional or alternative person profiles may be presented 404 by machine 100.

Figure 6:
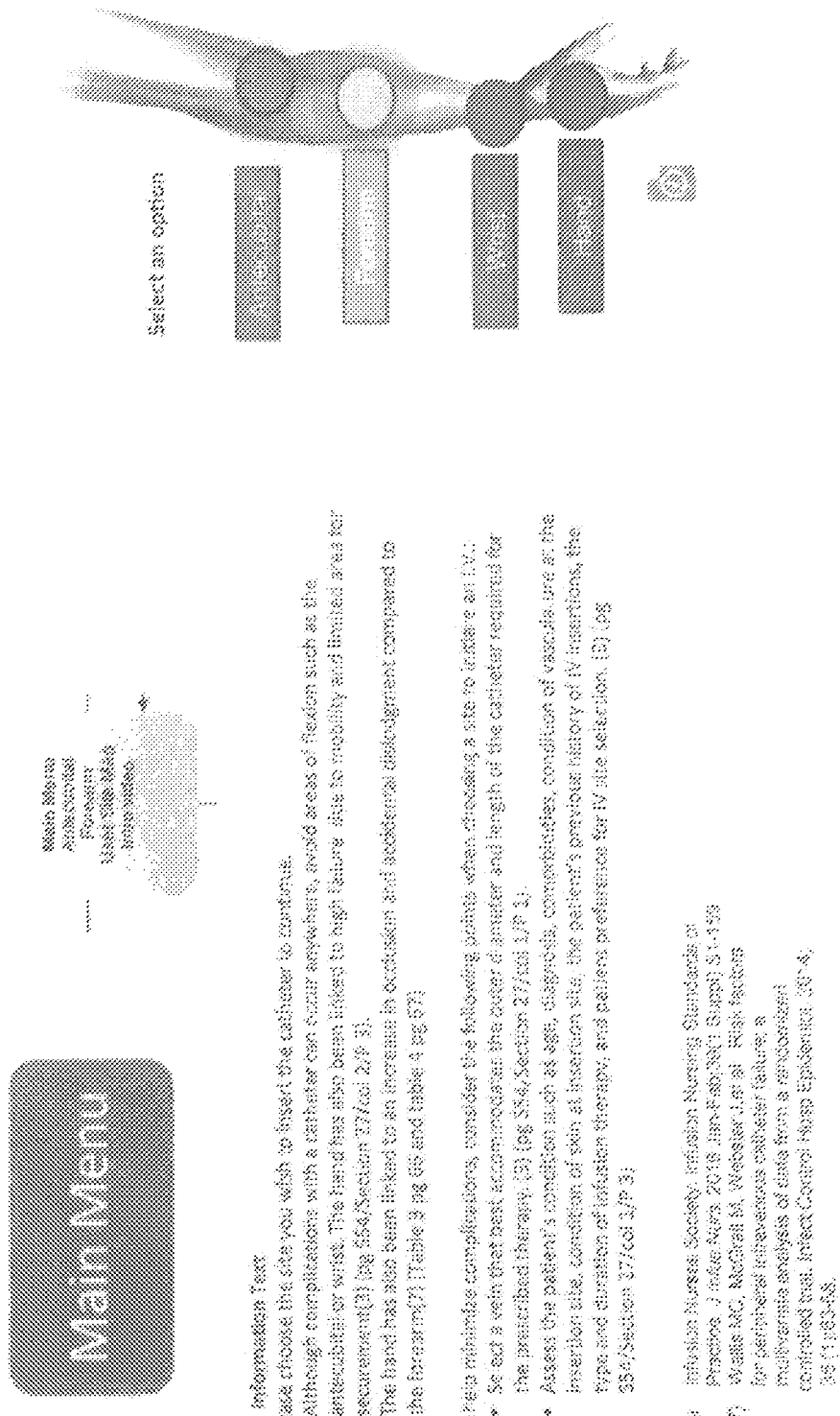
FIG. 6 is another example user interface, according to various embodiments.

Once the user selects one of the person profiles presented to the user, machine 100 prompts 406 the user to select an insertion site on a person's appendage (e.g., a person's arm) for inserting an IV catheter. As shown in FIG. 6, machine 100 displays a user interface indicating a plurality of insertion sites from which to select the insertion site. For example, as shown in FIG. 6, the user interface displays various options for selection including an antecubital insertion site, a forearm insertion site, a wrist insertion site, and a hand insertion site. The user interface may include a textual indicator and/or visual indicator, e.g., a color or highlighted option, indicating a preferred insertion site at least partially depending on the selected person profile. In particular embodiments, machine 100 indicates informational text providing guidance on selecting a most appropriate insertion site. For example, the informational text may advise the user of potential complications that can occur during catheter insertion and/or provide one or more points for the user to consider to minimize a potential for complications when selecting the insertion site for the IV. In certain embodiments, the informational text may include an indication that although complications with a catheter can occur anywhere, areas of flexion, such as at the antecubital insertion site or the wrist insertion site, should be avoided.

Further, the informational text may include additional information, such as the hand insertion site has been linked to an increase in occlusion and accidental dislodgement compared to other sites (e.g., a preferred insertion site such as the forearm insertion site). The informational text may also include additional points to consider to minimize complications including, for example, a selection of a vein that best accommodates an outer diameter and/or a length of the catheter required for the prescribed therapy and/or an assessment of a person's condition including, without limitation, an age of the person, a diagnosis, comorbidities, a condition of vasculature at the insertion site, a condition of the person's skin at the insertion site, a person's previous history of IV insertions, a type and/or a duration of infusion therapy, a person preference for IV site selection, or any suitable combination thereof.

Figure 8:
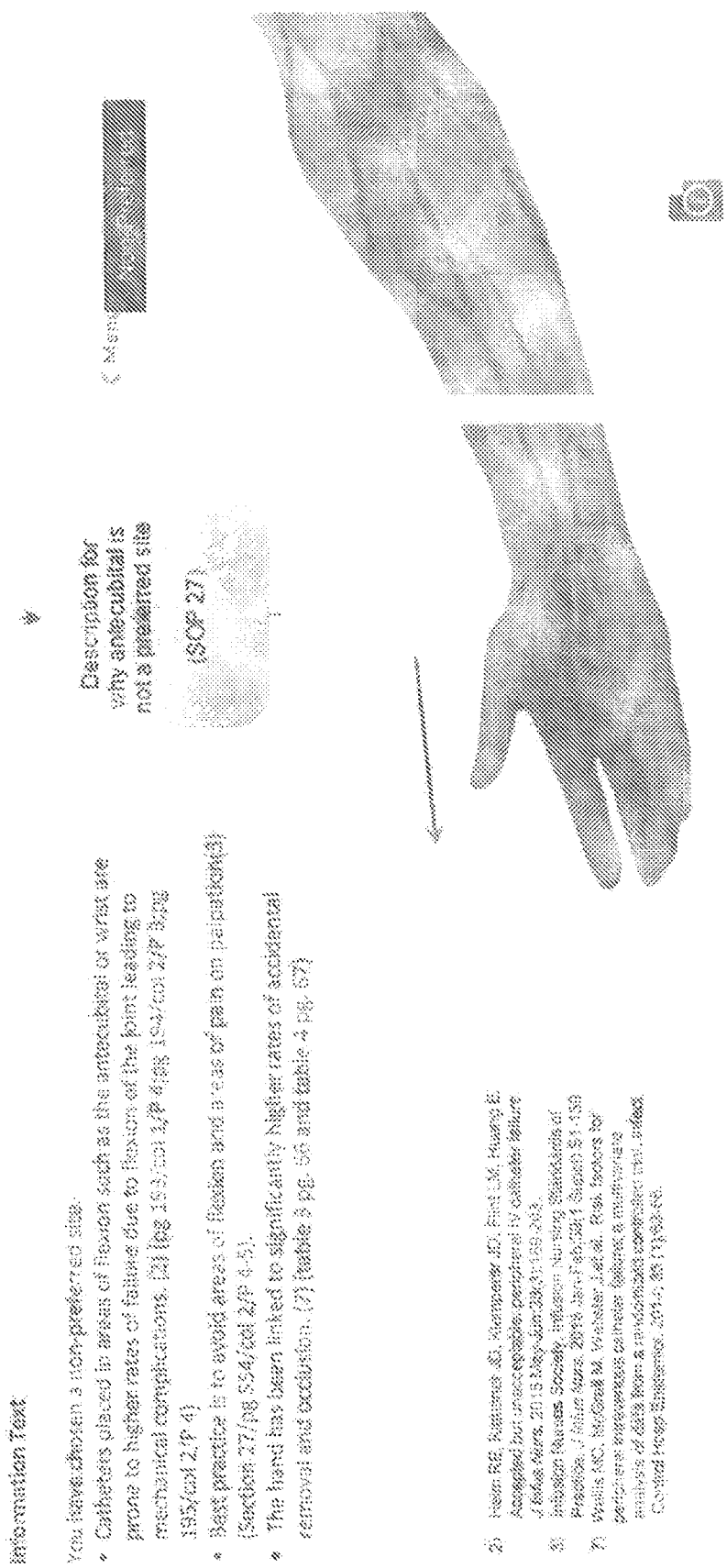
FIG. 8 is another example user interface, according to various embodiments.

At step 410, machine 100 determines whether the user selected a preferred insertion site or a non-preferred insertion site. If the user selects a non-preferred insertion site (e.g., the antecubital insertion site, the wrist insertion site, or the hand insertion site) in response to the prompting step 406, the processing device of machine 100, such as processor 702, renders a first graphical image of the selected arm and, at step 412, display 70 displays the first graphical image on a user interface as shown in FIG. 8. The user interface may include informational text indicating to the user that the user has chosen a non-preferred insertion site. The informational text may also include an indication that catheters placed in areas of flexion, such as the antecubital insertion site or the wrist insertion site, are prone to higher rates of failure due to flexion of the joint leading to mechanical complications. The informational text may also indicate a best practice to avoid areas of flexion and areas of pain on palpation. The informational text may also indicate that the hand insertion site has been linked to significantly higher rates of accidental removal and occlusion.

Figure 9:
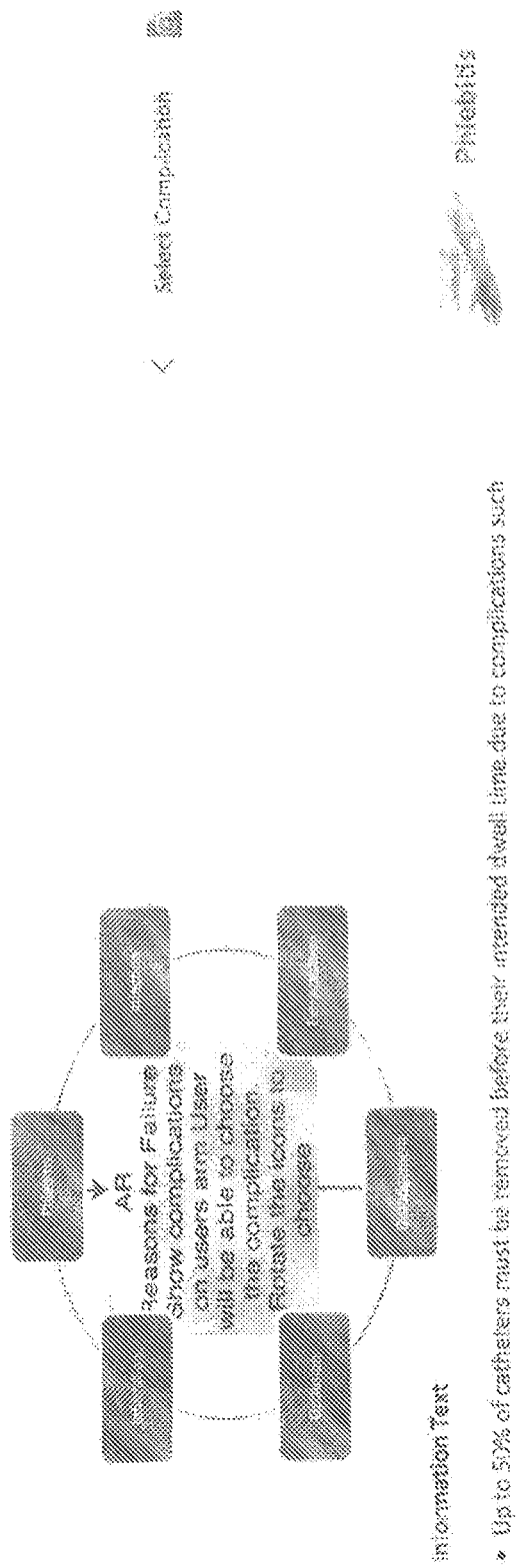
FIG. 9 is another example user interface, according to various embodiments.

At step 414, display 70 displays one or more complications associated with the chose non-preferred insertion site. For example, a user interface, as shown in FIG. 9, may indicate reasons for failure and/or complications associated with inserting the IV catheter in the non-preferred arm, such as phlebitis, infection, extravasation, dislodgment, occlusion, and infiltration, arranged in a menu having an arcuate or circular pattern on the user interface. To provide additional educational guidance, at step 416, machine 100 prompts the user to select one of the indicated complications for further information regarding the selected complication. The user interface may include informational text indicating that up to 50% of catheters must be removed before their intended dwell time due to complications such as displayed on the user interface and prompting the user to select one of the complications from the menu to learn more about the particular complication. In example embodiments, at step 418, the processing device of machine 100 renders a graphical image of the person's arm indicating the chosen complication and, at step 420, display 70 displays the graphical image on a user interface. The user interface may include informational text indicating which complication was selected, a definition of the complication, and/or an indication of risks associated with the selected complication.

Figures 10, 10A:
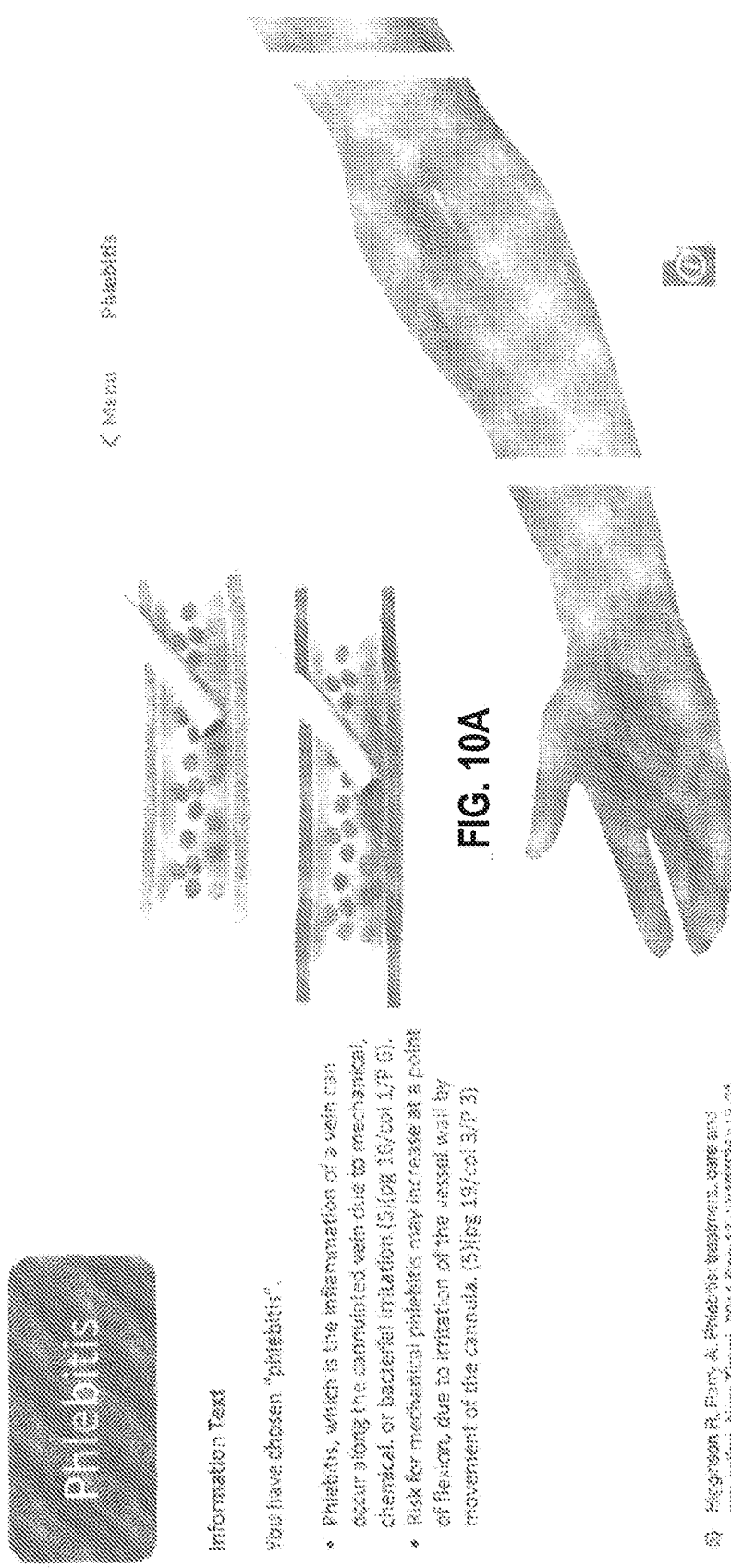
FIG. 10 is another example user interface, according to various embodiments.

For example, if, at step 416, the user chooses to learn more about phlebitis, at step 418, the processing device of machine 100 renders a graphical image of the person's arm indicating phlebitis and, at step 420, display 70 displays the graphical image on a user interface, as shown in FIG. 10. The user interface may include informational text indicating that the user has selected phlebitis and defining "phlebitis" as an inflammation of a vein that can occur along the cannulated vein due to mechanical, chemical, and/or bacterial irritation and/or an additional graphical image, such as shown in FIG. 10A, illustrating the effects of phlebitis. The informational text may also indicate risks associated with phlebitis, such as an increase at a point of flexion due to irritation of the vessel wall by movement of the cannula.

If, at step 416, the user chooses to learn more about infiltration, at step 418, the processing device of machine 100 renders a graphical image of the person's arm indicating infiltration and, at step 420, display 70 displays the graphical image on a user interface, as shown in FIG. 11. The user interface may include informational text indicating that the user has selected infiltration and defining "infiltration" as an inadvertent leakage of a non-vesicant solution into the surrounding tissue resulting from erosion or penetration of the catheter into or through the venous wall and/or an additional graphical image, such as shown in FIG. 11A, illustrating the effects of infiltration. The informational text may also indicate, for example, that infiltration is the most common catheter complication. The informational text may also indicate that peripheral IVs placed in areas of flexion (e.g., the antecubital insertion site or the wrist insertion site) are prone to have higher rates of infiltration, most likely due to the movement of the cannula tip against the vessel wall causing trauma which leads to poor venous wall integrity.

If, at step 416, the user chooses to learn more about infection, at step 418, the processing device of machine 100 renders a graphical image of the person's arm indicating infection and, at step 420, display 70 displays the graphical image on a user interface, as shown in FIG. 12. The user interface may include informational text indicating that the user has selected infection and defining "infection" as a presence and growth of a pathogenic microorganism(s) having a local or systemic effect and/or an additional graphical image, such as shown in FIG. 12A, illustrating the effects of infection. The informational text may also indicate, for example, that infection may be a result of poor skin disinfection during drug administration and/or a frequency of IV medication received, as well as other risk factors for infection.

If, at step 416, the user chooses to learn more about occlusion, at step 418, the processing device of machine 100 renders a graphical image of the person's arm indicating occlusion and, at step 420, display 70 displays the graphical image on a user interface, as shown in FIG. 13. The user interface may include informational text indicating that the user has selected occlusion and defining "occlusion" as an inability to infuse fluids and/or medication through a previously functioning catheter and/or an additional graphical image, such as shown in FIG. 13A, illustrating the effects of occlusion. The informational text may also indicate, for example, that catheter occlusion may occur as a result of a mechanical obstruction, such as kinking of the catheter, blood clots formed on and/or within the catheter, and/or migration of the catheter tip into the vessel wall without infiltration or extravasation. The informational text may also indicate risks for occlusion, such as insertion of a catheter in areas of flexion that are subject to movement and, therefore, bending and kinking and movement relative to the vessel wall can also cause injury to the tissue and subsequent thrombus formation.

Figures 14, 14A:
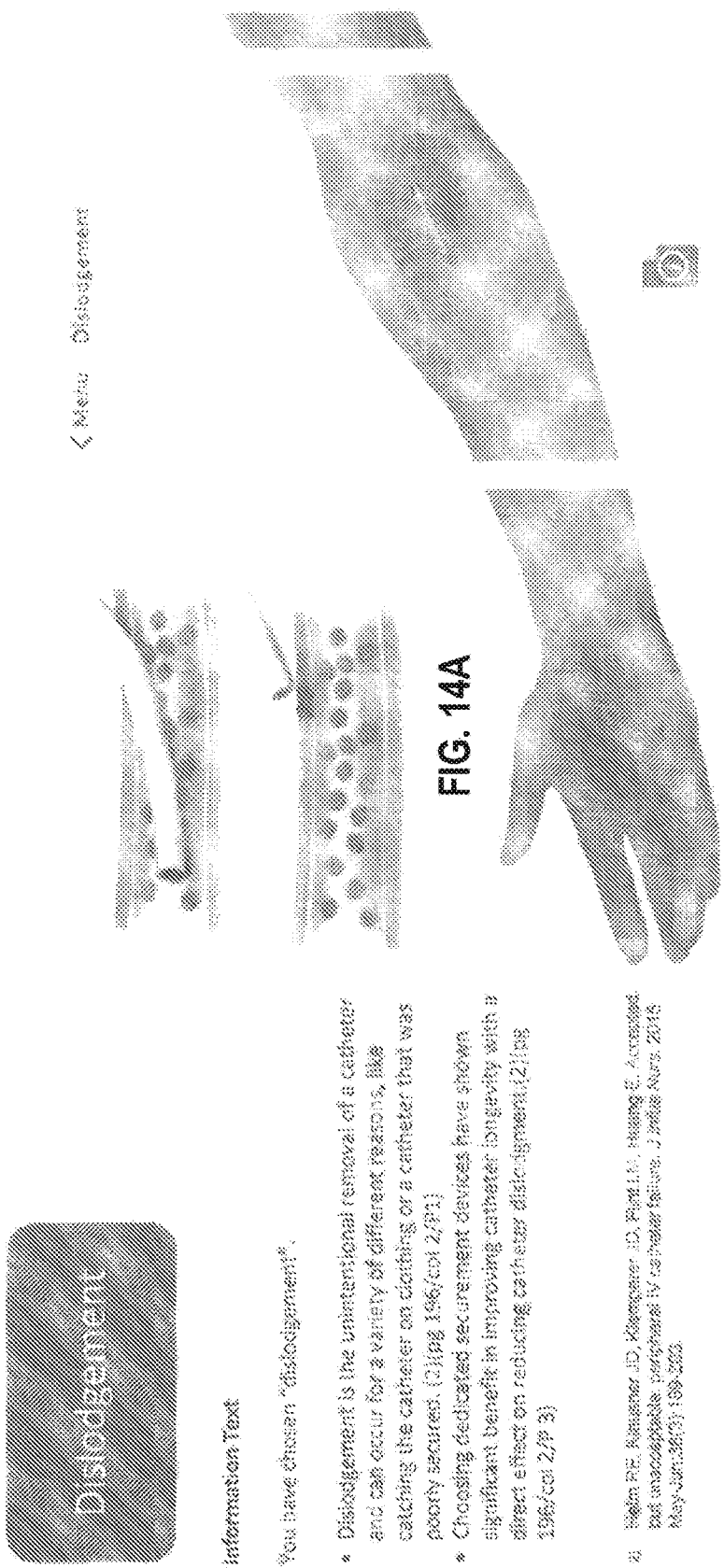
FIG. 14 is another example user interface, according to various embodiments.
FIG. 14A is another example user interface, according to various embodiments.

If, at step 416, the user chooses to learn more about dislodgement, at step 418, the processing device of machine 100 renders a graphical image of the person's arm indicating dislodgement and, at step 420, display 70 displays the graphical image on a user interface, as shown in FIG. 14. The user interface may include informational text indicating that the user has selected dislodgement and defining "dislodgement" as an unintentional removal of a catheter that can occur for a variety of reasons, such as catching the catheter on clothing or a catheter that was poorly secured and/or an additional graphical image, such as shown in FIG. 14A, illustrating the effects of dislodgement. The informational text may also indicate, for example, that choosing dedicated securement devices have shown significant benefit in improving catheter longevity with a direct effect on reducing catheter dislodgement.

Figure 15:
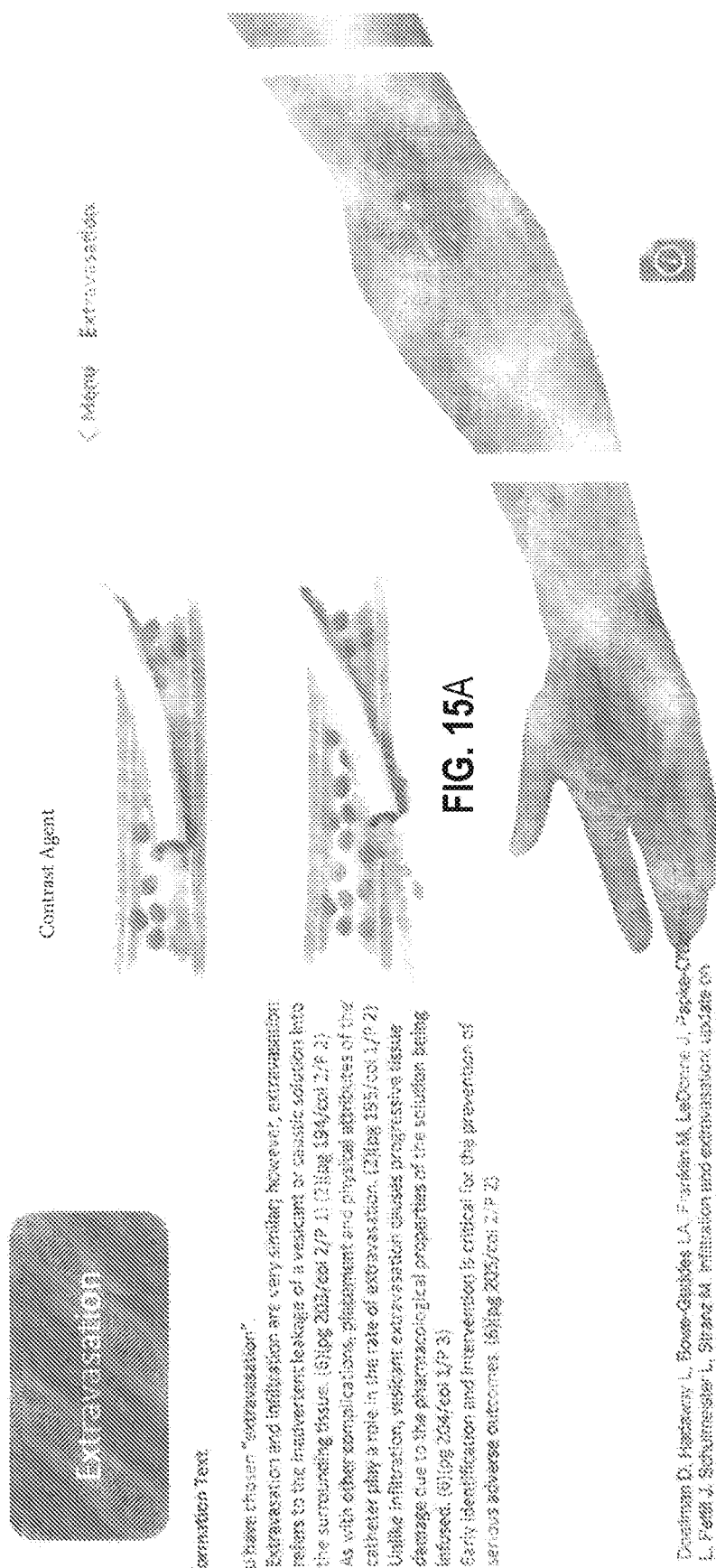
FIG. 15 is another example user interface, according to various embodiments.

If, at step 416, the user chooses to learn more about extravasation, at step 418, the processing device of machine 100 renders a graphical image of the person's arm indicating extravasation and, at step 420, display 70 displays the graphical image on a user interface, as shown in FIG. 15. The user interface may include informational text indicating that the user has selected extravasation and defining "extravasation" as an inadvertent leakage of a vesicant or caustic solution into the surrounding tissue and/or an additional graphical image, such as shown in FIG. 15A, illustrating the effects of extravasation. The informational text may also indicate, for example, that as with other complications, placement and physical attributes of the catheter play a role in the rate of extravasation. The informational text may also indicate that unlike infiltration, vesicant extravasation causes progressive tissue damage due to the pharmacological properties of the solution being infused and/or that early identification and intervention is critical for the prevention of serious adverse outcomes.

Figure 16:
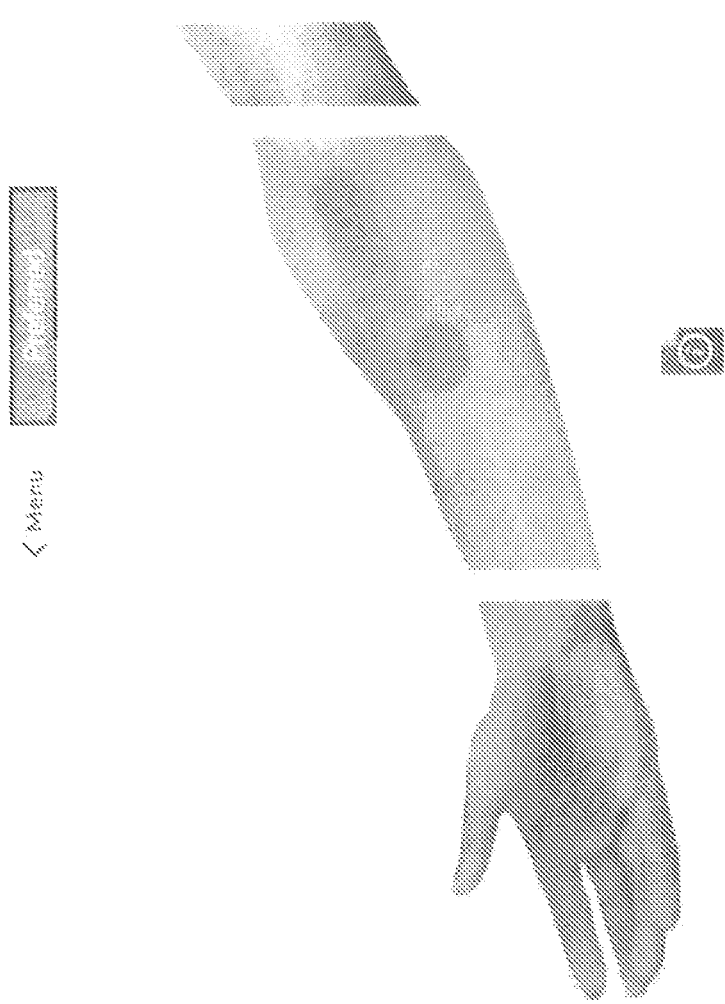
FIG. 16 is another example user interface, according to various embodiments.
Figure 17:
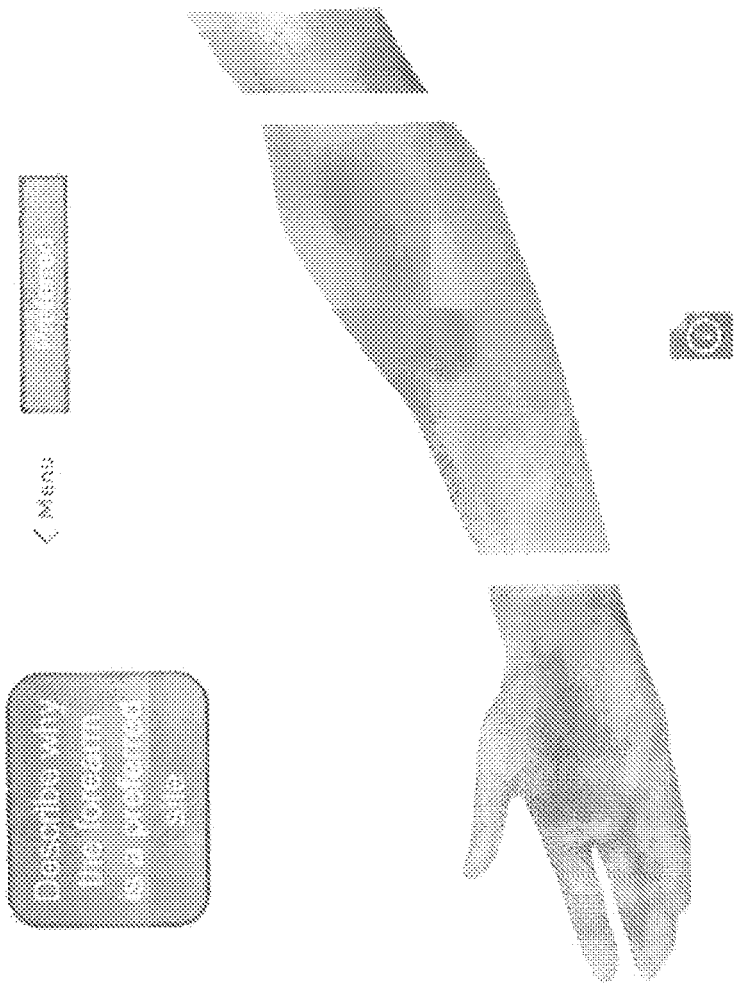
FIG. 17 is another example user interface, according to various embodiments.

However, if the user selects the preferred insertion site (e.g., the forearm insertion site) in response to the prompting step 406, the processing device of machine 100 renders a graphical image of the selected arm and, at step 422, display 70 displays the graphical image on a user interface, as shown in FIG. 16, indicating that the user correctly selected the preferred insertion site. The user interface may include informational text indicating to the user reasons the forearm insertion site is the preferred insertion site for a peripheral IV catheter including, for example, that there are lower risks of catheter complications associated with the forearm insertion site because there is no flexion (or minimal flexion) at the forearm insertion site and that studies have demonstrated that choosing the forearm insertion site over the hand insertion site or the antecubital insertion site can increase dwell time, decrease pain during dwell time, promote self-care, and prevent or limit accidental removal and occlusions. The informational text may also include additional guidance on catheter insertion, such as an indication that when selecting the forearm as the insertion site the user should avoid the ventral surface of the wrist due to pain on insertion and possible nerve damage and/or an indication that although the forearm is a preferred insertion site to the antecubital, wrist, or hand area, careful monitoring for clinical signs and symptoms of complications is still necessary.

Figure 18:
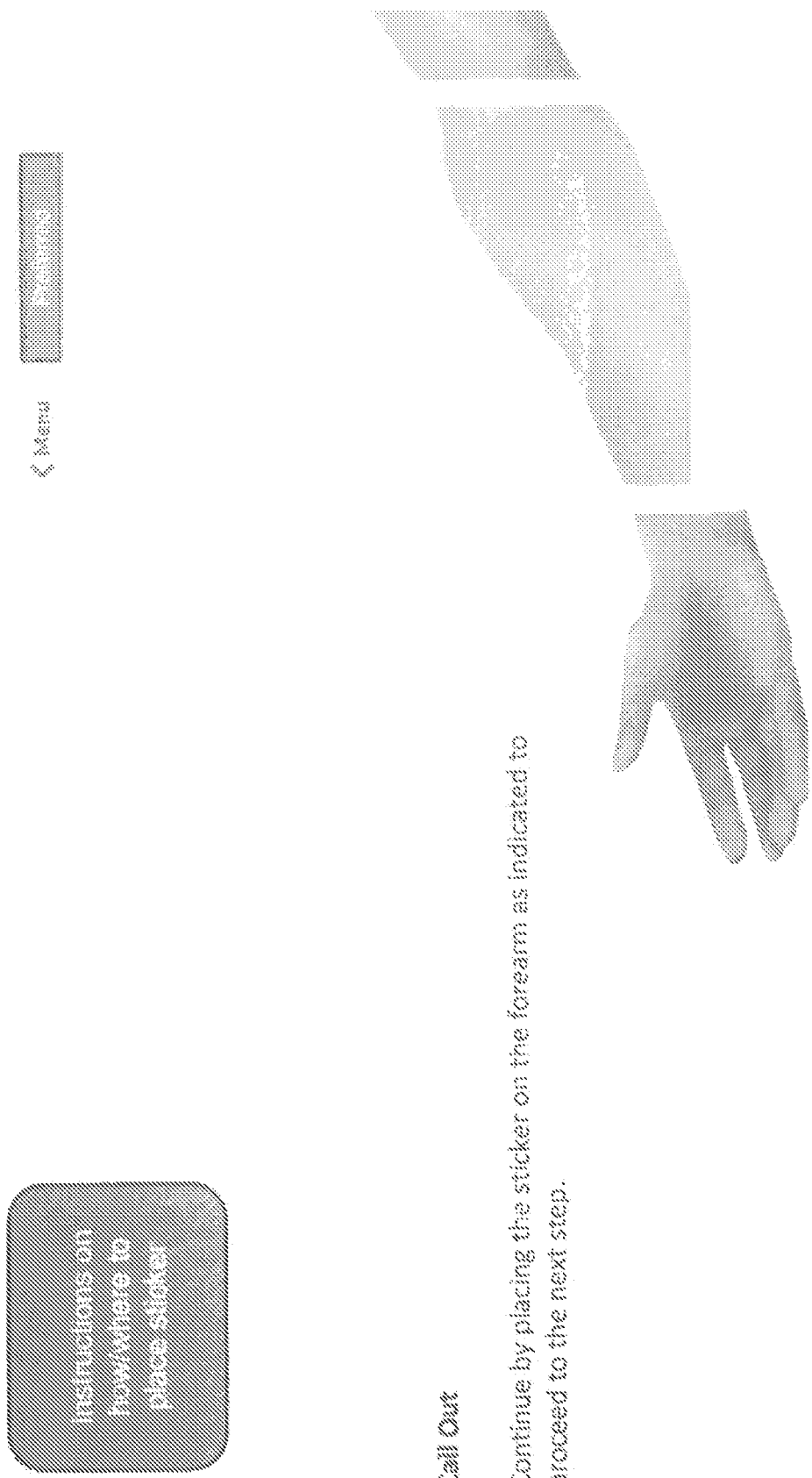
FIG. 18 is another example user interface, according to various embodiments.
Figure 19:
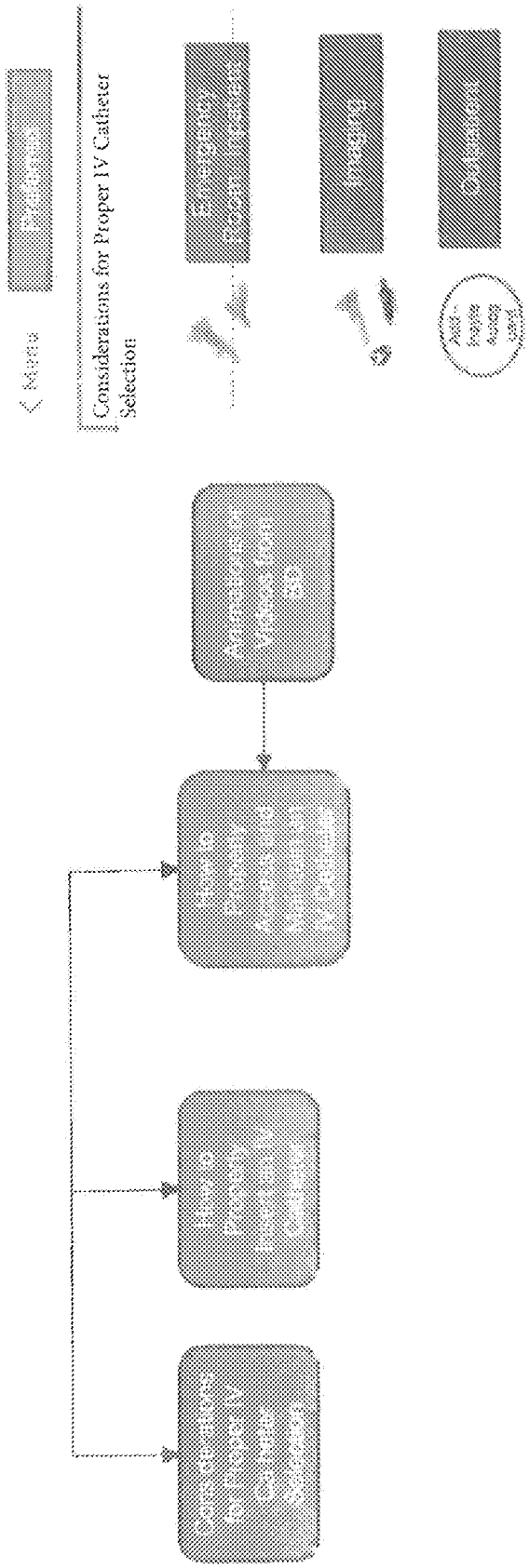
FIG. 19 is another example user interface, according to various embodiments.

In example embodiments, at step 424 machine 100 instructs the user to position sticker 50 at the preferred insertion site (e.g., the forearm insertion site) on the preferred arm (i.e., the right arm or the left arm) in order to proceed to the next step. As shown in FIG. 18, machine 100 displays a user interface indicating placement of sticker 50 at the preferred insertion site. The user interface may also indicate the proper alignment and orientation of sticker 50, e.g., an arrow displayed on sticker 50 pointing toward the person's wrist on the chosen arm.

With sticker 50 properly positioned at the forearm insertion site, machine 100 then queries the user, at step 426, whether the user is interested in learning more about proper peripheral IV therapy. If the user indicates that he or she is interested in learning more about proper peripheral IV therapy, machine 100 provides 428 the user with one or more learning topics including, for example, considerations for proper IV catheter selection, instructional information for properly inserting an IV catheter, and/or instructional information for properly accessing and maintaining an IV catheter.

Figure 20:
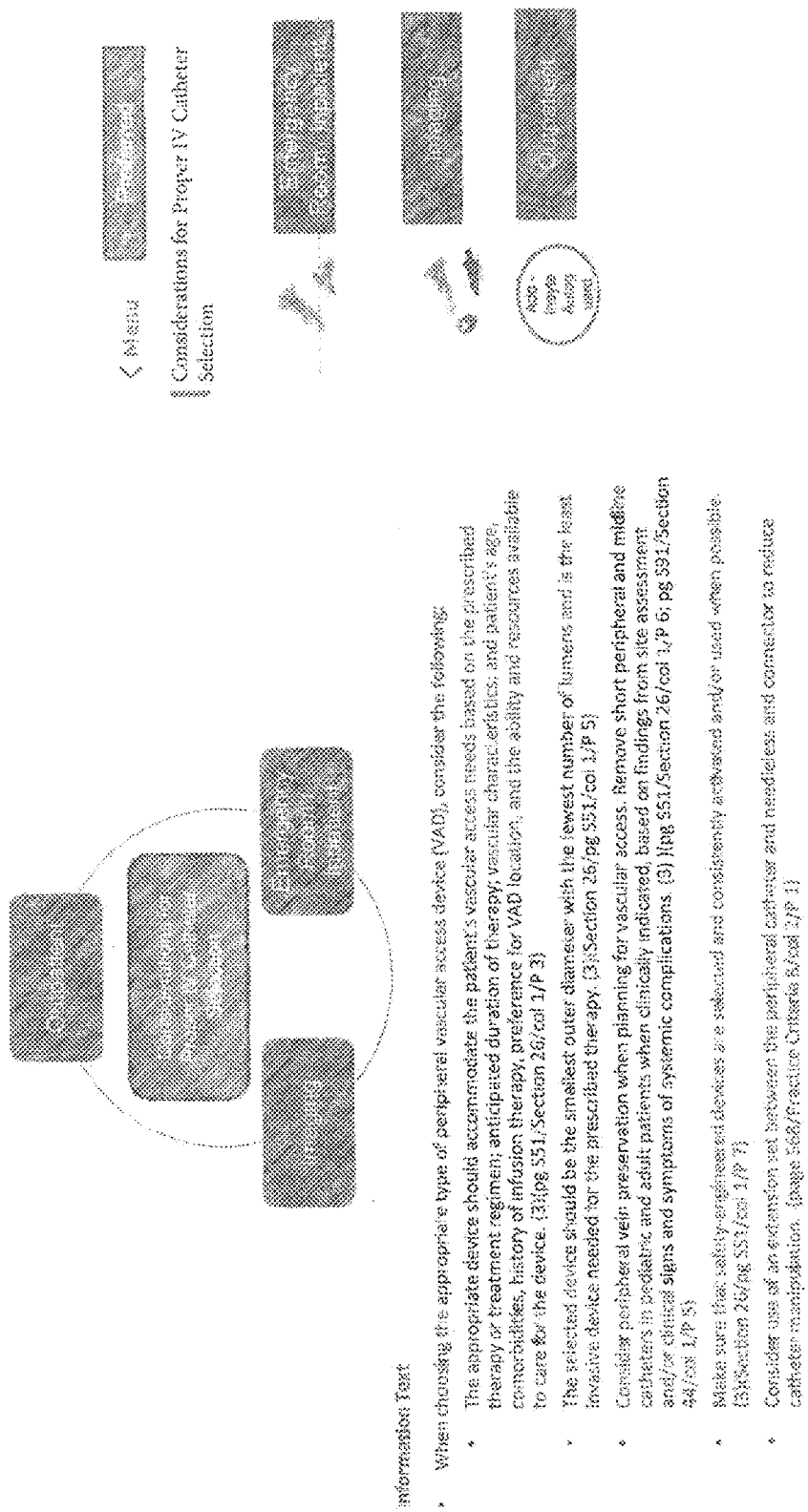
FIG. 20 is another example user interface, according to various embodiments.

If, for example, the user selects to learn more about considerations for proper IV catheter selection, display 70 displays a user interface, as shown in FIG. 20, indicating one or more topics of consideration when selecting a proper IV catheter including, for example, an environment in which the person will be situated, such as an outpatient environment, an imaging environment, or an emergency room or inpatient environment. The user interface may include informational text indicating to the user that an appropriate type of peripheral vascular access device (VAD) may be selected depending at least in part on the patient environment and several considerations may influence which VAD to use in the particular patient environment.

For example, the informational text may indicate to the user that the appropriate VAD should accommodate the person's vascular access needs based on the prescribed therapy or treatment regimen, the anticipated duration of therapy, the person's vascular characteristics, and the person's age, comorbidities, history of infusion therapy, preference for VAD location, and the ability and resources available to care for the device. The informational text may indicate that the selected VAD should have the smallest outer diameter with the fewest number of lumens and is the least invasive device needed for the prescribed therapy. Further, peripheral vein preservation might be considered when planning for vascular access. Short peripheral and midline catheters in pediatric and adult persons might be removed when clinically indicated, based on findings from site assessment and/or clinical signs and symptoms of systemic complications. Safety-engineered devices might be selected and consistently activated and/or used when possible. Use of an extension set between the peripheral catheter and connector might be considered to reduce catheter manipulation. In alternative embodiments, such informational text may be different, e.g., include added recommendations, delete certain recommendations, and/or change certain recommendations.

Figure 21:
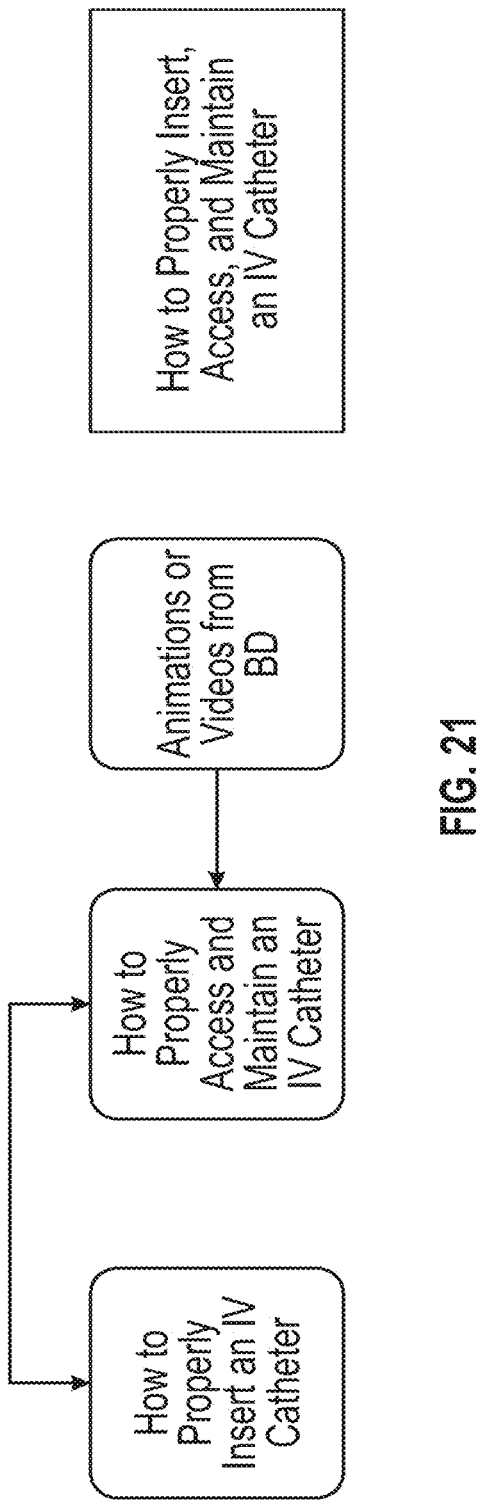
FIG. 21 is another example user interface, according to various embodiments.

Referring to FIG. 21, if the user selects to learn more about considerations for properly inserting an IV catheter, display 70 displays a user interface that may include informational text indicating to the user that initially skin antisepsis is performed and indicating that the most recent INS Standards of Practice recommend using the skin antiseptic agent of greater than 0.5% chlorhexidine in alcohol solution. Further, the informational text may indicate that if there is a contraindication to an alcoholic chlorhexidine solution, a tincture of iodine, an iodophor (povidone-iodine), or a 70% alcohol may also be used. The informational text may indicate that the antiseptic agent should be allowed to fully dry before insertion, a new pair of disposable gloves should be used along with a "no-touch" technique for peripheral IV insertion, meaning that the insertion site is not palpated after skin antisepsis, for example. The informational text may also indicate additional considerations including, without limitation, using vascular visualization technology to increase success for persons with the difficult vascular access, selecting the smallest-gauge peripheral catheter that will accommodate the prescribed therapy and person need, and/or a warning the peripheral catheters should not be used for continuous vesicant therapy, parenteral nutrition, or infusates with an osmolarity greater than 900 mOsm/L, for example. In certain example embodiments, machine 100 is configured to display on display 70 a video illustrating best practices for inserting a peripheral IV catheter including such information as shown in FIG. 23.

Figure 24:
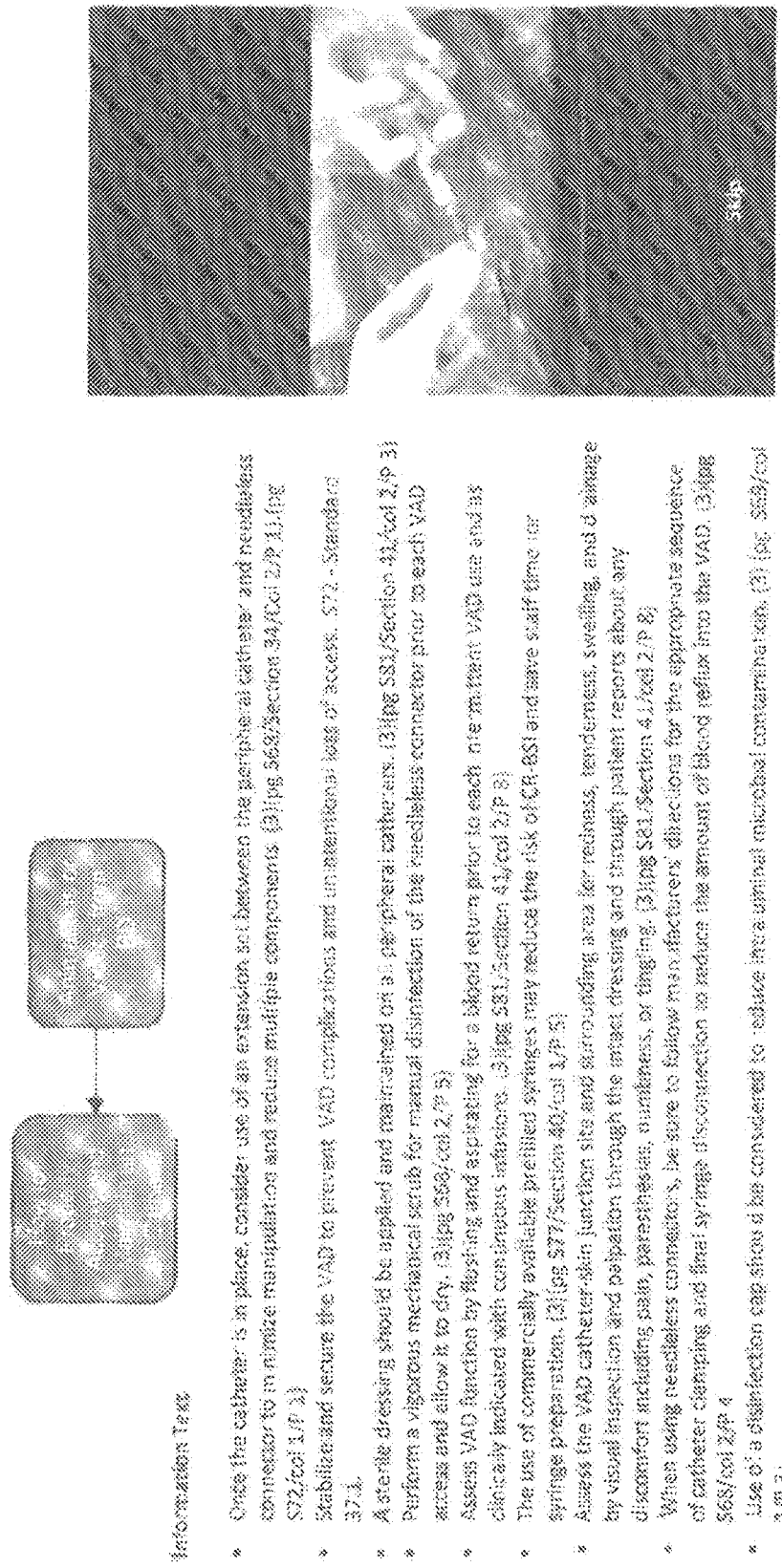
FIG. 24 is another example user interface, according to various embodiments.

Referring to FIG. 24, if the user selects to learn more about considerations for properly accessing and maintaining an IV catheter, display 70 displays a user interface that may include informational text indicating to the user that once the catheter is in place, the user should consider: whether to use of an extension set between the peripheral catheter and the needleless connector to minimize manipulation and reduce multiple components; stabilizing and securing the VAD to prevent VAD complications and unintentional loss of access; applying and maintaining a sterile dressing on all peripheral catheters; performing a vigorous mechanical scrub for manual disinfection of the needleless connector prior to each VAD access and allow it to dry; accessing VAD function by flushing and aspirating for a blood return prior to each intermittent VAD use and as clinically indicated with continuous infusions; whether to use a commercially available prefilled syringe that may reduce the risk of CR-BSI and save staff time for syringe preparation; accessing the VAD catheter-skin junction site and surrounding area for redness, tenderness, swelling, and/or drainage by visual inspection and palpation through the intact dressing and through person reports about any discomfort including pain, paresthesias, numbness, or tingling; when using needleless connectors, assuring that the manufacturers' directions for the appropriate sequence of catheter clamping and final syringe disconnection are followed to reduce the amount of blood reflux into the VAD; and/or considering the use of a disinfection cap to reduce intraluminal microbial contamination, for example. In certain example embodiments, machine 100 is configured to display on display 70 a video illustrating best practices for accessing and maintaining a peripheral IV catheter including such information as shown in FIG. 25.

Figure 27:
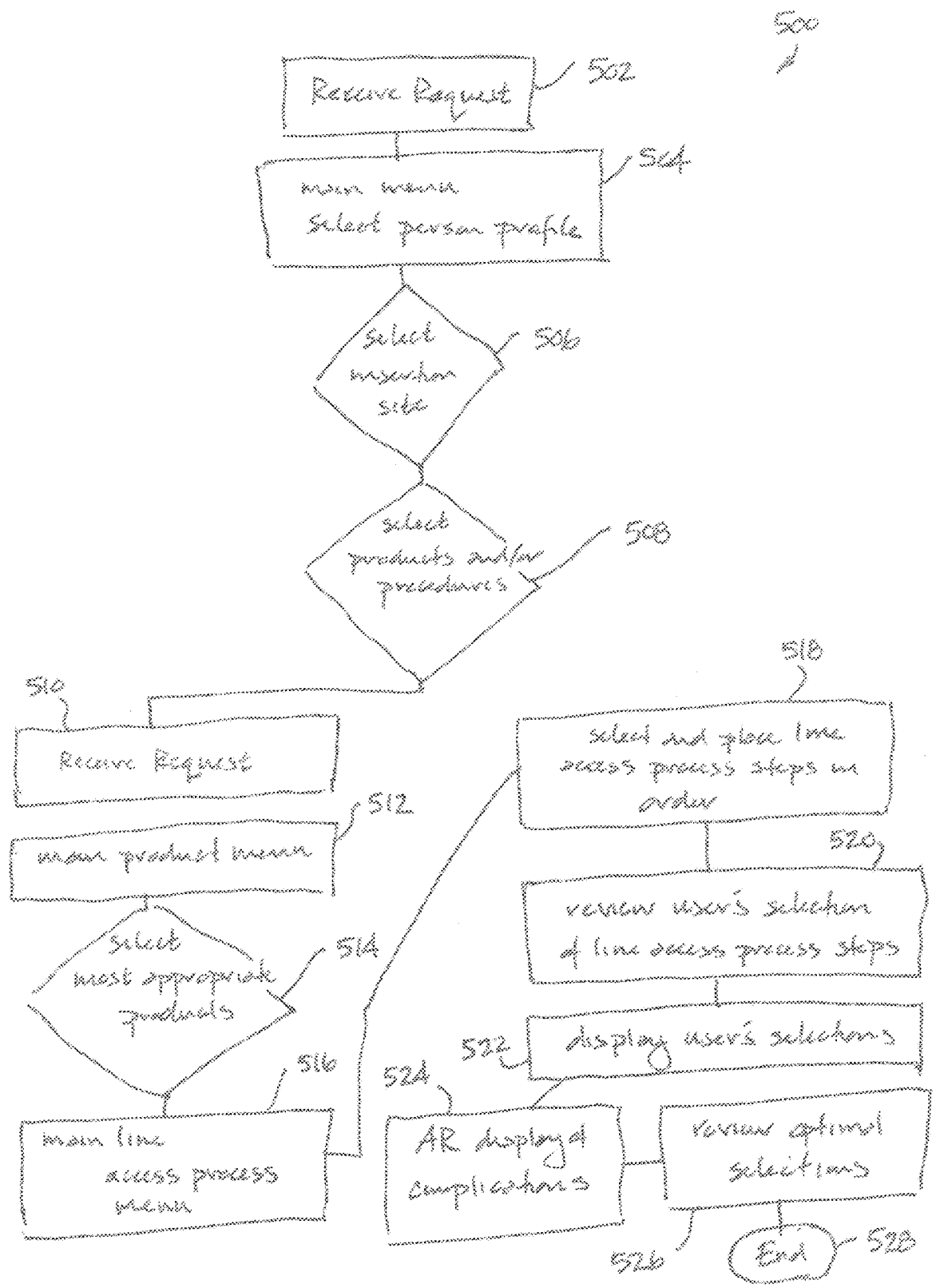
FIG. 27 is an example method for providing educational guidance for peripheral IV therapy using a consequence-based learning (CBL) program, according to various embodiments.
Figure 28:
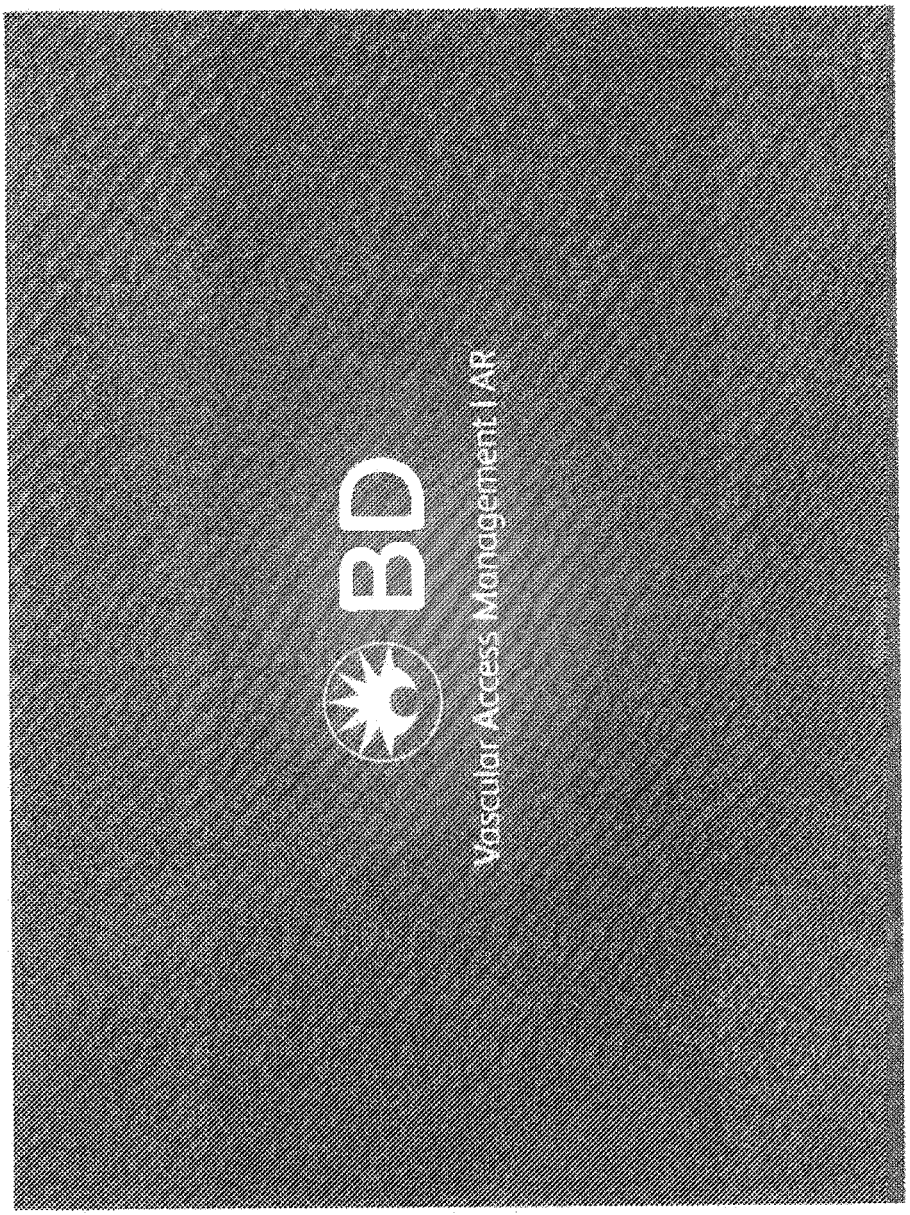
FIG. 28 is an example user interface displayed on the example machine during the method of FIG. 27, according to various embodiments.
Figure 119:
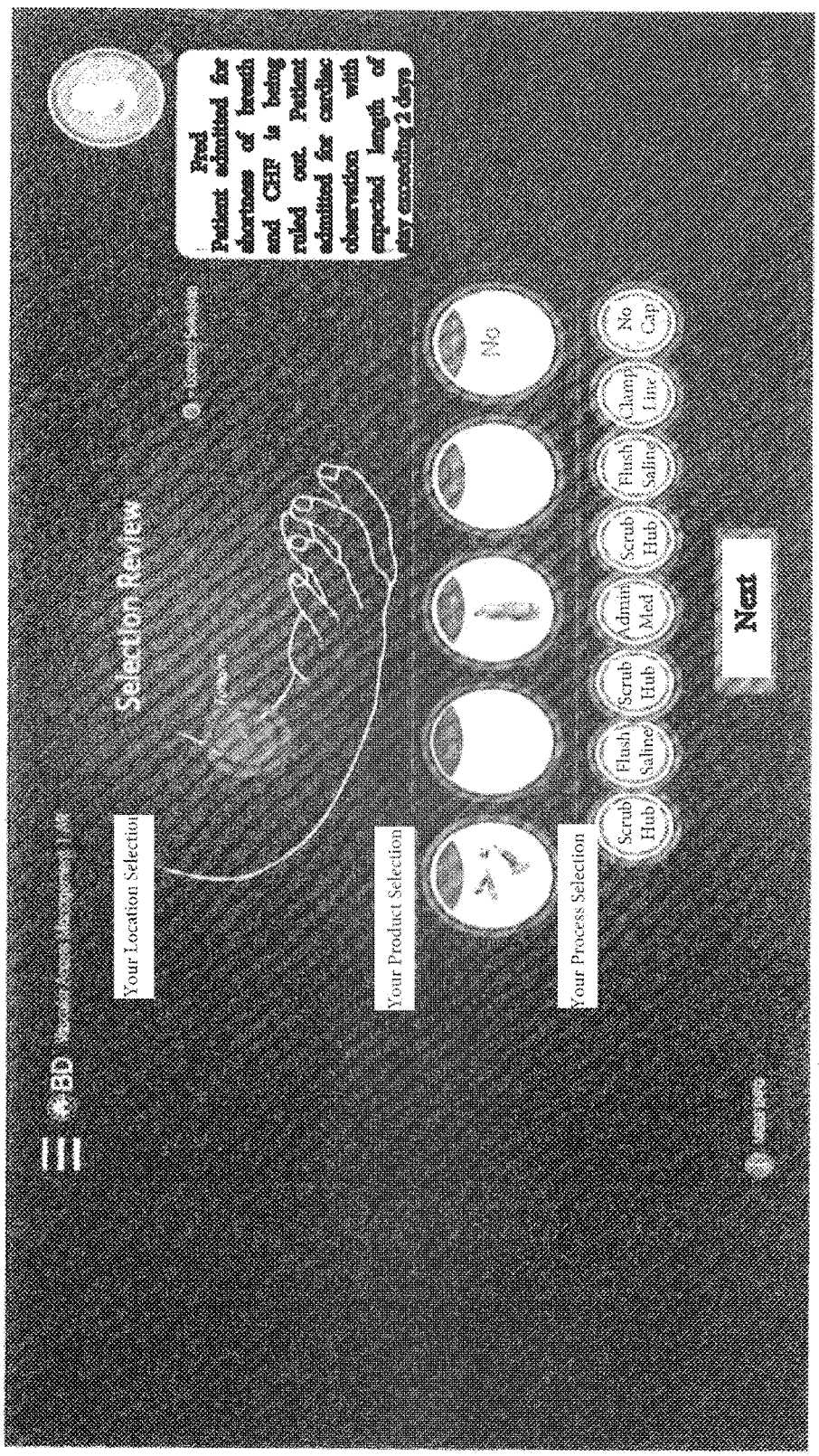
Figure 120:
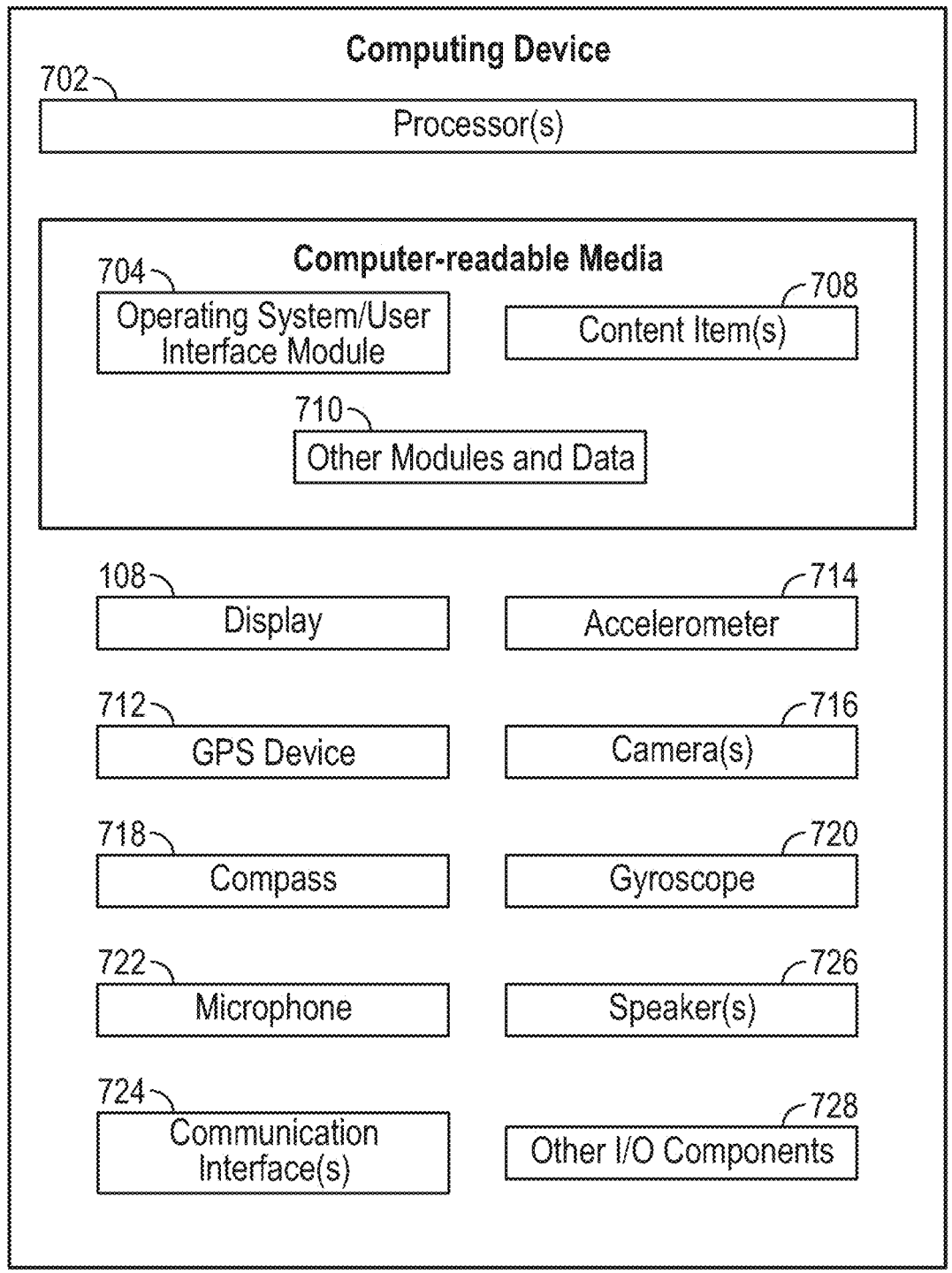

Referring now to FIGS. 27-120, in example embodiments, machine 100 may be implemented as part of a method for providing educational guidance for peripheral IV therapy using suitable learning programs such as a consequence-based learning (CBL) program or application. Machine 100 may implement logic, similar to or different from the logic shown in the flow diagrams of FIGS. 3A-3C, as part of a method in accordance with various embodiments. For instance, various circuitry elements discussed above and/or various components of machine 100, such as one or more processing devices, may be configured to implement some or all of the logic implemented by machine 100 during the CBL program or application. FIG. 27 shows a flow diagram of logic 500 that machine 100 may implement as part of a method in accordance with various embodiments. FIGS. 28-119 illustrate example user interfaces associated with various steps of logic 500 and displayed on display 70 of machine 100 during the CBL program or application.

Figure 29:
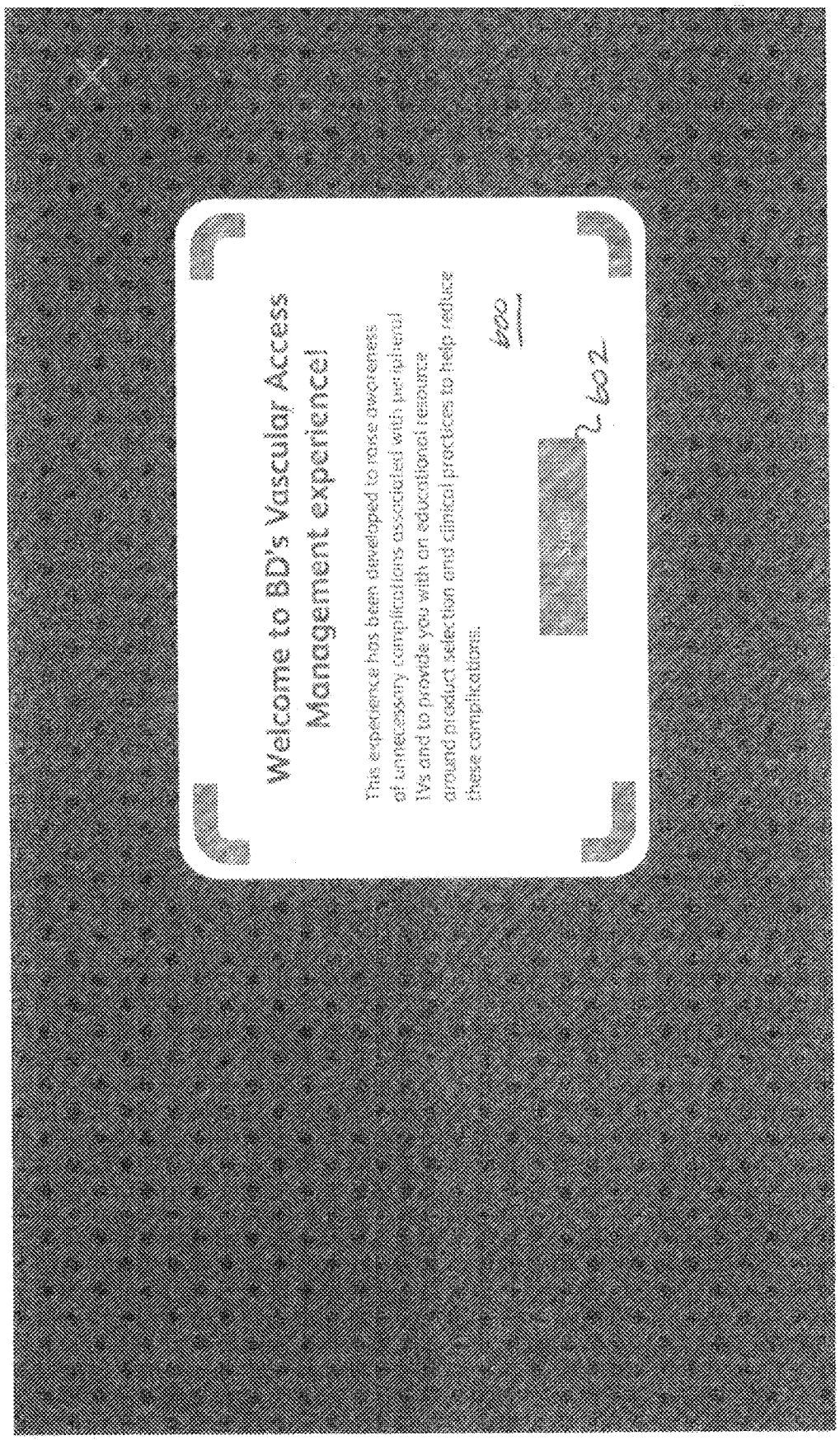
FIG. 29 is another example user interface, according to various embodiments.
Figure 30:
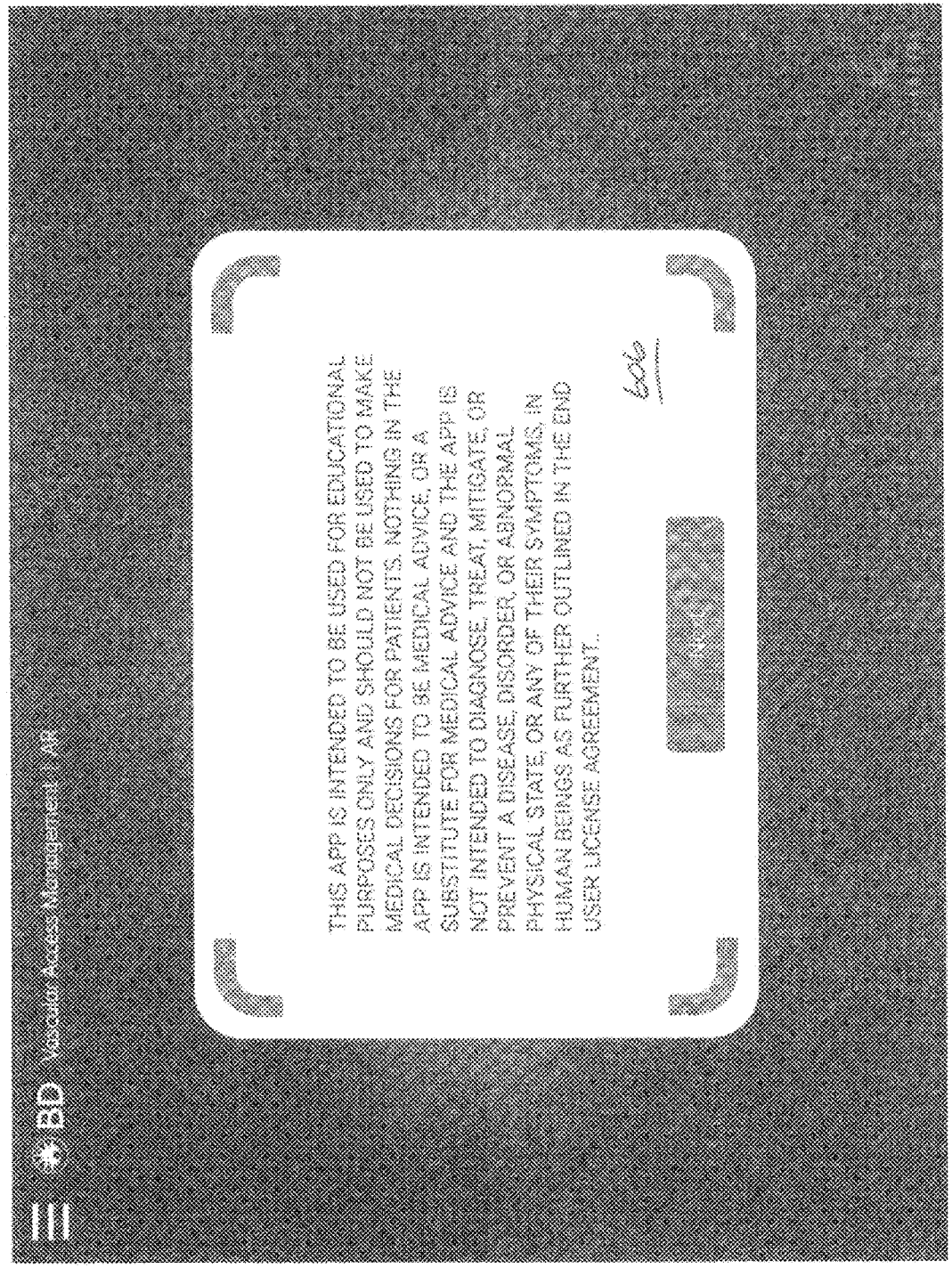
FIG. 30 is another example user interface, according to various embodiments.
Figure 31:
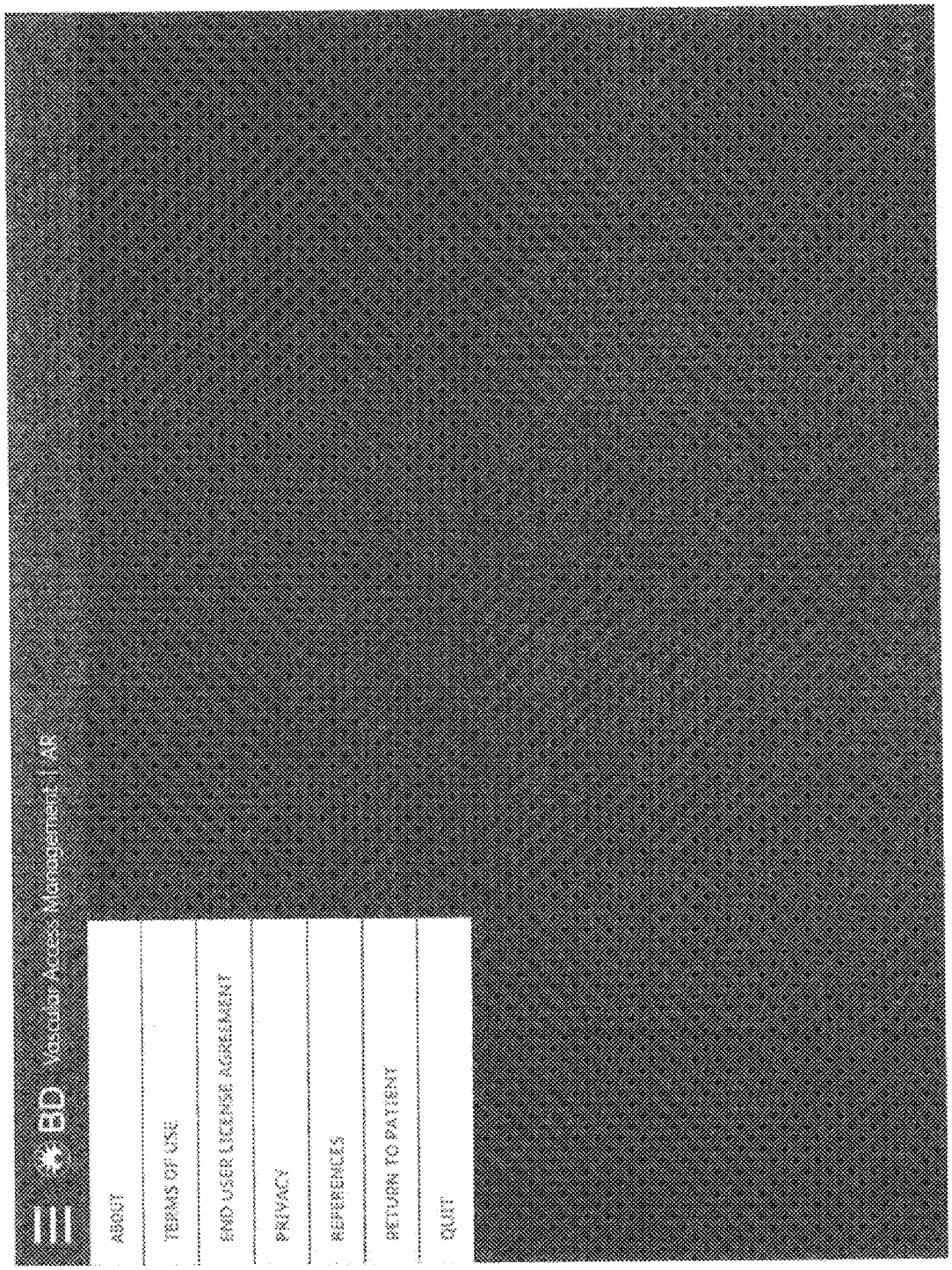
FIG. 31 is another example user interface, according to various embodiments.
Figure 32:
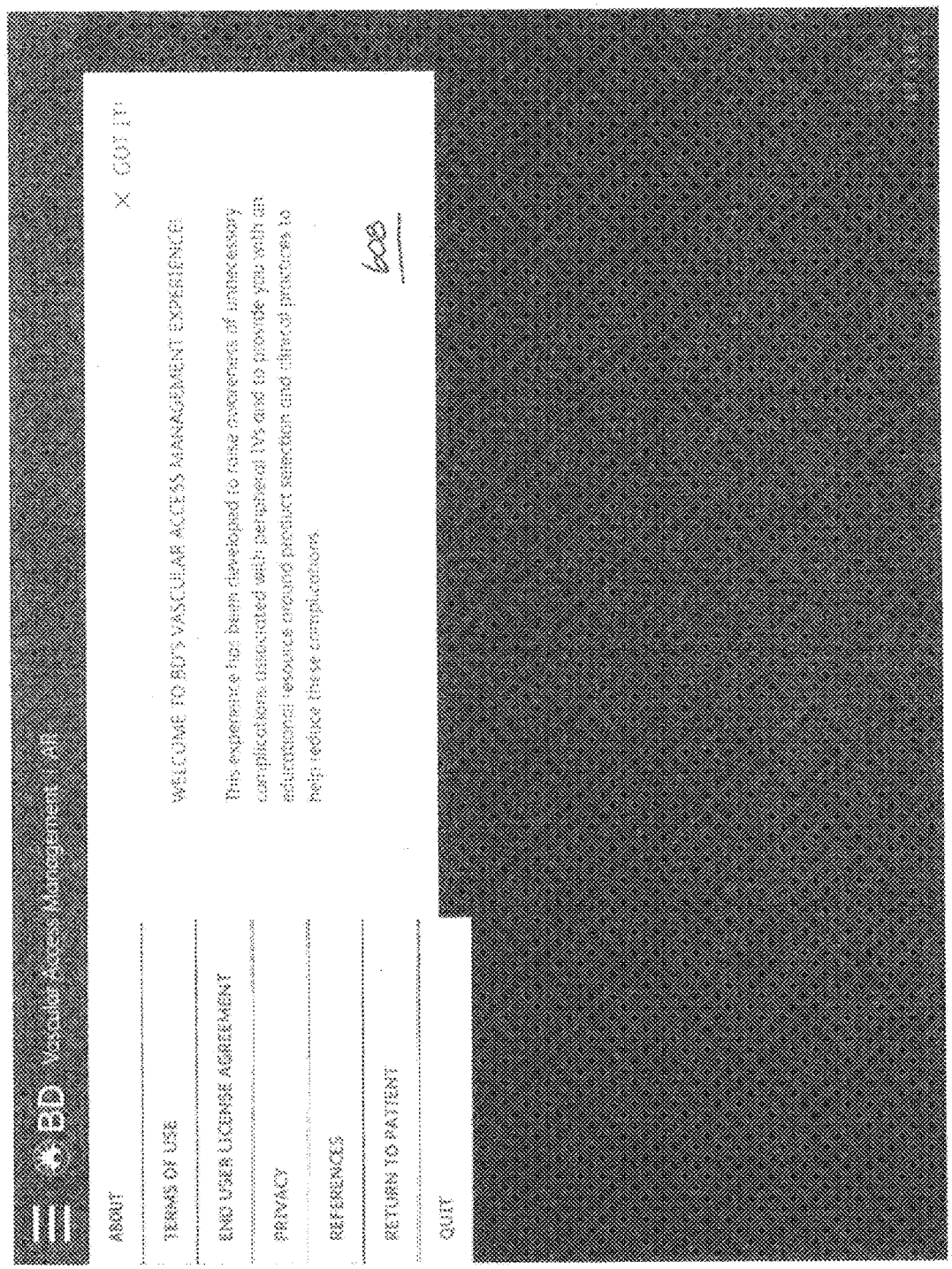
FIG. 32 is another example user interface, according to various embodiments.
Figure 33:
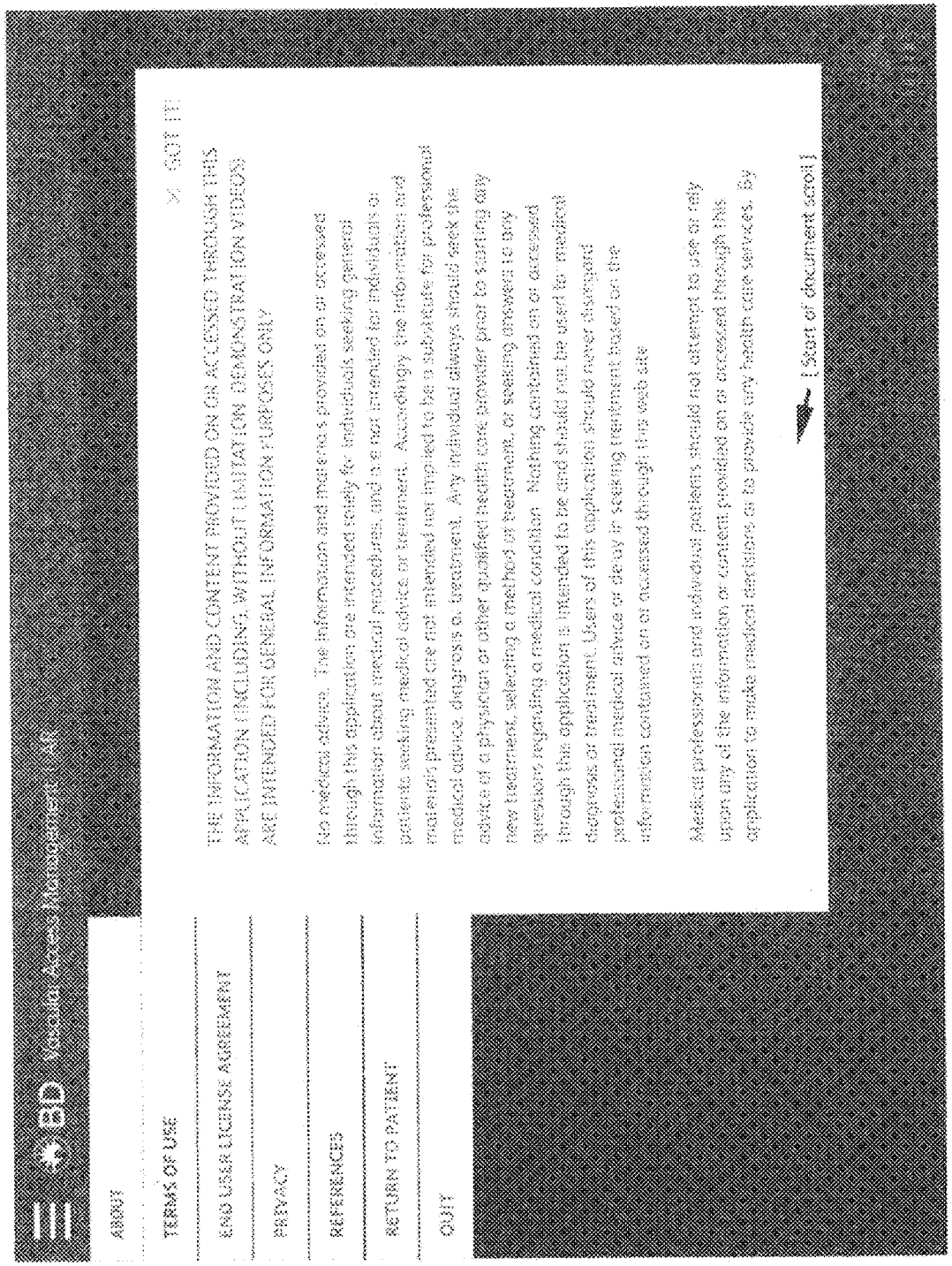
FIG. 33 is another example user interface, according to various embodiments.
Figure 34:
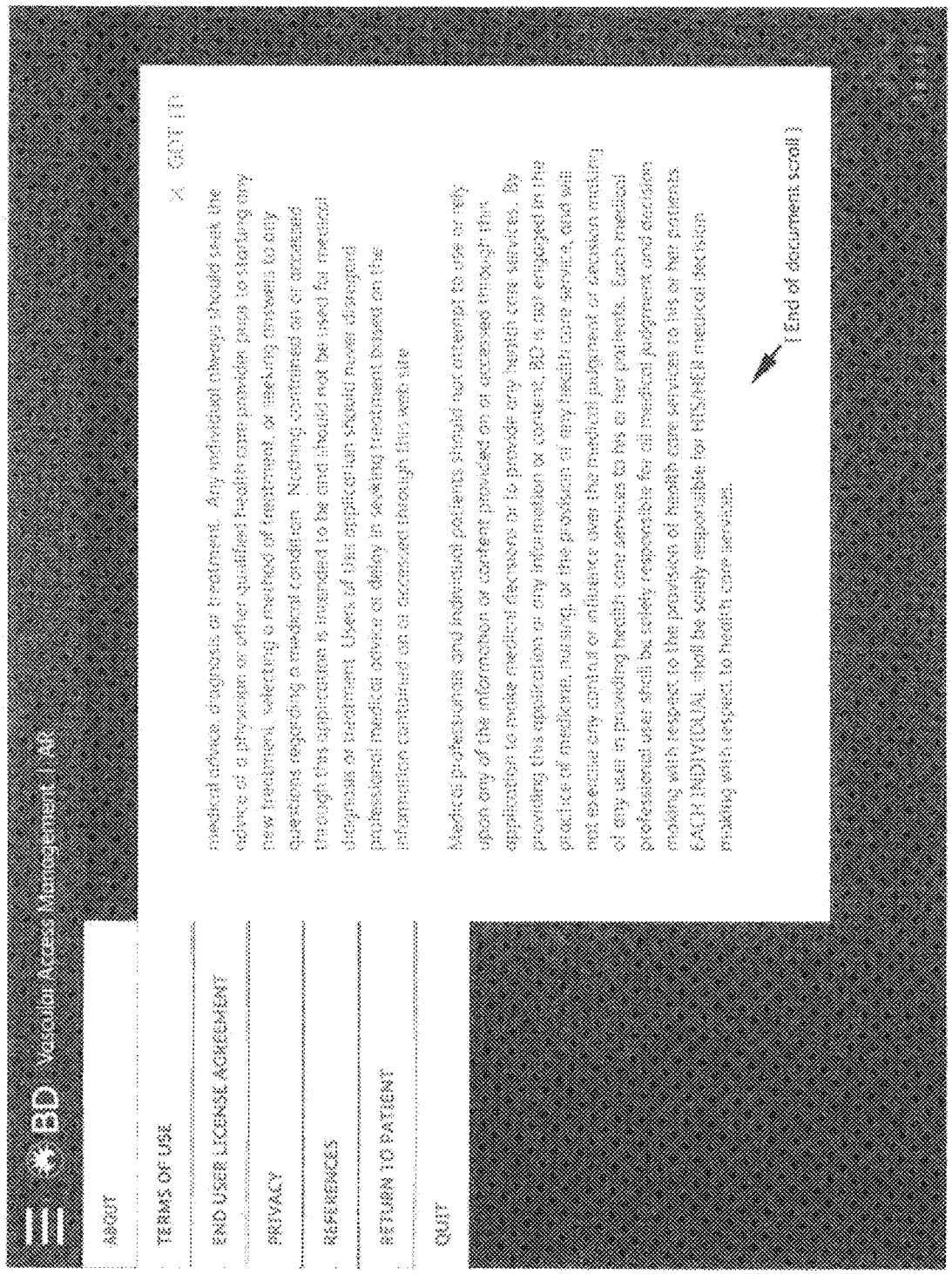
FIG. 34 is another example user interface, according to various embodiments.
Figure 35:
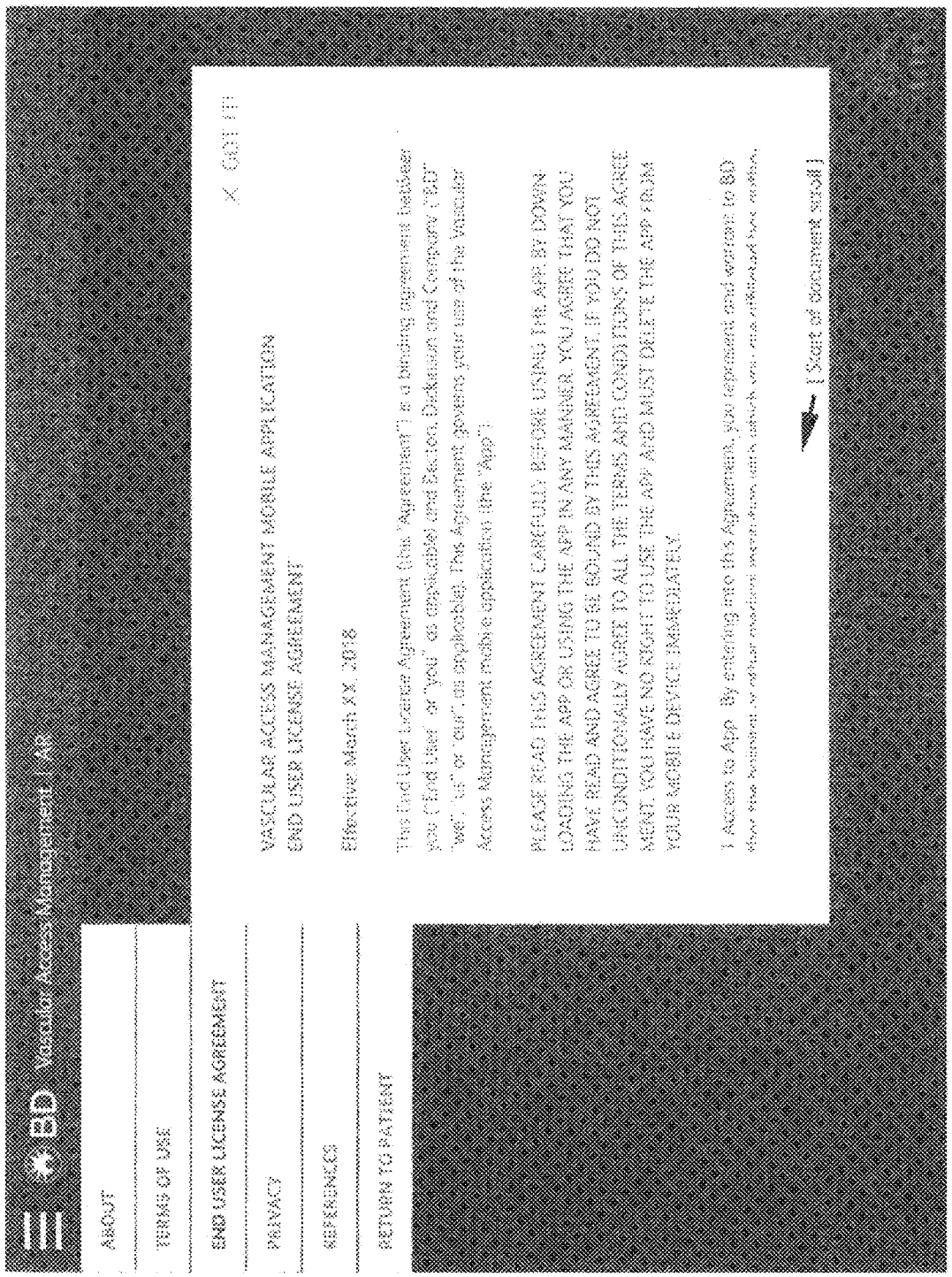
FIG. 35 is another example user interface, according to various embodiments.
Figure 36:
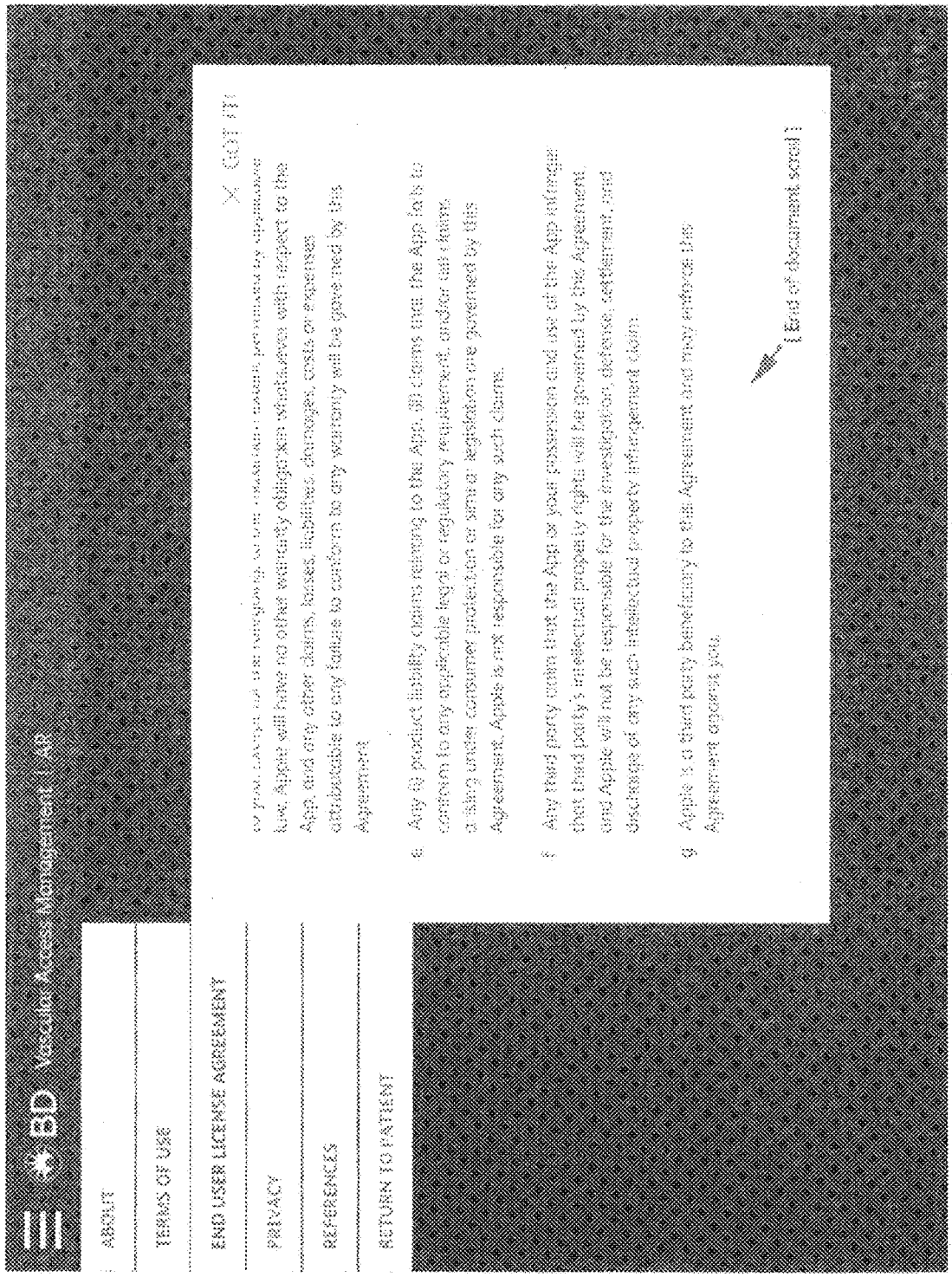
FIG. 36 is another example user interface, according to various embodiments.
Figure 37:
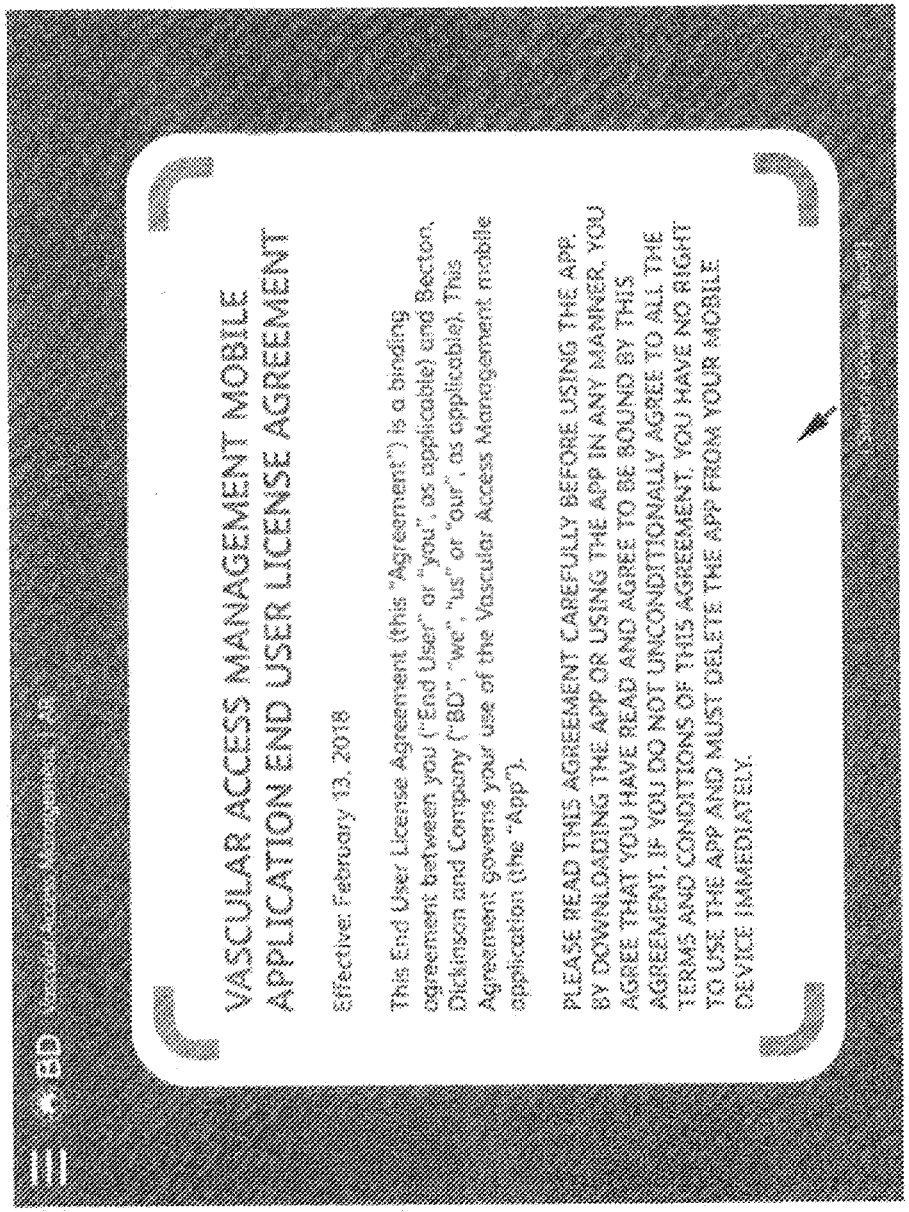
FIG. 37 is another example user interface, according to various embodiments.
Figure 38:
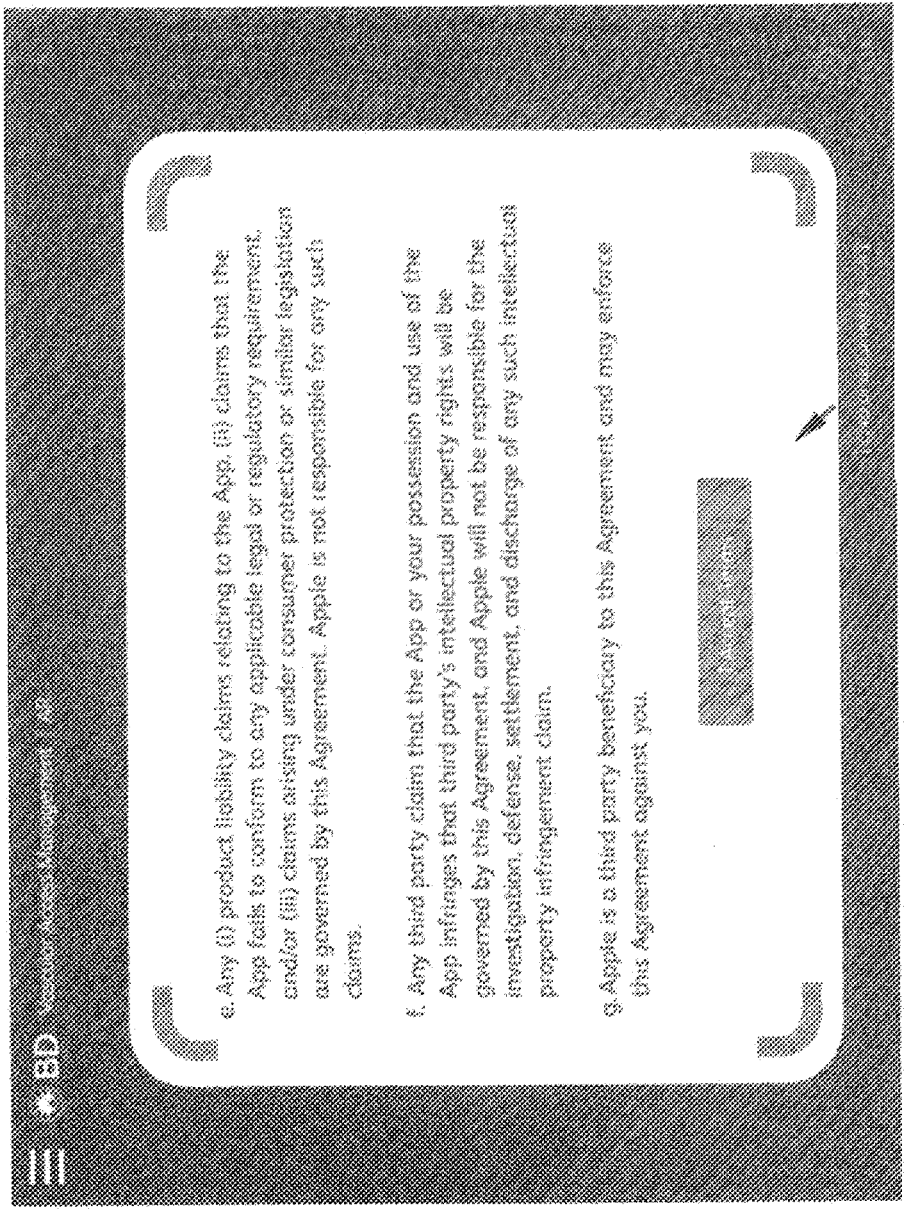
FIG. 38 is another example user interface, according to various embodiments.
Figure 39:
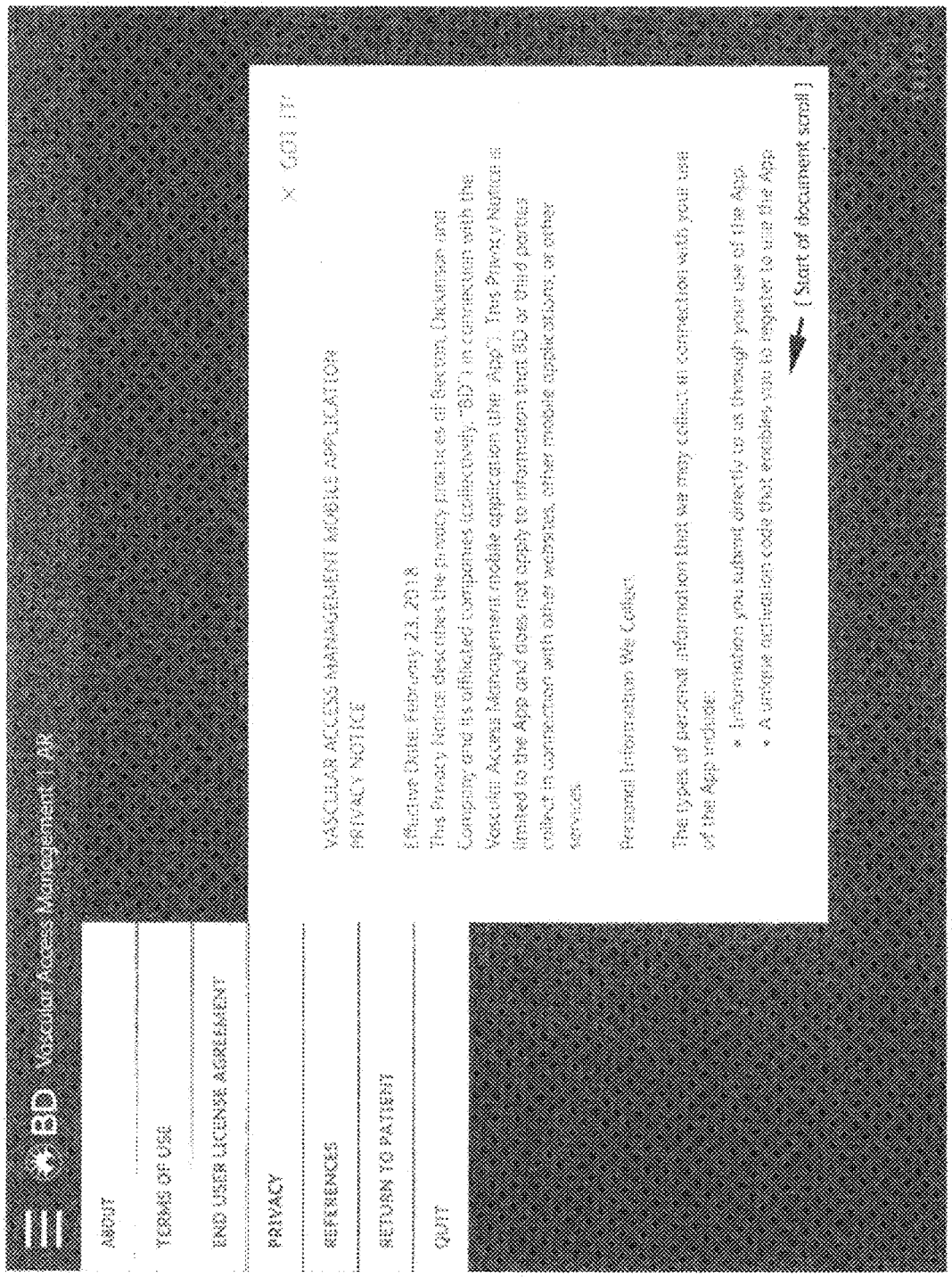
FIG. 39 is another example user interface, according to various embodiments.
Figure 40:
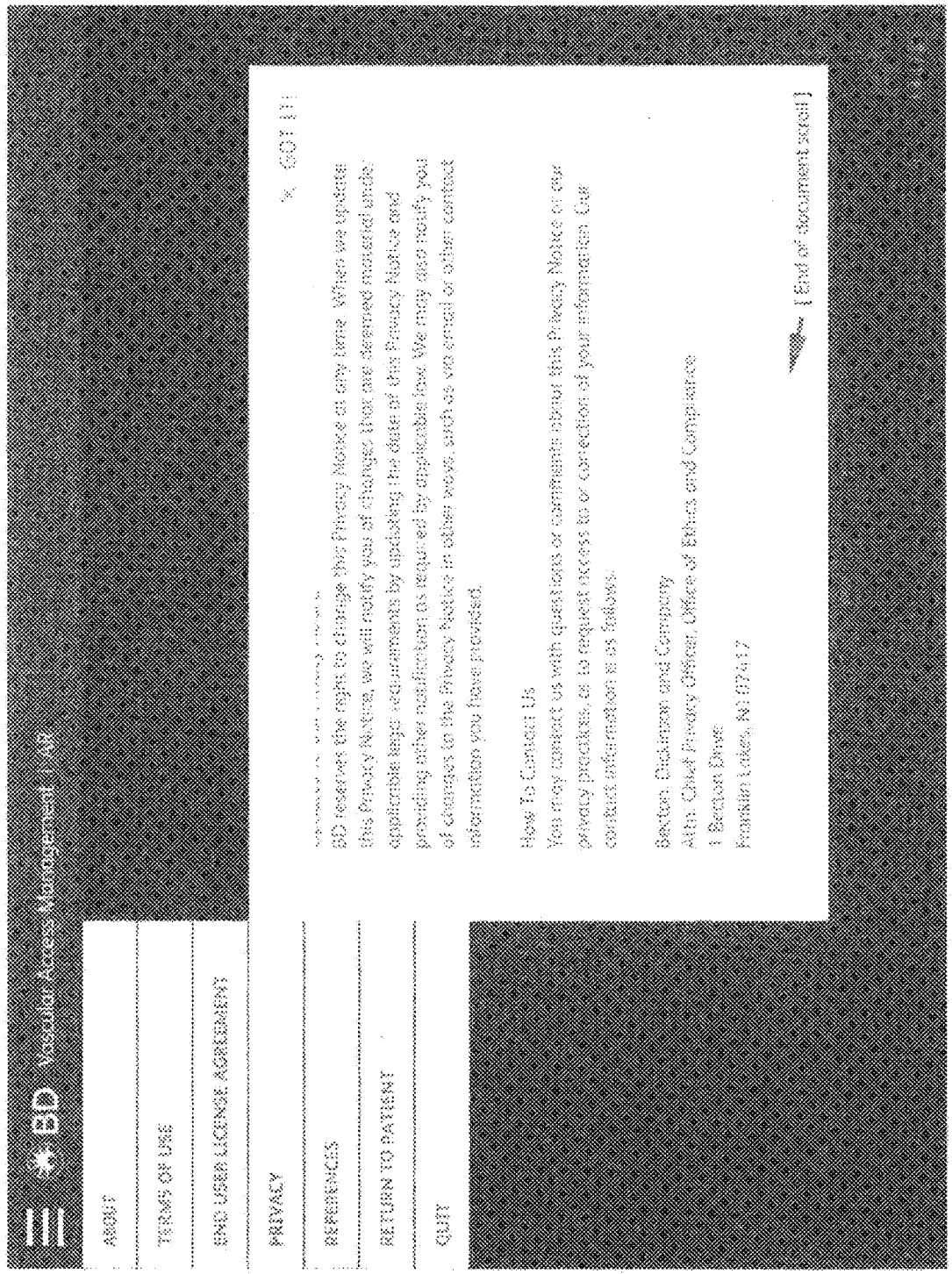
FIG. 40 is another example user interface, according to various embodiments.
Figure 41:
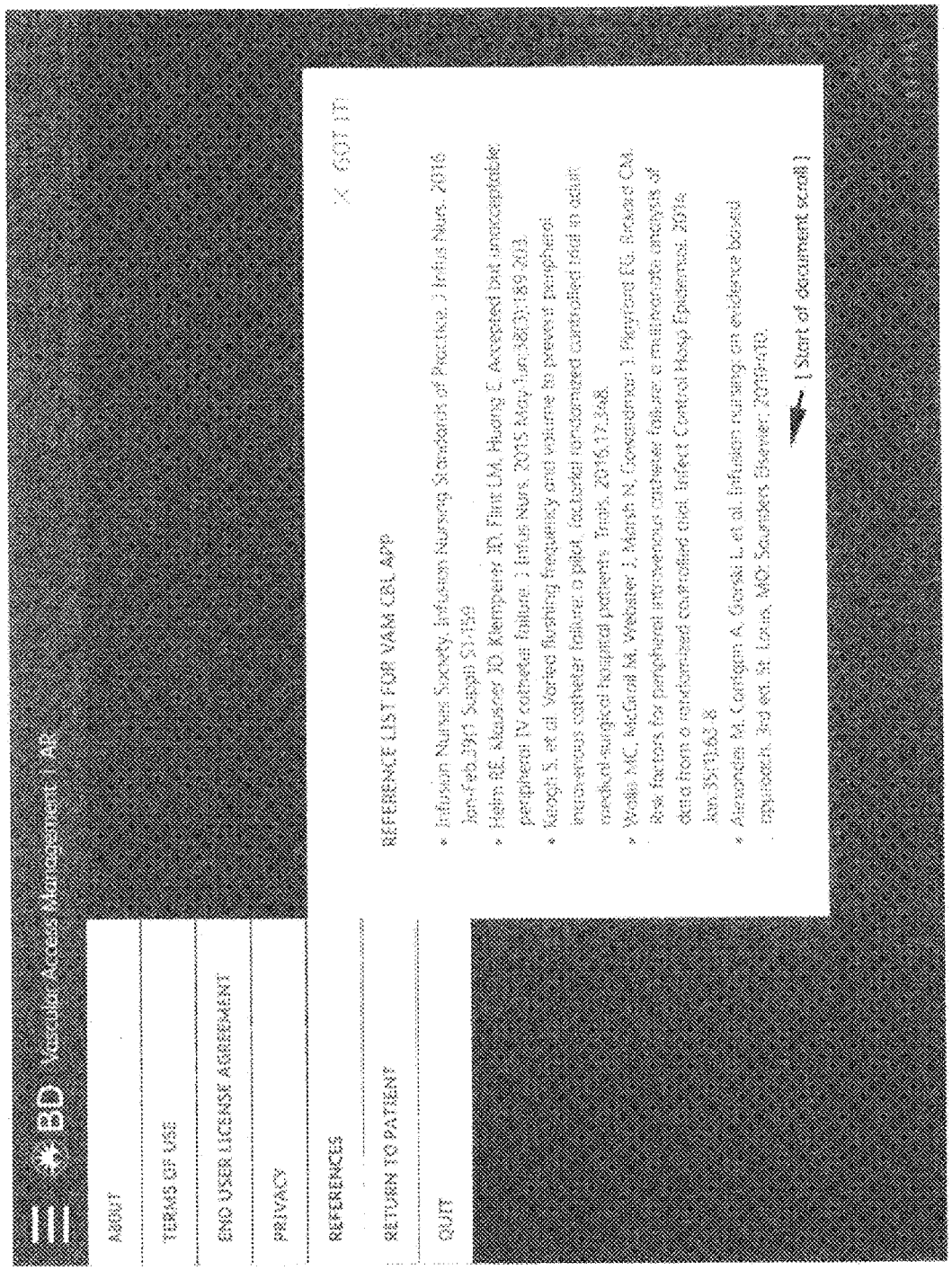
FIG. 41 is another example user interface, according to various embodiments.
Figure 42:
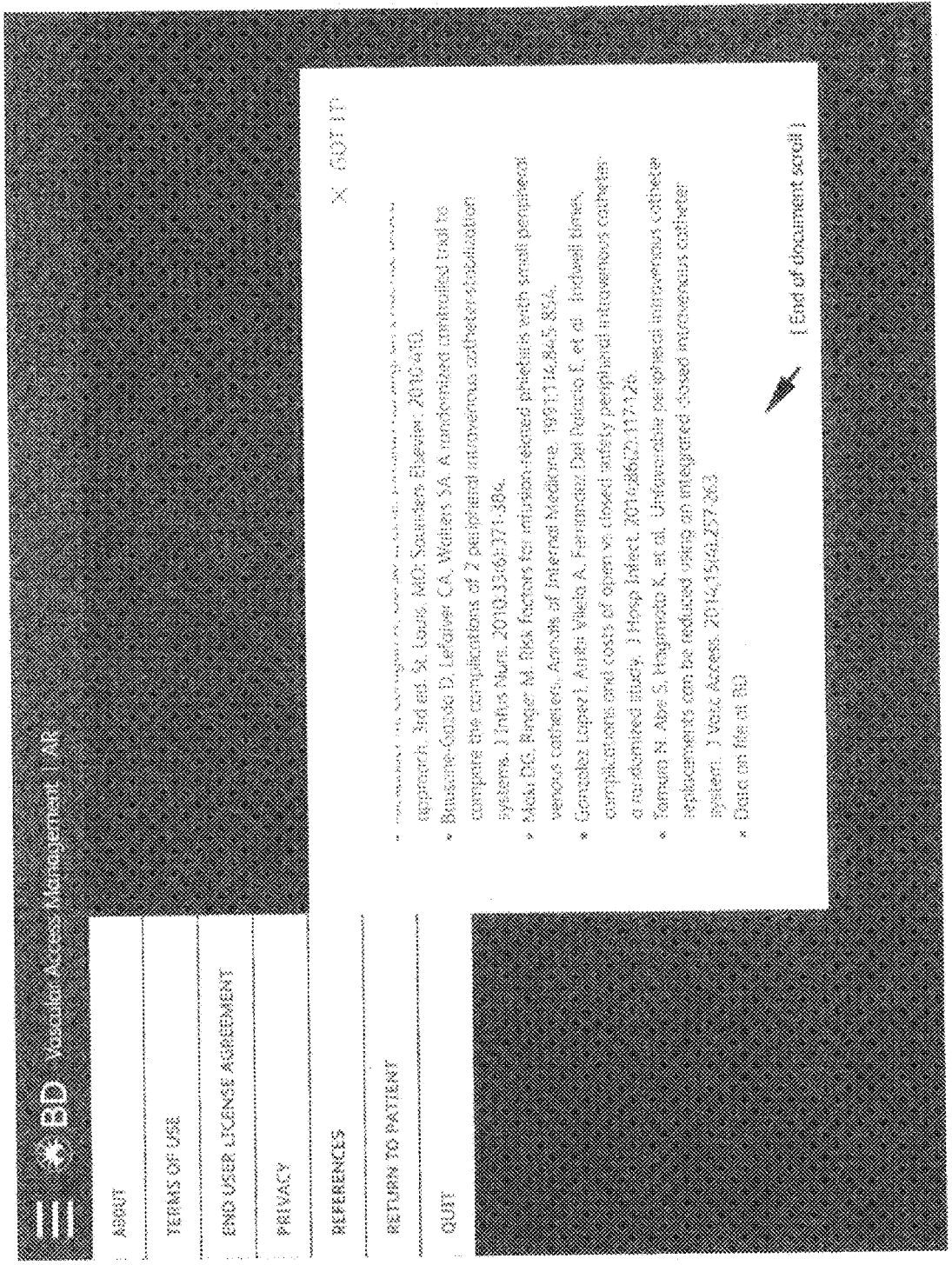
FIG. 42 is another example user interface, according to various embodiments.

In example embodiments, the CBL program or application begins with a welcome screen 600, such as shown in FIG. 29, which includes a "Start" button 602. By the user pressing the Start button 602, at step 502, machine 100 receives, via a network 114, a request for initiating a CBL program from a user and, in response to the request, machine 100 presents 504 the user with a main menu including a plurality of example person profiles from which to choose. Before presenting the main menu, the CBL program or application may launch an introductory video summarizing the purpose and/or the process of the CBL program or application. In certain embodiments, machine 100 presents a screen including a suitable disclaimer 606, such as shown in FIG. 30, and/or a welcome message 608, such as shown in FIG. 32, stating this experience has been developed to raise awareness of unnecessary complications associated with peripheral IV therapy and provide educational resources around product selection and clinical practices to help reduce these complications, for example. Additional introductory screens may be included in certain embodiments. For example, machine 100 may present a Terms of Use screen as shown in FIG. 33, a Mobile Application End User License Agreement as shown in FIG. 35, a Mobile Application Privacy Notice screen as shown in FIG. 39, and/or a References screen as shown in FIG. 41.

Figure 43:
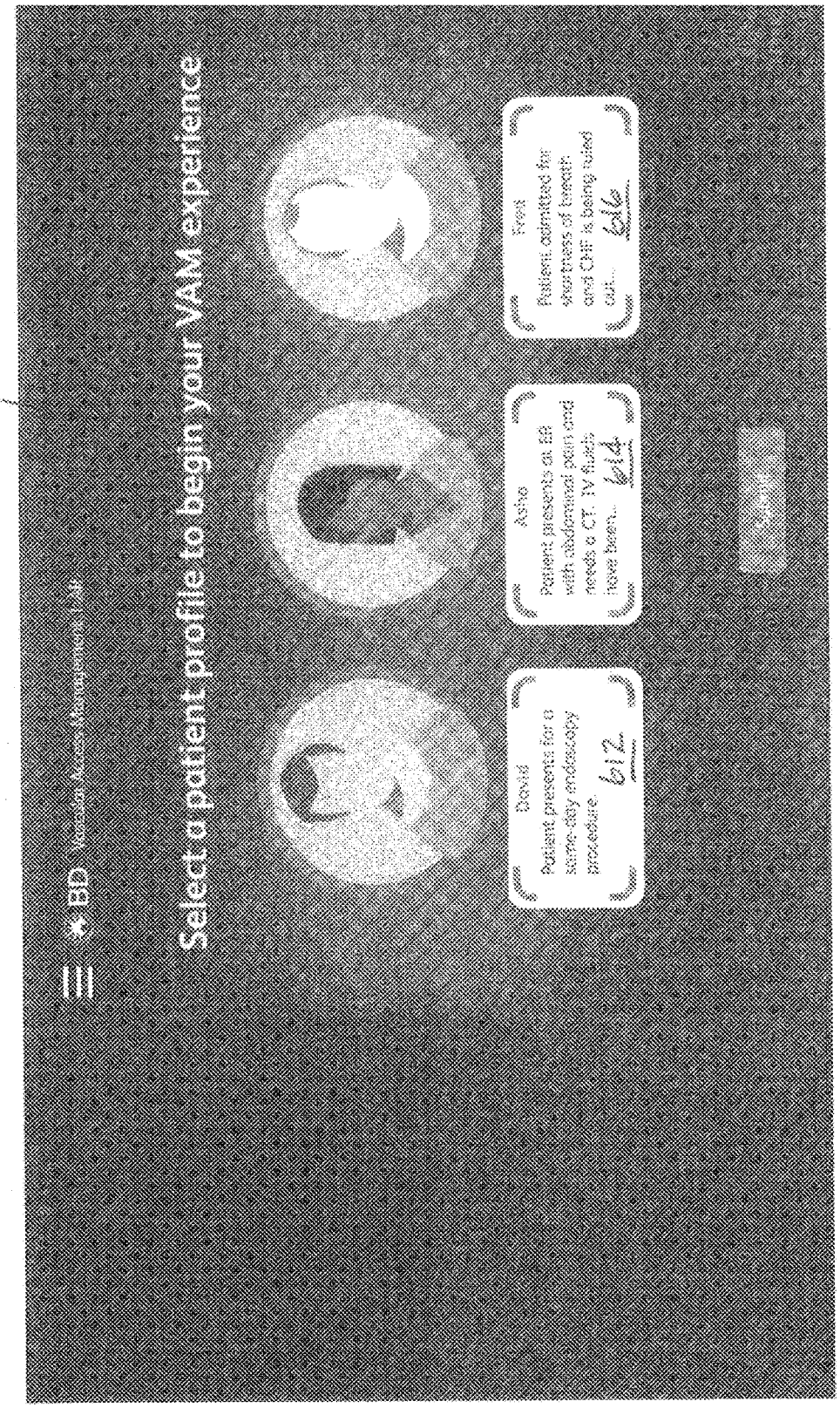
FIG. 43 is another example user interface, according to various embodiments.
Figure 44:
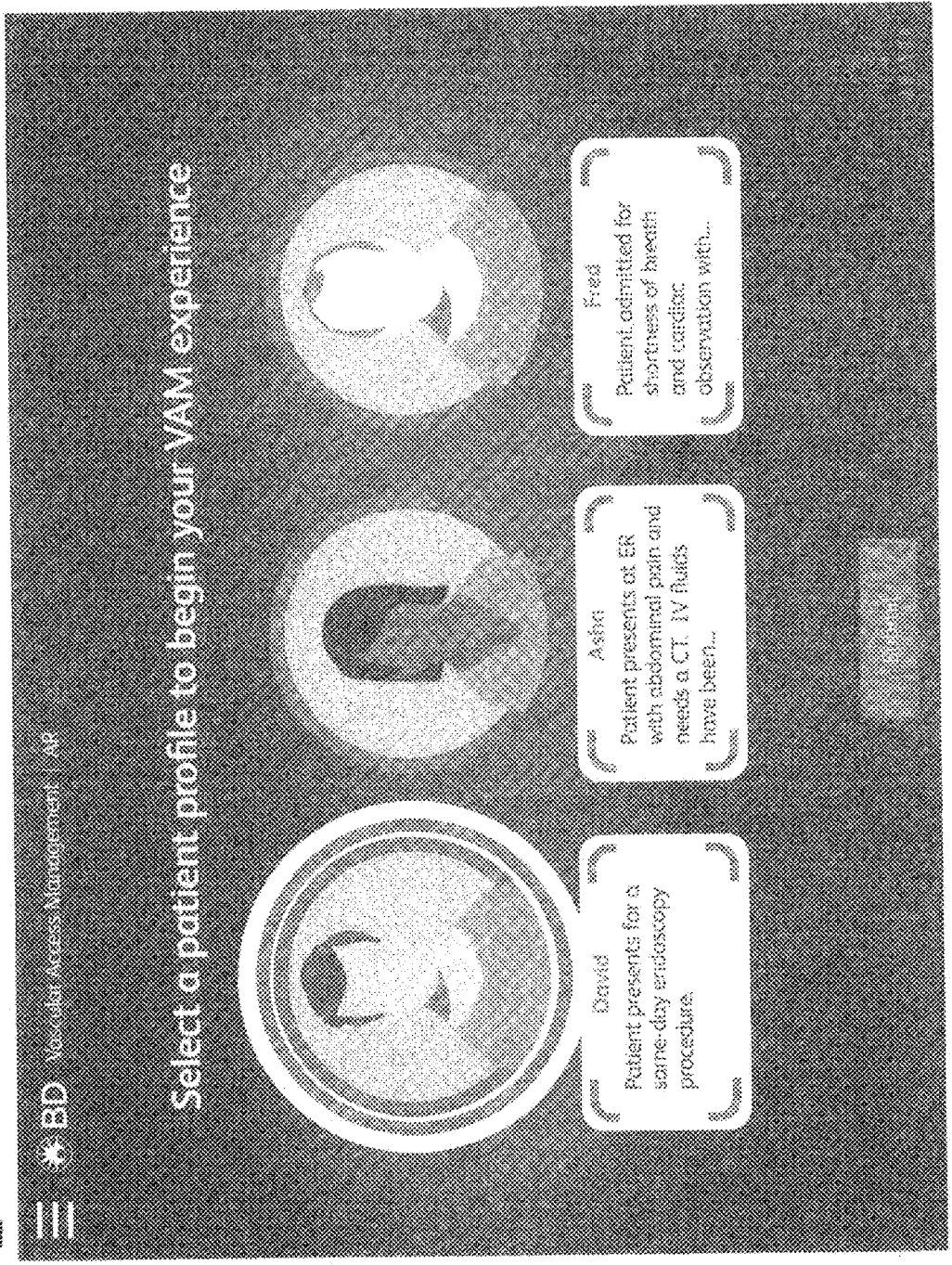
FIG. 44 is another example user interface, according to various embodiments.
Figure 45:
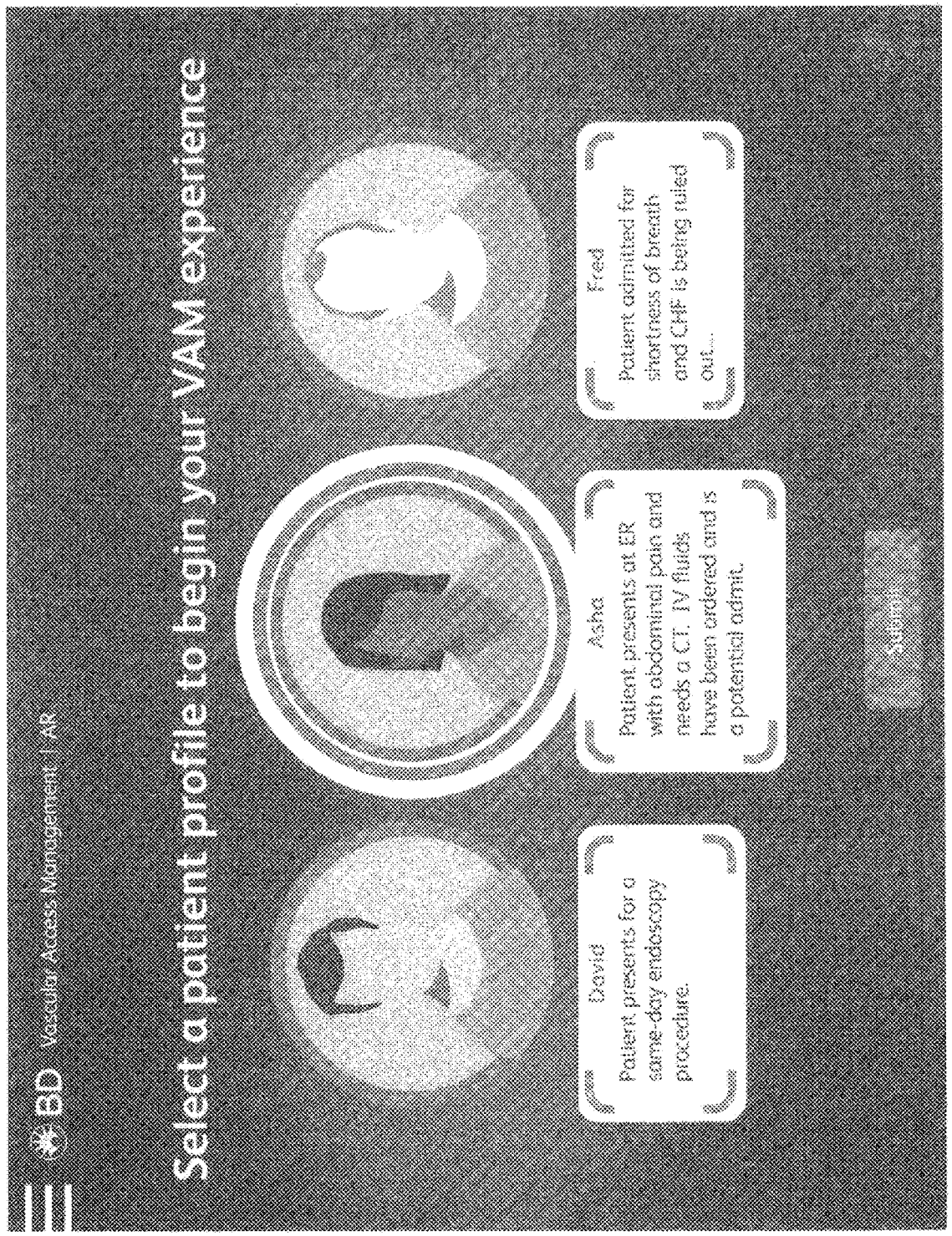
FIG. 45 is another example user interface, according to various embodiments.
Figure 46:
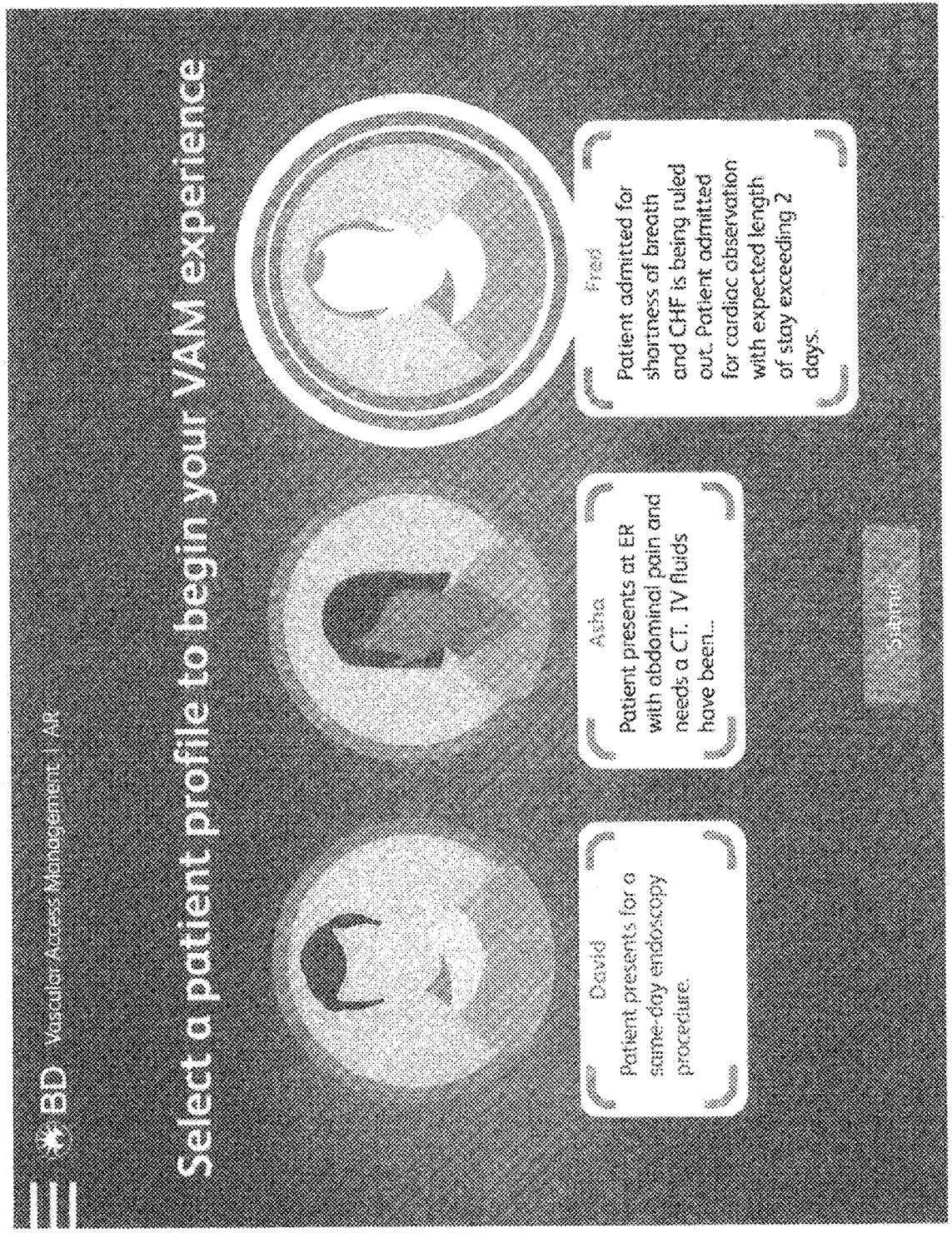
FIG. 46 is another example user interface, according to various embodiments.
Figure 47:
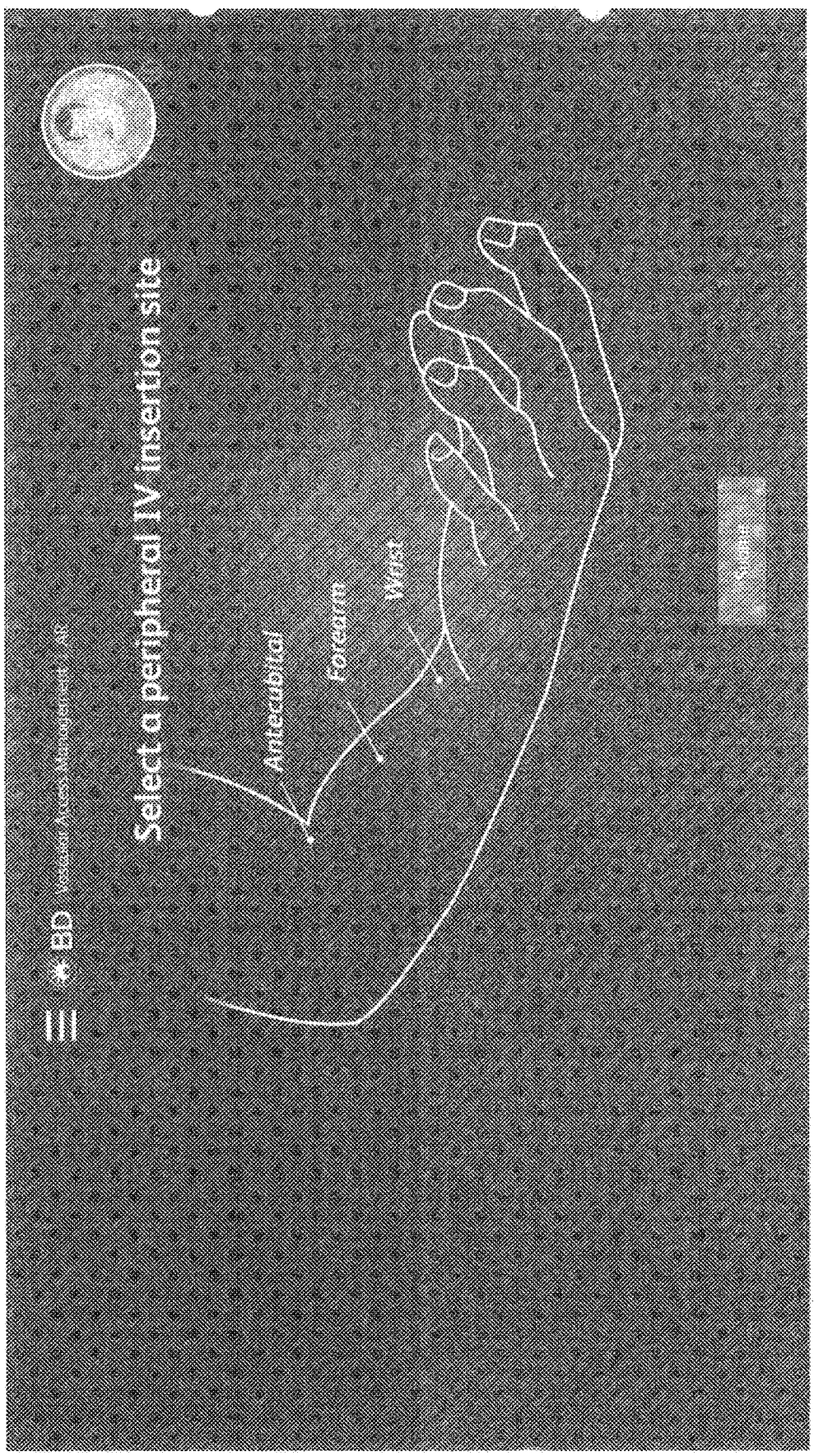
FIG. 47 is another example user interface, according to various embodiments.

In example embodiments, at step 504, machine 100 presents a main menu 610 that includes a plurality of example person profiles 612, 614, and 616 from which to select a person profile to begin the user's Vascular Access Management ("VAM") experience. For example, as shown in FIG. 43, main menu 610 may present a first person profile 612 identified as "David" indicating a person presenting for a same-day endoscopy procedure; a second person profile 614 identified as "Asha" indicating a person presenting at an emergency room with abdominal pain and need for a CT, noting that IV fluids have been ordered and that Asha is a potential admit; and a third person profile 616 identified as "Fred" indicating a person admitted for shortness of breath and cardiac observation with an expected length of hospital stay exceeding two (2) days. Additional or alternative person profiles may be presented 504 by machine 100. Each of these person profiles may require a different set of "correct," "optimal," or "appropriate" procedures and/or products for IV therapy, although machine 100 does not display the correct or most appropriate procedures and/or products to the user at this time in the CBL program.

Figure 48:
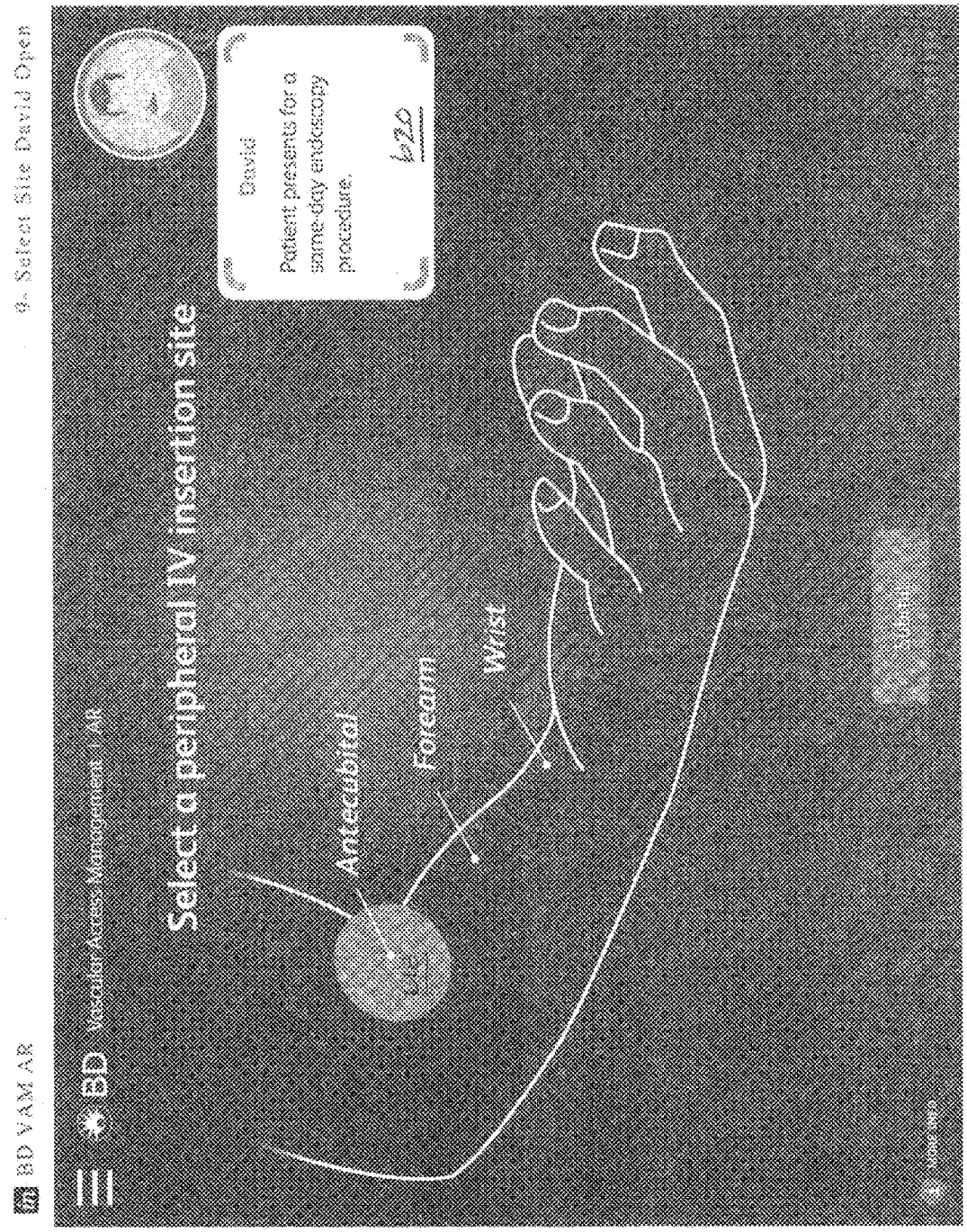
FIG. 48 is another example user interface, according to various embodiments.
Figure 49:
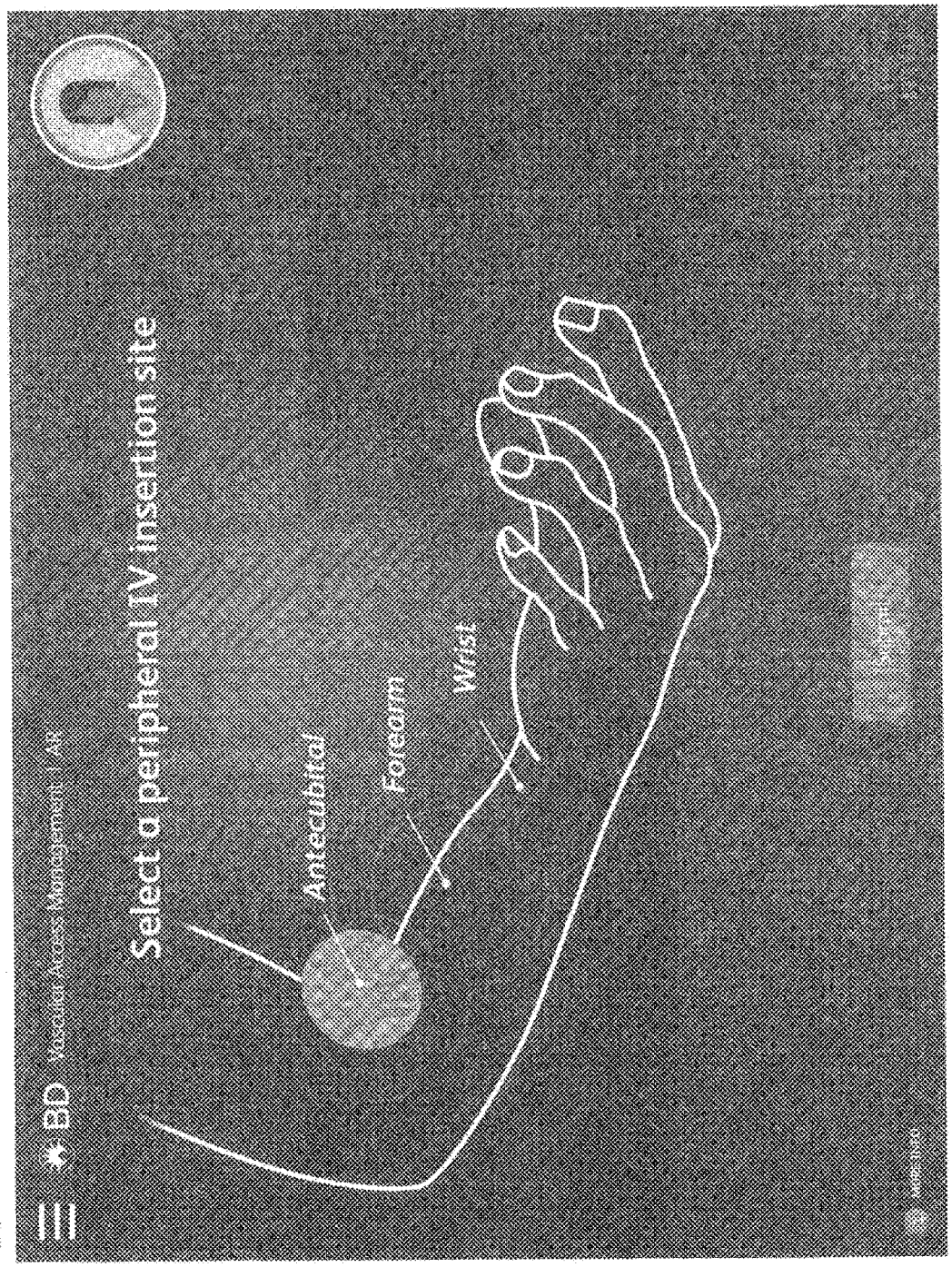
FIG. 49 is another example user interface, according to various embodiments.
Figure 50:
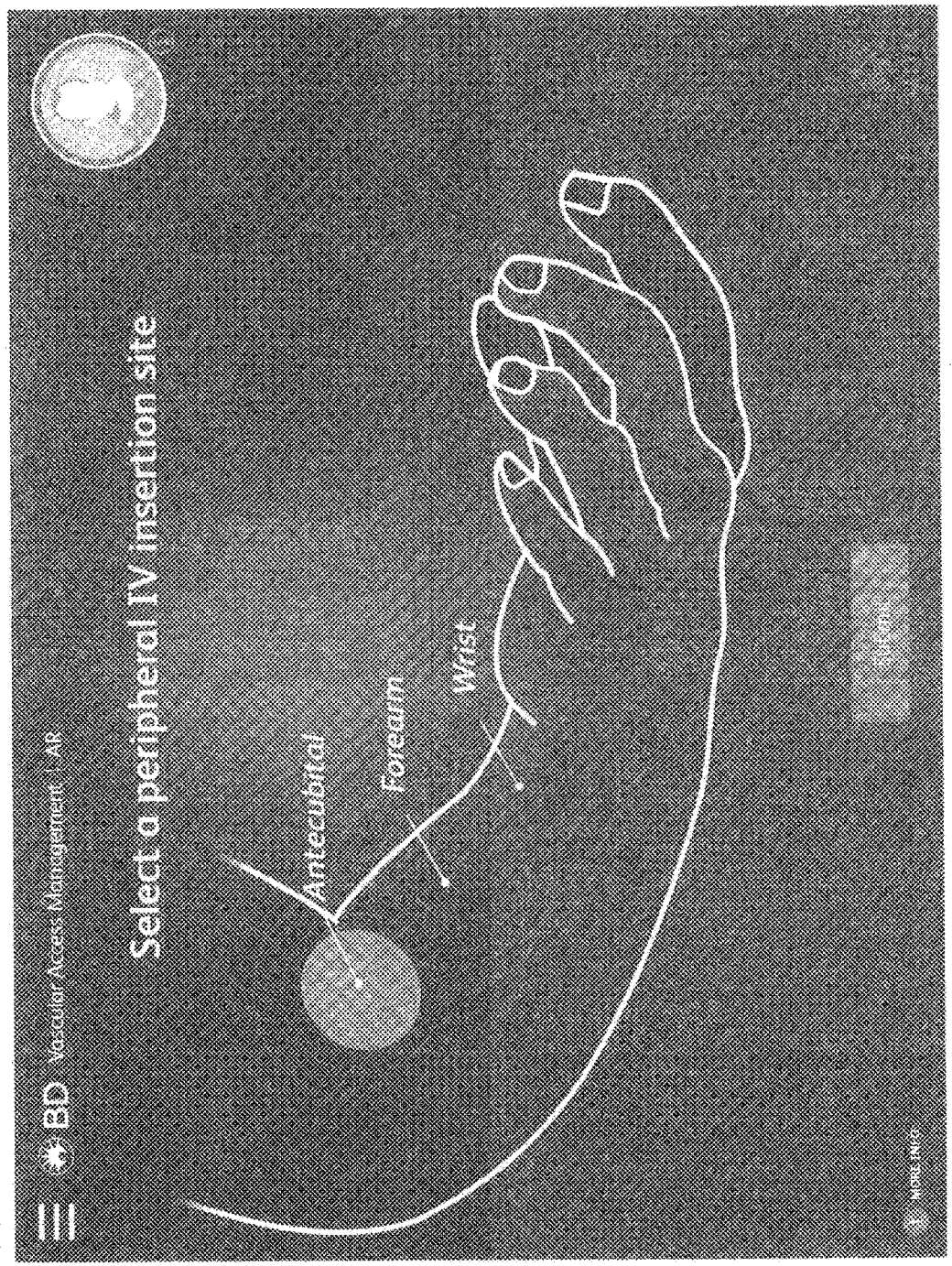
FIG. 50 is another example user interface, according to various embodiments.

Once the user selects one of the person profiles presented to the user, machine 100 prompts 506 the user to select an insertion site on a person's appendage (e.g., a person's arm) for inserting an IV catheter. As shown in FIG. 48, machine 100 displays a user interface indicating a plurality of insertion sites from which to select the insertion site. For example, as shown in FIG. 48, after the user selects first person profile 612 identified as "David," the user interface displays various options for selection of an insertion site including an antecubital insertion site, a forearm insertion site, and a wrist insertion site. Similarly, if the user selects second person profile 614 identified as "Asha" (see FIG. 49) or third person profile 616 identified as "Fred" (see FIG. 50), the user interface displays various options for selection of an insertion site including an antecubital insertion site, a forearm insertion site, and a wrist insertion site.

The user interface may include a textual indicator and/or visual indicator 618, e.g., a color or highlighted option, indicating a preferred insertion site at least partially depending on the selected person profile. The user interface may also include a summary 620 of the selected person profile. In particular embodiments, machine 100 generates informational text providing guidance on selecting a most appropriate insertion site. For example, the informational text may advise the user of potential complications that can occur during catheter insertion and/or provide one or more points for the user to consider to minimize a potential for complications when selecting the insertion site for the IV. In certain embodiments, the informational text may include an indication that although complications with a catheter can occur anywhere, areas of flexion, such as at the antecubital insertion site or the wrist insertion site, should be avoided.

Further, the informational text may include additional information, such as the hand insertion site has been linked to an increase in occlusion and accidental dislodgement compared to other sites (e.g., a preferred insertion site such as the forearm insertion site). The informational text may also include additional points to consider to minimize complications including, for example, a selection of a vein that best accommodates an outer diameter and/or a length of the catheter required for the prescribed therapy and/or an assessment of a person's condition including, without limitation, an age of the person, a diagnosis, comorbidities, a condition of vasculature at the insertion site, a condition of the person's skin at the insertion site, a person's previous history of IV insertions, a type and/or a duration of infusion therapy, a person's preference for IV site selection, or any suitable combination thereof.

At step 508, machine 100 instructs the user to select the appropriate products and/or procedures for properly inserting the IV catheter in the person's arm at the selected insertion site, based on the person profile selected by the user. For example, a person identified in a first person profile might require a first catheter, an extension set or no extension set, a suitable skin preparation, such as skin antisepsis or 70% isopropyl alcohol, a suitable connector, and a dressing choice of either film with a border or film without a border. A person identified in a second person profile might require a second catheter, a suitable skin preparation, a suitable connector, and a transparent film with a border; however, this person profile may not require an extension set. A person identified in a third person profile might require a third catheter, a suitable skin preparation, a suitable connector, and a transparent film with a border; however, this person profile does not require an extension set.

Figure 51:
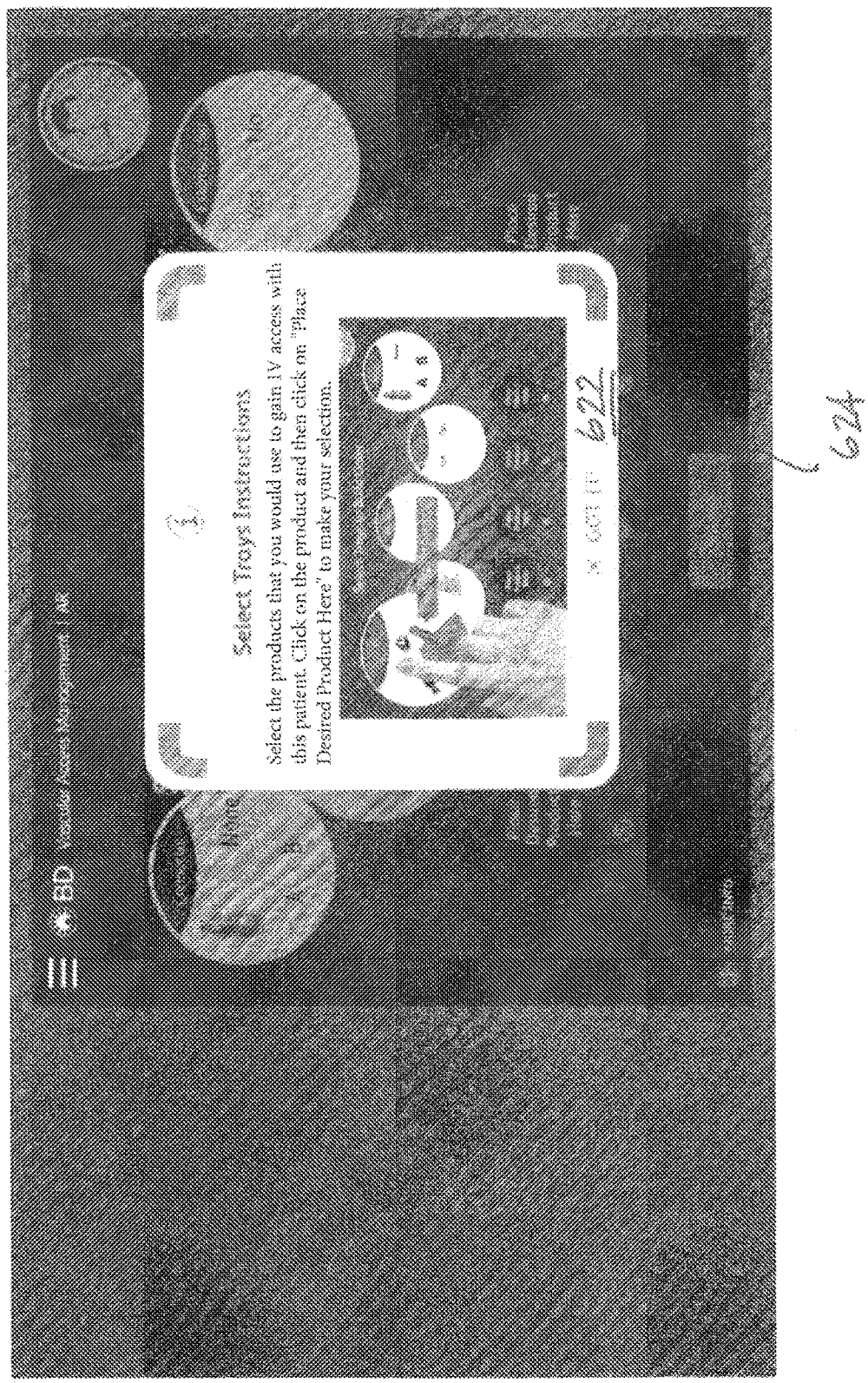
FIG. 51 is another example user interface, according to various embodiments.
Figure 52:
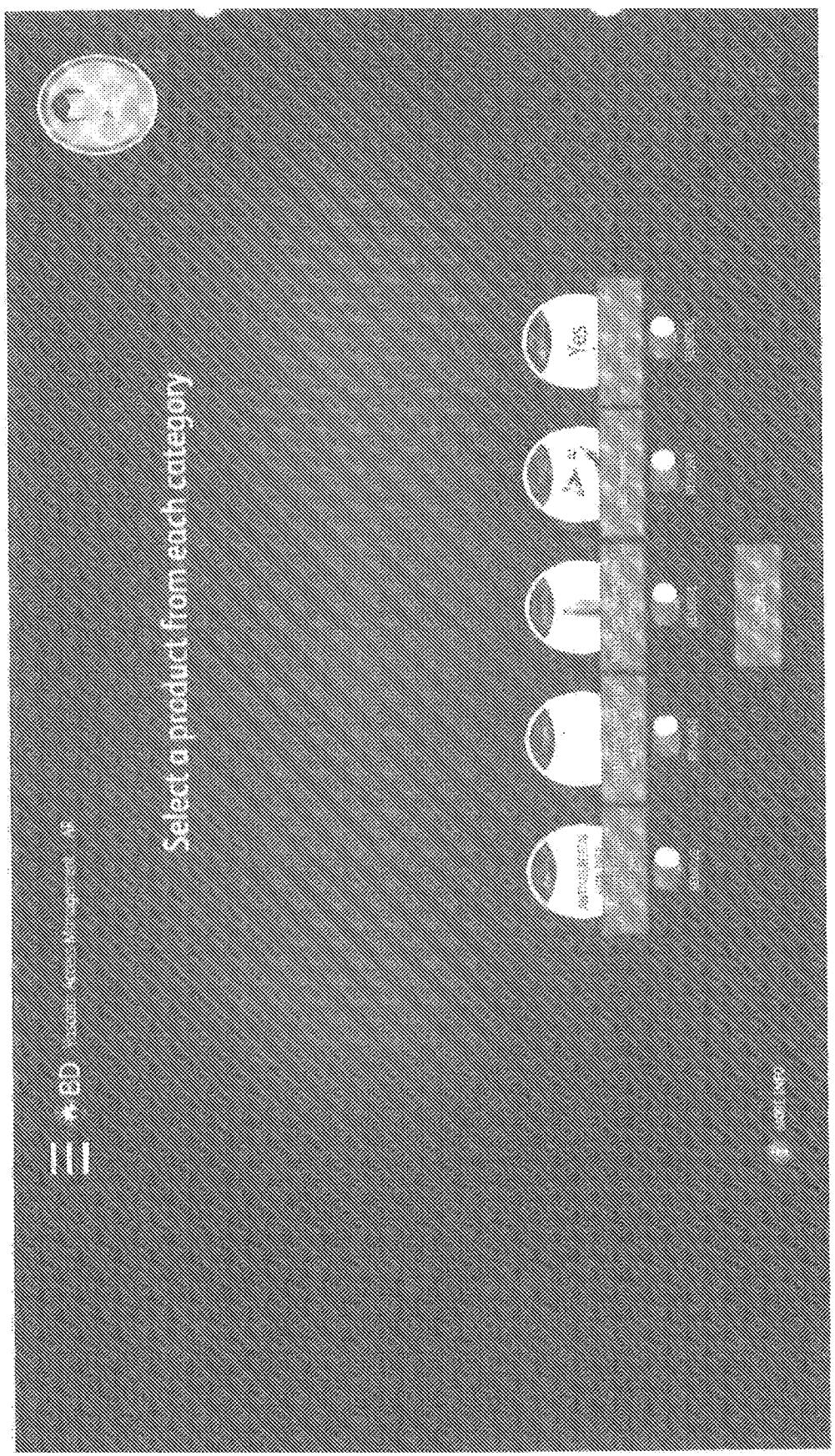
FIG. 52 is another example user interface, according to various embodiments.

In example embodiments, the CBL program or application then continues with a tray selection instruction screen 622, such as shown in FIG. 51. For example, try selection instruction screen 622 may indicate that the user will be required to select one or more products that the user would use to gain IV access with the person identified in the selected person profile. When the user presses the submit button 624, at step 510, machine 100 receives, via a network 114, a request for initiating the product selection portion of the CBL program or application and, in response to the request, machine 100 presents 512 the user with a main product menu including a plurality of example product categories that may be utilized to gain IV access, as shown in FIG. 53.

In an example embodiment, machine 100 may display available products on a tray and instruct 514 the user to select, e.g., click and drag, the most appropriate products to be used to gain IV access. In these embodiments, by selecting what the user believes to be the most appropriate products for the procedure, the user is required to connect the most appropriate products and practice. For example, in a particular embodiment, a proper procedure may include, in sequence, selecting the most appropriate peripheral IV catheter, preparing the insertion site for insertion of the catheter, providing and coupling a connector to the IV catheter, providing appropriate dressing at or around the insertion sire, providing an extension set, if required, and then proceeding with a line access process.

In example embodiments, the user selects the most appropriate catheter for the selected person profile. A plurality of catheters, such as a first catheter, a second catheter, and a third a third catheter, may be displayed on display 70 from which the user is prompted to select the most appropriate catheter for the procedure. The user also selects the most appropriate process for preparing the site for insertion. A plurality of possible preparation steps may be displayed on display 70, such as whether to prepare the insertion site with chlorhexidine in alcohol solution or whether to prepare the insertion site with only alcohol. The user also selects the most appropriate connector, if necessary, to couple to the selected catheter. For example, machine 100 may display a plurality of choices for a connector, such as a first connector, a second connector, a third connector, or no connector. The user selects what the user believes is the most appropriate connector selection for the person profile. Similarly, the user selects the most appropriate dressing from a plurality of dressing choices. For example, machine 100 may display on display 70 several choices including a transparent film dressing and a transparent film dressing with a border. The user may further determine whether an extension set is required. For example, machine 100 may display an option for using an extension set, indicated as "Yes," and an option for not using an extension set, indicated as "No."

Figure 53:
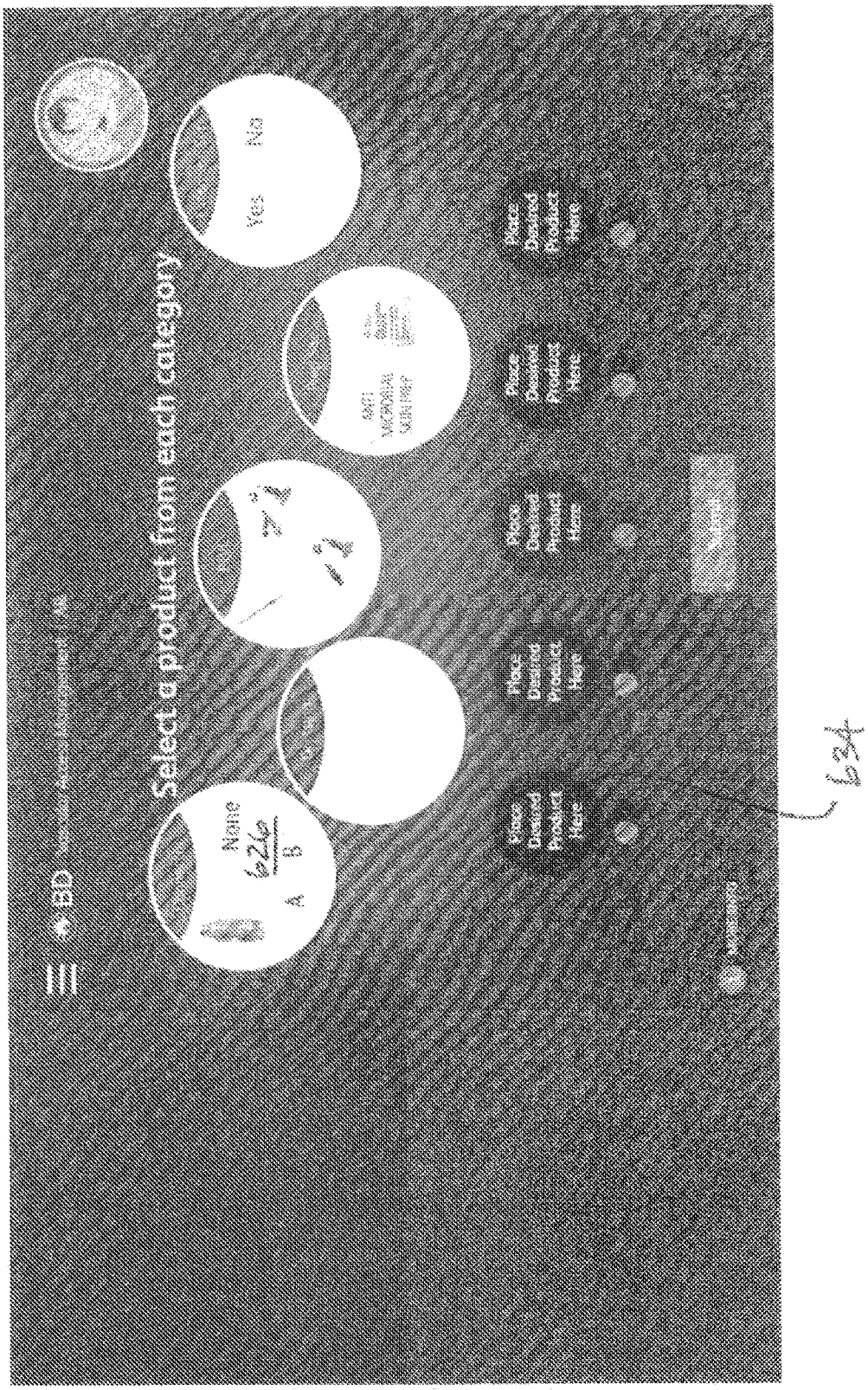
FIG. 53 is another example user interface, according to various embodiments.
Figure 54:
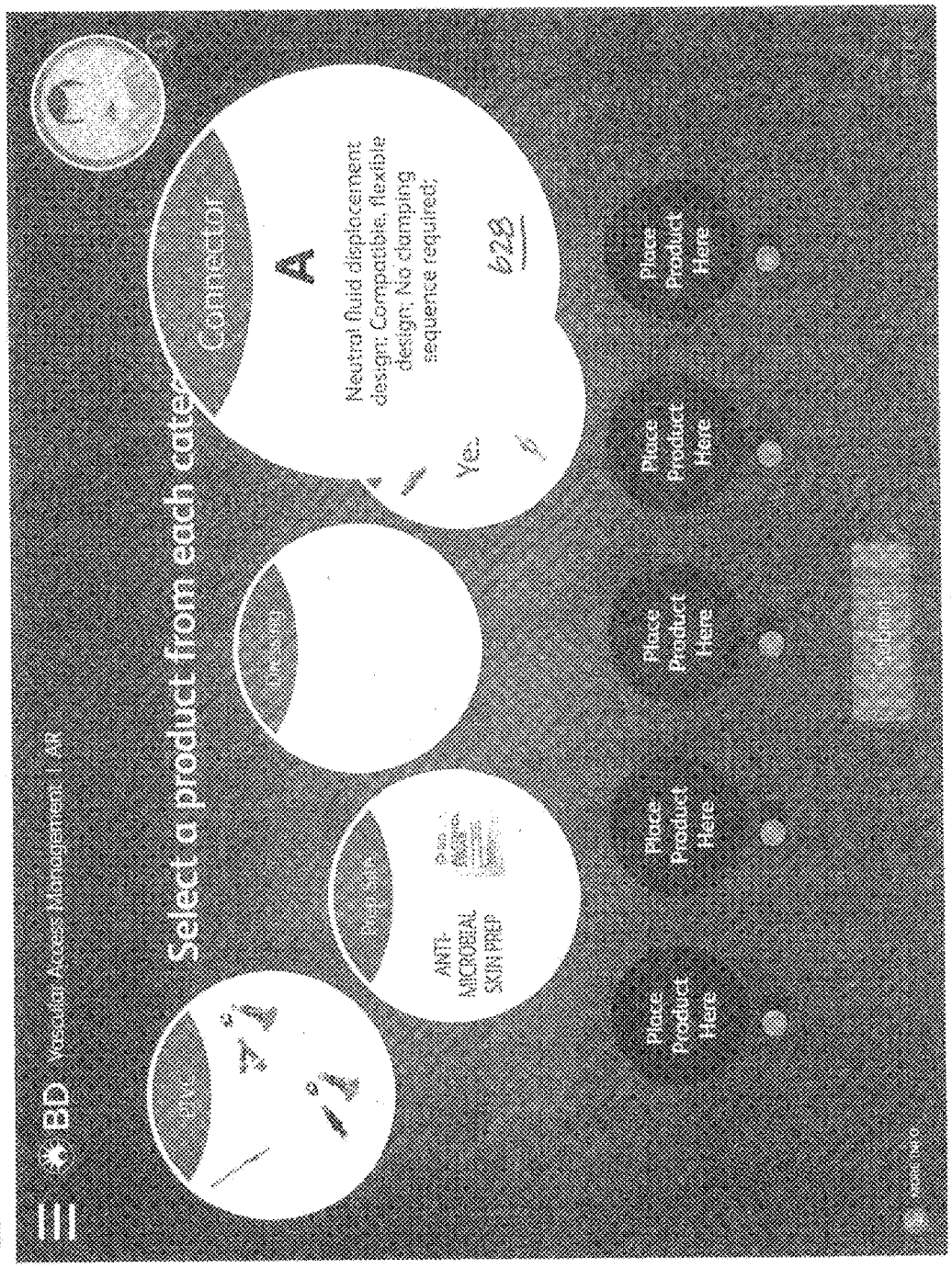
FIG. 54 is another example user interface, according to various embodiments.
Figure 55:
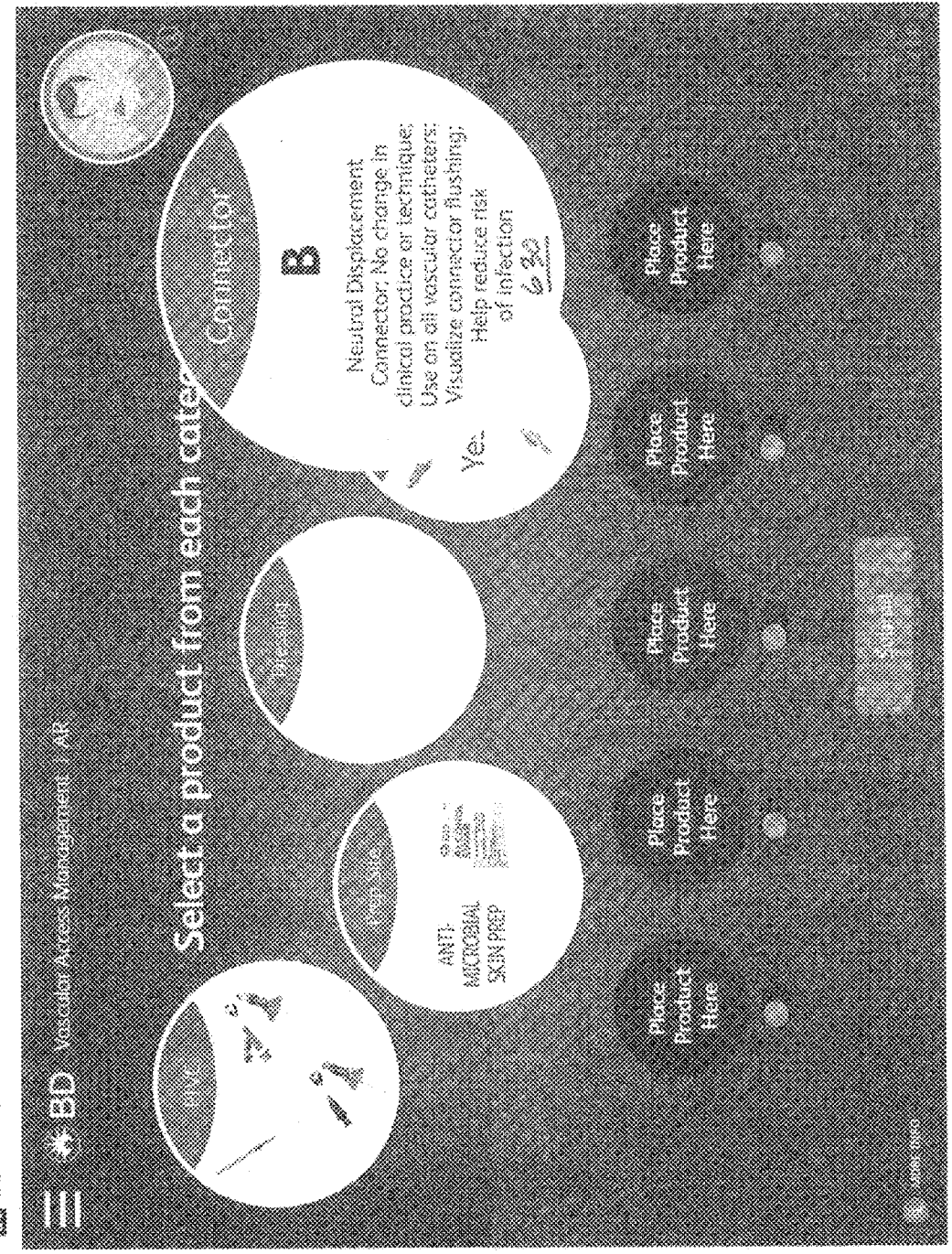
FIG. 55 is another example user interface, according to various embodiments.
Figure 56:
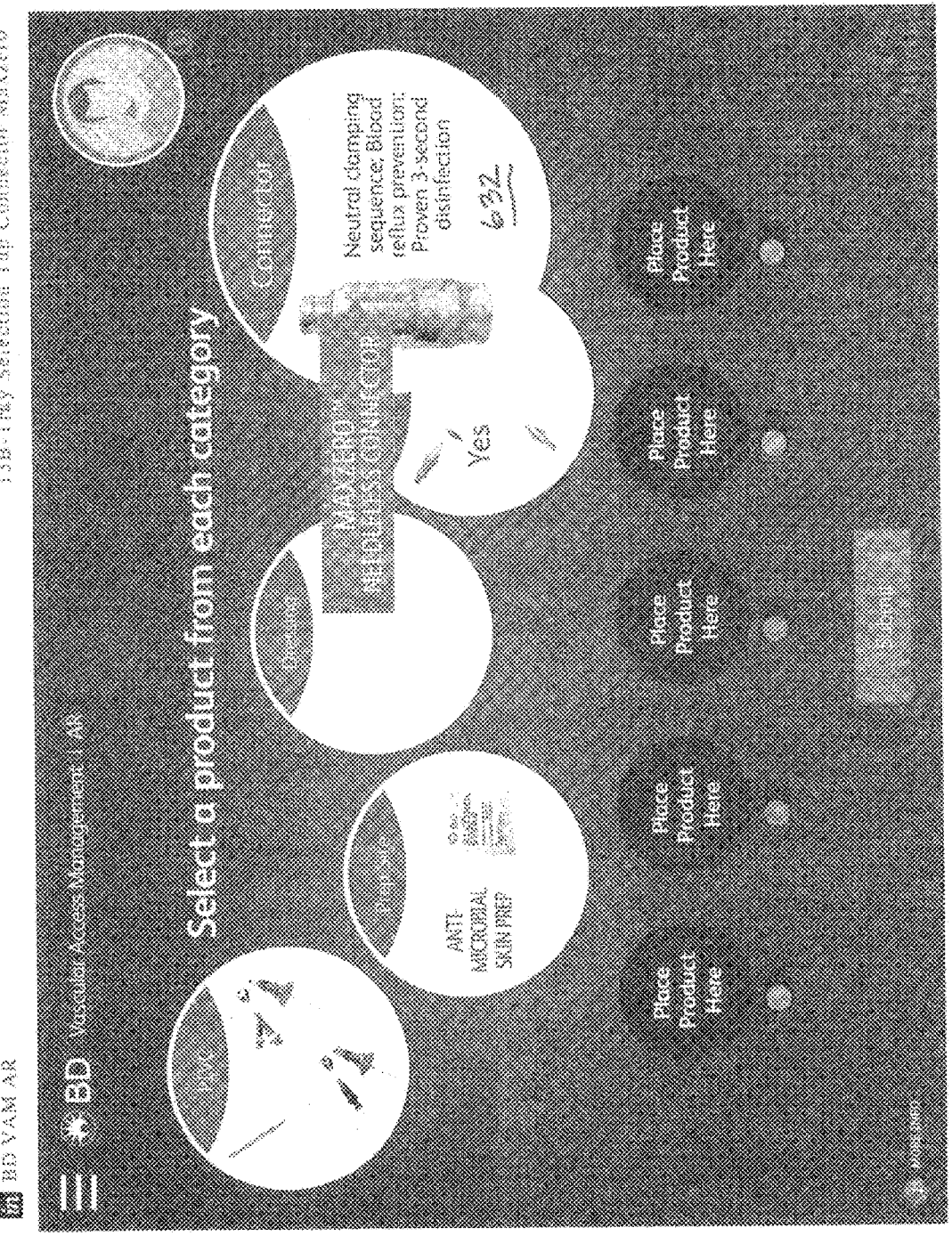
FIG. 56 is another example user interface, according to various embodiments.
Figure 57:
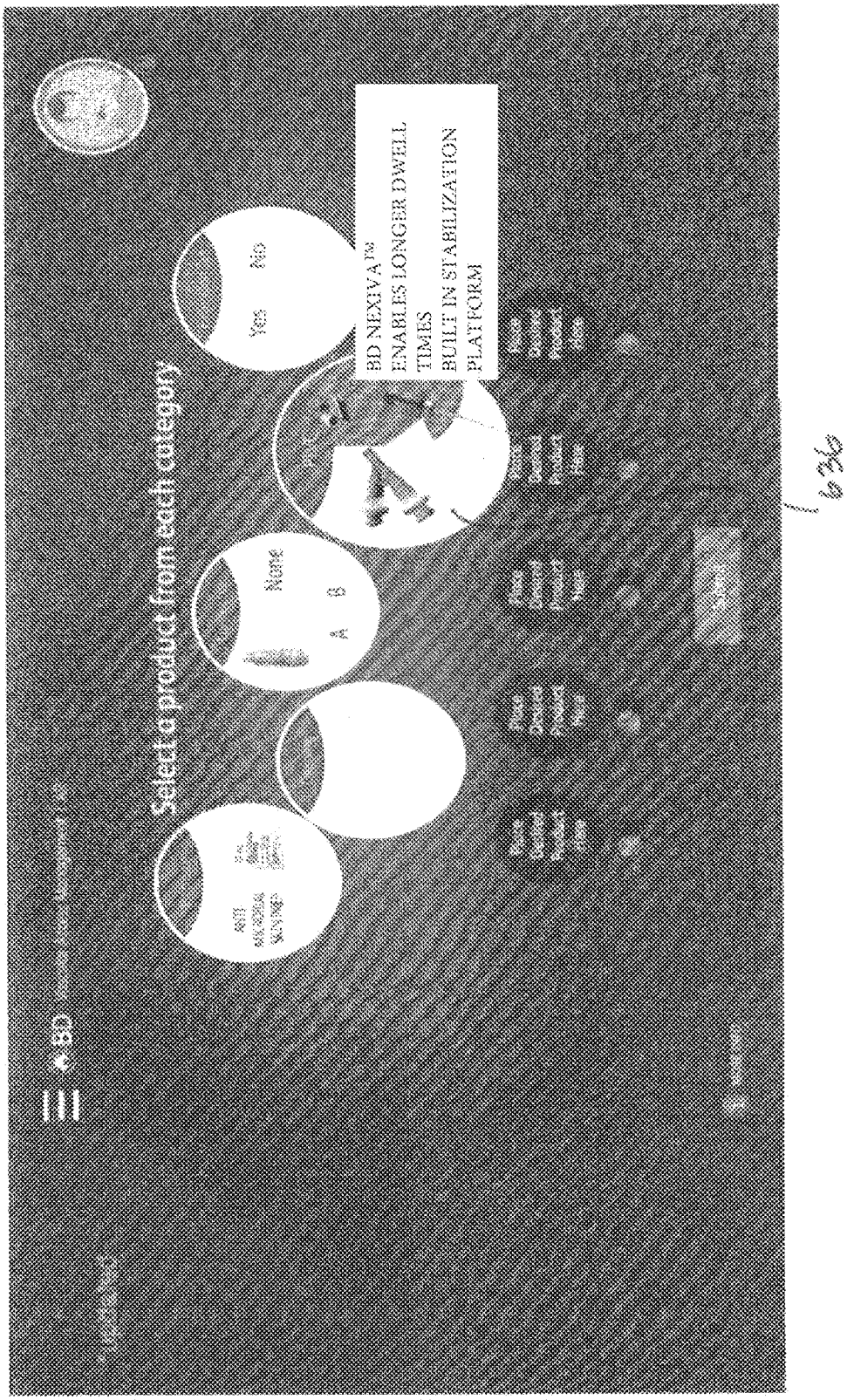
FIG. 57 is another example user interface, according to various embodiments.
Figure 58:
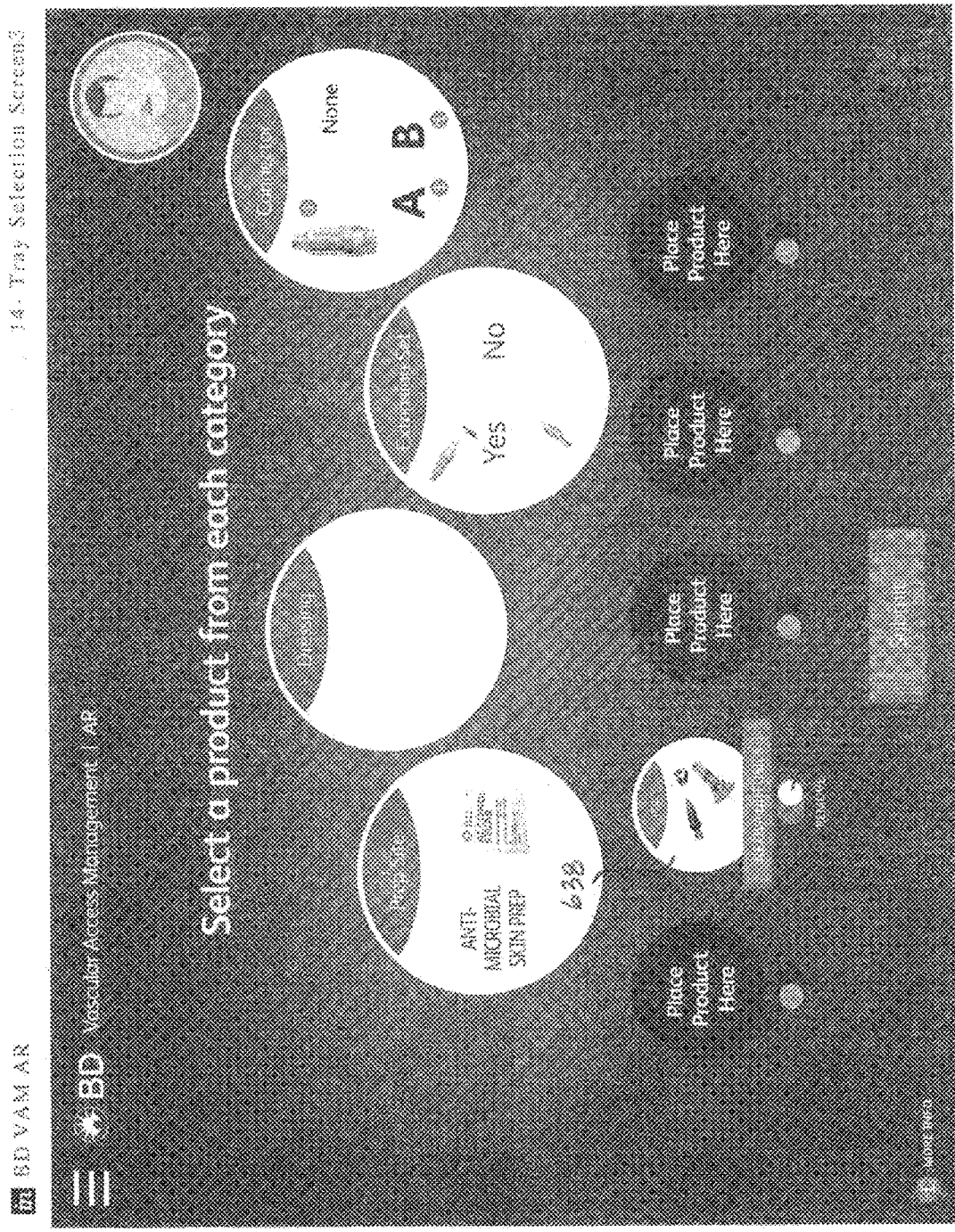
FIG. 58 is another example user interface, according to various embodiments.
Figure 59:
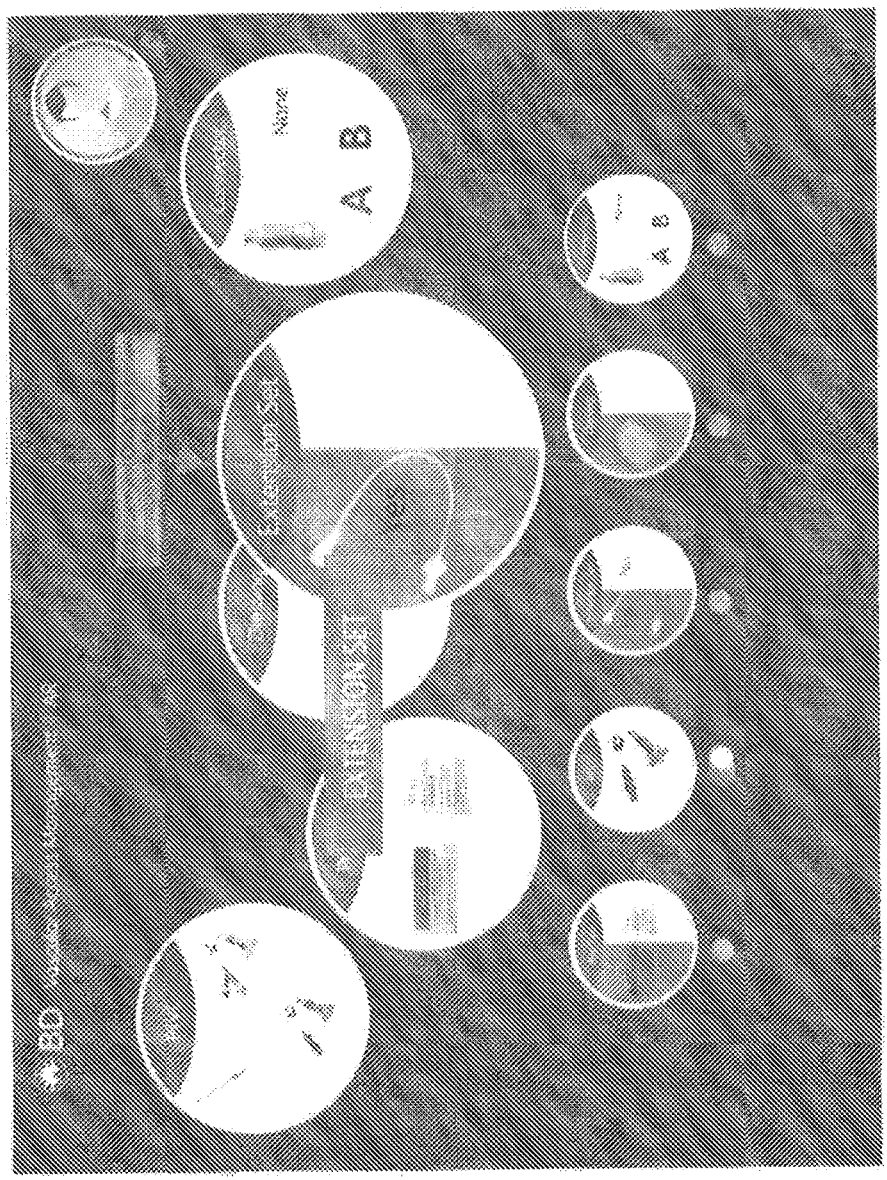
FIG. 59 is another example user interface, according to various embodiments.
Figure 60:
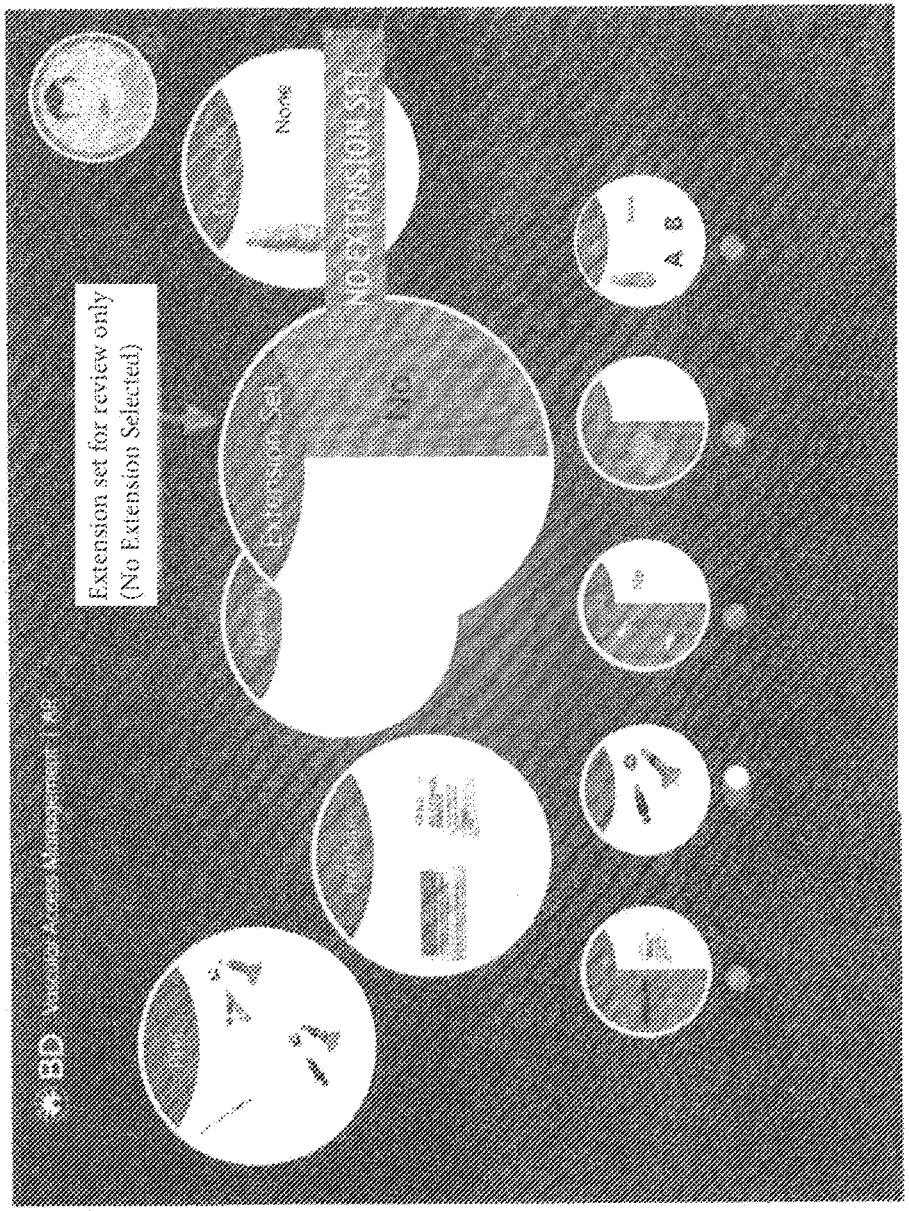
FIG. 60 is another example user interface, according to various embodiments.

Referring to FIGS. 53-56, in example embodiments, if the user selects a "Connector" window 626, e.g., by clicking on Connector window 626, the user may select Connector A 628 identified in FIG. 54, Connector B 630 identified in FIG. 55, or Connector C 632, e.g., a Maxzero™ needleless connector, identified in FIG. 56. In order to select the connector which the user believes to be the most appropriate connector associated with the person profile, the user can click and drag the selected connector and move it to a marker 634, such as shown in FIG. 53, including text that reads "Place Product Here." Similarly, as shown in FIG. 57, the user selects a peripheral intravenous catheter ("PIVC"), e.g., by clicking on a PIVC window 636. Within PIVC window 636, the user may select a suitable or most appropriate PIVC for the selected person profile from one or more available PIVCs, such as a first catheter, e.g., a BD Nexiva™ Diffusics™ catheter, a second catheter, and a third catheter, displayed on display 70. Referring further to FIG. 58, in order to select the PIVC which the user believes to be the most appropriate PIVC associated with the person profile for the procedure, the user can click and drag the selected PIVC and move it to a marker 638 including text that reads "Place Product Here." In a particular embodiment, the user is able to remove the selected PIVC using a remove button 640, as shown in FIG. 58, and replace it with a different PIVC that the user believes is more appropriate for the procedure.

Figure 61:
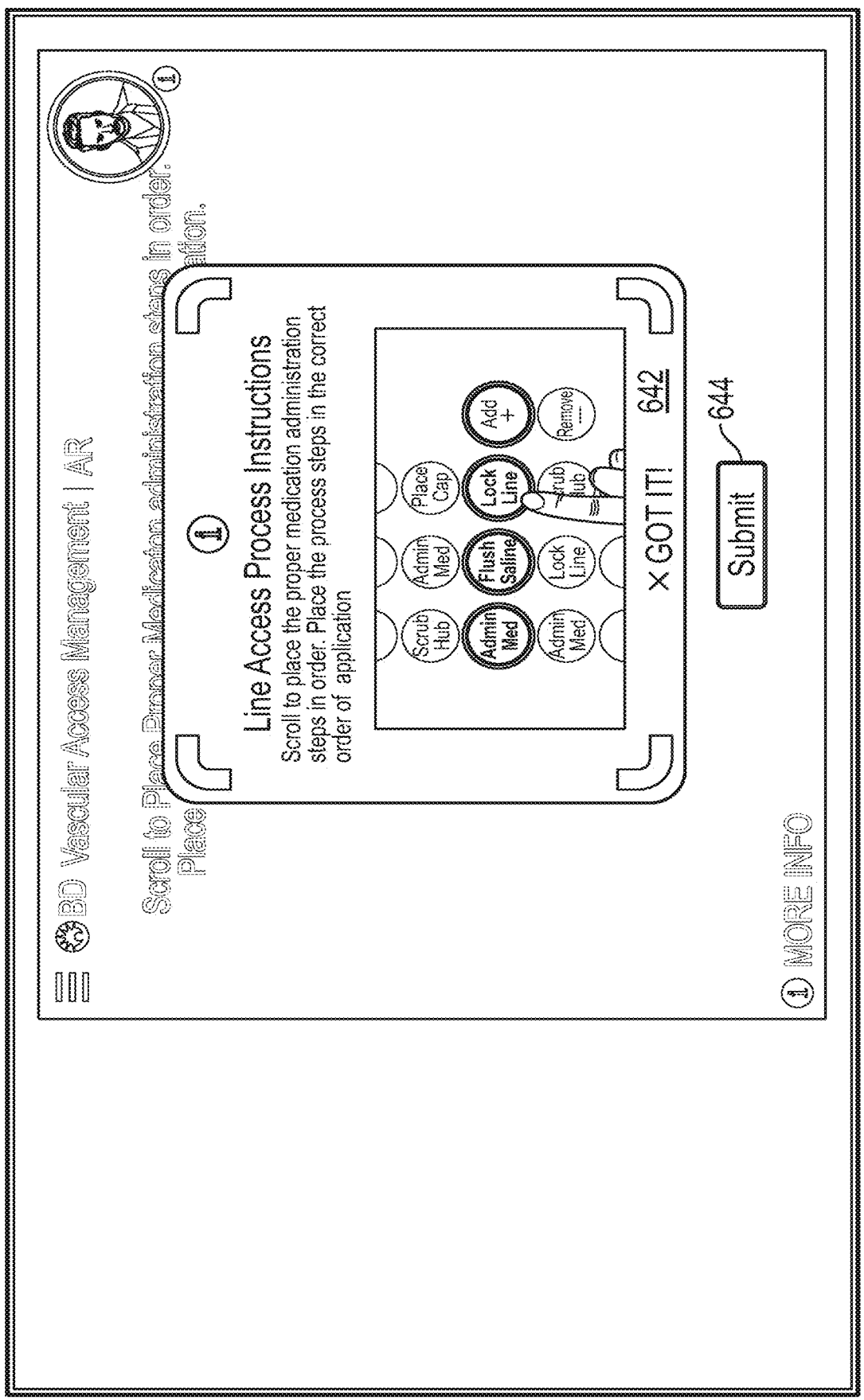
FIG. 61 is another example user interface, according to various embodiments.

Once the user has selected the products which the user believes are the most appropriate products for the selected person profile, the CBL program or application continues with a line access process. In example embodiments, the CBL program or application continues with a line access process instruction screen 642, such as shown in FIG. 61. For example, screen 642 may indicate that the user will be required to place the proper medication administration steps in a most appropriate order or sequence. A video, for example, may run on screen 642 to provide the user with suitable instructions. When the user presses a submit button 644, at step 516, machine 100 receives, via a network 114, a request for initiating the line access process portion of the CBL program or application and, in response to the request, machine 10 presents the user with a main line access process menu including a plurality of example line access process steps that may be utilized to gain IV access, as shown in FIGS. 62 and 65.

Figure 62:
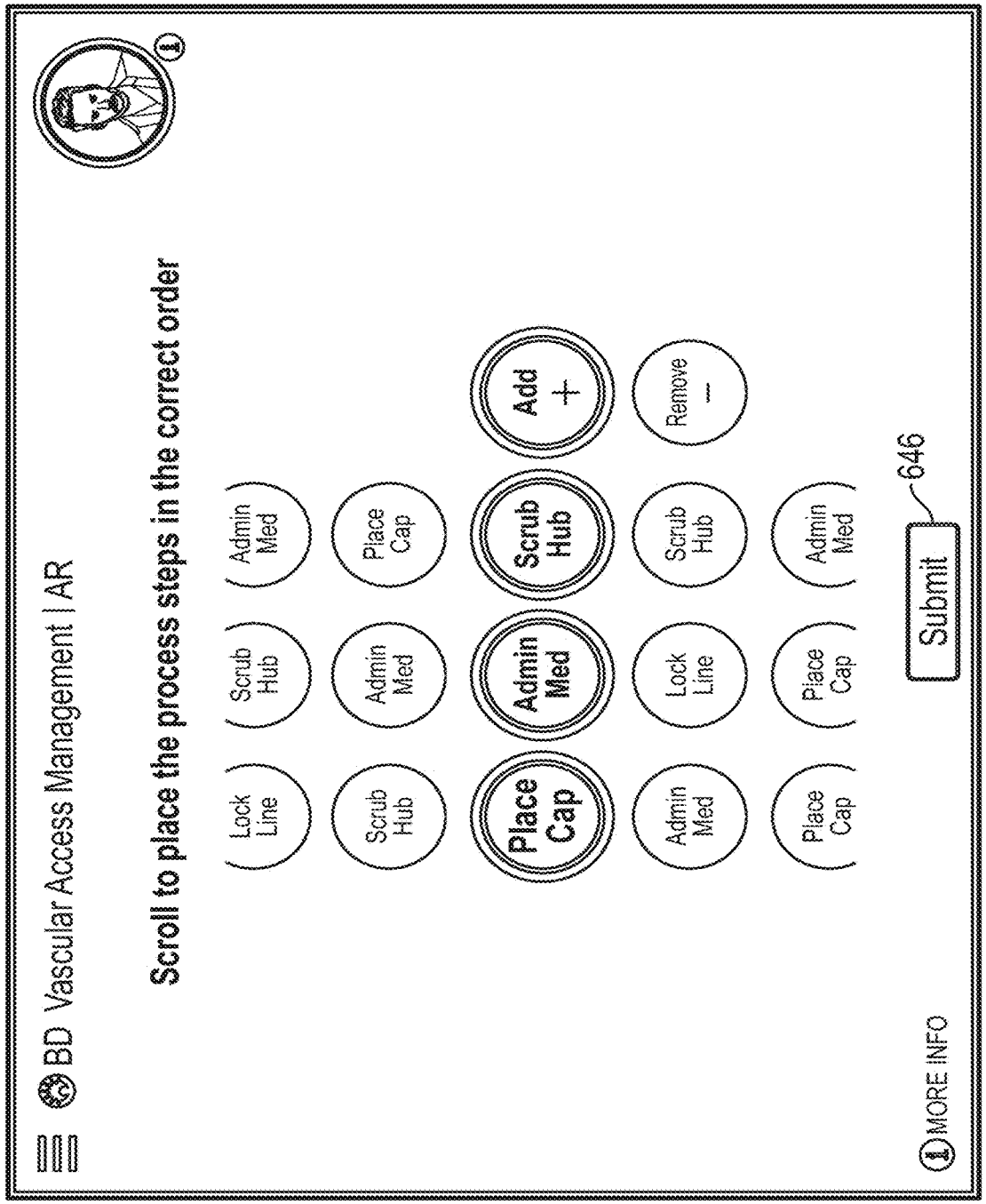
FIG. 62 is another example user interface, according to various embodiments.
Figure 63:
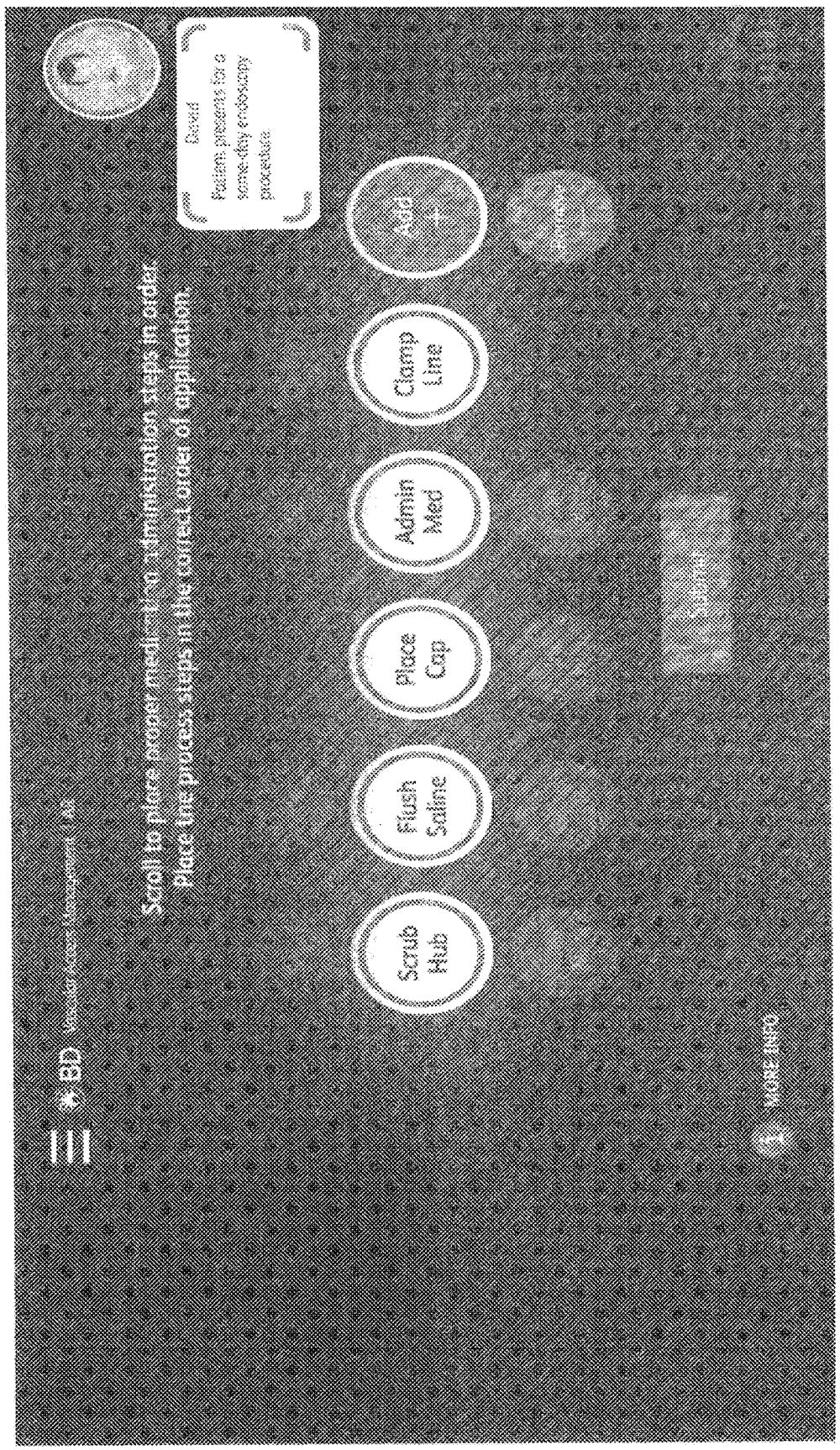
FIG. 63 is another example user interface, according to various embodiments.
Figure 64:
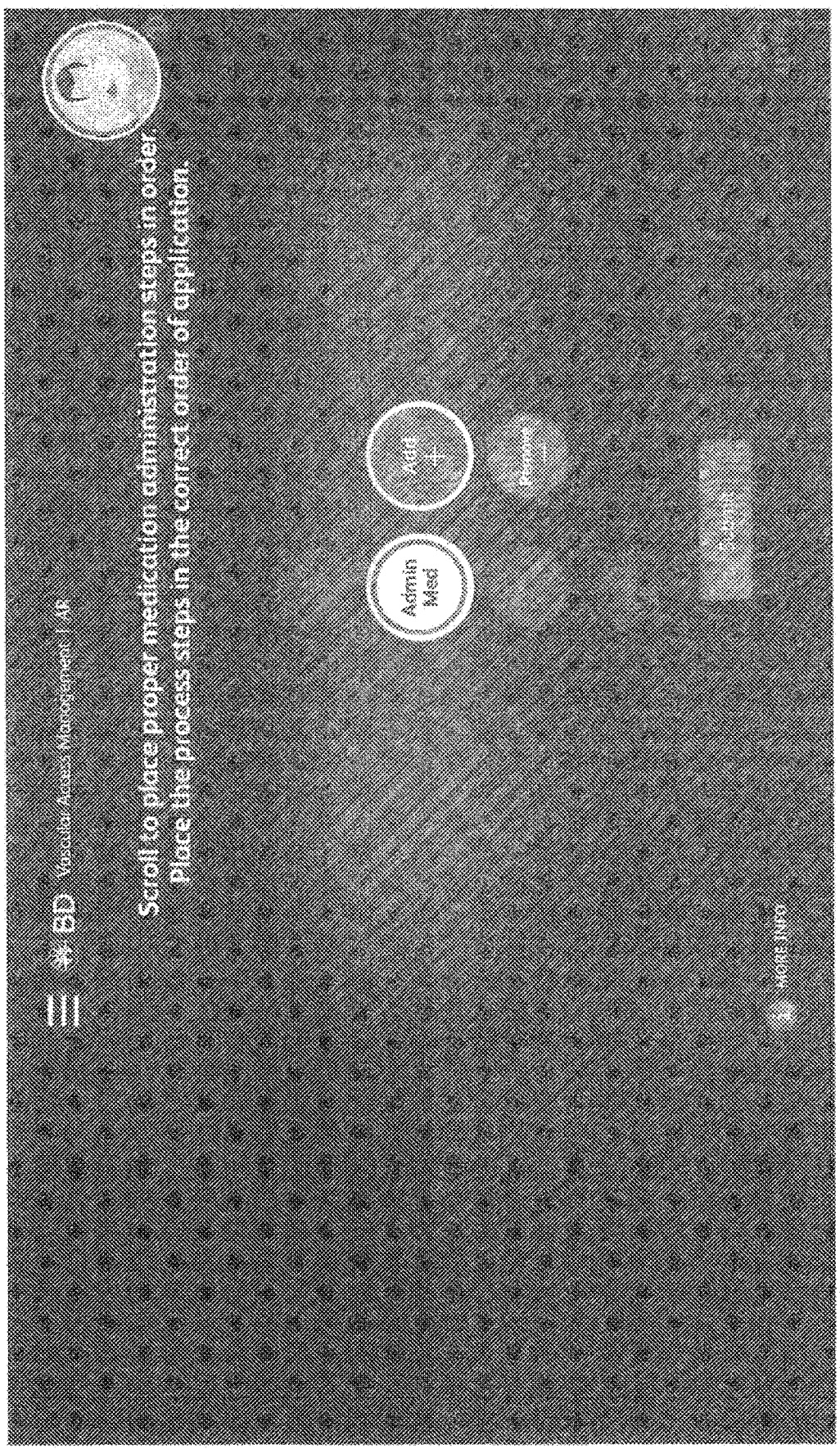
FIG. 64 is another example user interface, according to various embodiments.
Figure 66:
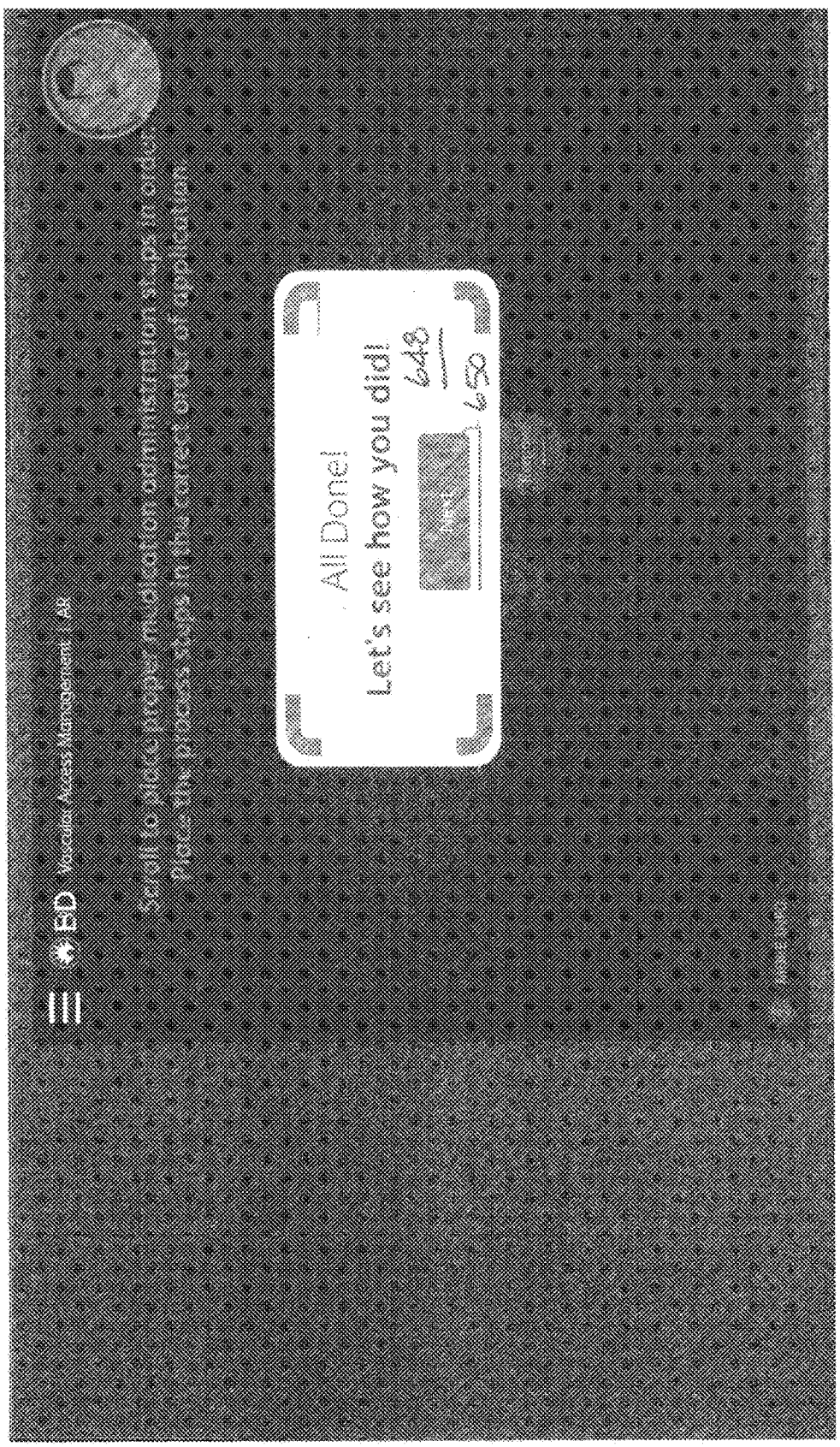
FIG. 66 is another example user interface, according to various embodiments.

During the line access process, the user positions or places 518 a plurality of process steps in a most appropriate sequential order by clicking, dragging, and dropping each process step in an appropriate numbered process step location, as shown in FIGS. 62 and 65. For example, machine 100 may display the various steps of the line access process including, for example, "Scrub Hub," "Place Cap," "Administer Med," "Flush Saline," and/or "Lock Line" in a non-sequential listing on display 70. The user is then required to properly place the line access process steps in a most appropriate sequential order within the numbered line access process step locations displayed on display 70. The selected line access process steps can be added or removed using appropriate buttons displayed on display 70. In example embodiments, one or more of the line access process steps may be required more than once during an appropriate line access process. With the line access process steps positioned in what the user believes is the most appropriate sequential order, such as shown in FIG. 65, the user presses a submit button 646. In example embodiments, when the user presses submit button 646, at step 520, machine 100 receives, via a network 114, a request for initiating a review of the user's selection of the most appropriate sequential line access process steps and, in response to the request, machine 100 presents the user with a screen 648 including a "Next" button 650, as shown in FIG. 66, allowing the user to continue the CBL program or application to learn: (a) whether the user selected the most appropriate access site for gaining IV access for the person identified in the selected person profile; (b) whether the user selected the most appropriate products for one or more product categories for gaining IV access for the person identified in the selected person profile (see FIGS. 29-58); and/or (c) whether the user selected the most appropriate sequential line access steps utilized to gain IV access, (see FIGS. 61-65).

In certain embodiments, once the user places the line access process steps in what the user believes is the most appropriate sequential order, machine 100 instructs the user to position sticker 50 at the selected insertion site (e.g., the antecubital insertion site, the forearm insertion site, the wrist insertion site, or the hand insertion site) on the chosen arm (i.e., the right arm or the left arm) in order to proceed to the next step. In certain example embodiments, machine 100 displays a user interface indicating placement of sticker 50 at the selected insertion site.

Figure 67:
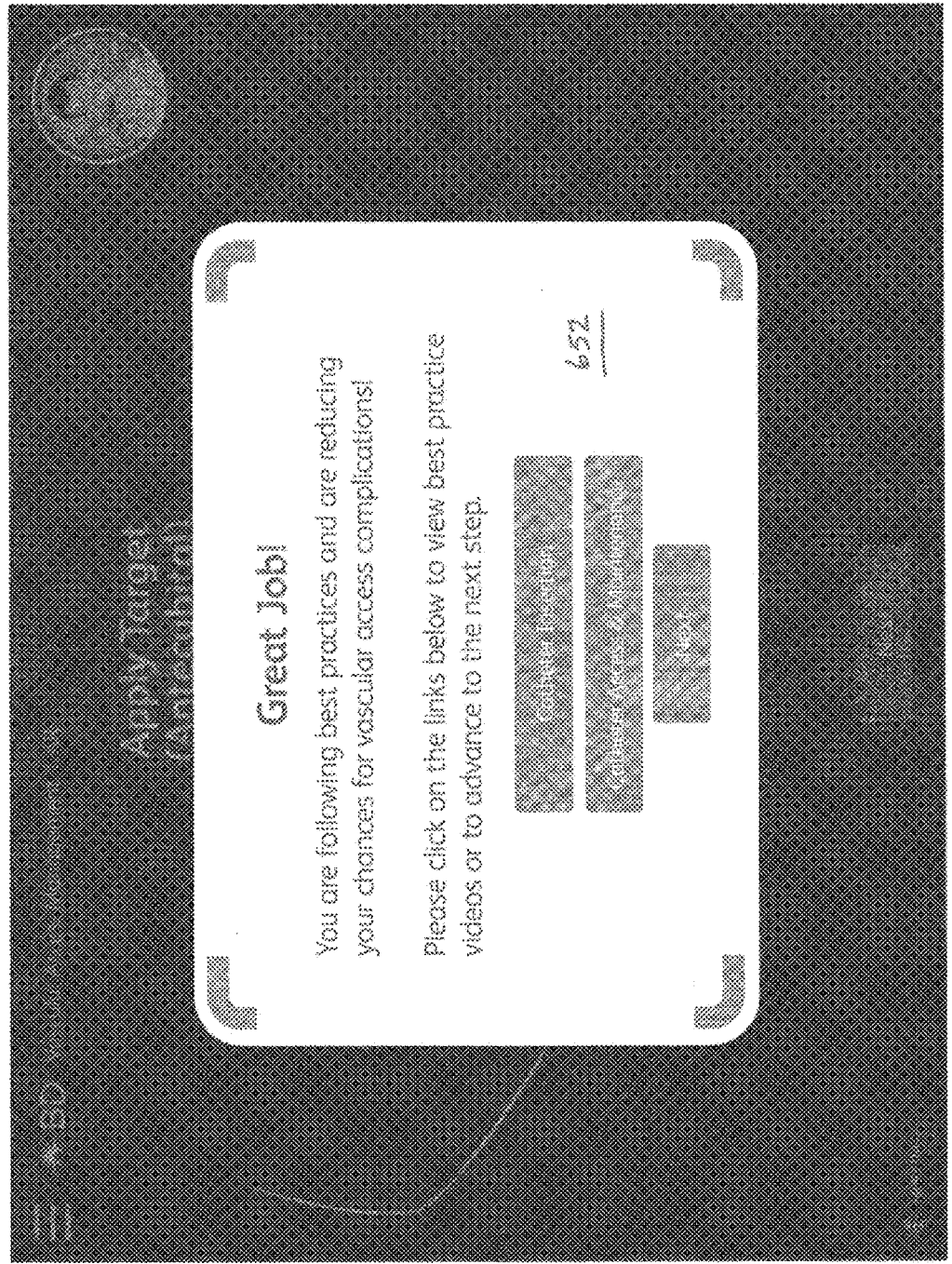
FIG. 67 is another example user interface, according to various embodiments.

In example embodiments, at step 522, machine 100 displays on display 70 (or another suitable display operatively coupled to machine 100) the results of the user's catheter build and listing of the selected line access process steps. If every user selection is most appropriate, i.e., the catheter was properly built and the listing of the line access process steps were in most appropriate sequential order, machine 100 displays on a screen 652 of display 70 a congratulatory response for positive reinforcement, such as "Great Job!" such as shown in FIG. 67. In certain embodiments, display 70 may include a link to view best practice videos, such as a "Catheter Insertion" best practice video or a "Catheter Access and Maintenance" best practice video, and/or advance to a next step.

Figure 68:
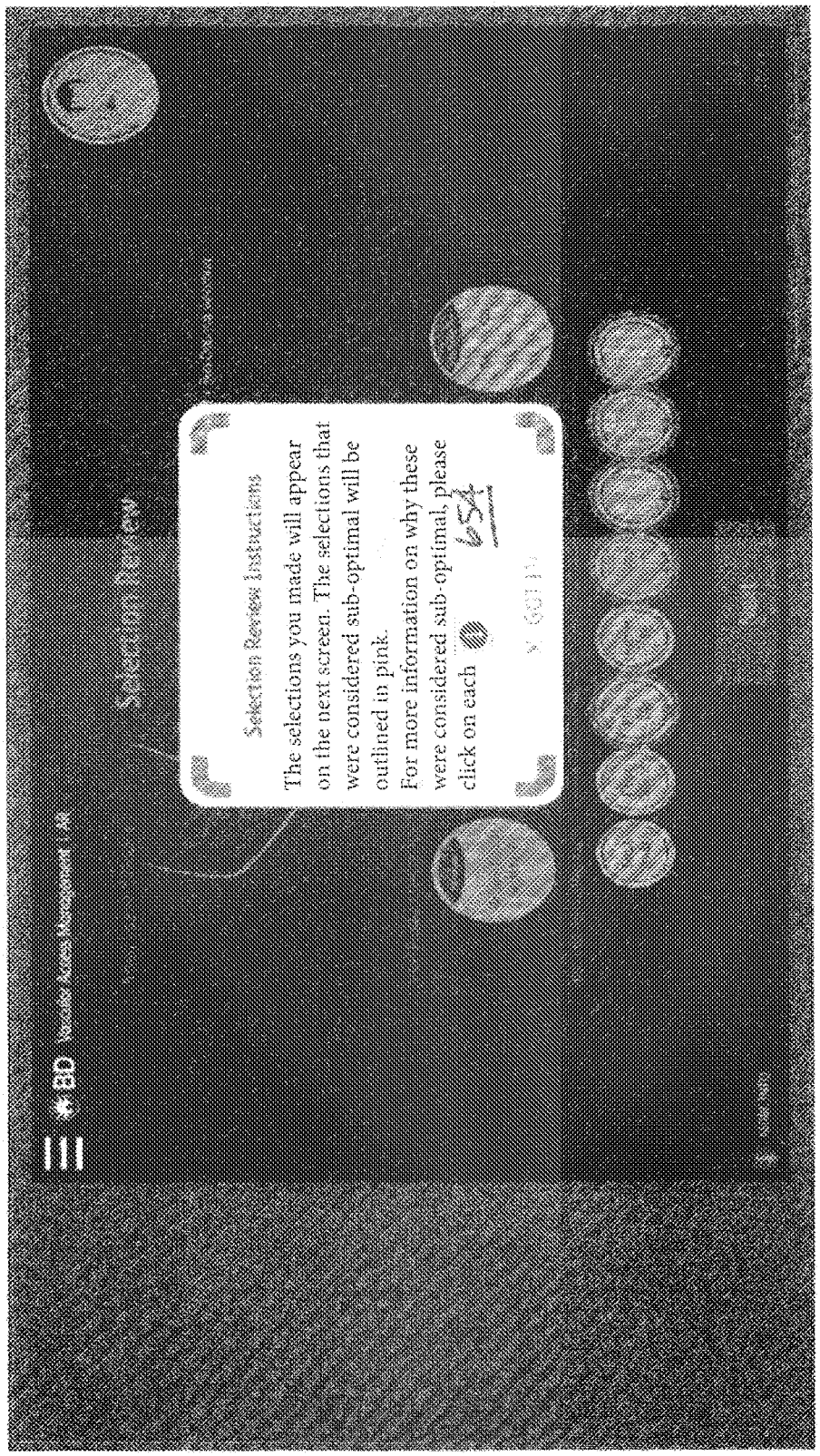
FIG. 68 is another example user interface, according to various embodiments.
Figure 69:
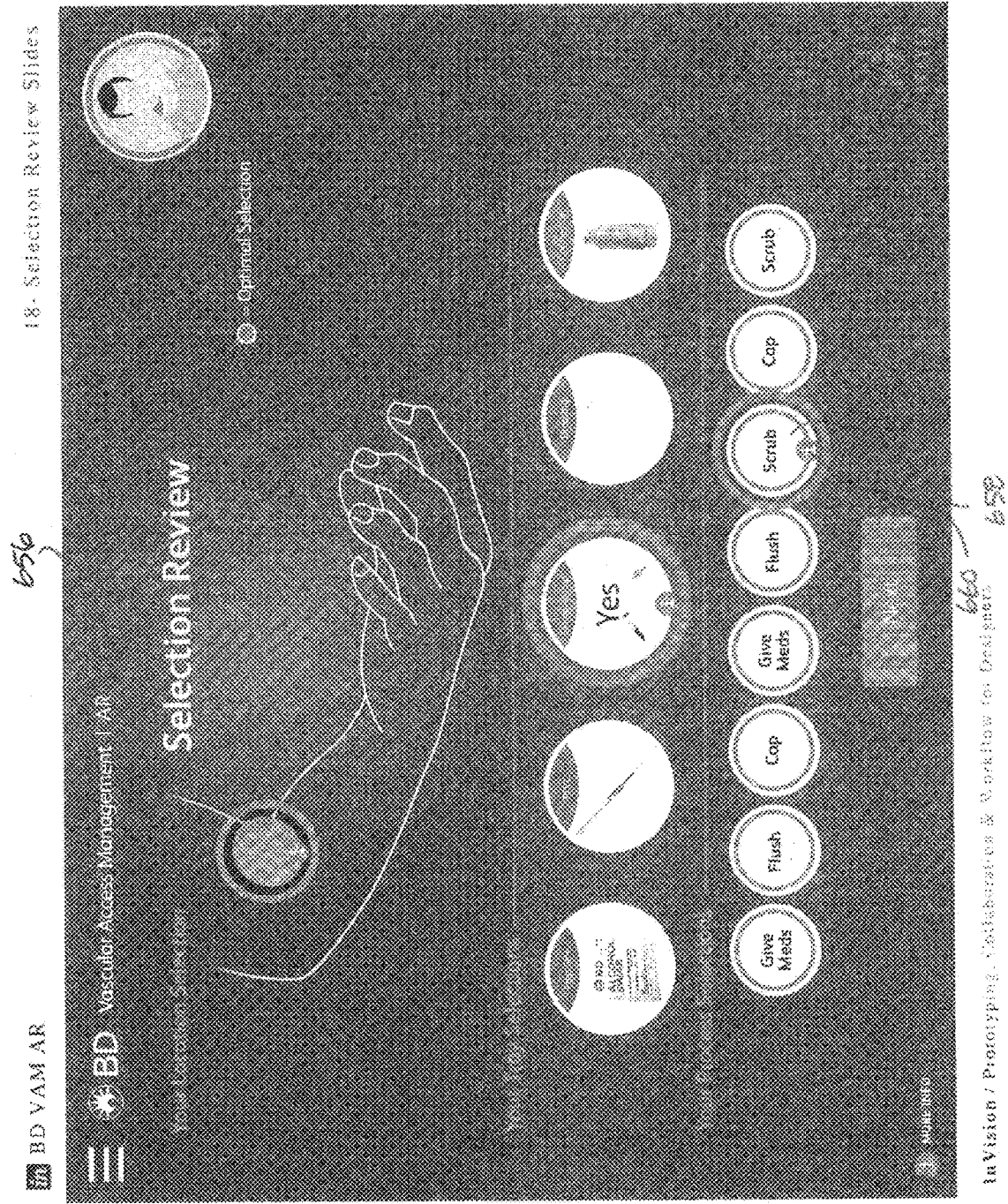
FIG. 69 is another example user interface, according to various embodiments.
Figure 70:
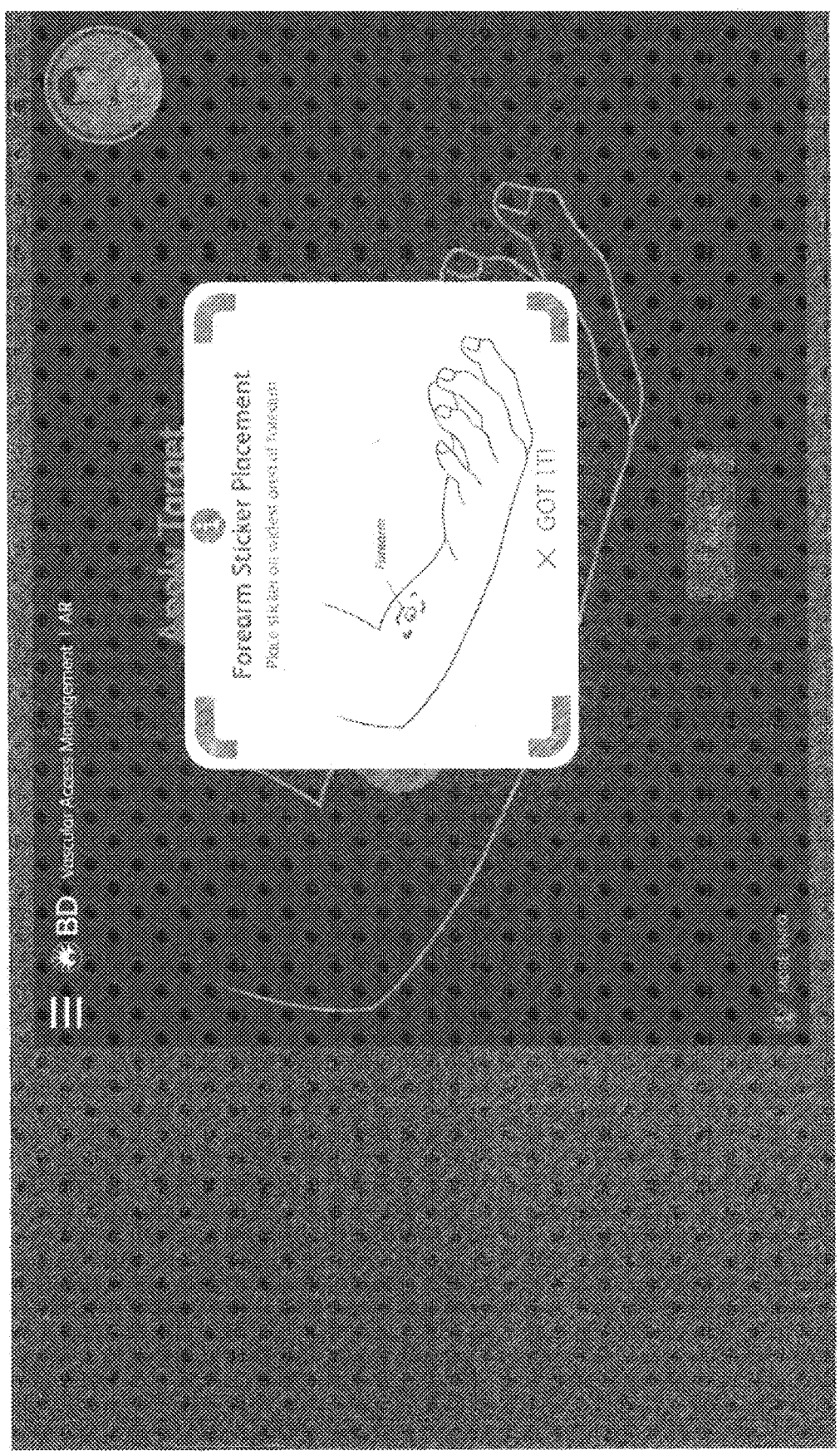
FIG. 70 is another example user interface, according to various embodiments.
Figure 71:
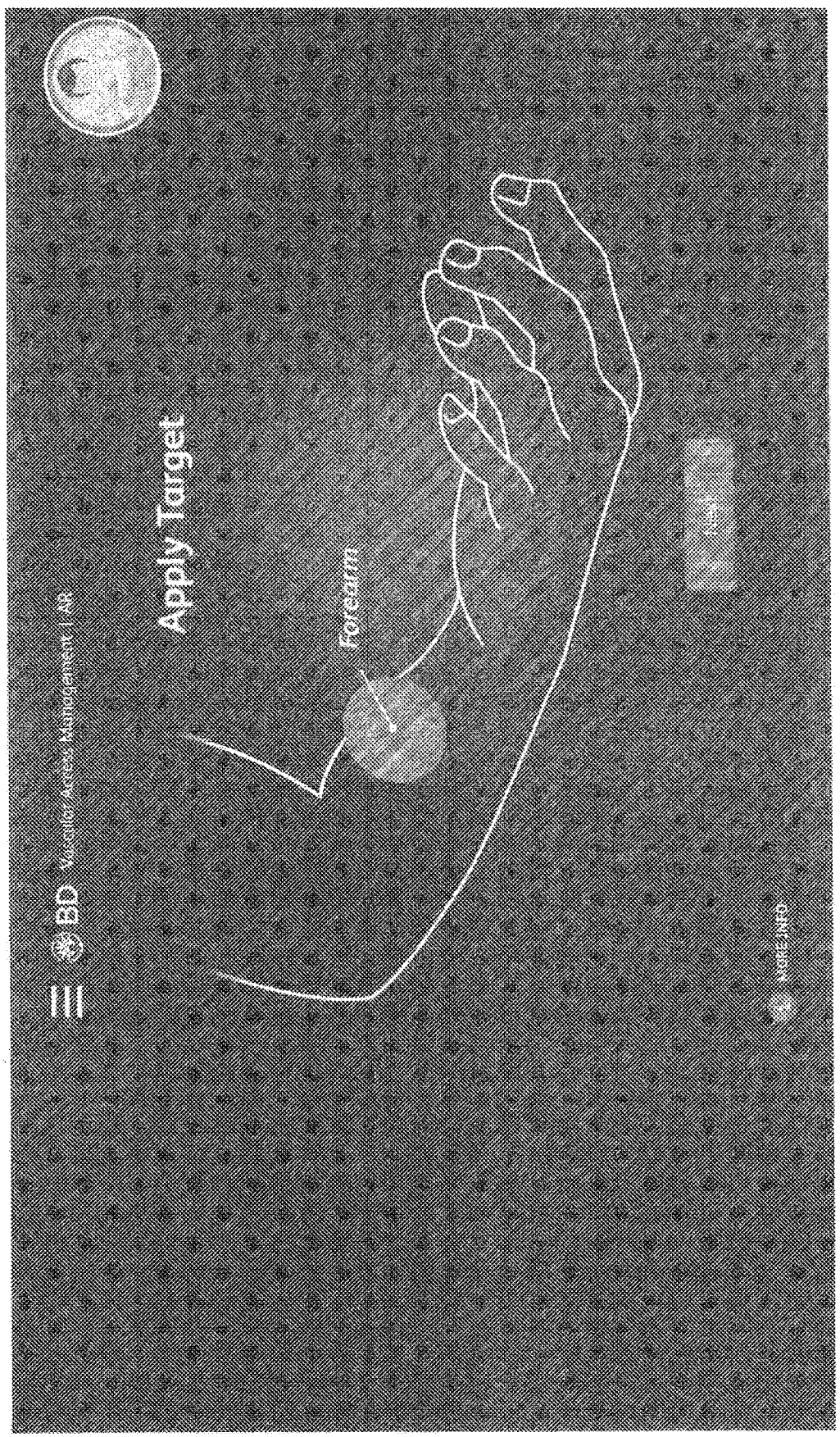
FIG. 71 is another example user interface, according to various embodiments.
Figure 72:
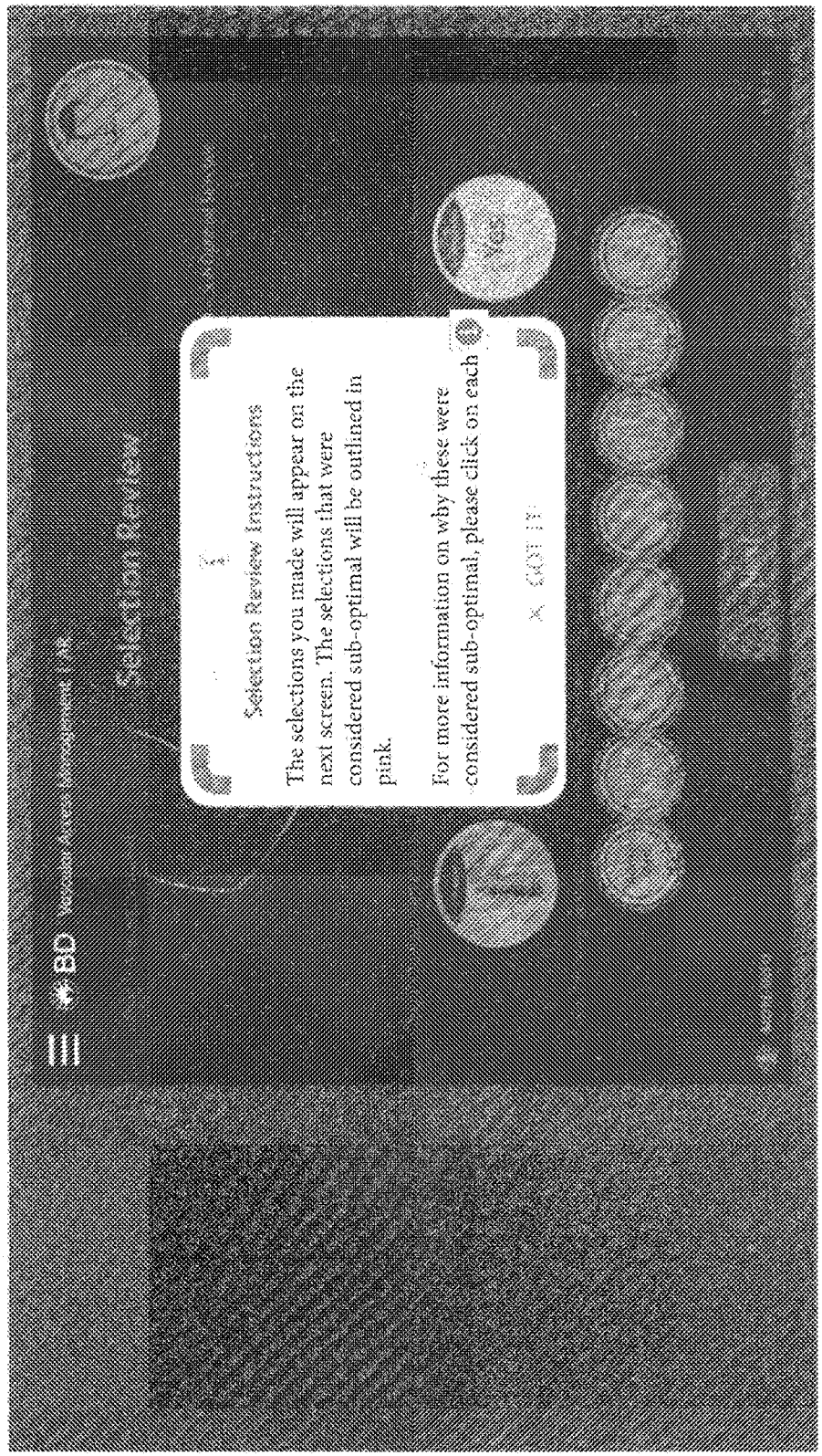
FIG. 72 is another example user interface, according to various embodiments.
Figure 73:
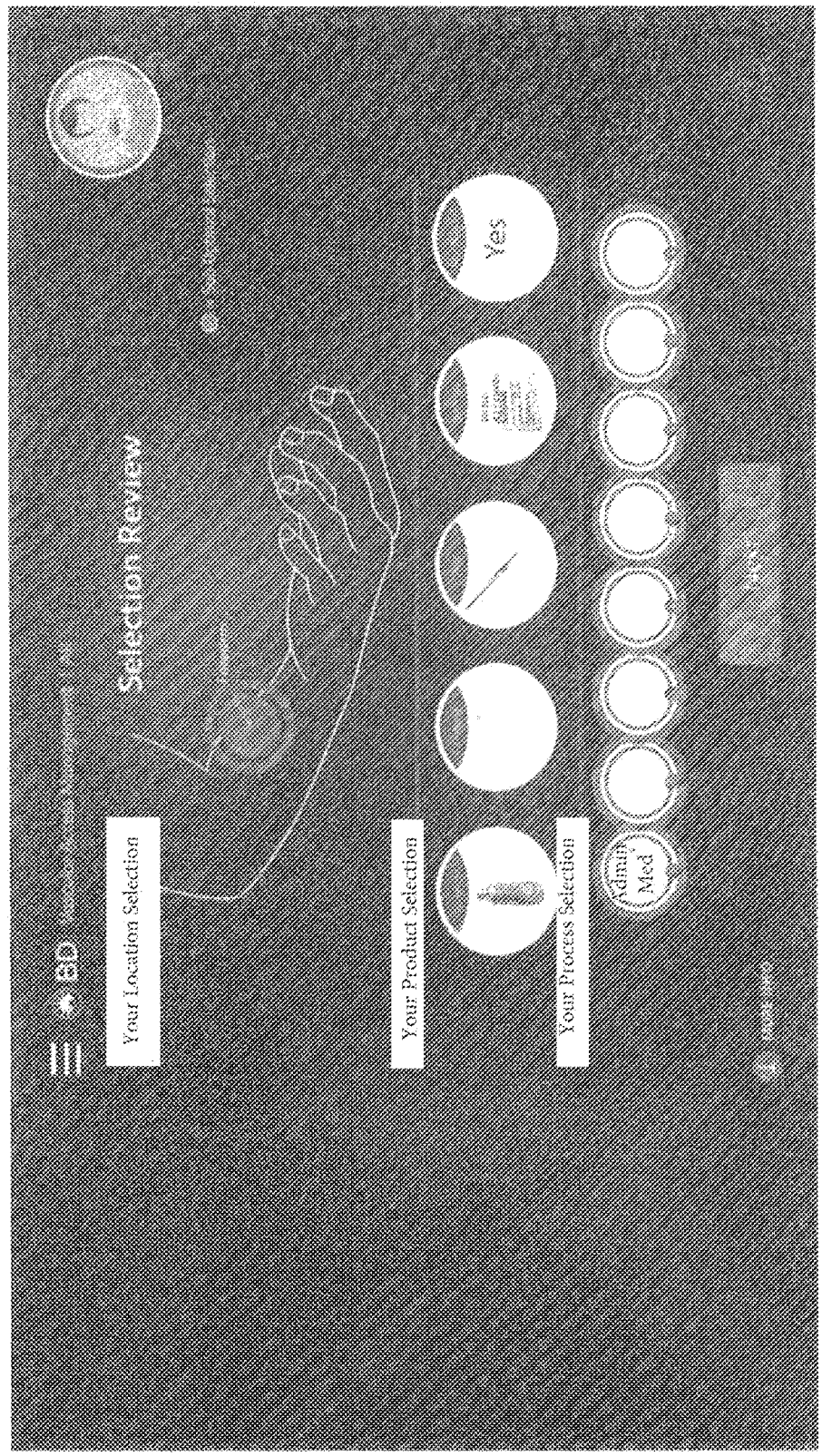
FIG. 73 is another example user interface, according to various embodiments.
Figure 74:
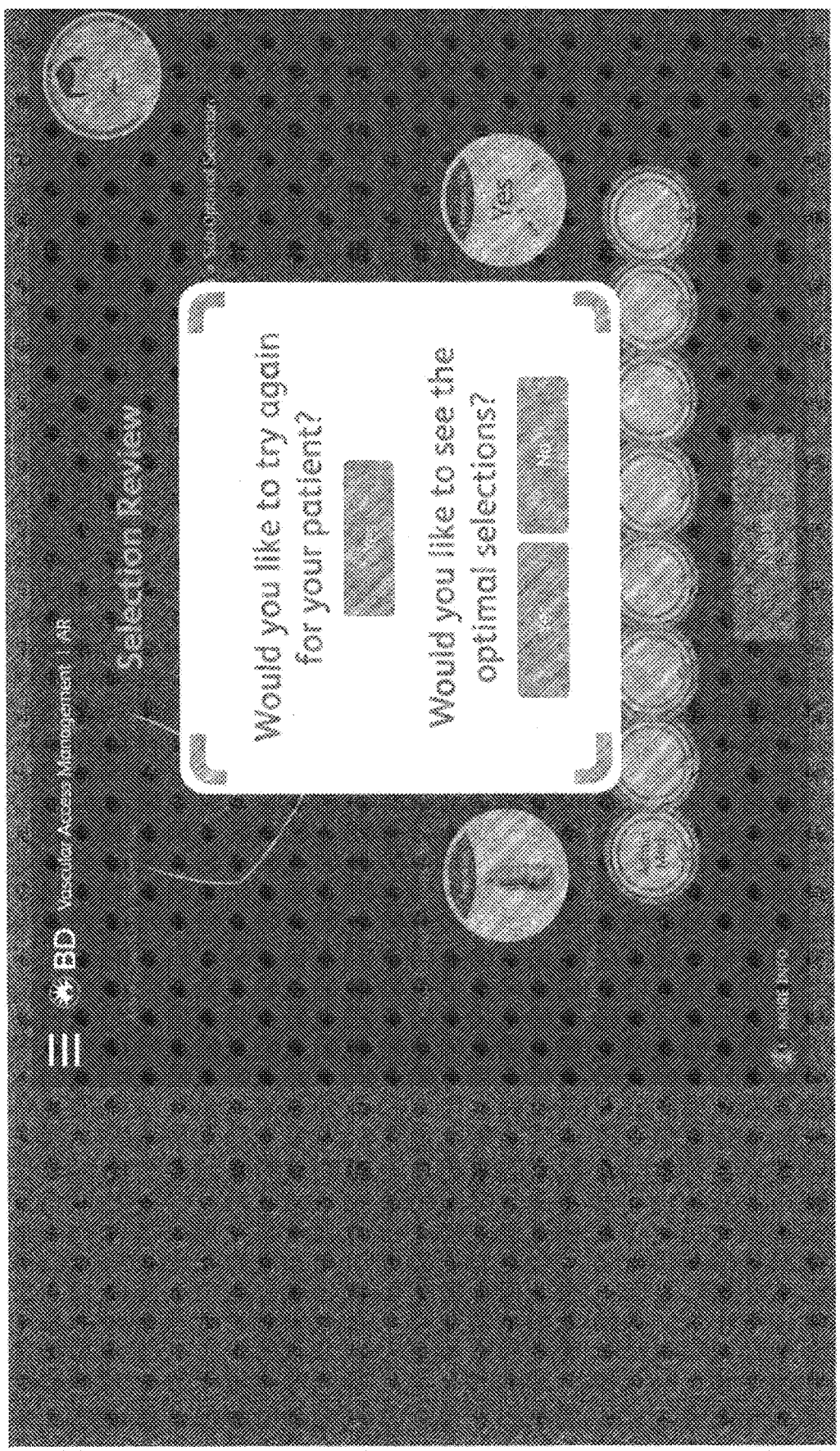
FIG. 74 is another example user interface, according to various embodiments.
Figure 75:
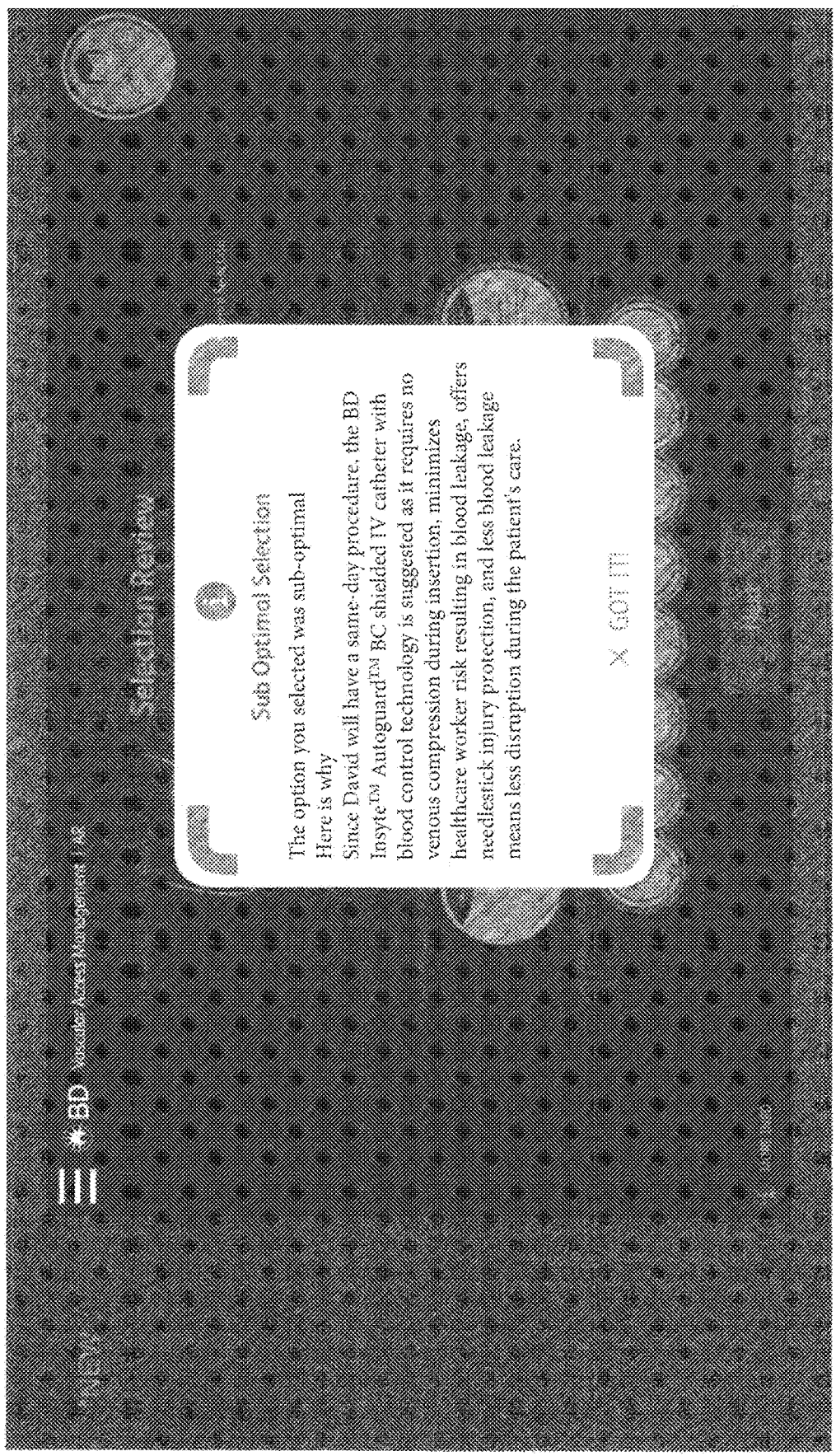
FIG. 75 is another example user interface, according to various embodiments.
Figure 76:
FIG. 76 is another example user interface, according to various embodiments.

If, however, one or more selections or process steps were not the most appropriate, machine 100 displays a selection review screen 654 of display 70, as shown in FIG. 68. Selection review screen 654 may indicate that the selections the user made will appear on the next screen and that one or more of the selections are considered sub-optimal selections. In certain embodiments, the sub-optimal selections will be highlighted or outlined, e.g., outlined in pink, on a selection review screen 656, as shown in FIG. 69. The selection review screens may include an information icon to provide access to more information on why these selections are considered sub-optimal selections.

Figure 77:
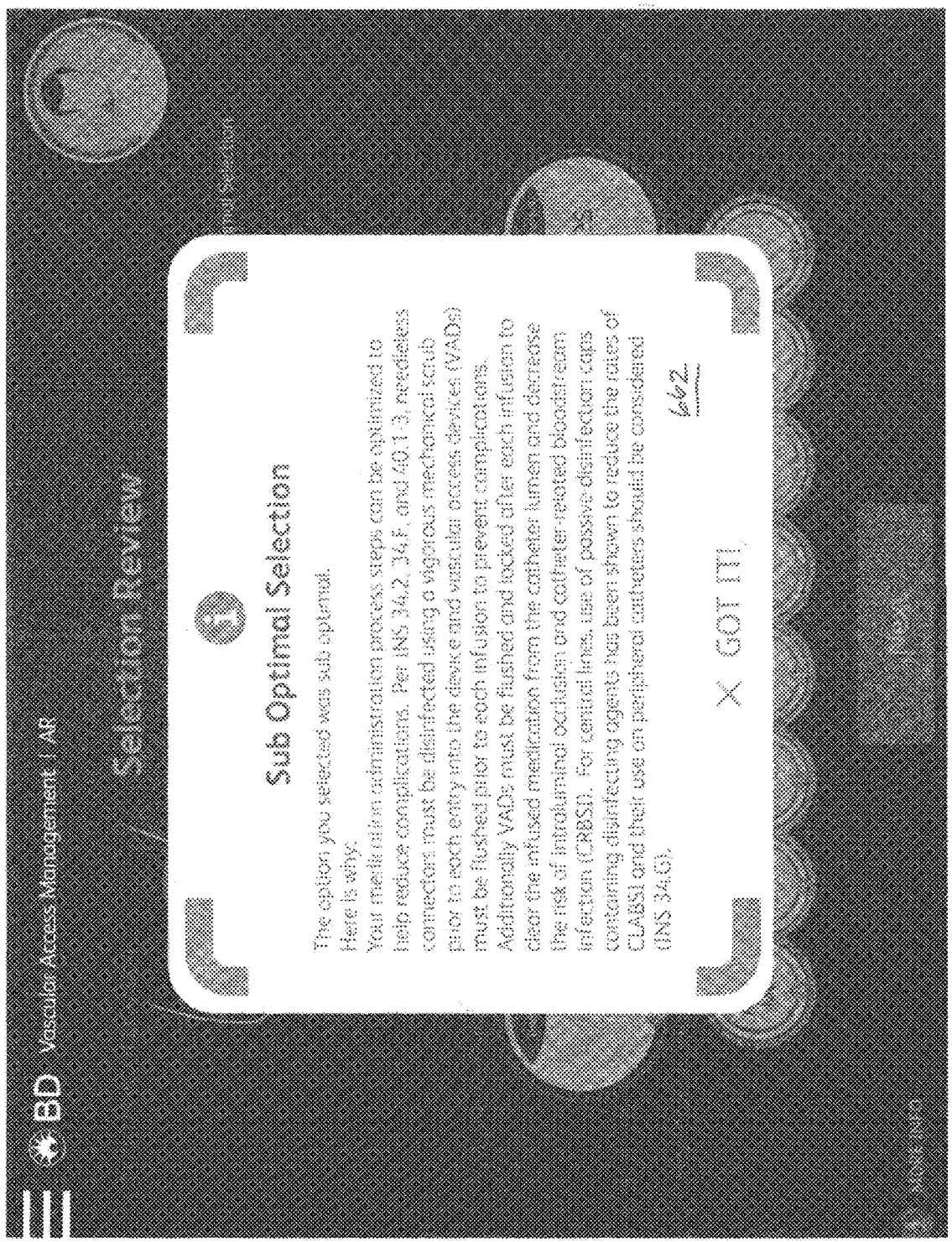
FIG. 77 is another example user interface, according to various embodiments.

Referring further to FIG. 69, the user's selections, for example, the location selection, the tray selections, and/or the process selections are displayed on selection review screen 656. In this embodiment, the sub-optimal selections are outlined in a suitable color, e.g., pink. Each sub-optimal selection also includes an information icon to provide a link to more information on why the particular selection is considered sub-optimal. For example, in FIG. 69, selection review screen 656 includes a "Scrub" line access process selection 658 that is considered a sub-optimal selection as indicated by the pink outlining. The "scrub" line access process selection 658 also includes an information icon 660. If the user clicks on information icon 660, a suboptimal selection screen 662, such as shown in FIG. 77, is displayed on display 70. In example embodiments, sub-optimal selection screen 662 includes one or more instructions and/or one or more recommendations for optimizing the line access process steps and the medication administration process steps.

Figure 78:
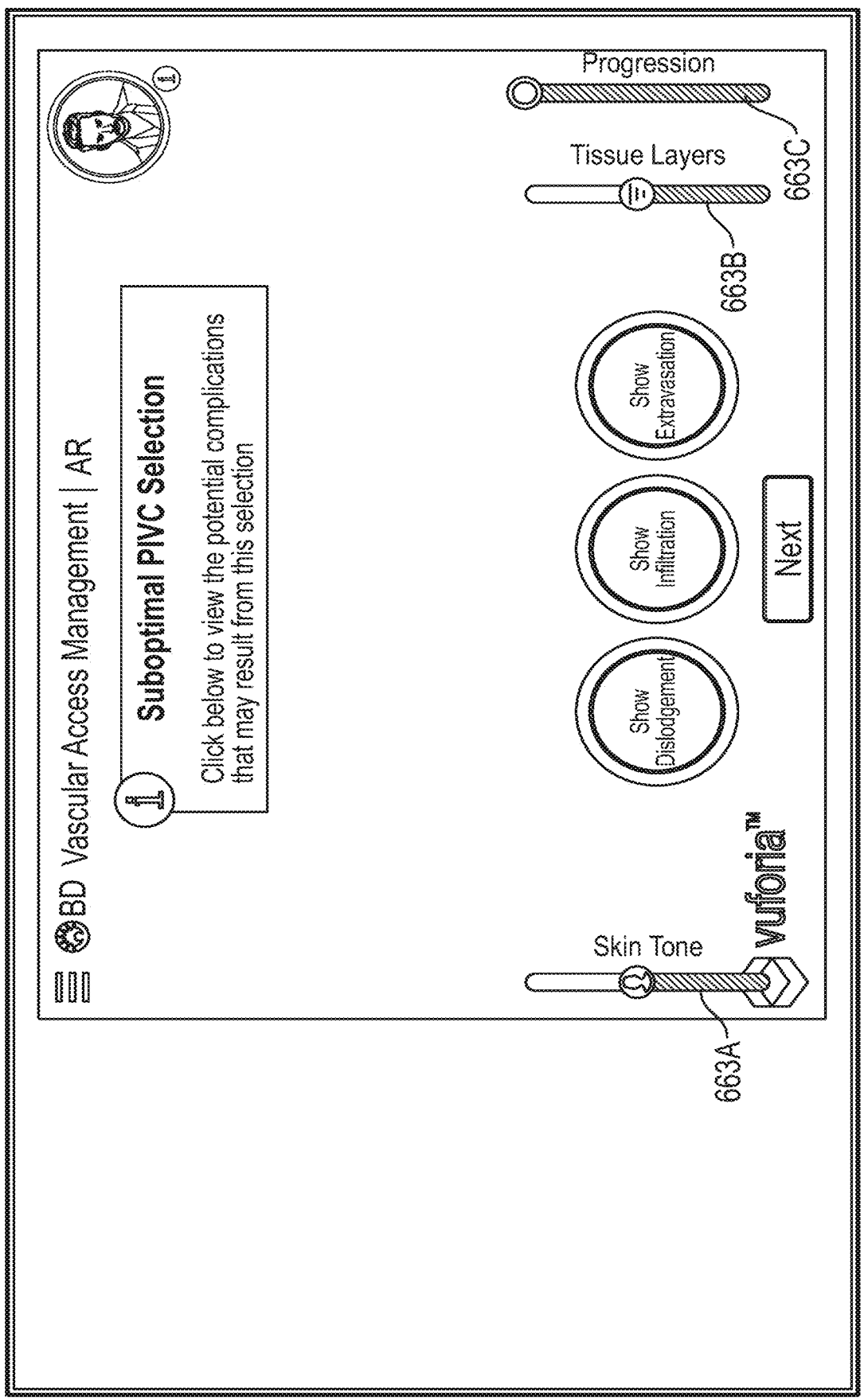
FIG. 78 is another example user interface, according to various embodiments.
Figure 79:
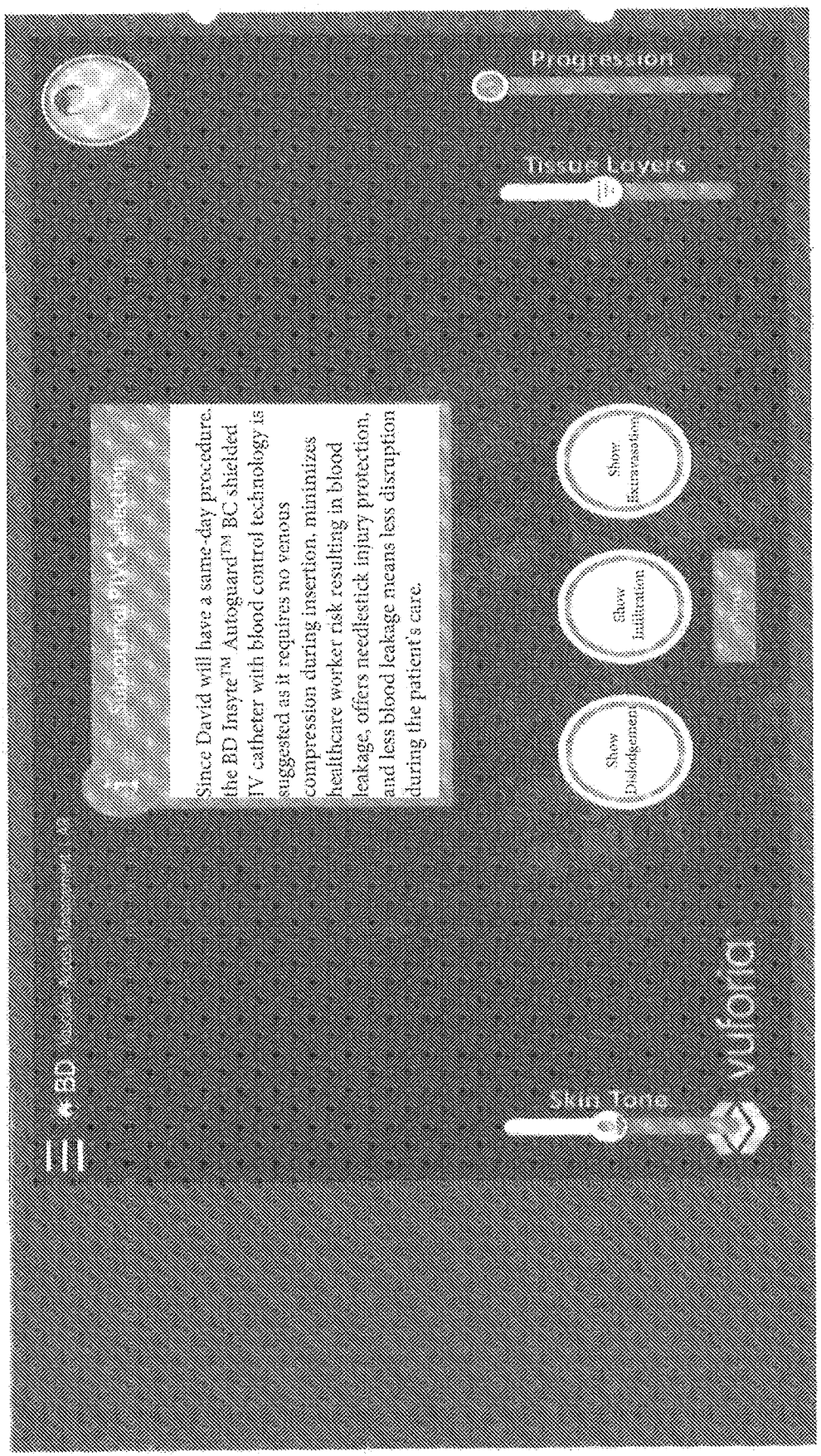
FIG. 79 is another example user interface, according to various embodiments.
Figure 80:
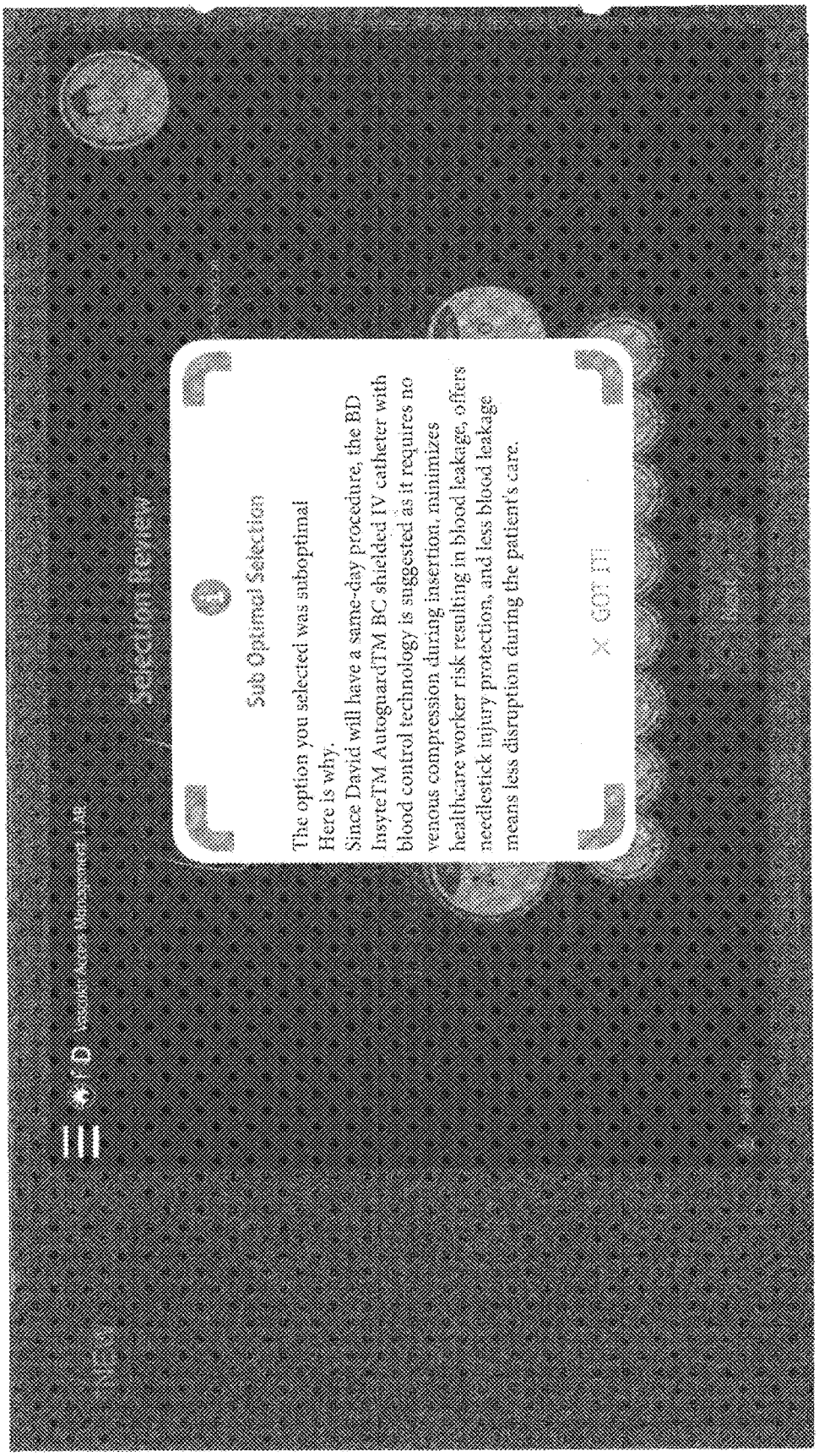
FIG. 80 is another example user interface, according to various embodiments.
Figure 81:
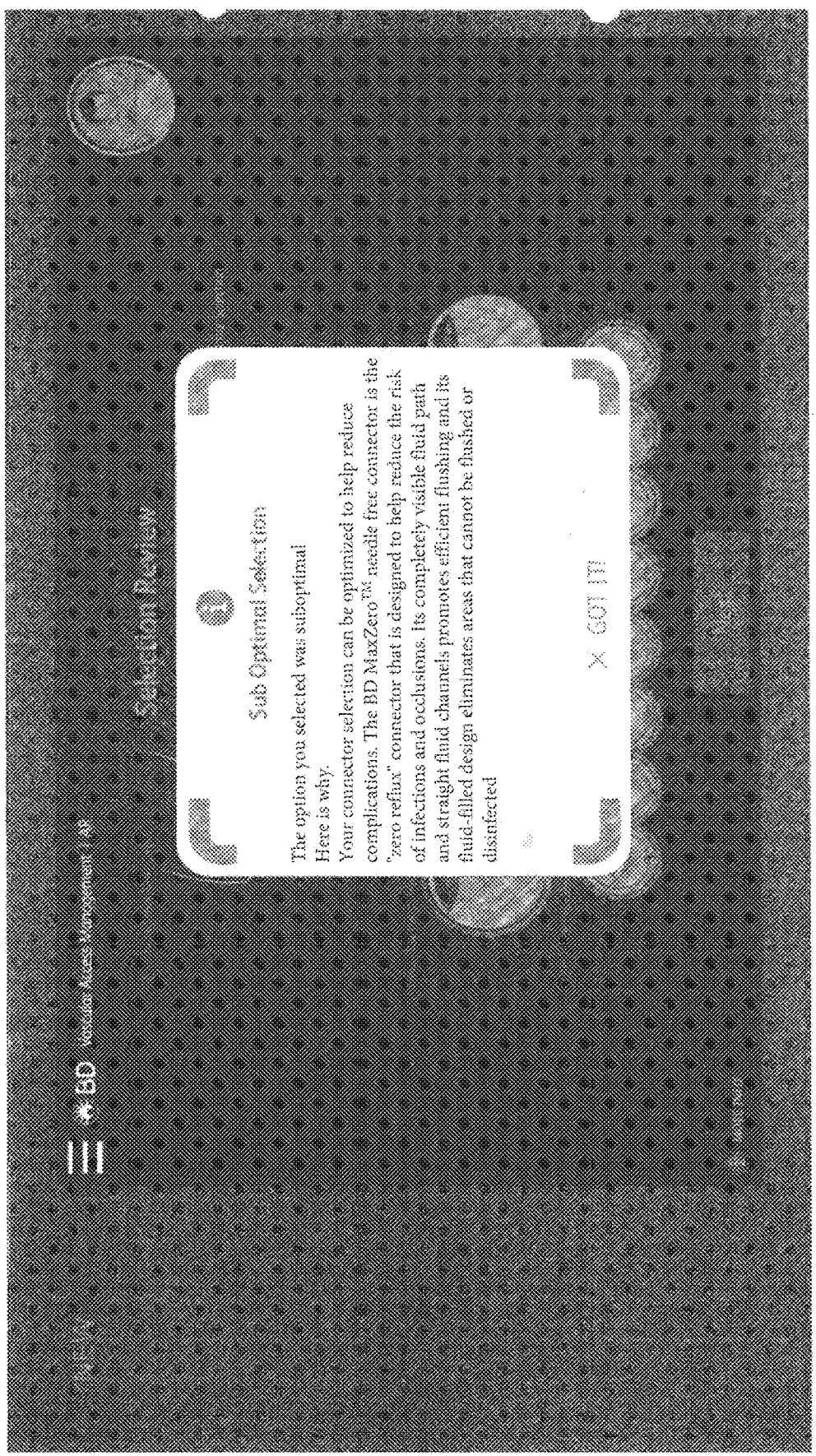
FIG. 81 is another example user interface, according to various embodiments.

Referring to FIGS. 78-83, in example embodiments, in additional screens, such as described herein, machine 100 displays 524 on a screen of display 70 complications, if any, associated with one or more improper selections. Referring to FIG. 78, if the user incorrectly selected the catheter based on the selected person profile, machine 100 instructs the user to place machine 100 over sticker 50 to learn of potential results of and/or complications associated with the user's product and/or practice selection for the corresponding person profile. For example, according to certain example embodiments, if the user selected an incorrect catheter under the circumstances, e.g., for gaining IV access for the person identified in first person profile 612, machine 100 displays on display 70 potential complications as a consequence of the incorrect catheter selection. For example, referring further to FIG. 78, selecting a sub-optimal catheter may lead to one or more complications, such as extravasation, infiltration, and/or dislodgment. In this instance, machine 100 displays on display 70 potential complications as a consequence of the incorrect catheter selection. In example embodiments, utilizing AR techniques, the machine includes a suitable actuator, such as one or more slider buttons 663A, 663B, and 663C shown in FIG. 78, configured to provide and manipulate the augmented reality aspects of the disclosed embodiments. For example, in certain embodiments, the machine is configured to provide data items such as varying skin tones, e.g., indicating irritation, inflammation, and/or infection, a varying depth of the person's vasculature, and/or a time-lapse image of the complications, e.g., extravasation, infiltration, and/or dislodgment, arising and progressing as the slider buttons are manipulated by the user.

If the user chooses to learn more about extravasation, in certain example embodiments, the processing device of machine 100 renders a graphical image of the person's arm indicating extravasation and display 70 displays the graphical image on a user interface. In these embodiments, the user interface may include informational text indicating that the user has selected extravasation and defining "extravasation" as an inadvertent leakage of a vesicant or caustic solution into the surrounding tissue and/or an additional graphical image illustrating the effects of extravasation. The informational text may also indicate, for example, that as with other complications, placement and physical attributes of the catheter play a role in the rate of extravasation. The informational text may also indicate that unlike infiltration, vesicant extravasation causes progressive tissue damage due to the pharmacological properties of the solution being infused and/or that early identification and intervention is critical for the prevention of serious adverse outcomes.

If the user chooses to learn more about infiltration, in certain example embodiments, the processing device of machine 100 renders a graphical image of the person's arm indicating infiltration and display 70 displays the graphical image on a user interface. In these embodiments, the user interface may include informational text indicating that the user has selected infiltration and defining "infiltration" as an inadvertent leakage of a non-vesicant solution into the surrounding tissue resulting from erosion or penetration of the catheter into or through the venous wall and/or an additional graphical image illustrating the effects of infiltration. The informational text may also indicate, for example, that infiltration is the most common catheter complication. The informational text may also indicate that peripheral IVs placed in areas of flexion (e.g., the antecubital insertion site or the wrist insertion site) are prone to have higher rates of infiltration, most likely due to the movement of the cannula tip against the vessel wall causing trauma which leads to poor venous wall integrity.

If the user chooses to learn more about dislodgement, in certain example embodiments, the processing device of machine 100 renders a graphical image of the person's arm indicating dislodgement and display 70 displays the graphical image on a user interface. In these embodiments, the user interface may include informational text indicating that the user has selected dislodgement and defining "dislodgement" as an unintentional removal of a catheter that can occur for a variety of reasons, such as catching the catheter on clothing or a catheter that was poorly secured and/or an additional graphical image illustrating the effects of dislodgement. The informational text may also indicate, for example, that choosing dedicated securement devices have shown significant benefit in improving catheter longevity with a direct effect on reducing catheter dislodgement.

Figure 82:
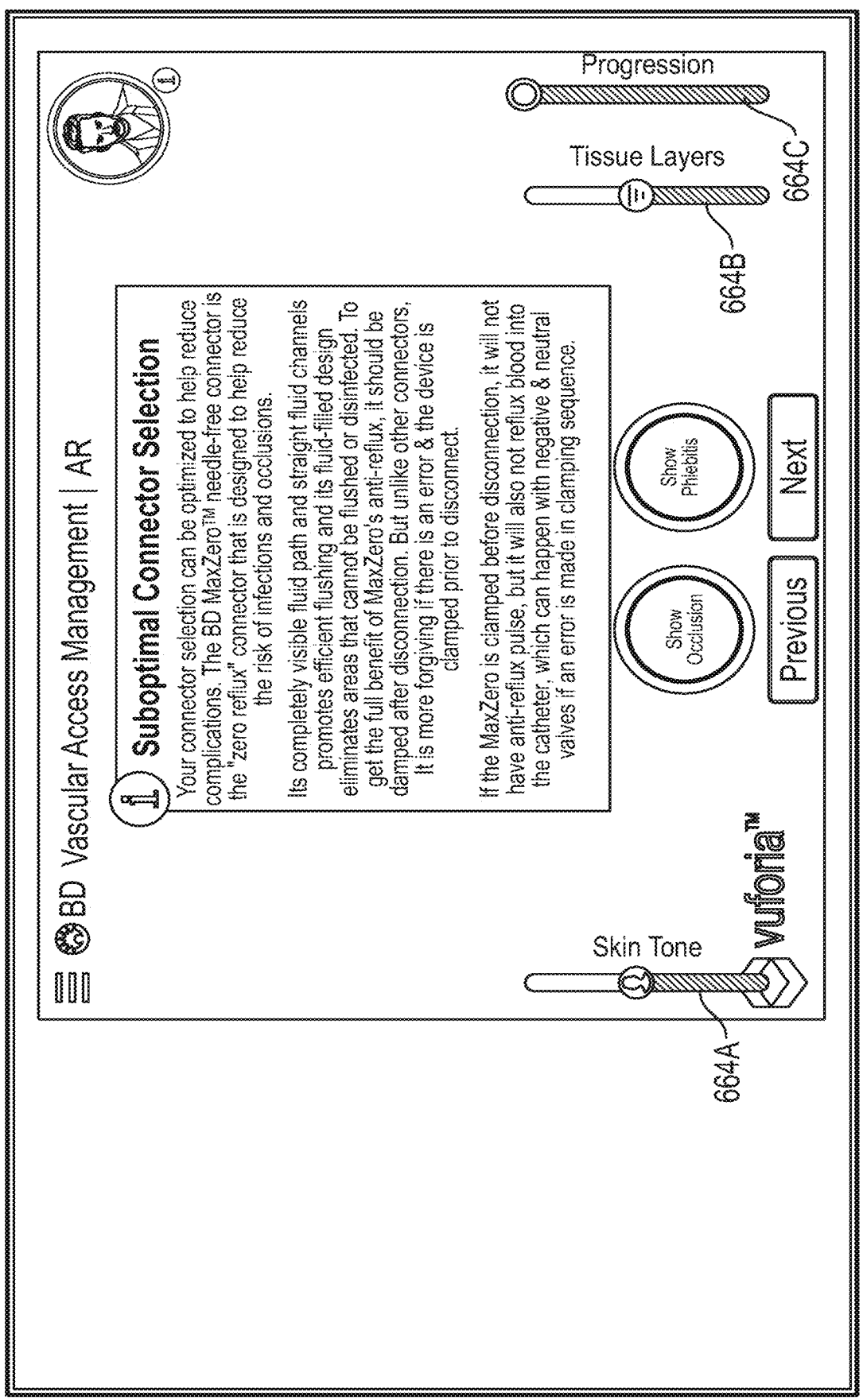
FIG. 82 is another example user interface, according to various embodiments.

Similarly, referring further to FIG. 82, if the user incorrectly selected the connector based on the selected person profile, machine 100 instructs the user to place machine 100 over sticker 50 to learn of potential results of and/or complications associated with the user's product and/or practice selection for the corresponding person profile. For example, according to certain embodiments, if the user selected an incorrect connector, machine 100 displays potential complications as a consequence of the incorrect connector selection, including, for example, phlebitis and/or occlusion. In example embodiments, the machine includes a suitable actuator, such as one or more slider buttons 664A, 664B, and 664C shown in FIG. 82, configured to provide and manipulate the augmented reality aspects of the disclosed embodiments.

Additionally, if the user incorrectly selected the dressing based on the selected person profile, machine 100 instructs the user to place machine 100 over sticker 50 to learn of potential results of and/or complications associated with the user's product and/or practice selection for the corresponding person profile. For example, according to certain embodiments, if the user selected an incorrect dressing, machine 100 displays potential complications as a consequence of the incorrect dressing selection, including, for example, phlebitis and/or dislodgement. If the user incorrectly selected whether to use an extension set based on the selected person profile, machine 100 instructs the user to place machine 100 over sticker 50 to learn of potential results and/or complications associated with the user's product and/or practice selection for the corresponding person profile. For example, according to certain embodiments, if the user selected to incorrectly use or not use an extension set, machine 100 displays potential complications as a consequence of the incorrect selection, including, for example, a potential result of infiltration, phlebitis and/or dislodgement.

Figure 83:
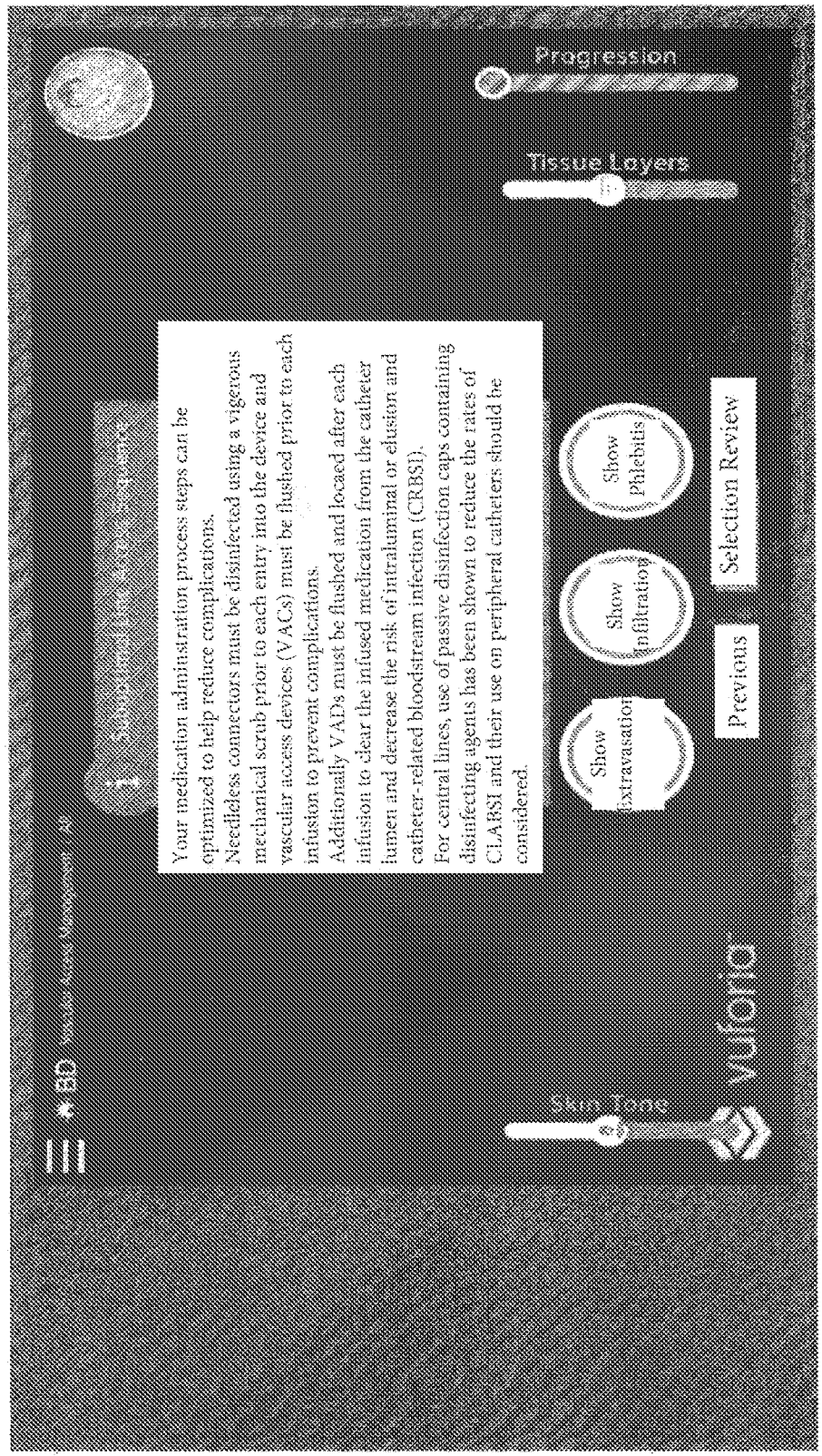
FIG. 83 is another example user interface, according to various embodiments.
Figure 84:
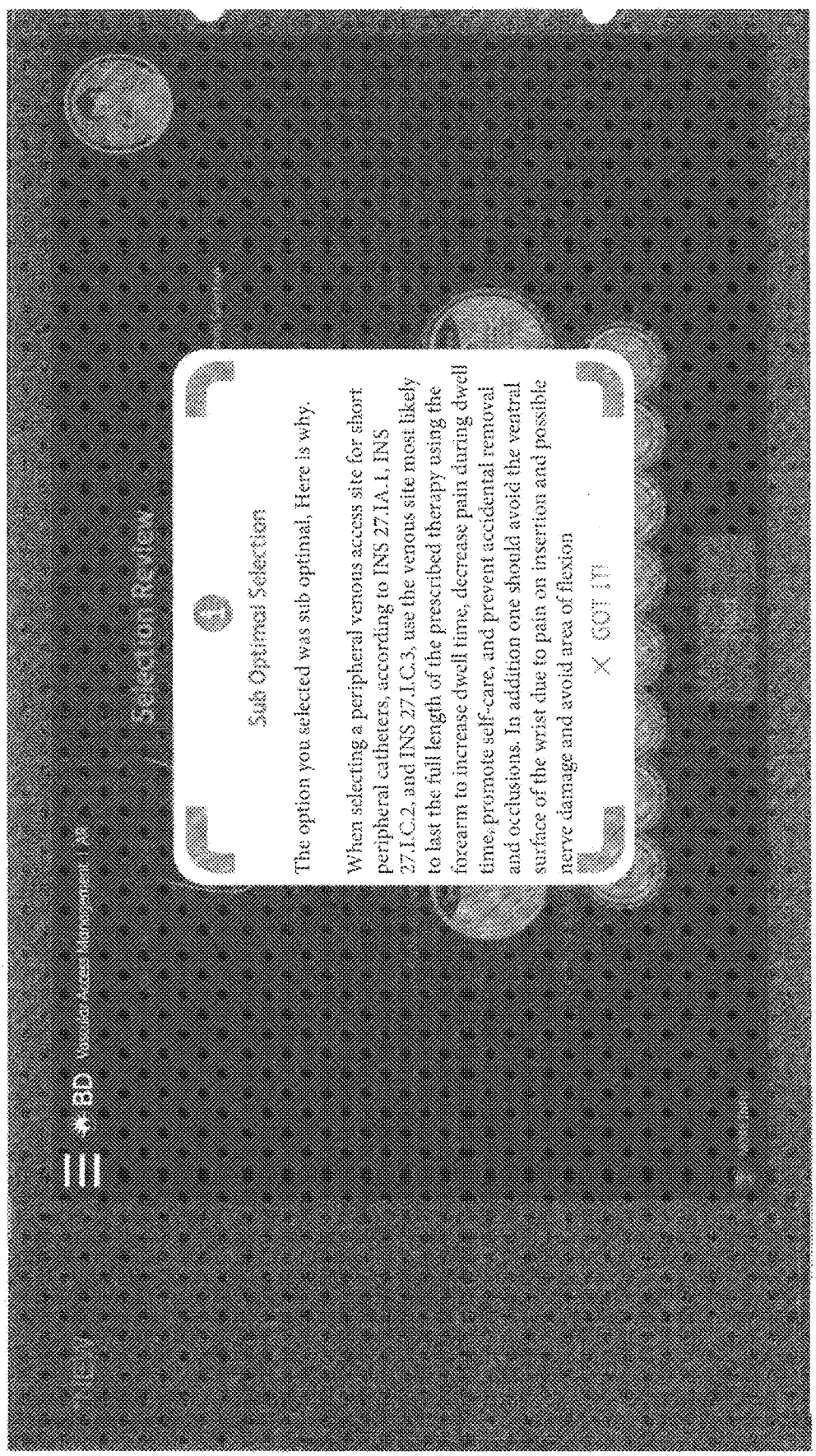
FIG. 84 is another example user interface, according to various embodiments.

Referring further to FIG. 83, if the user incorrectly selected one or more of the line access process steps, machine 100 instructs the user to place machine 100 over sticker 50 to learn of potential results and/or complications associated with the user's product and/or practice selection. For example, according to certain embodiments, if the user incorrectly selected one or more of the line access process steps, machine 100 displays potential complications as a consequence of the incorrect selection, including, for example, a potential result of extravasation, infiltration, dislodgement, phlebitis, occlusion, and/or other potential complications that may occur.

In example embodiments, if the user selects a non-preferred or suboptimal catheter placement or insertion site, the processing device of machine 100, such as processor 702, renders a first graphical image of the selected arm and display 70 displays the first graphical image on a user interface. The user interface may include informational text indicating to the user that the user has chosen a non-preferred insertion site. The informational text may also include an indication that catheters placed in areas of flexion, such as the antecubital insertion site or the wrist insertion site, are prone to higher rates of failure due to flexion of the joint leading to mechanical complications. The informational text may also indicate a best practice to avoid areas of flexion and areas of pain on palpation. The informational text may also indicate that the hand insertion site has been linked to significantly higher rates of accidental removal and occlusion.

Display 70 may also display one or more complications associated with the selected non-preferred insertion site. For example, a user interface may indicate reasons for failure and/or complications associated with inserting the IV catheter in the non-preferred arm, such as phlebitis, infection, extravasation, dislodgment, occlusion, and/or infiltration. To provide additional educational guidance, machine 100 may prompt the user to select one of the indicated complications for further information regarding the selected complication. In example embodiments, the processing device of machine 100 renders a graphical image of the person's arm indicating the chosen complication and display 70 displays the graphical image on a user interface. The user interface may include informational text indicating which complication was selected, a definition of the complication, and/or an indication of risks associated with the selected complication.

For example, if the user chooses to learn more about phlebitis, in certain example embodiments the processing device of machine 100 renders a graphical image of the person's arm indicating phlebitis and display 70 displays the graphical image on a user interface. The user interface may include informational text indicating that the user has selected phlebitis and defining "phlebitis" as an inflammation of a vein that can occur along the cannulated vein due to mechanical, chemical, and/or bacterial irritation and/or an additional graphical image illustrating the effects of phlebitis. The informational text may also indicate risks associated with phlebitis, such as an increase at a point of flexion due to irritation of the vessel wall by movement of the cannula.

Figure 85:
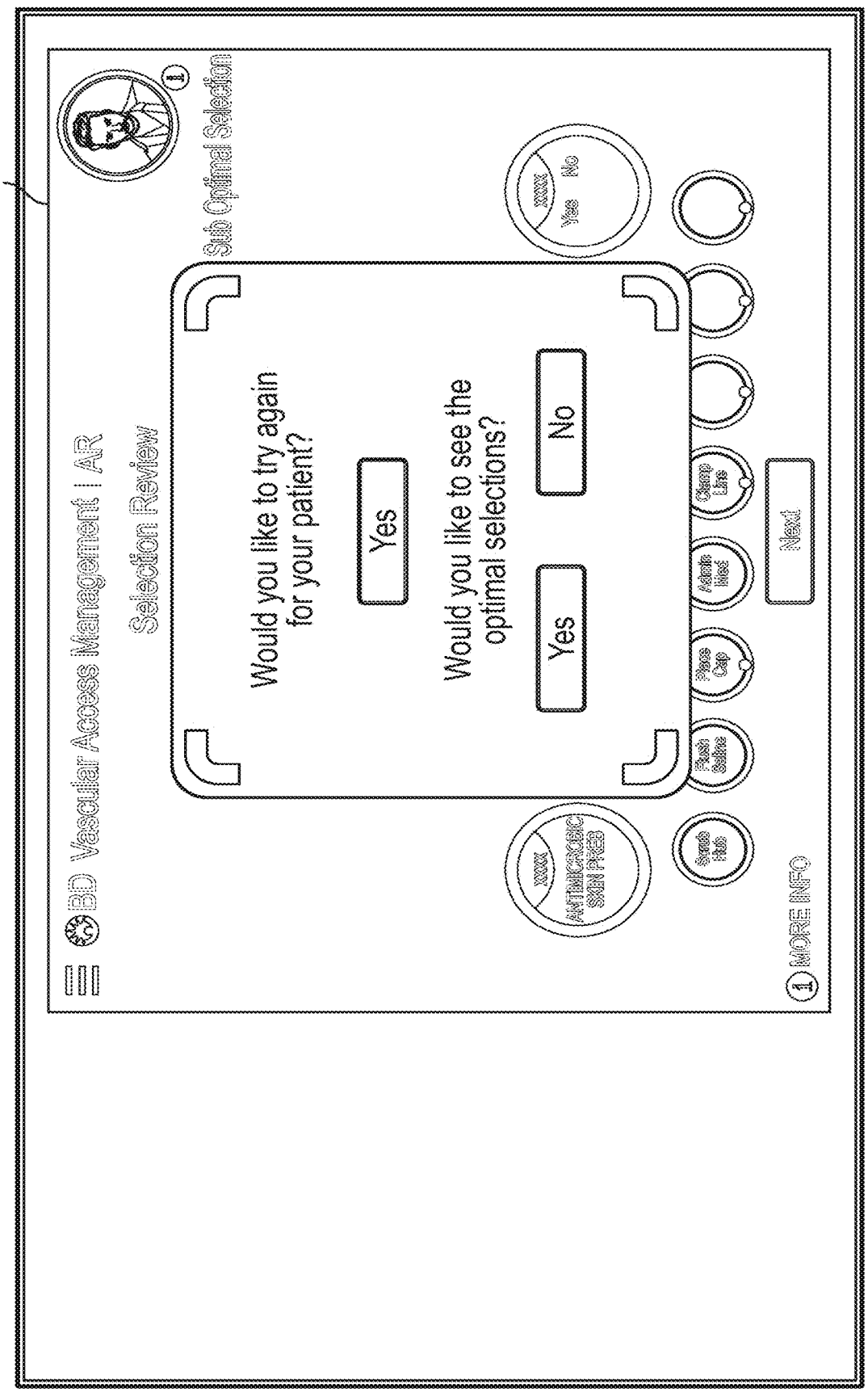
FIG. 85 is another example user interface, according to various embodiments.

Once machine 100 displays to the user the incorrect selections and the complications and/or potential risks resulting from the incorrect selection or selections, machine 100 displays on a screen 665, as shown in FIG. 85, querying the user whether the user would like to try again for your patient and/or whether the user would like to see the optimal selections. The user may decide to continue with the CBL program or application to learn how to achieve a better result for the person. If the user is not interested in learning more, the CBL program or application is closed. In one embodiment, machine 100 provides the user with a link to a suitable site, for example, a microsite that provides the results of the application evaluation and/or directs the user to a proper site or a microsite providing a survey for the user to complete.

Figure 86:
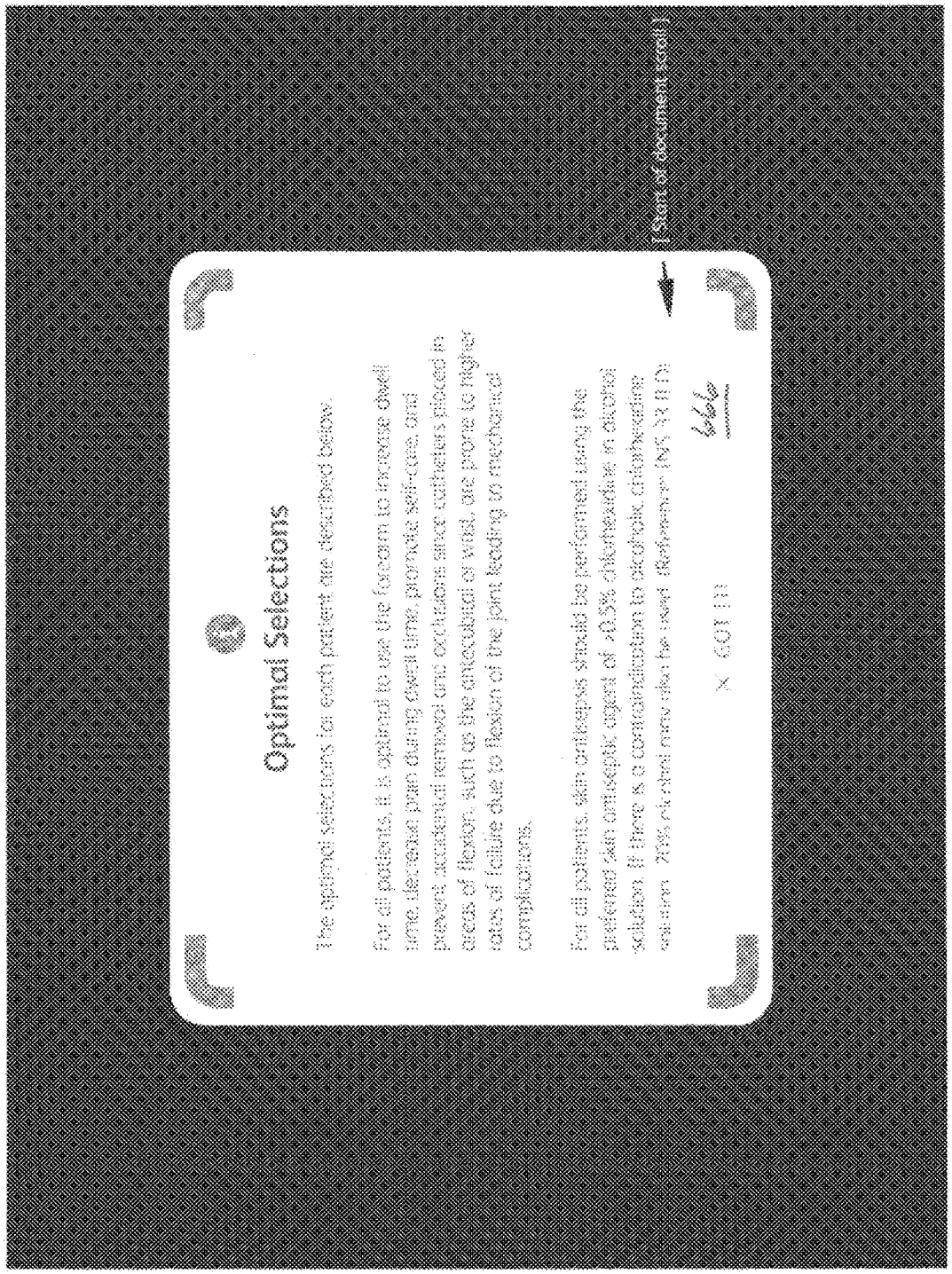
FIG. 86 is another example user interface, according to various embodiments.
Figure 87:
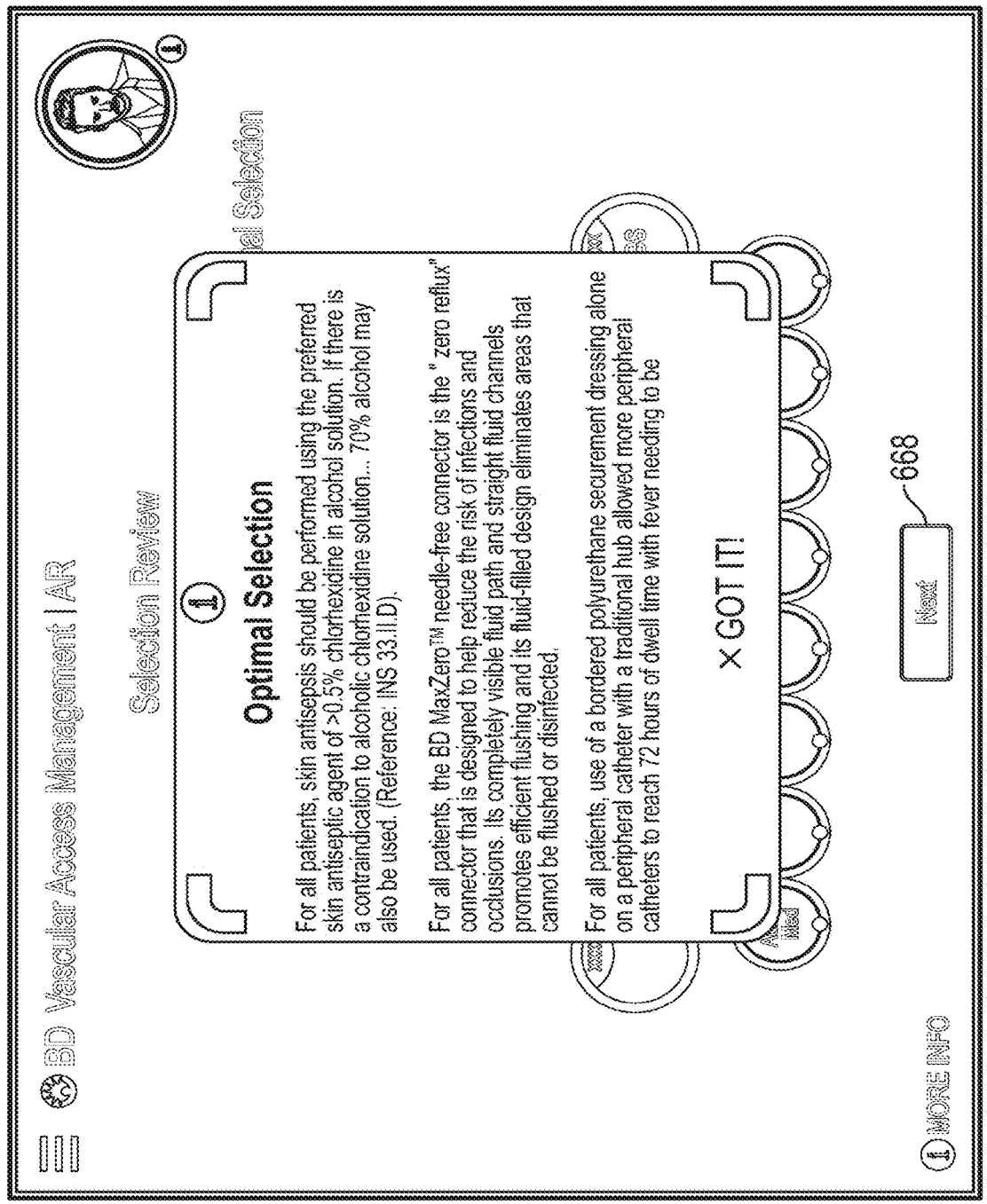
FIG. 87 is another example user interface, according to various embodiments.
Figure 88:
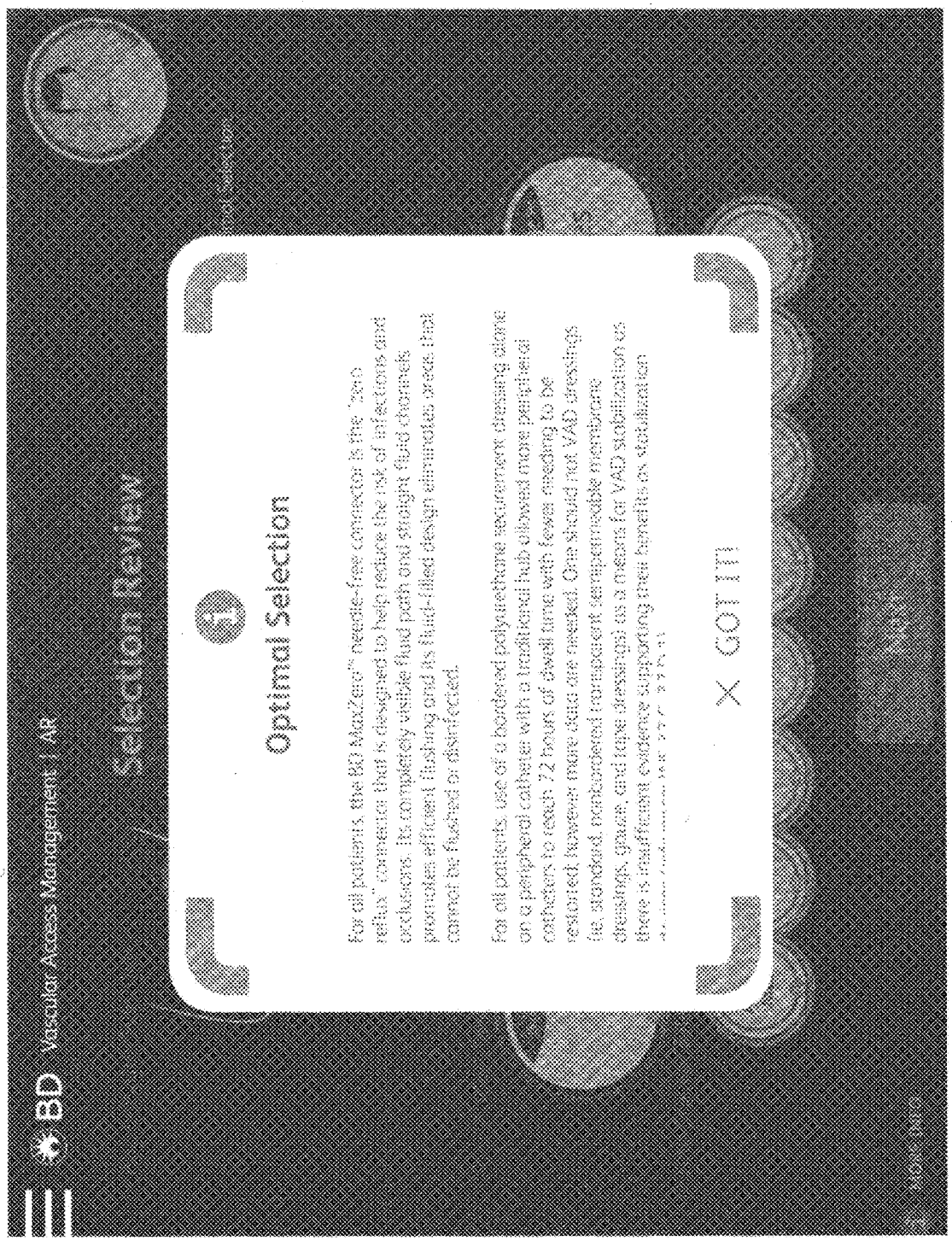
FIG. 88 is another example user interface, according to various embodiments.
Figure 89:
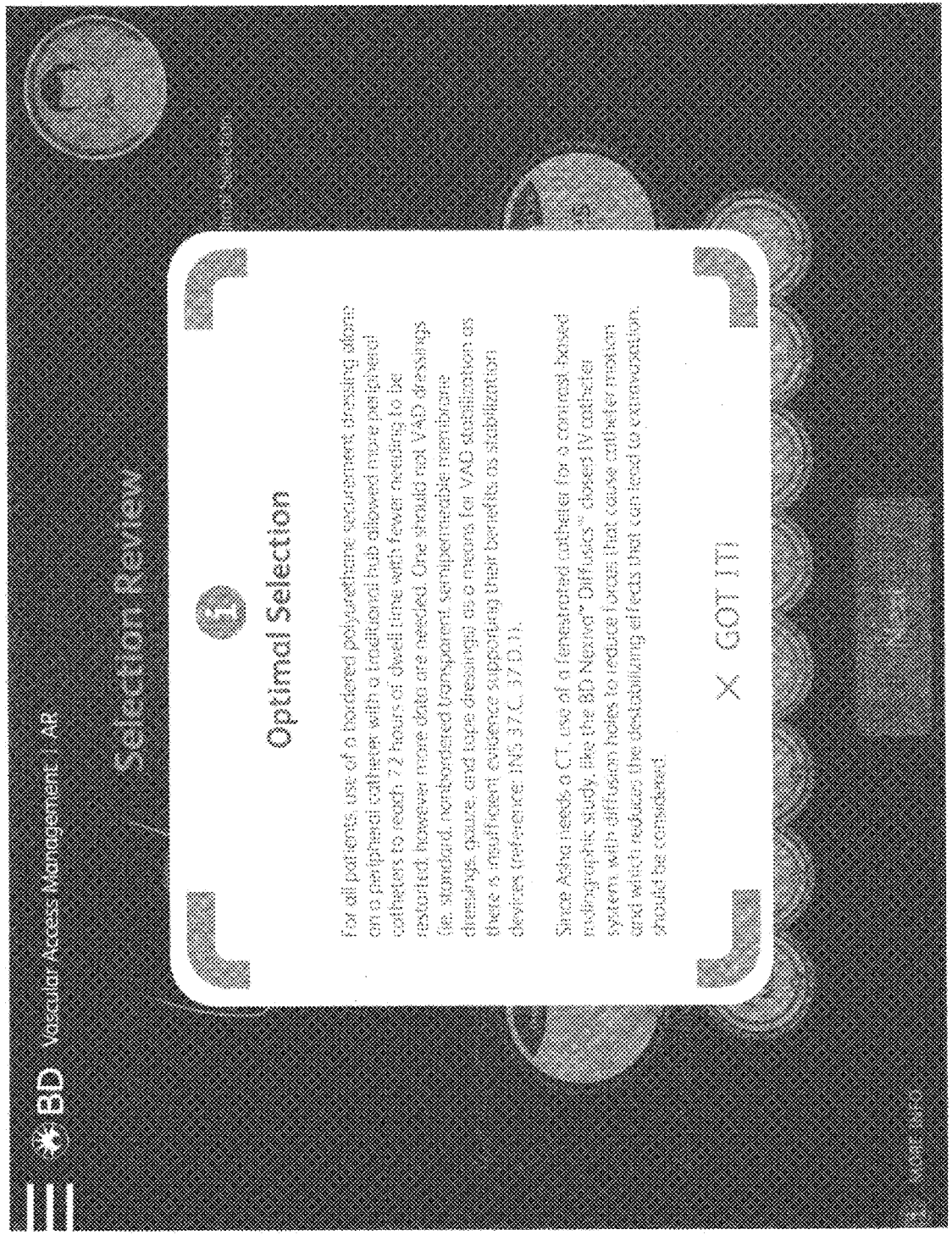
FIG. 89 is another example user interface, according to various embodiments.
Figure 90:
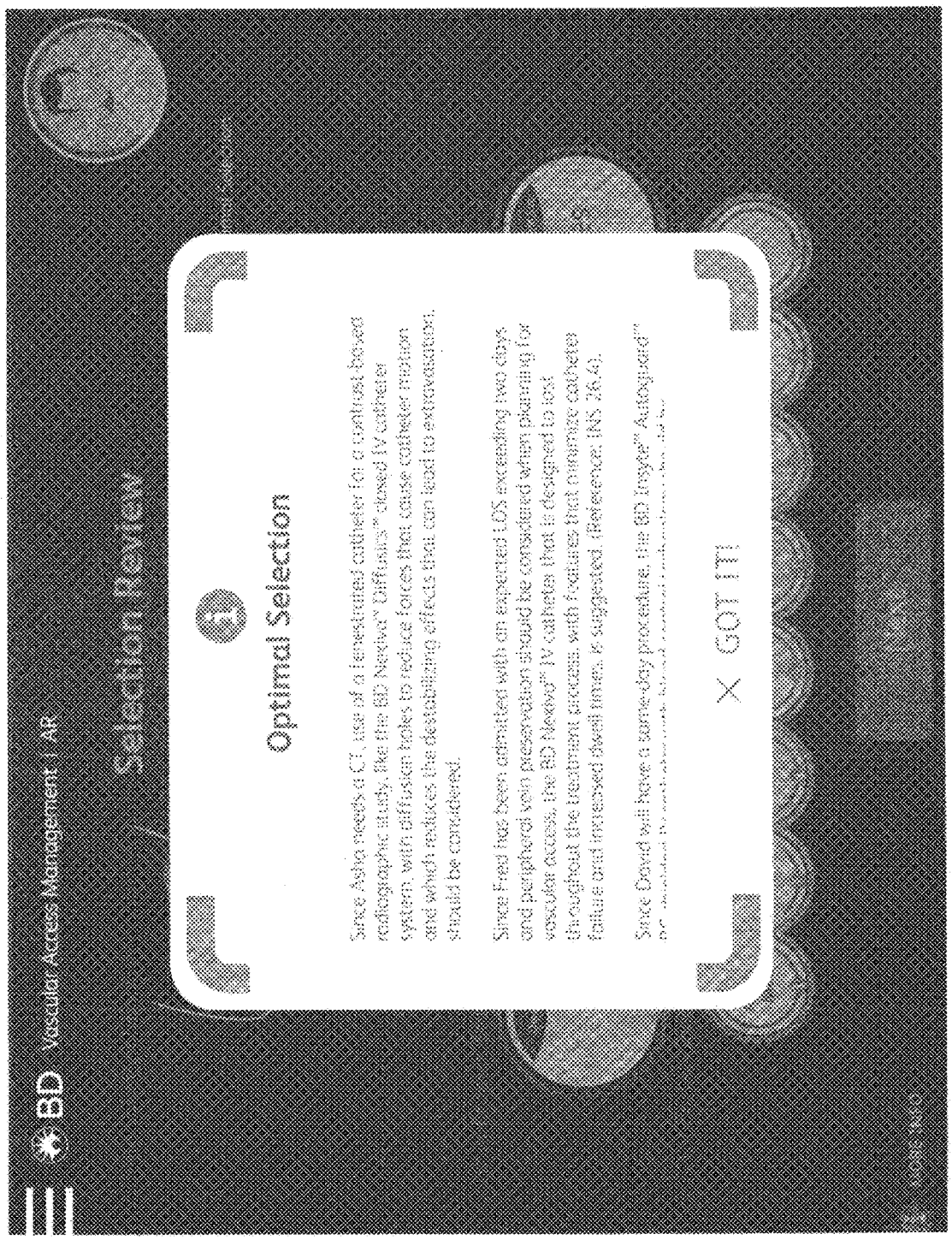
FIG. 90 is another example user interface, according to various embodiments.
Figure 91:
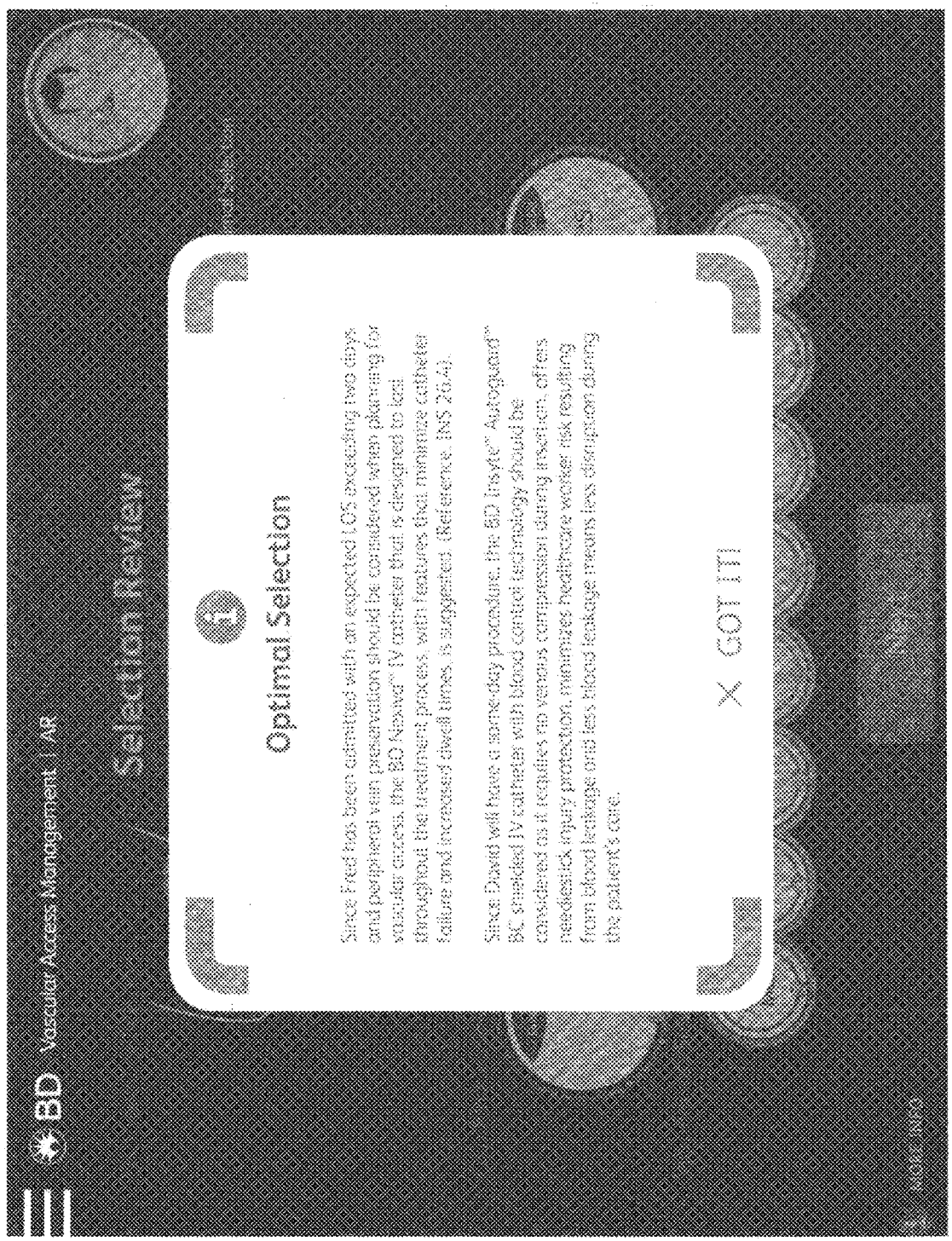
FIG. 91 is another example user interface, according to various embodiments.
Figure 92:
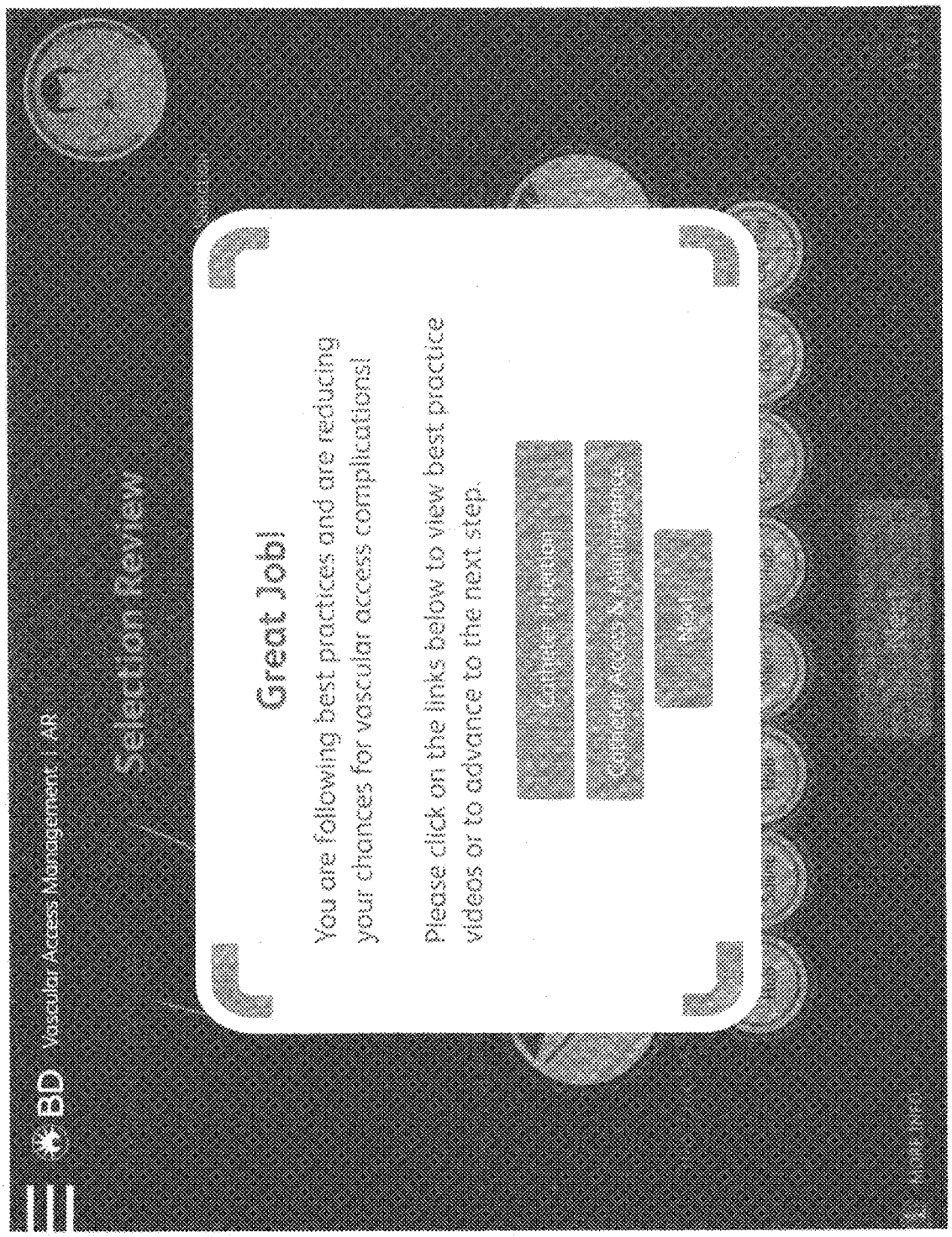
FIG. 92 is another example user interface, according to various embodiments.
Figure 93:
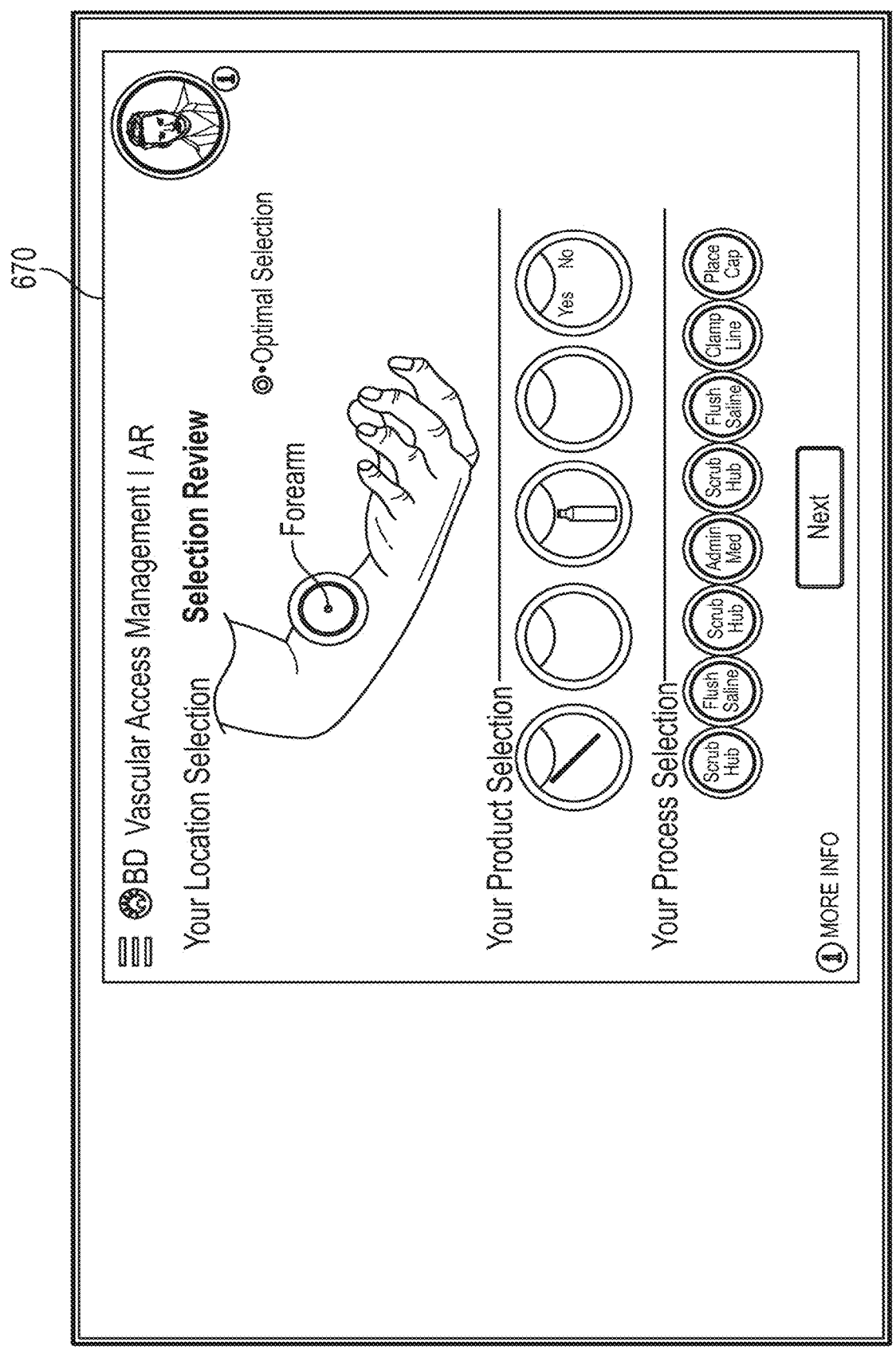
FIG. 93 is another example user interface, according to various embodiments.
Figure 94:
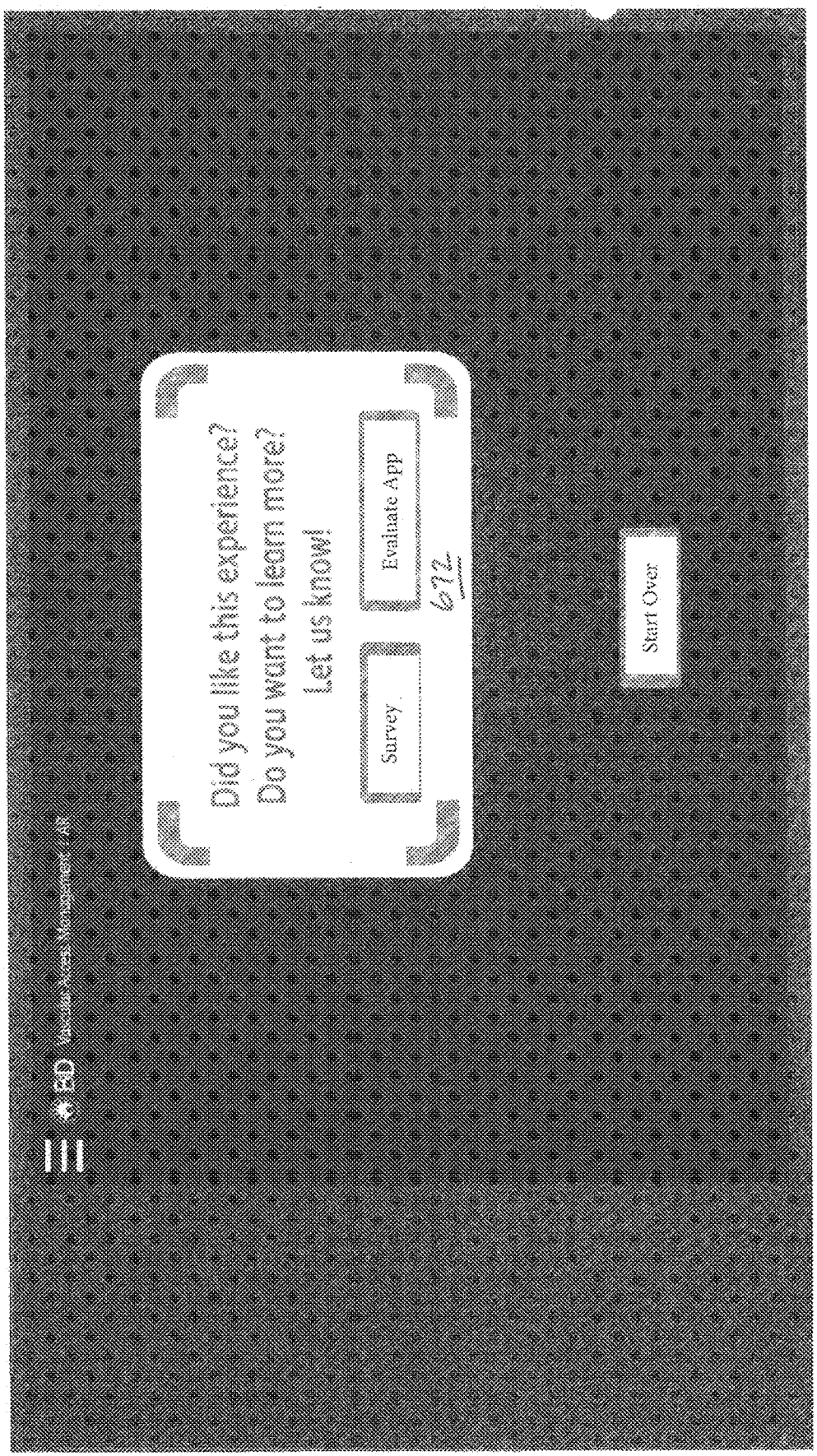
FIG. 94 is another example user interface, according to various embodiments.
Figure 95:
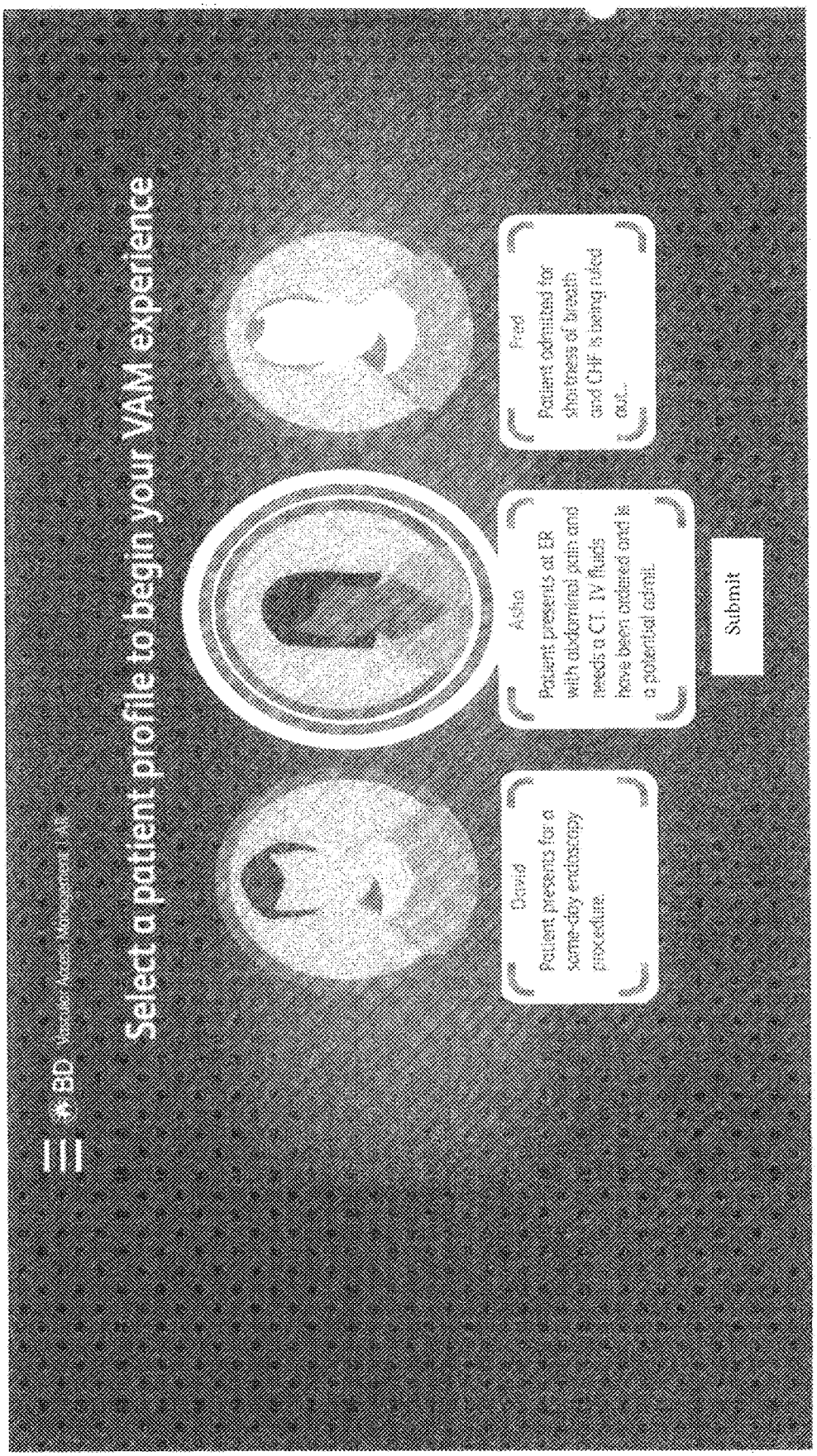
FIG. 95 is another example user interface, according to various embodiments.
Figure 96:
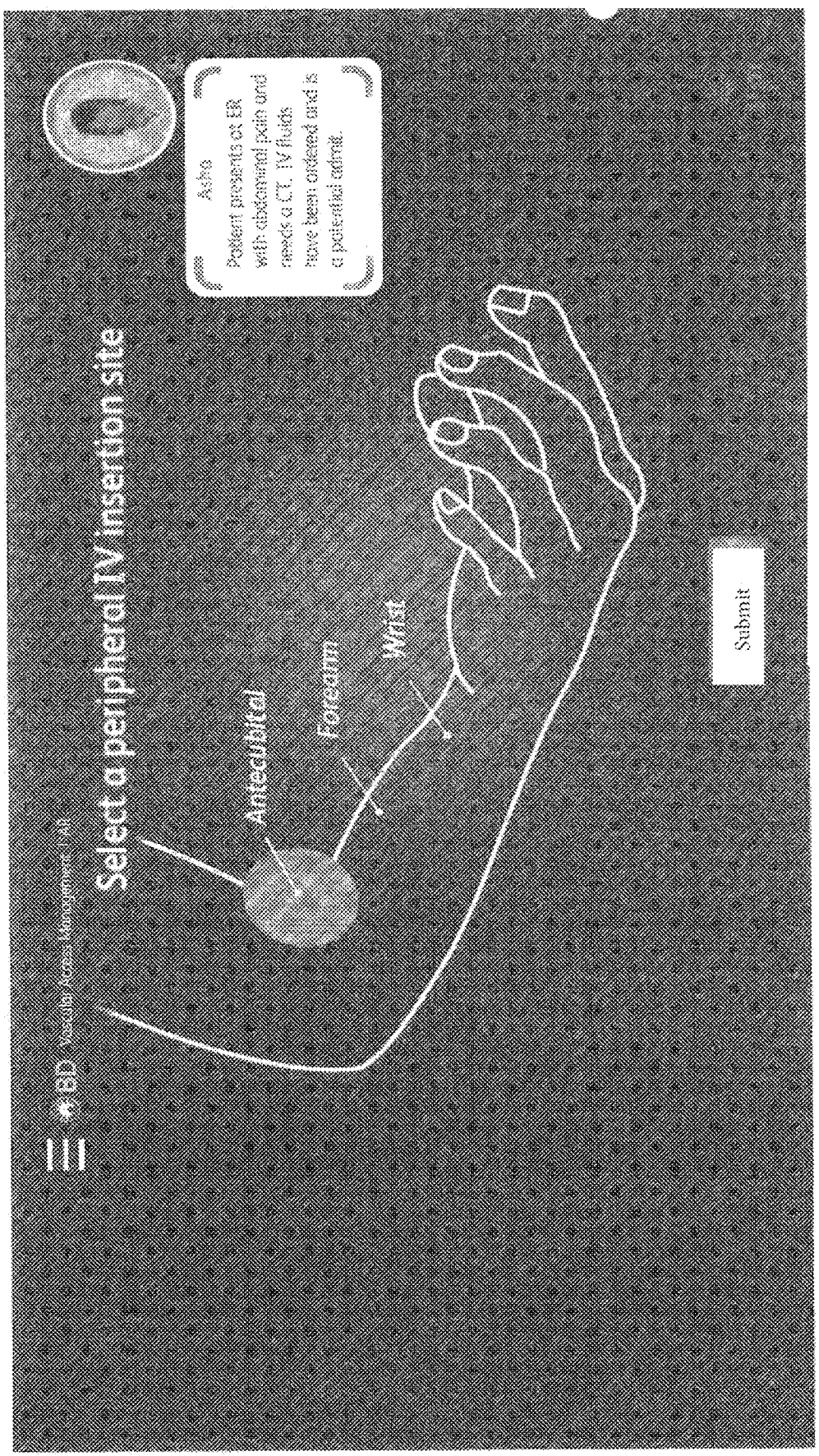
FIG. 96 is another example user interface, according to various embodiments.
Figure 97:
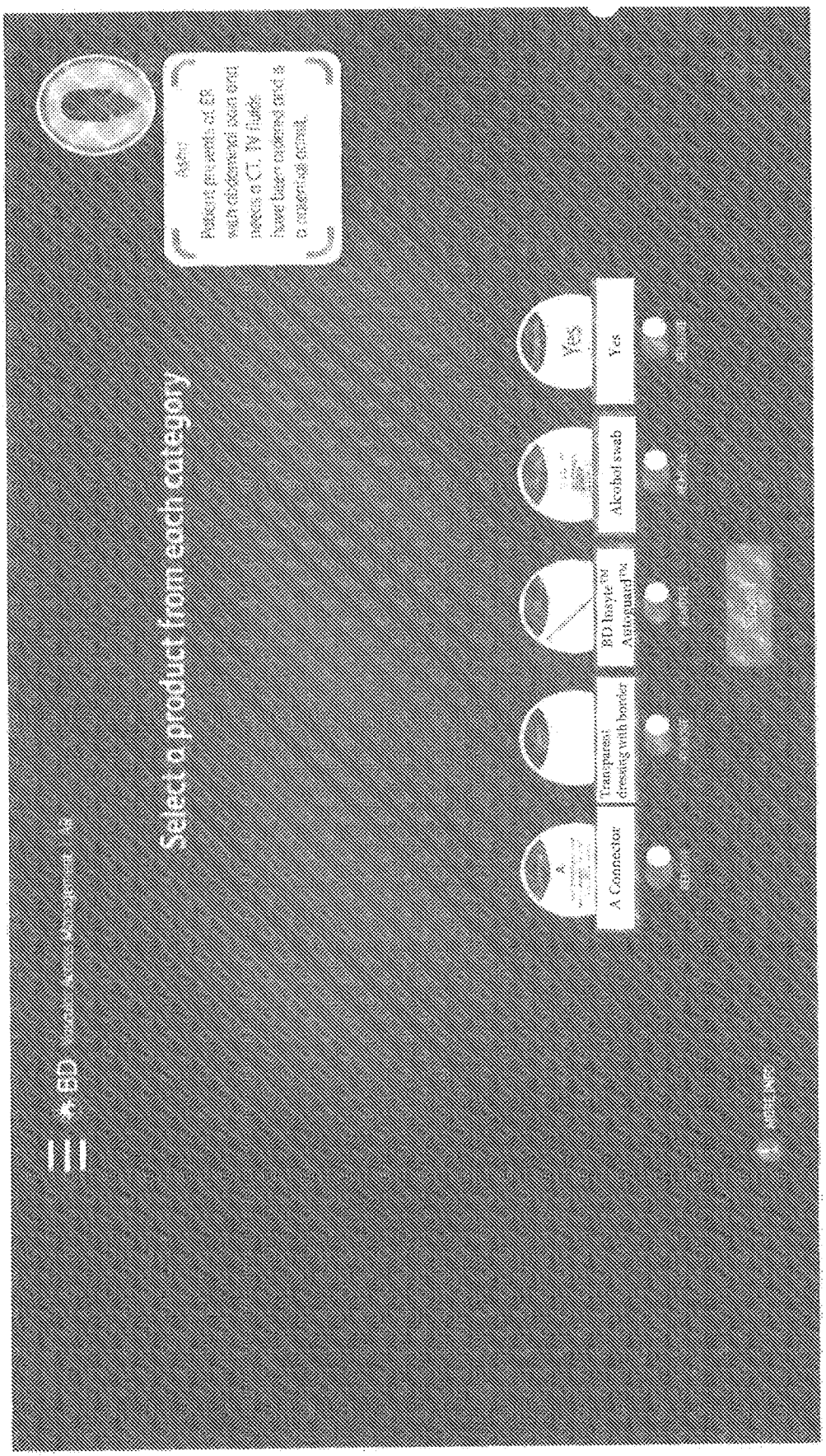
FIG. 97 is another example user interface, according to various embodiments.
Figure 98:
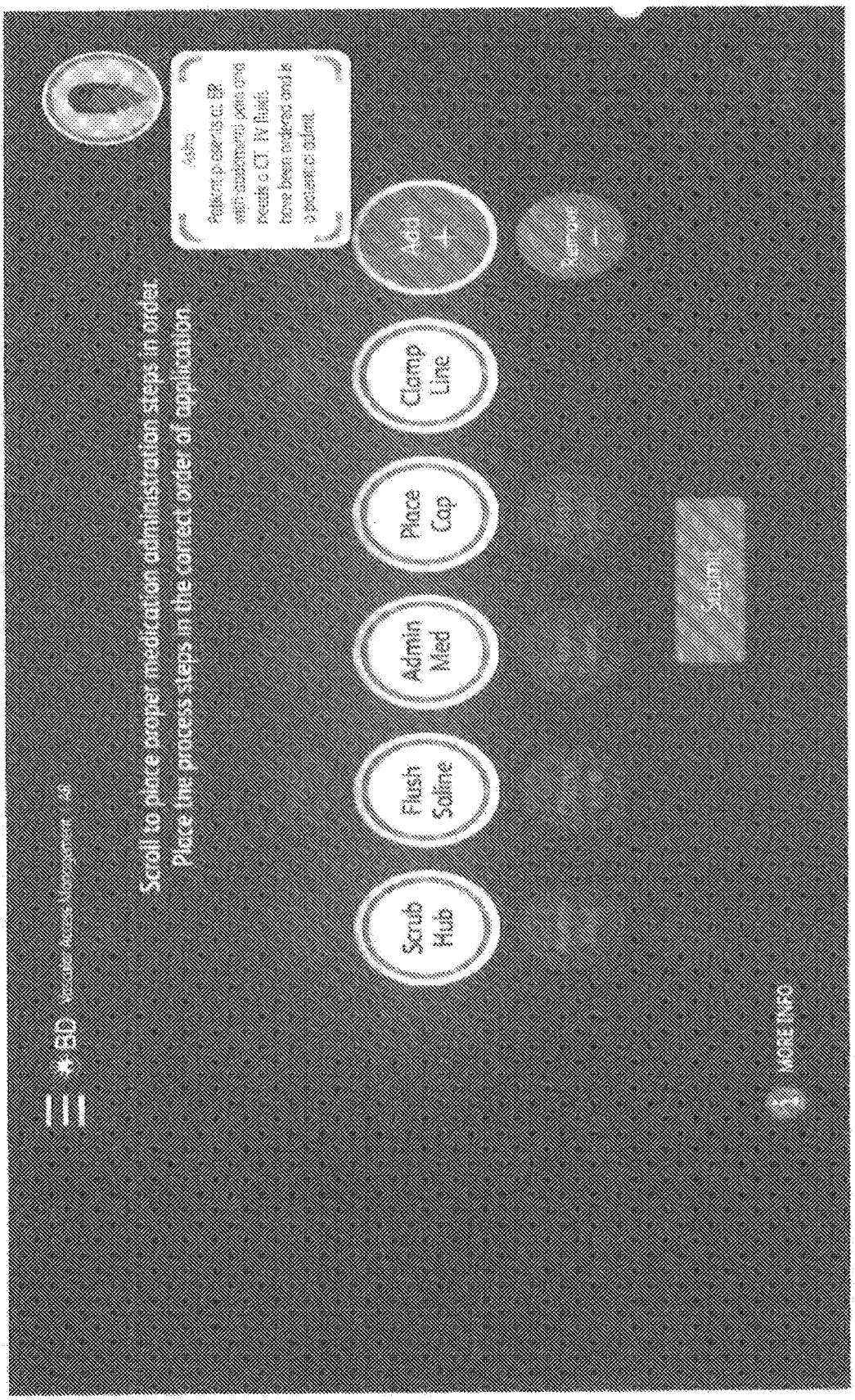
FIG. 98 is another example user interface, according to various embodiments.
Figure 99:
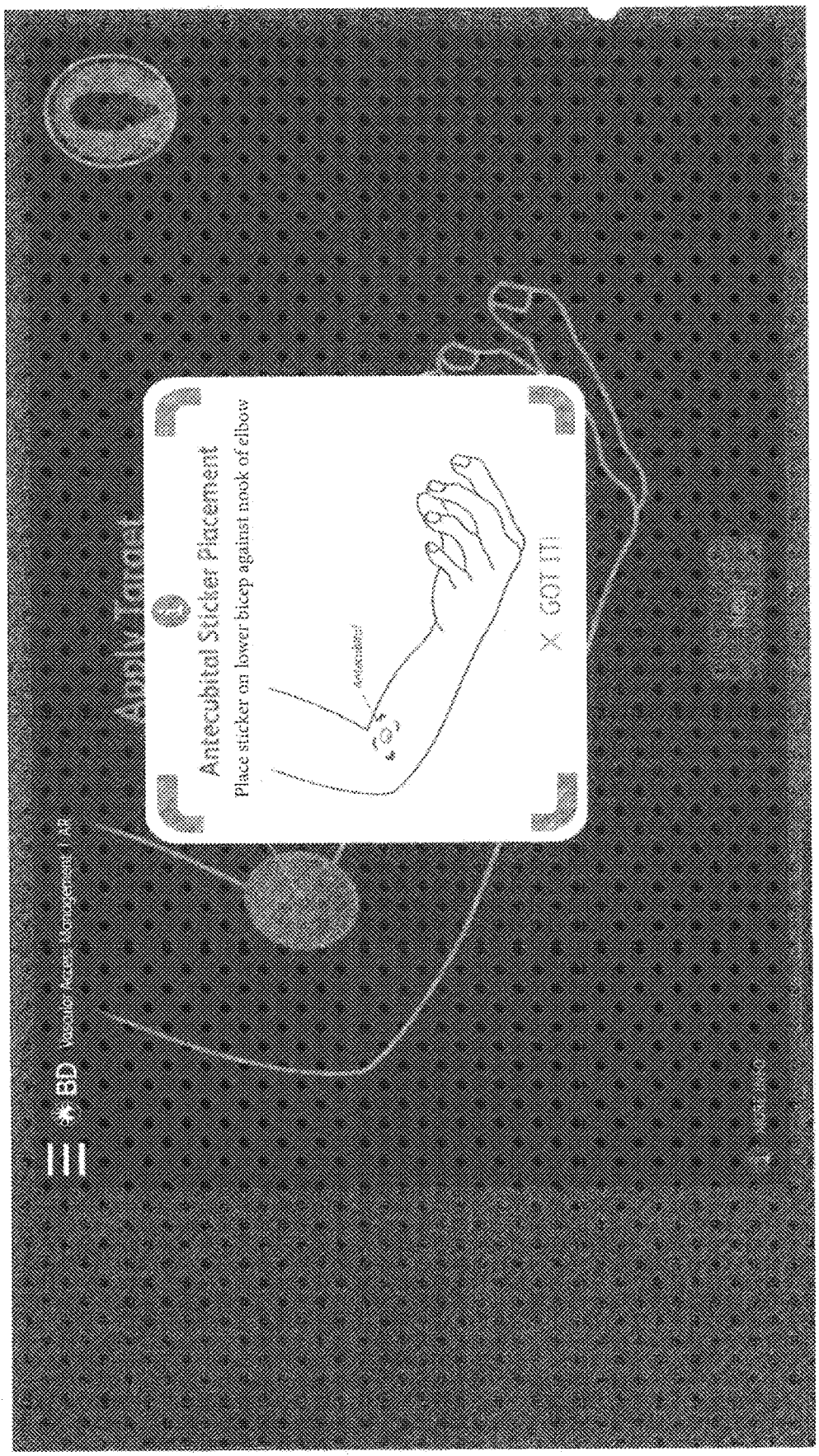
FIG. 99 is another example user interface, according to various embodiments.
Figure 100:
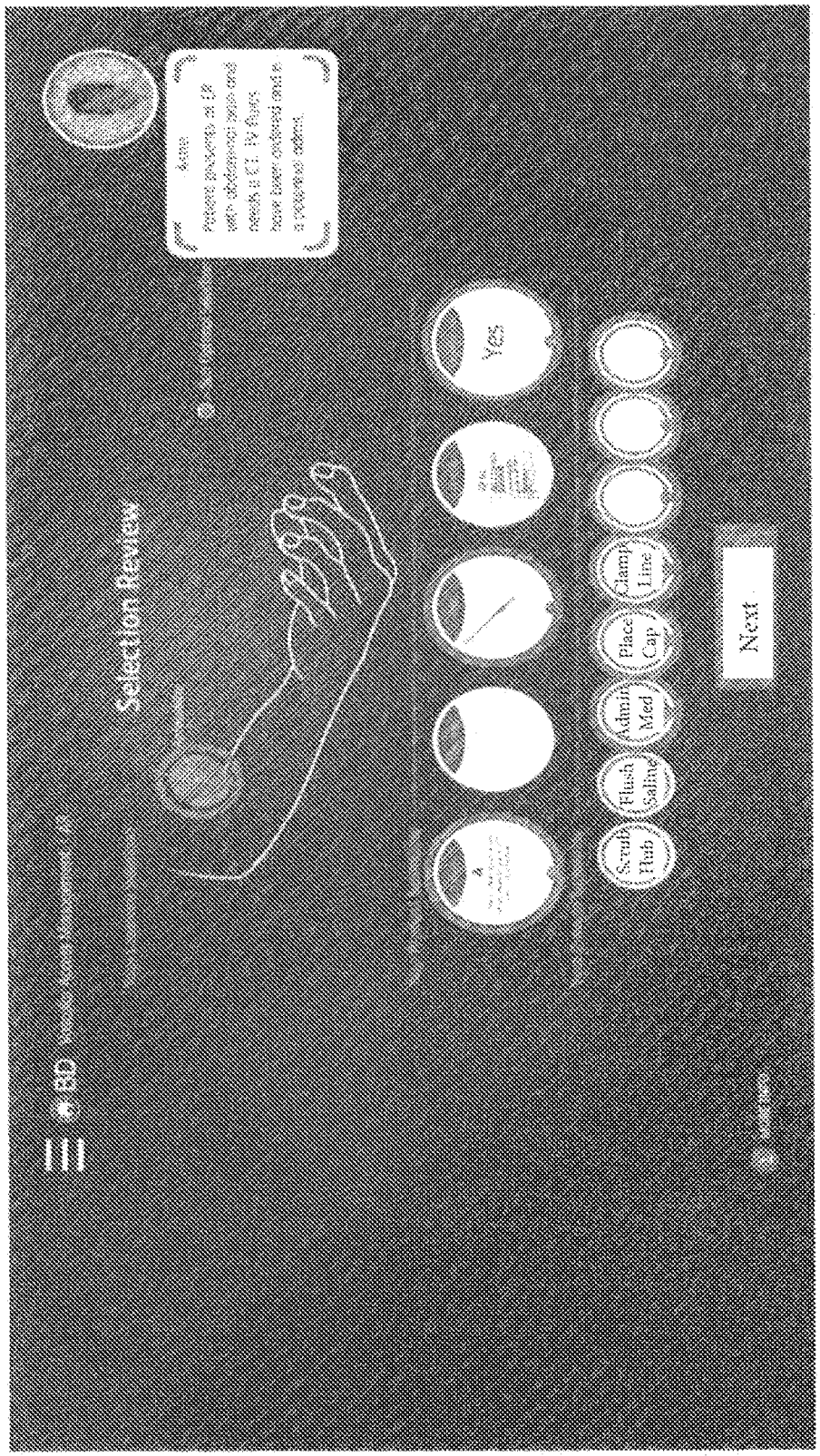
FIG. 100 is another example user interface, according to various embodiments.
Figure 101:
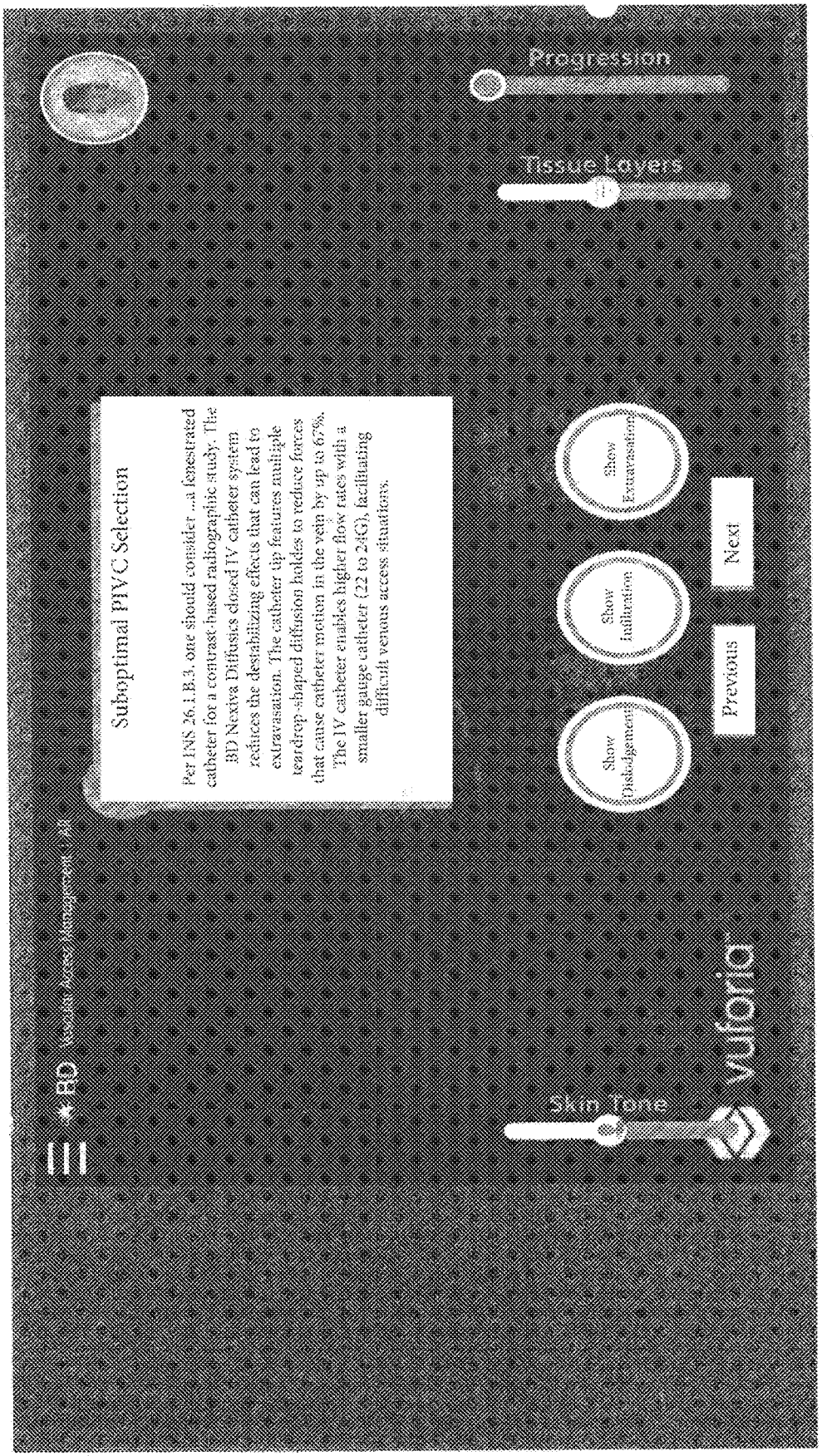
FIG. 101 is another example user interface, according to various embodiments.
Figure 102:
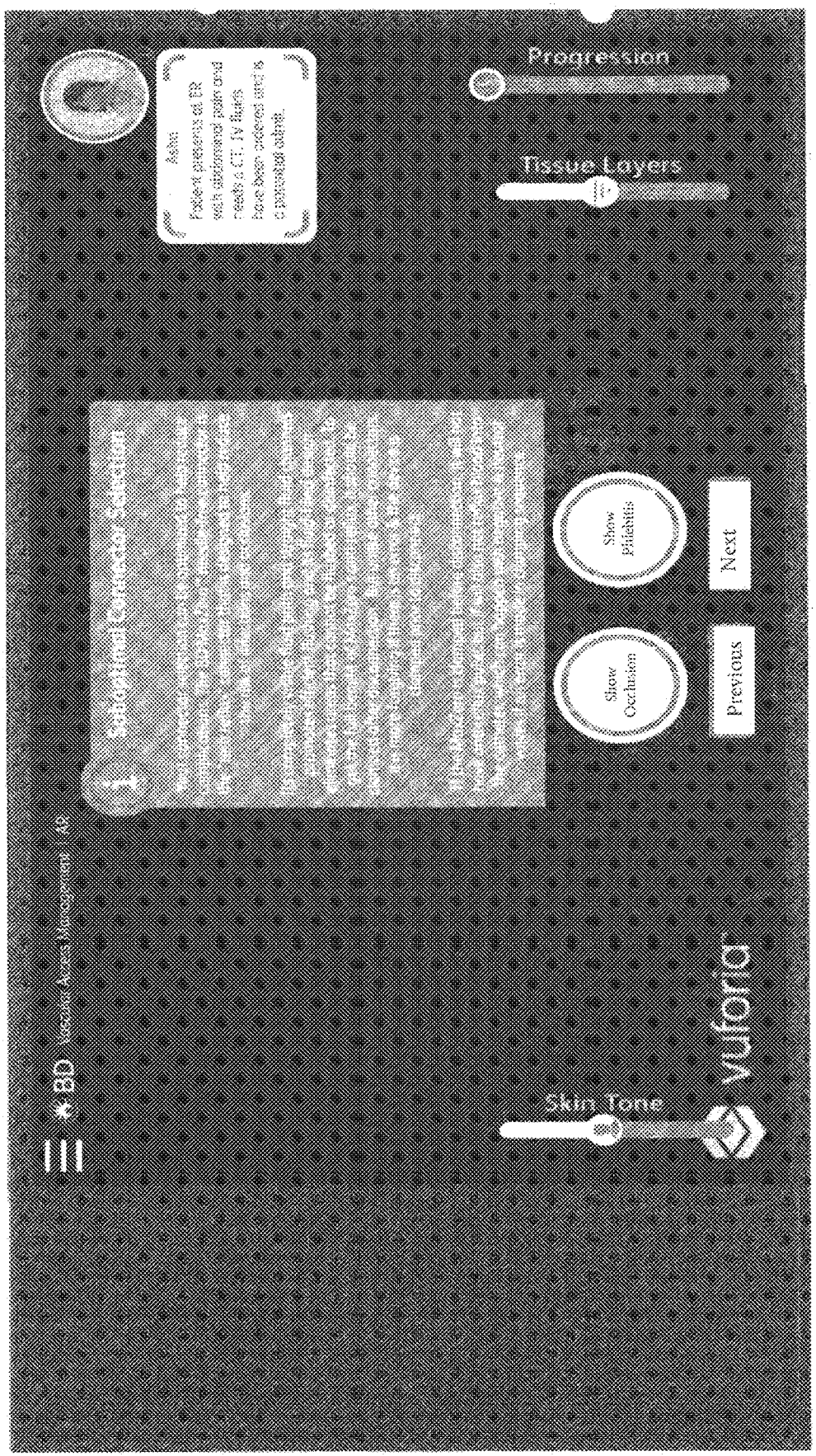
FIG. 102 is another example user interface, according to various embodiments.
Figure 103:
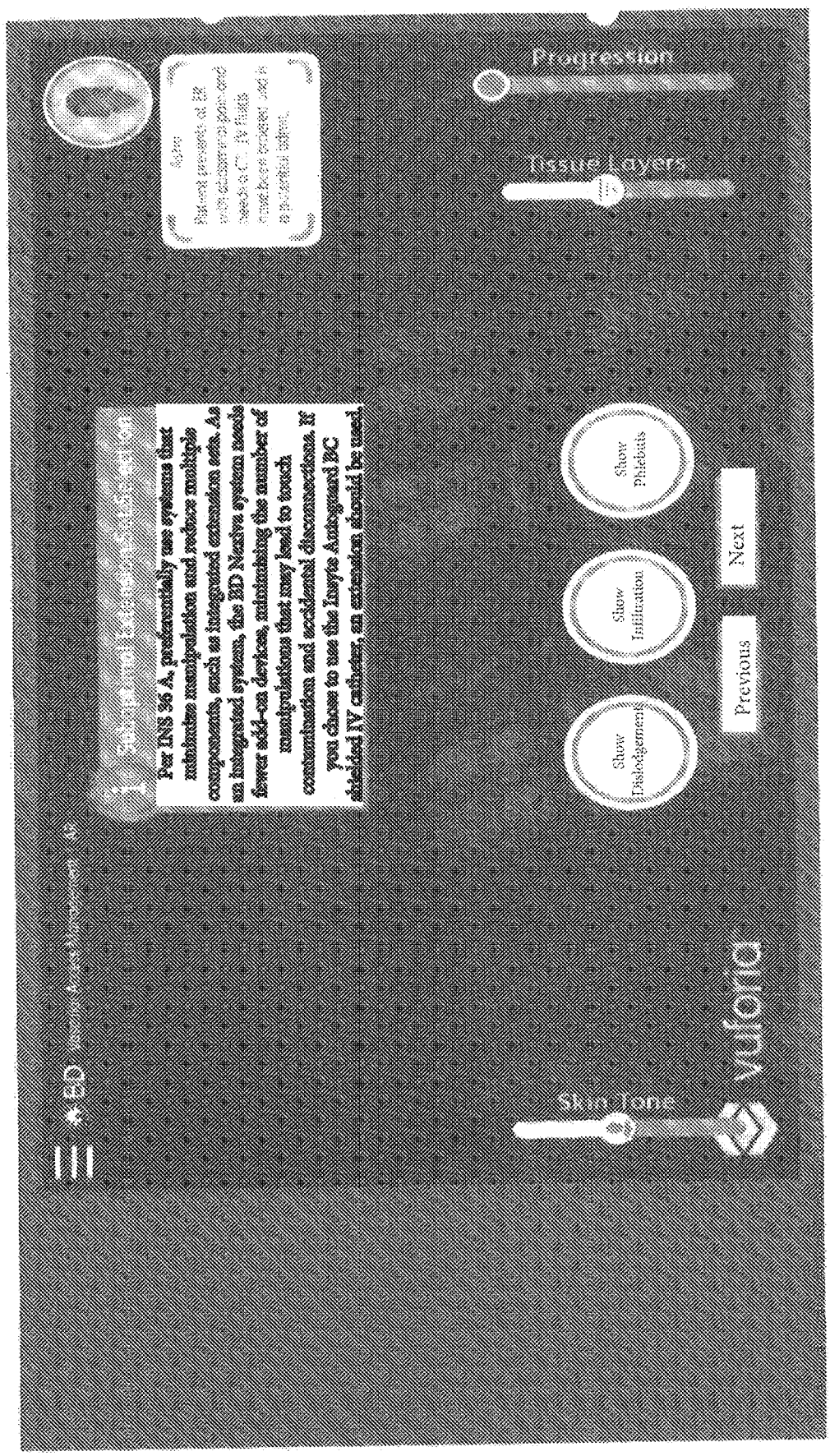
FIG. 103 is another example user interface, according to various embodiments.
Figure 104:
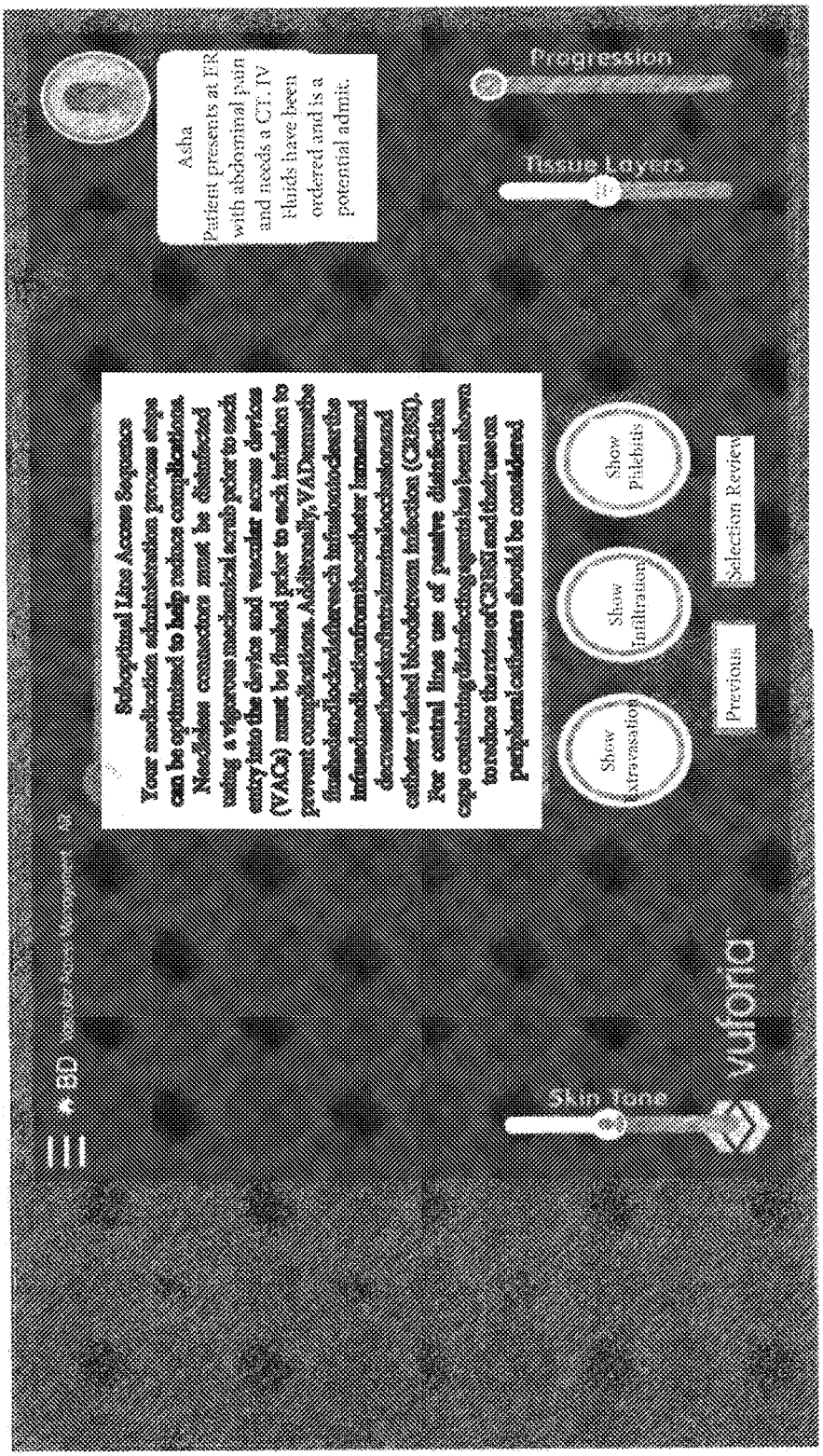
FIG. 104 is another example user interface, according to various embodiments.
Figure 105:
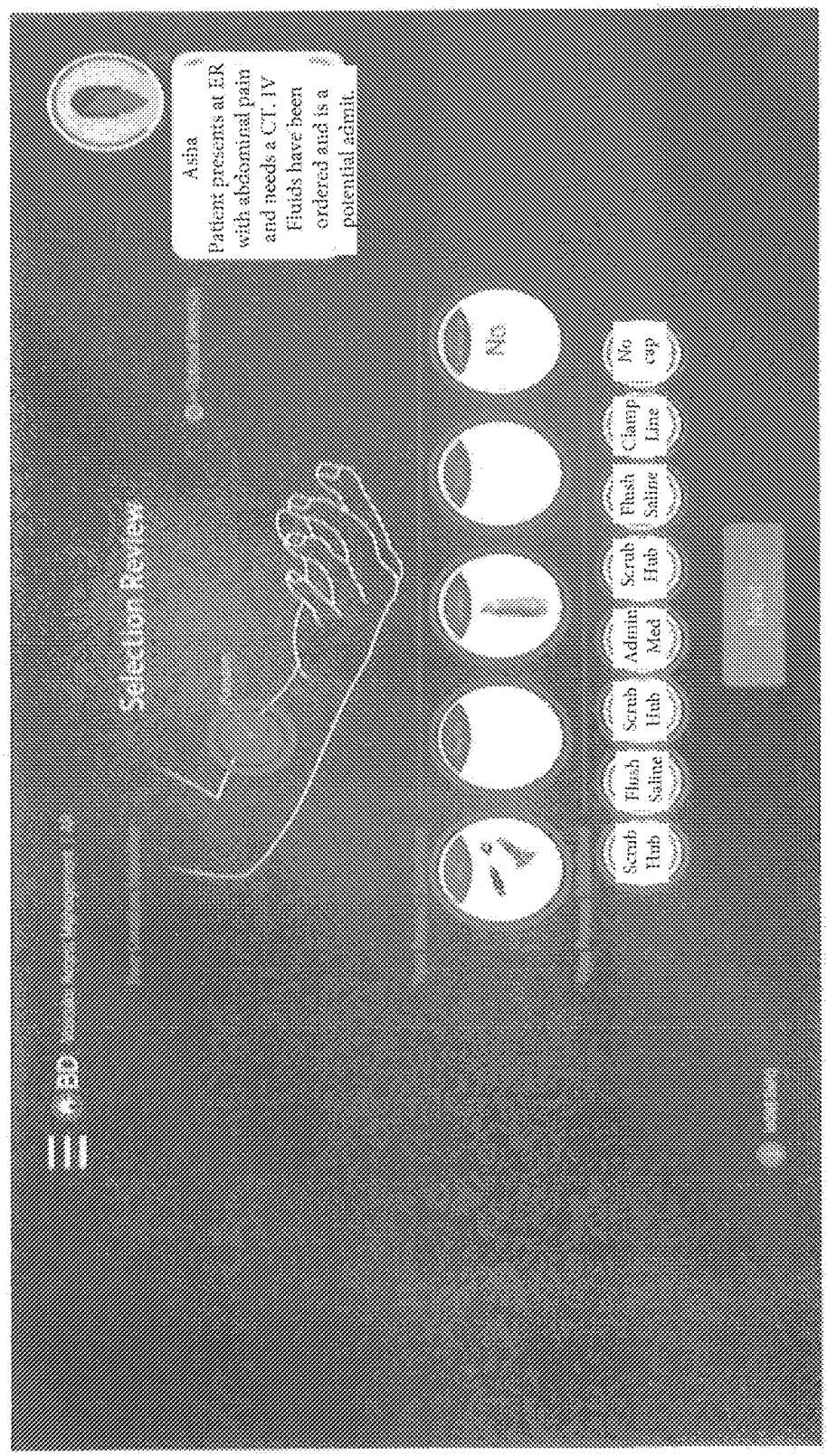
FIG. 105 is another example user interface, according to various embodiments.
Figure 106:
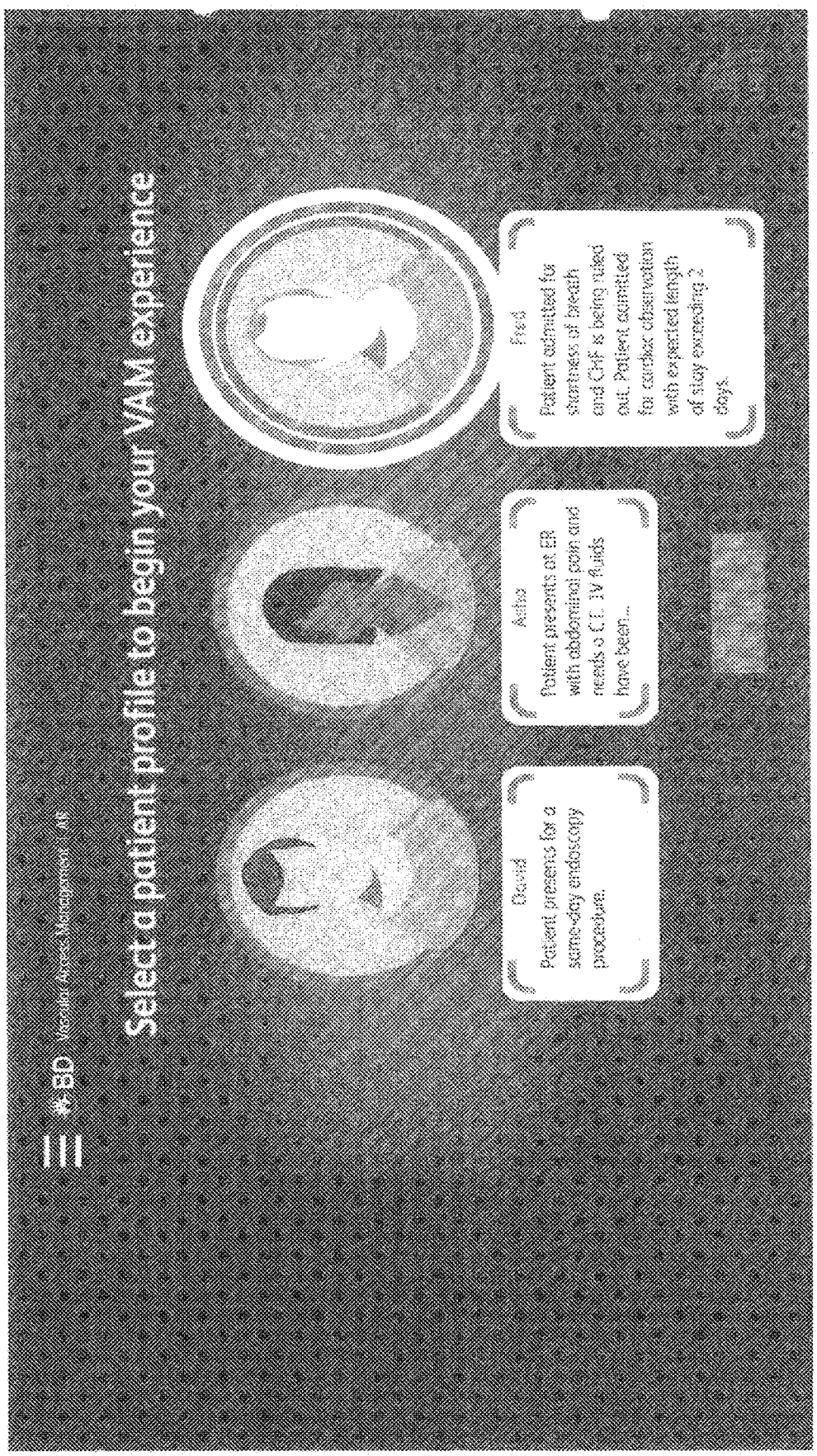
FIG. 106 is another example user interface, according to various embodiments.
Figure 107:
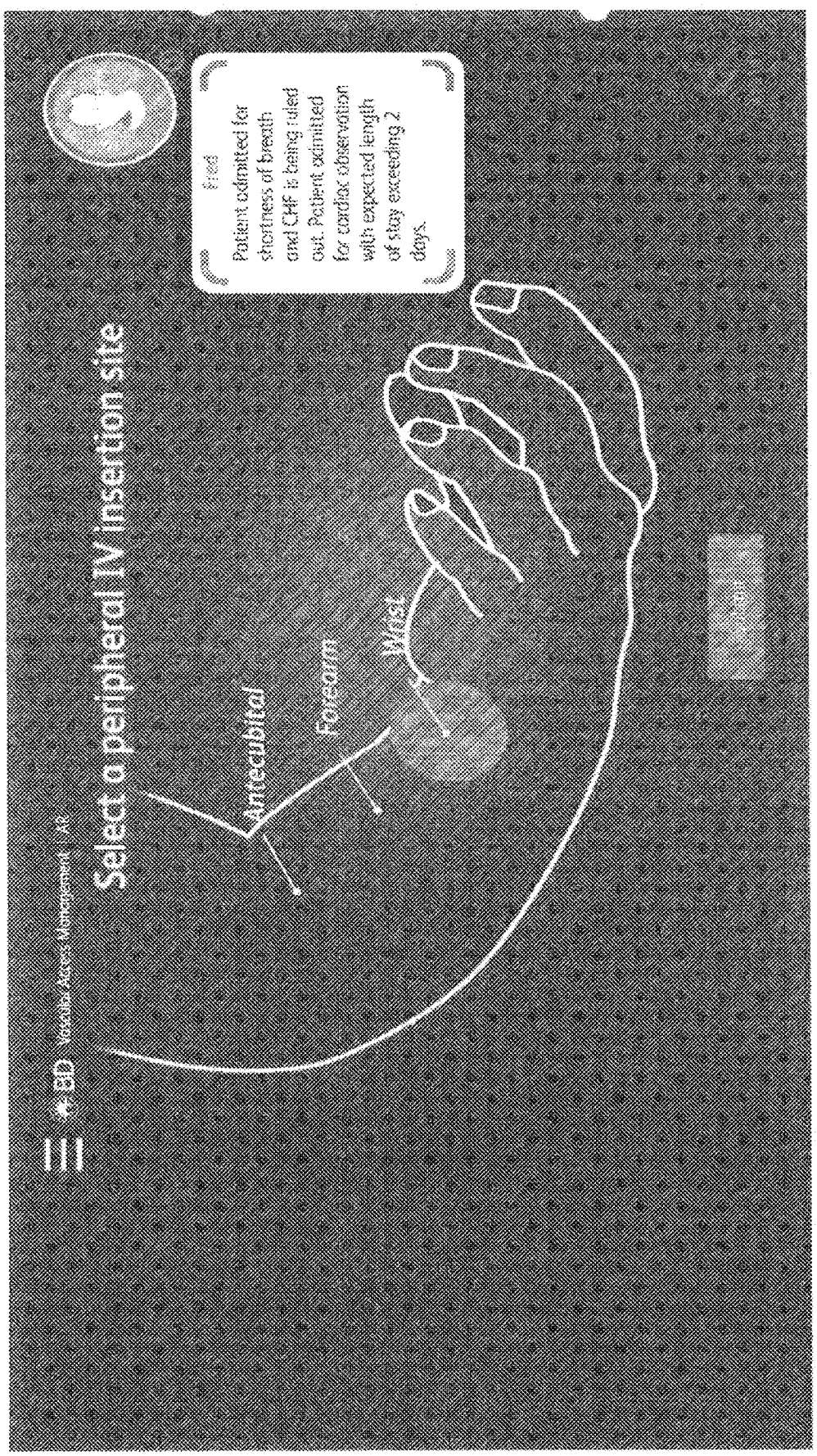
FIG. 107 is another example user interface, according to various embodiments.
Figure 108:
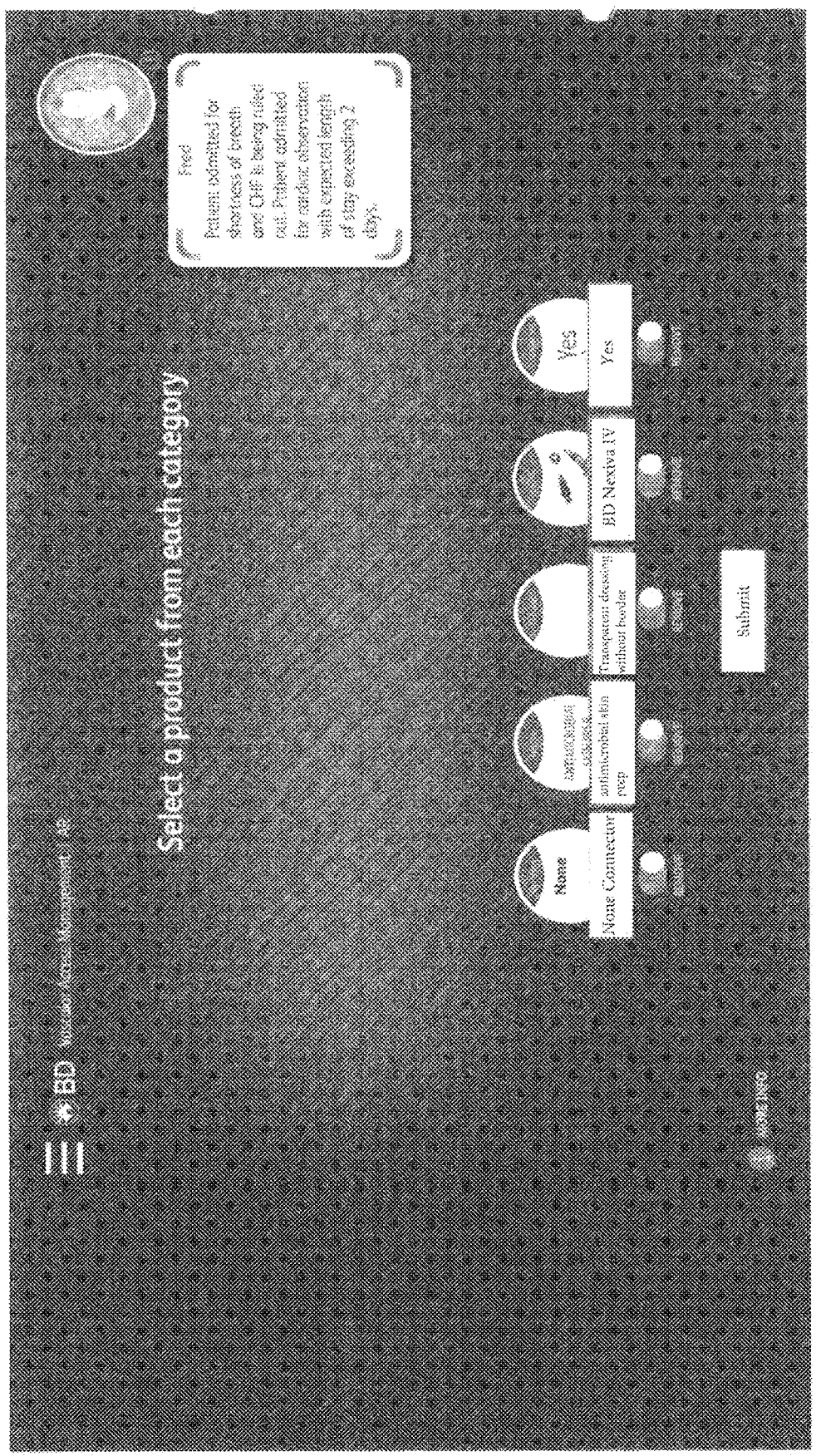
FIG. 108 is another example user interface, according to various embodiments.
Figure 109:
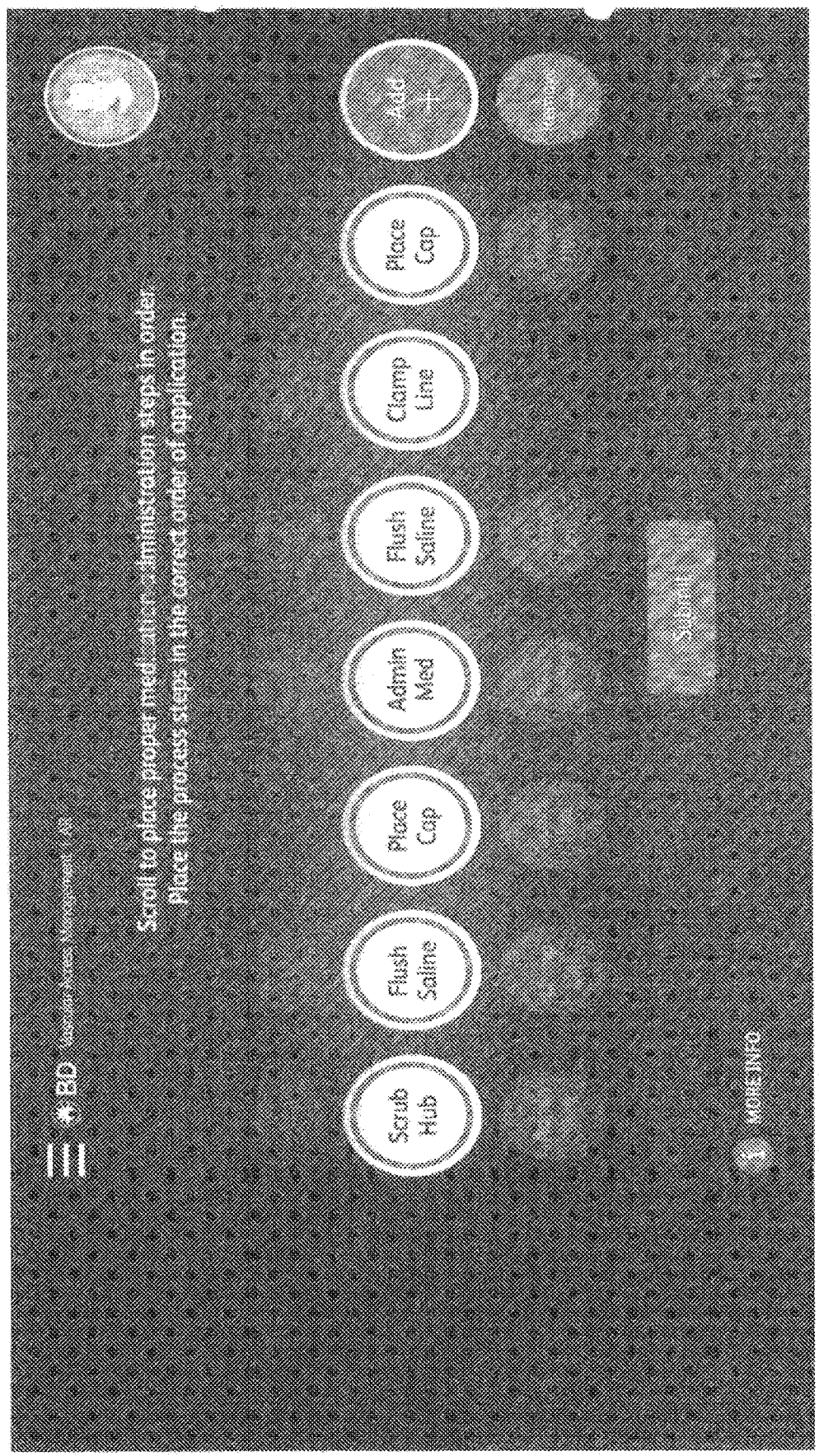
FIG. 109 is another example user interface, according to various embodiments.
Figure 110:
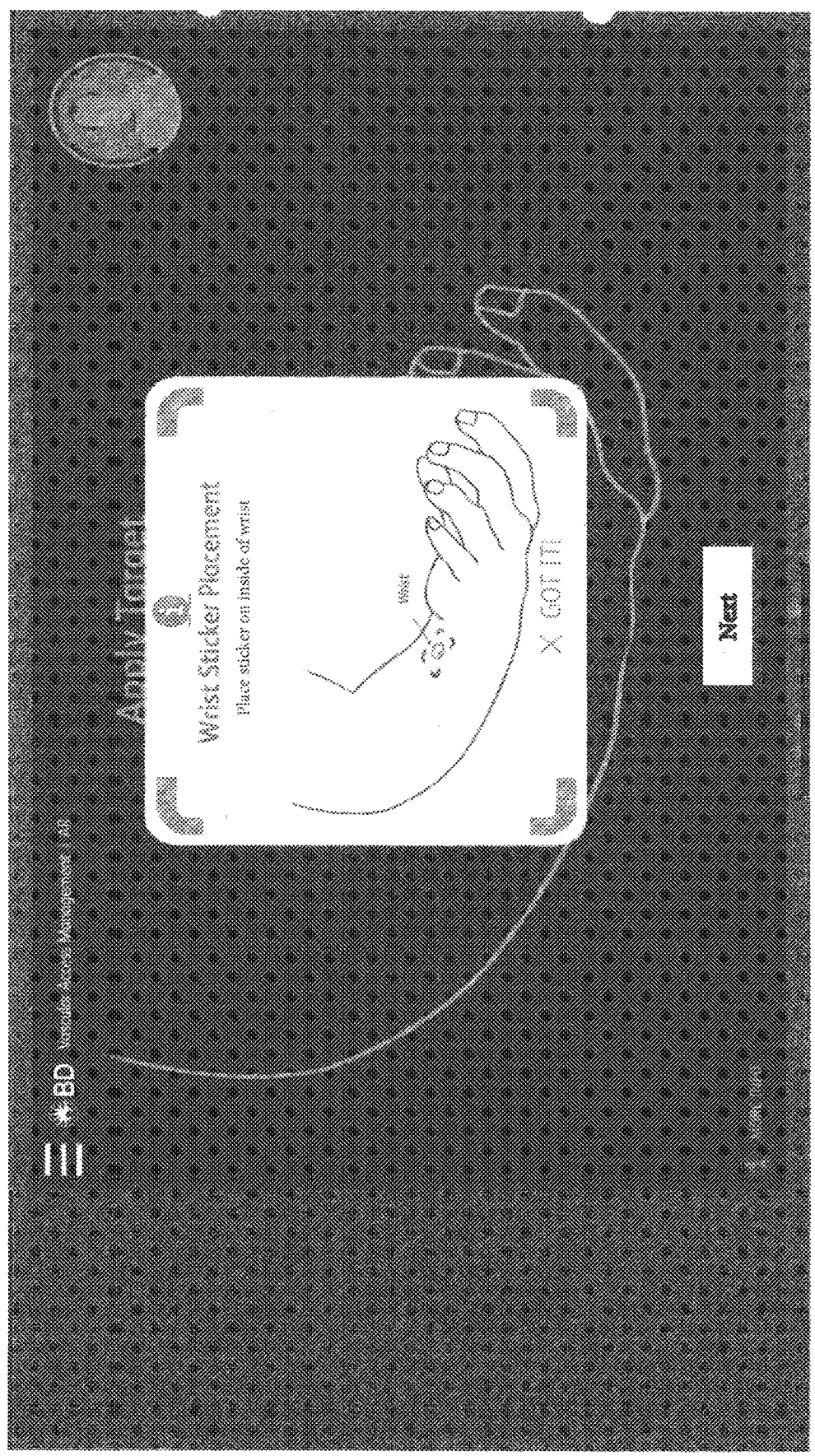
Figure 111:
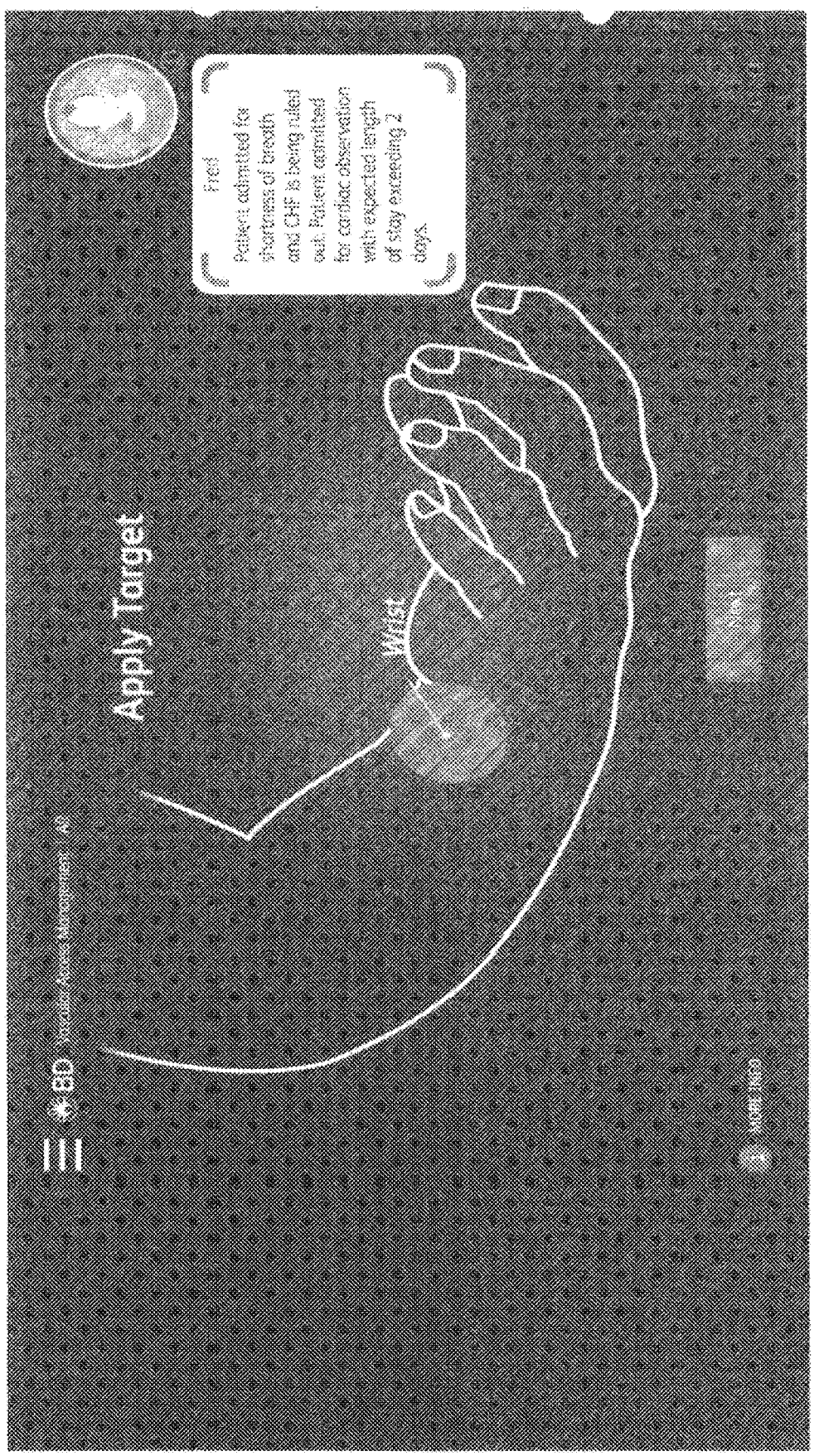
Figure 112:
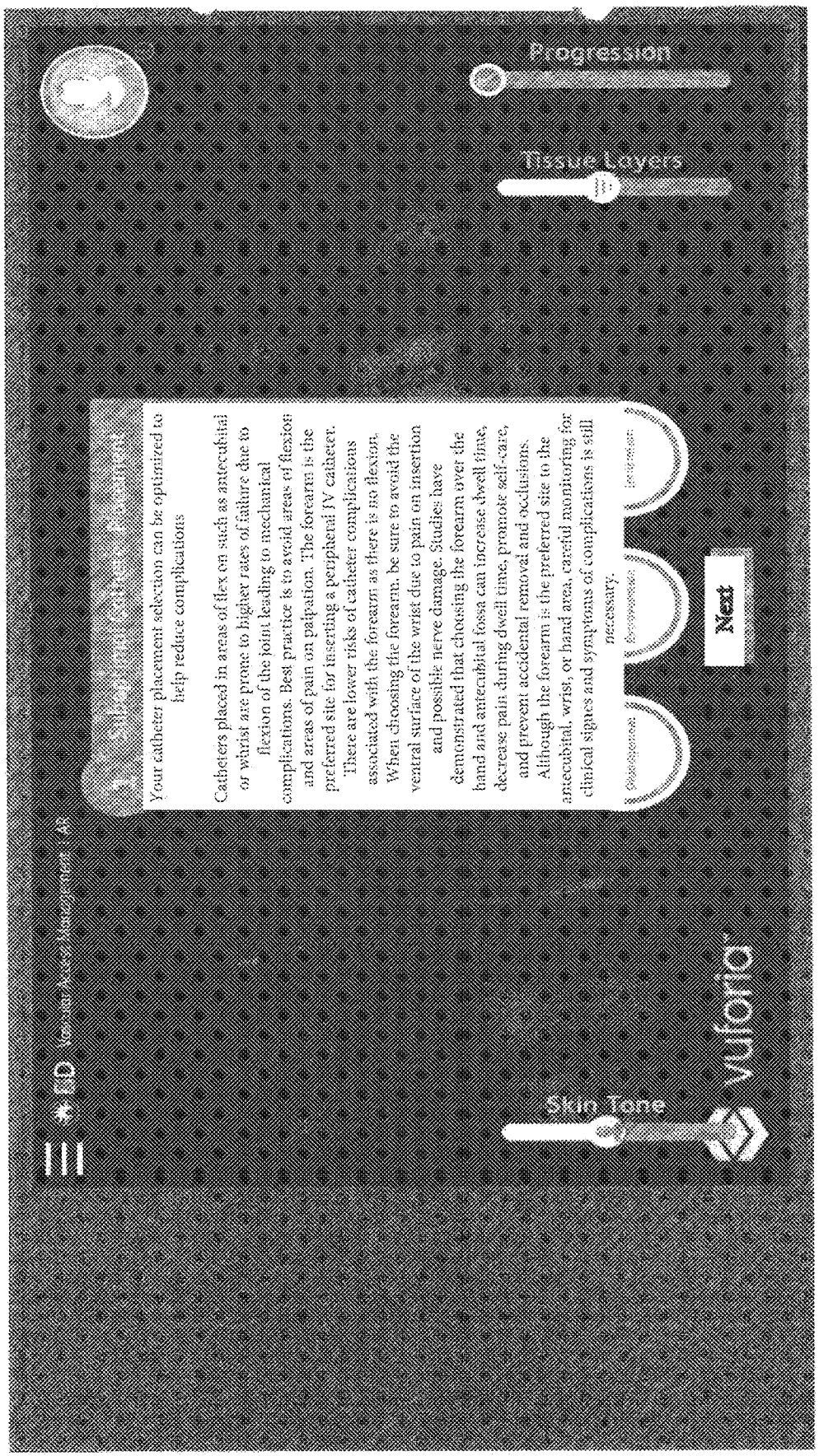
Figure 113:
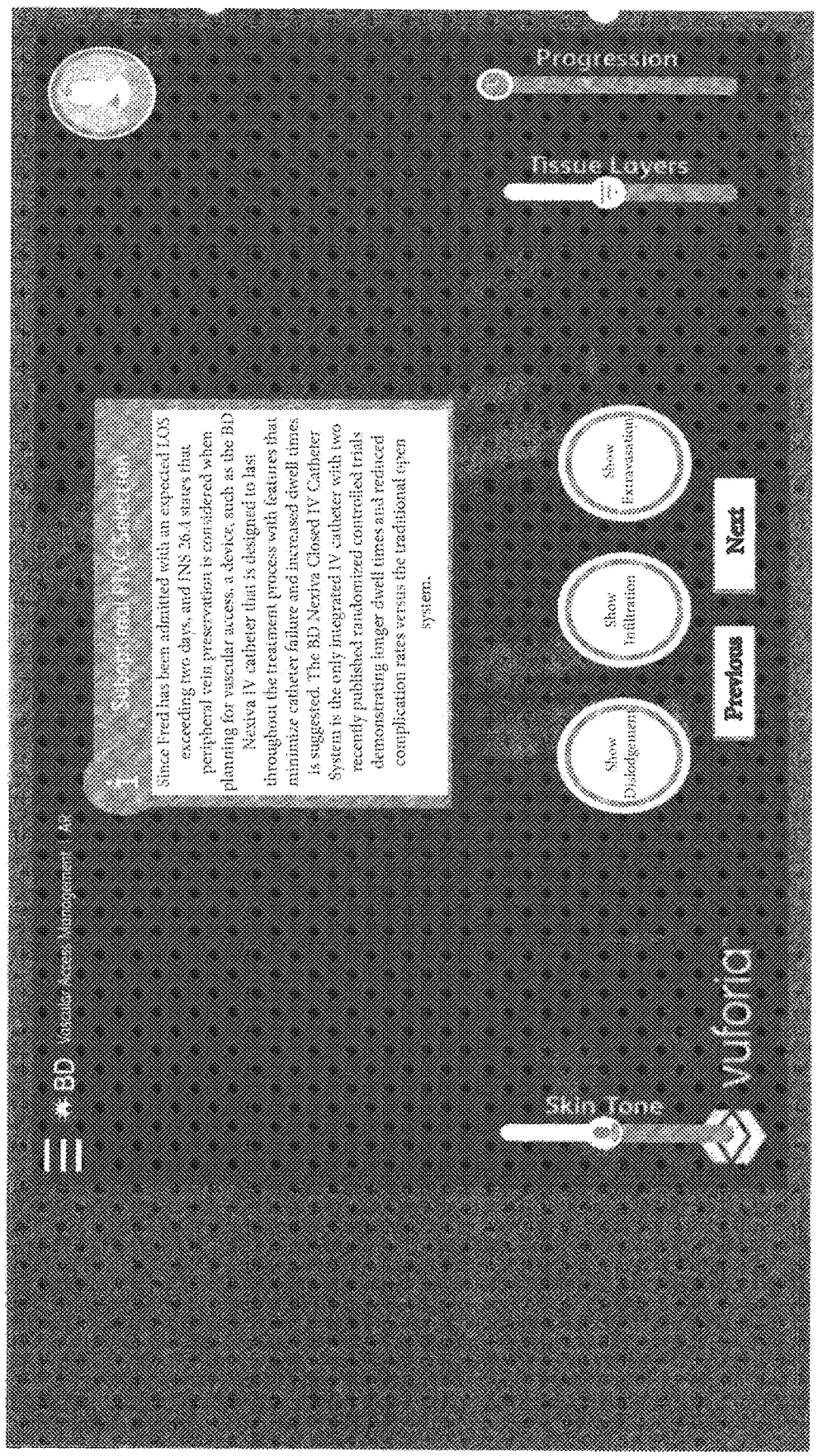
Figure 114:
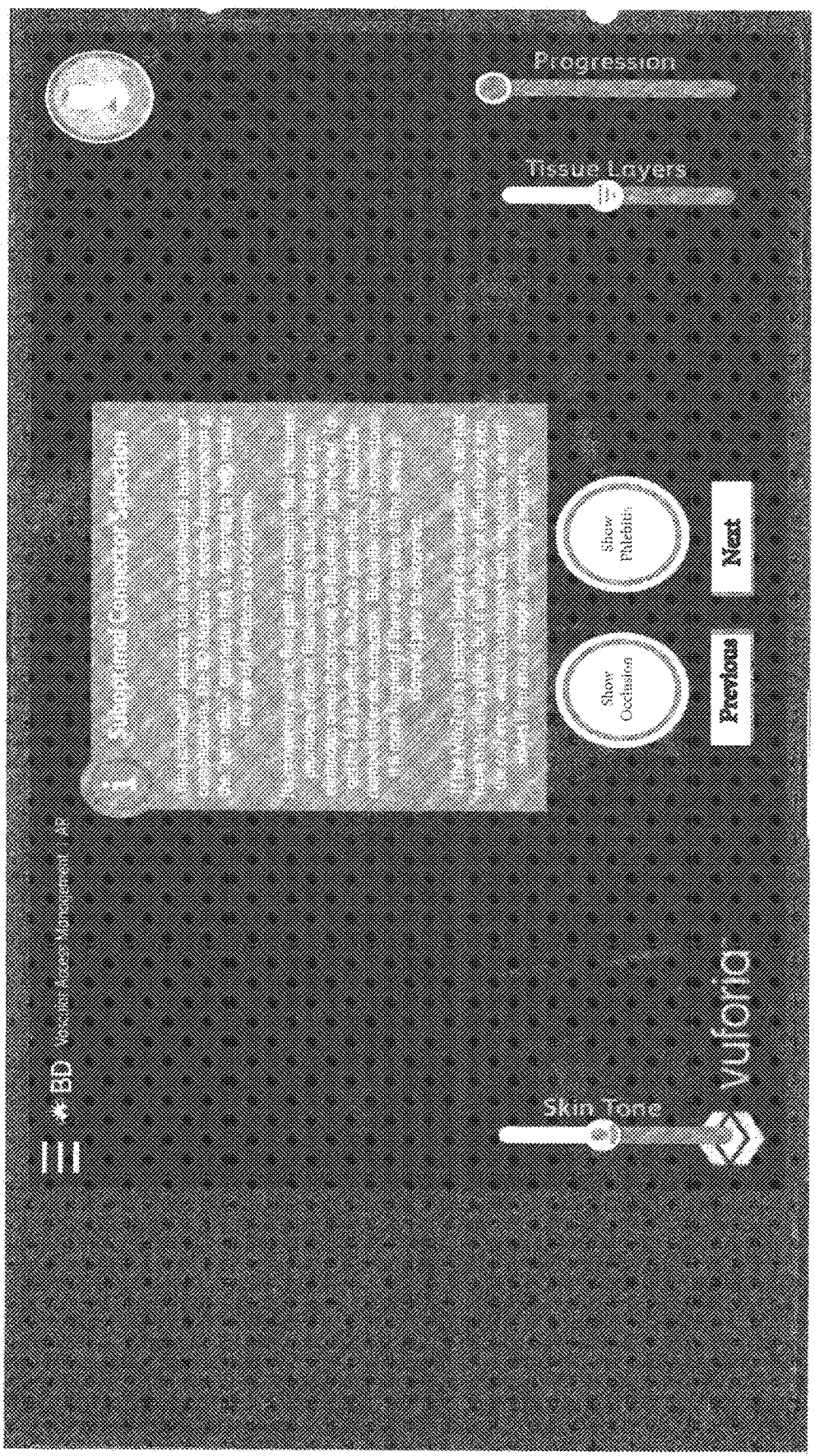
Figure 115:
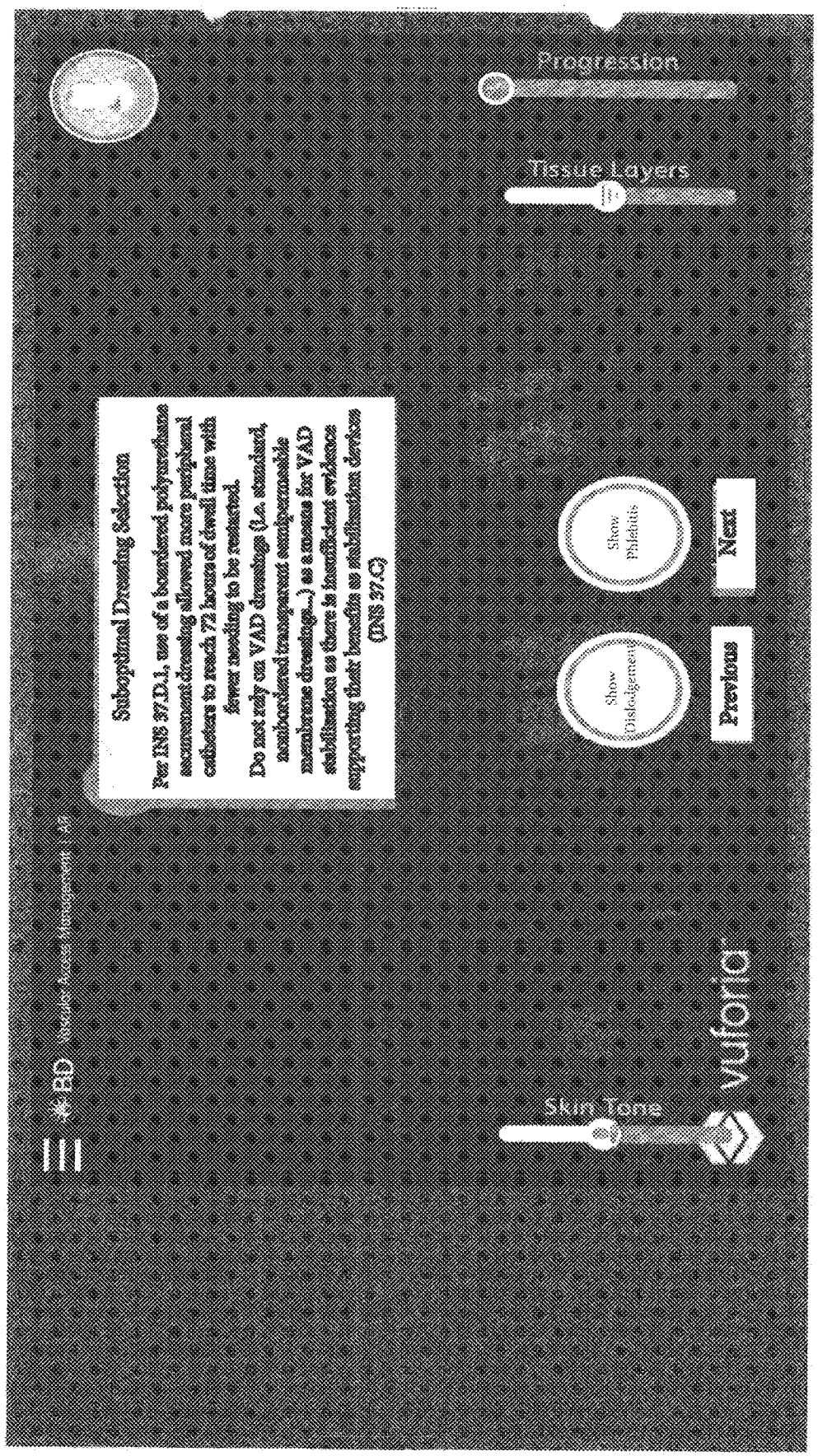
Figure 116:
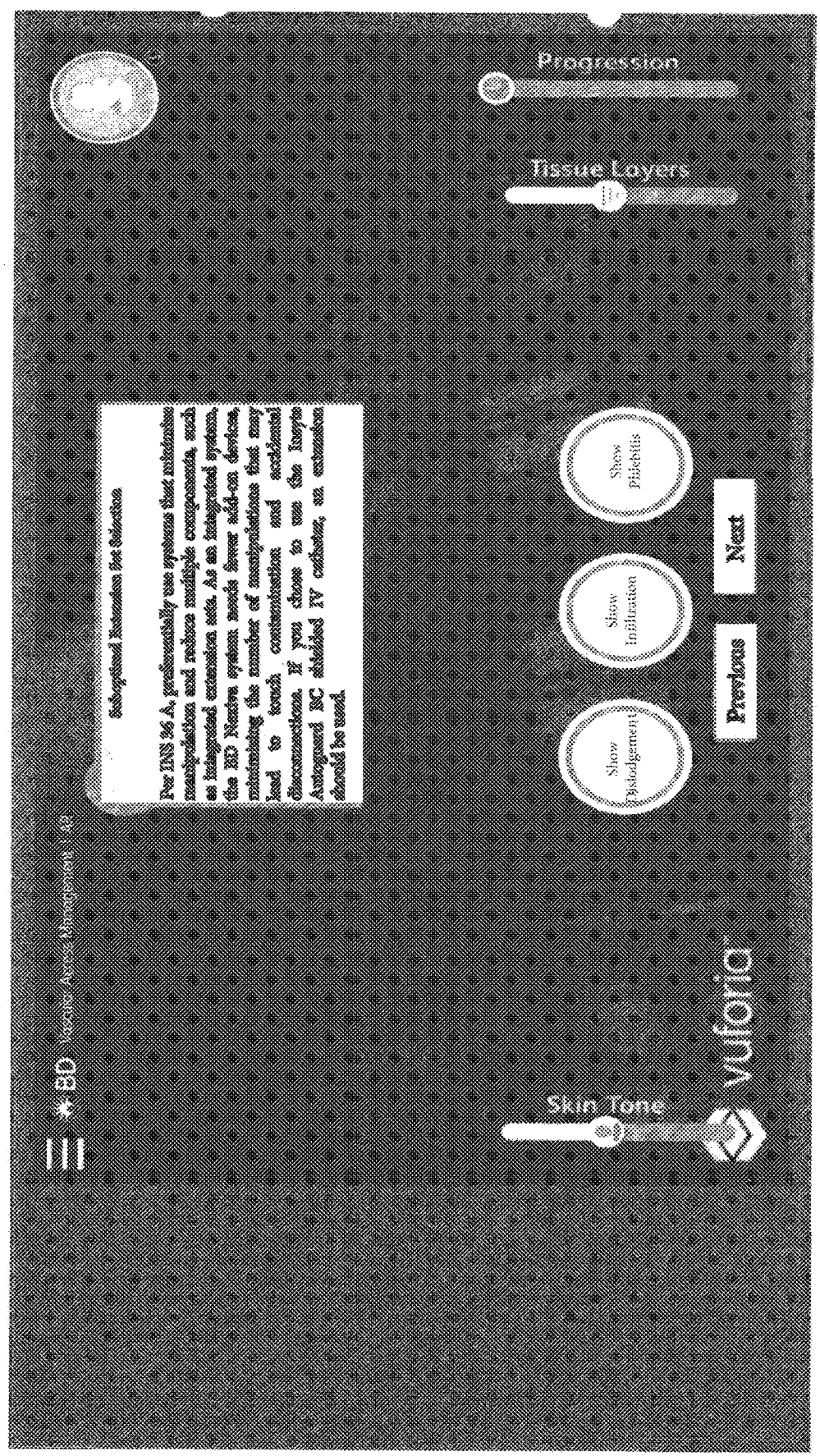
Figure 117:
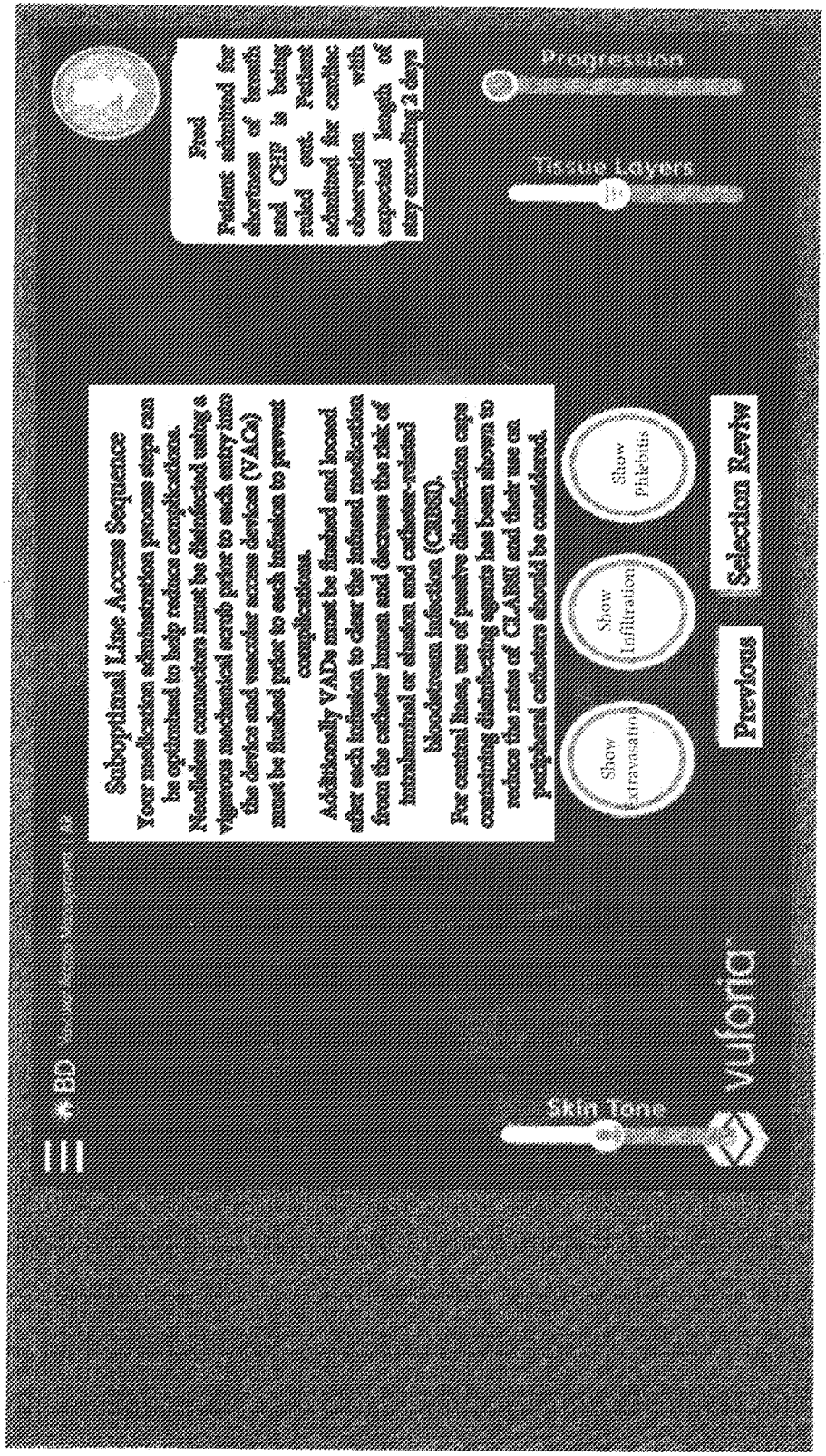
Figure 118:
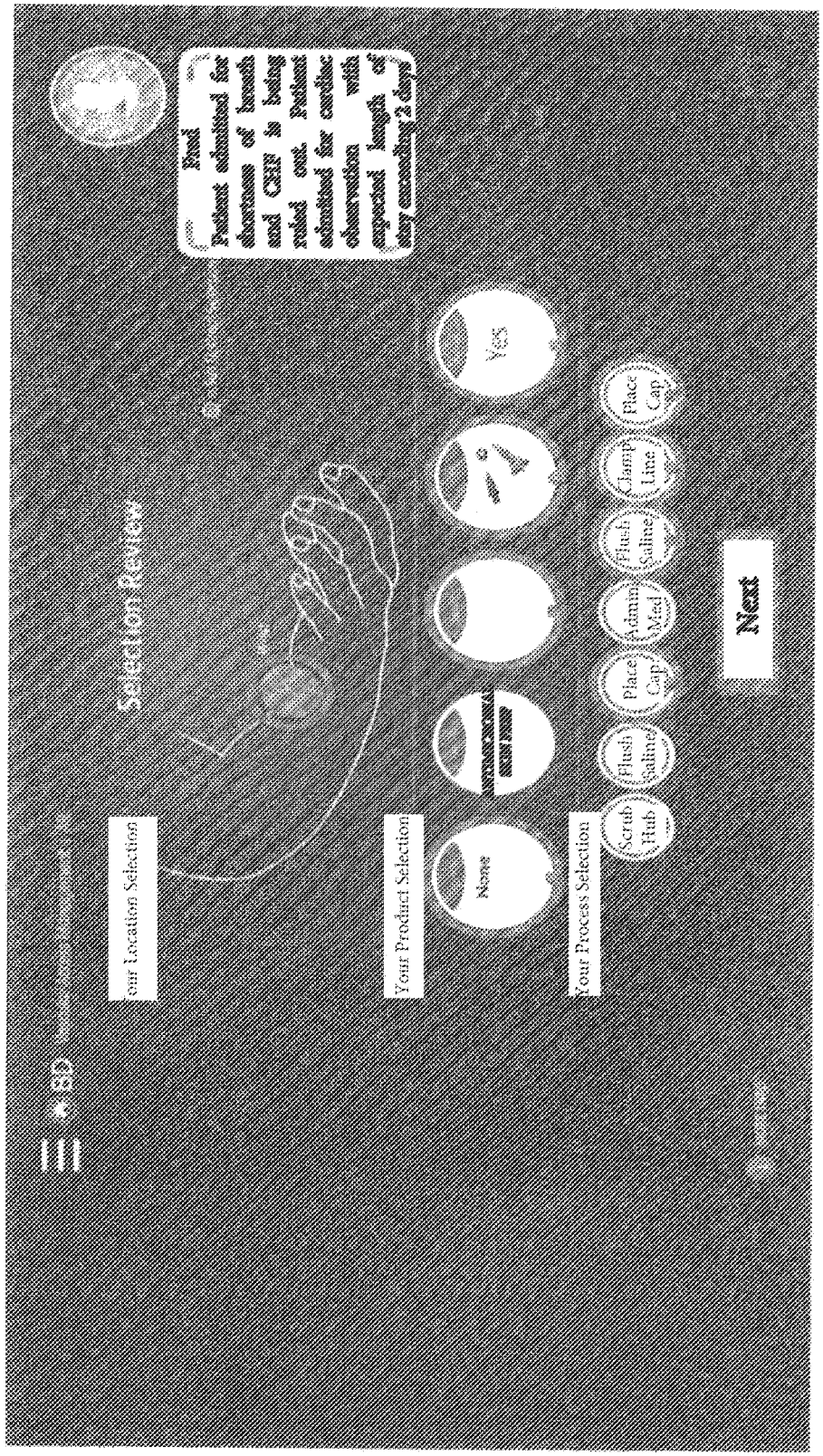

Referring to FIGS. 86, 87, and 93, during the review process in accordance with example embodiments, machine 100 displays the optimal selections to properly gain IV access for the person identified in the select person profile. For example, machine 100 may display a screen 666, such as shown in FIGS. 86 and 87, indicating that the optimal selections will be displayed. Screen 666 includes a "Next" button 668 as shown in FIG. 87 allowing the user to continue the CBL program or application to learn the optimal selections during the selection review process. When the user presses "Next" button 668, at step 526, machine 100 receives, via a network 114, a request for initiating a review of the optimal selections associated with the selected person profile. As shown in FIG. 93, machine 100 displays a selection review screen 670 on display 70 including the most appropriate selections, e.g., the most appropriate location selection, the most appropriate tray selections, and the most appropriate process selections. In certain embodiments, the optimal or most appropriate selections will be highlighted or outlined, e.g., outlined in teal, on selection review screen 670. As shown in FIG. 94, after the review process is complete, machine 100 may display a screen 672 querying the user whether the user would like to complete a survey and/or evaluate the application, for example. If the user does not select the link to complete the survey or evaluate the application, the application ends 528.

In example embodiments, consequence-based learning application usage collects metrics to enable a user to target select customers with targeted messaging (e.g., customer X made inordinately more suboptimal selections or spent inordinately more time in the catheter selection portion of the app, target education/sales messaging to focus on catheter selection).

In example embodiments, the application uses a virtual reality (VR) or mixed reality (MR) environment to serve as a simulation lab for nurses and/or residents to learn about inserting and/or maintaining an IV to help overcome scheduling and facilities restrictions and to help build insertion competency.

In example embodiments, the application includes ultrasound technology built into the system or operatively coupled to the system that can communicate with the machine via the application leverage, in certain embodiments, augmented reality, virtual reality, and/or mixed reality technology. This can enable customized training based on the person's actual vasculature. This can also enable ultrasound-guided insertion support.

In example embodiments, the application enables a group or community of users to take videos, pictures, and/or VR/MR video to show their successful approach to catheter insertion in difficult vein access persons. This will build a library of community-sourced content and/or case studies to support training and education on DVA insertion techniques.

In example embodiments, the application will enable better site assessment by matching a vascular access device site image by comparing against image libraries and enable early risk identification and mitigation preparation.

In example embodiments, the application uses virtual reality and/or mixed reality technology to enable tactile feedback to help with insertion training and real-life catheter insertion.

In example embodiments, the application "gamifies" vascular access and training and education by allowing a community of users to compete against each other in best practice knowledge, best practice adherence, training drills, etc. This application may be used in nursing schools (enabling them to teach vascular access and care, which they currently do not have time or facilities to accomplish). It may also be combined with the following: the application enables user-inputted data to help a clinician keep track of how many times he or she has assessed the IV site, how many stick attempts he or she experienced, if he or she allowed adequate dry time after skin antisepsis, if he or she flushed the line per best practices, if he or she scrubbed the hub and allowed adequate dry time, and/or how many times he or she needed to pull out a catheter earlier than desired. This provides a reward system for early assessment and/or a personal dashboard of IV success; and/or the application enables benchmarking within IDNs and across IDNs for that listed above.

In example embodiments, the application provides person and/or caretaker education on vascular access and maintenance. This will help with person transitions from acute care to non-acute care and/or home settings. The system may track usage metrics to enable IDNs to manage their risk pools through population health management.

In example embodiments, the application includes a checklist and/or technical support to enable appropriate selection of vascular access device selection.

FIG. 120 illustrates select example components of an example machine 100 according to some implementations. Machine 100 may be implemented as any of a number of different types of electronic devices including a processor 702 and memory (e.g., computer-readable media 704) for controlling the display of a map according to the techniques described herein.

In various configurations, machine 100 includes, or accesses, components such as at least one control logic circuit, central processing unit, or processing device ("processor") 702, and one or more computer-readable media 704 (e.g., memory). Each processor 702 may itself comprise one or more processors or processing cores. For example, processor 702 can be implemented as one or more microprocessors, microcomputers, microcontrollers, digital signal processors, central processing units, state machines, logic circuitries, and/or any devices that manipulate signals based on operational instructions. In some cases, processor 702 may be one or more hardware processors and/or logic circuits of any suitable type specifically programmed or configured to execute the algorithms and processes described herein. Processor 702 can be configured to fetch and execute computer-readable instructions stored in computer-readable media 704 or other computer-readable media. Processor 702 can perform one or more of the functions attributed to the machine 100, and in particular attributed to the rendering circuitry 102, the network interface circuitry 104, and/or the user interface circuitry 110.

Depending on the configuration of the machine 100, computer-readable media 704 may be an example of tangible non-transitory computer storage media and may include volatile and nonvolatile memory and/or removable and non-removable media implemented in any type of technology for storage of information such as computer-readable instructions, data structures, program modules or other data. Computer-readable media 704 may include, but is not limited to, RAM, ROM, EEPROM, flash memory or other computer readable media technology, CD-ROM, digital versatile disks (DVD) or other optical storage, magnetic cassettes, magnetic tape, solid-state storage and/or magnetic disk storage. Further, in some cases, machine 100 may access external storage, such as RAID storage systems, storage arrays, network attached storage, storage area networks, cloud storage, or any other medium that can be used to store information and that can be accessed by processor 702 directly or through another computing device or network. Accordingly, computer-readable media 704 may be computer storage media able to store instructions, modules or components that may be executed by processor 702.

Computer-readable media 704 may be used to store and maintain any number of functional components that are executable by processor 702. In some implementations, these functional components comprise instructions or programs that are executable by processor 702 and that, when executed, implement operational logic for performing the actions attributed above to machine 100. Functional components of machine 100 stored in computer-readable media 704 may include the operating system and user interface module 706 for controlling and managing various functions of machine 100, and for generating one or more user interfaces on display device 108 of machine 100.

In addition, computer-readable media 704 may also store data, data structures and the like, that are used by the functional components. For example, data stored by computer-readable media 704 may include user information and, optionally, one or more content items 708. Depending on the type of machine 100, computer readable media 704 may also optionally include other functional components and data, such as other modules and data 710, which may include programs, drivers and so forth, and the data used by the functional components. Further, machine 100 may include many other logical, programmatic and physical components, of which those described are merely examples that are related to the discussion herein. Further, while the figures illustrate the functional components and data of machine 100 as being present on machine 100 and executed by processor 702 on machine 100, it is to be appreciated that these components and/or data may be distributed across different computing devices and locations in any manner.

FIG. 120 further illustrates examples of other components that may be included in machine 100. Such examples include various types of sensors, which may include, for example, the display device 108, a GPS device 712, an accelerometer 714, one or more cameras 716, a compass 718, a gyroscope 720, and/or a microphone 722. Display device 108 may be an LCD display, a cholesteric display, an electrophoretic display, an electrofluidic pixel display, a photonic ink display, or an electrowetting display panel.

Machine 100 may further include one or more communication interfaces 724, which may comprise all or portions of the structure and functionality of the network interface circuitry 104. The communication interfaces 724 may support both wired and wireless connection to various networks, such as cellular networks, radio, Wi-Fi networks, close-range wireless connections, near-field connections, infrared signals, local area networks, wide area networks, and/or the Internet, for example. Communication interfaces 724 may further allow a user to access storage on or through another device, such as a remote computing device, a network attached storage device, or cloud storage. Additionally, the communication interfaces 724 may include system busses to effect intercommunication between various elements, components, and circuitry portions of the machine 100. Example system bus implementations include Peripheral Component Interconnect Express (PCIe), Serial or Parallel Advanced Technology Attachment (SATA or PATA), and integrated drive electronics (IDE) based buses.

Machine 100 may further be equipped with one or more speakers 726 and various other input/output (I/O) components 728. The I/O components 728 may form portions of the user interface circuitry 110. Such I/O components 728 may include, for example, a touchscreen and various user controls (e.g., buttons, a joystick, a keyboard, and/or a keypad), a haptic or tactile output device, connection ports, and/or physical condition sensors. For example, operating system 706 of machine 100 may include suitable drivers configured to accept input from a keypad, keyboard, or other user controls and devices included as I/O components 728. Additionally, machine 100 may include various other components that are not shown, examples of which include removable storage, a power source, such as a battery and power control unit, and/or a PC Card component. Various instructions, methods and techniques described herein may be considered in the general context of computer-executable instructions, such as program modules stored on computer storage media and executed by the processors herein. Generally, program modules include, for example, routines, programs, objects, components, and/or data structures, for performing particular tasks or implementing particular abstract data types. These program modules, and the like, may be executed as native code or may be downloaded and executed, such as in a virtual machine or other just-in-time compilation execution environment. Typically, the functionality of the program modules may be combined or distributed as desired in various implementations. An implementation of these modules and techniques may be stored on computer storage media or transmitted across some form of communication.

The methods, devices, processing, circuitry, structures, architectures, and logic described above may be implemented in many different ways and in many different combinations of hardware and software. For example, all or parts of the implementations may be circuitry that includes an instruction processor, such as a Central Processing Unit (CPU), microcontroller, or a microprocessor; or as an Application Specific Integrated Circuit (ASIC), Programmable Logic Device (PLO), or Field Programmable Gate Array (FPGA); or as circuitry that includes discrete logic or other circuit components, including analog circuit components, digital circuit components or both; or any combination thereof. The circuitry may include discrete interconnected hardware components or may be combined on a single integrated circuit die, distributed among multiple integrated circuit dies, or implemented in a Multiple Chip Module (MCM) of multiple integrated circuit dies in a common package, as examples.

Accordingly, the circuitry may store or access instructions for execution, or may implement its functionality in hardware alone. The instructions may be stored in one or more non-transitory computer-readable mediums that may include a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HOD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings. The computer-readable medium may include instructions that, when executed by circuitry elements, cause the circuitry elements to perform a method including one or more steps discussed in this disclosure.

The implementations may be distributed. For instance, the circuitry may include multiple distinct system components, such as multiple processors and memories, and may span multiple distributed processing systems. Parameters, databases, and other data structures may be separately stored and managed, may be incorporated into a single memory or database, may be logically and physically organized in many different ways, and may be implemented in many different ways. Example implementations include linked lists, program variables, hash tables, arrays, records (e.g., database records), objects, and implicit storage mechanisms. Instructions may form parts (e.g., subroutines or other code sections) of a single program, may form multiple separate programs, may be distributed across multiple memories and processors, and may be implemented in many different ways. Example implementations include stand-alone programs, and as part of a library, such as a shared library like a Dynamic Link Library (DLL). The library, for example, may contain shared data and one or more shared programs that include instructions that perform any of the processing described above or illustrated in the drawings, when executed by the circuitry.

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims. One skilled in the art will realize that a virtually unlimited number of variations to the above descriptions are possible, and that the examples and the accompanying figures are merely to illustrate one or more examples of implementations. It will be understood by those skilled in the art that various other modifications can be made, and equivalents can be substituted, without departing from claimed subject matter. Additionally, many modifications can be made to adapt a particular situation to the teachings of claimed subject matter without departing from the central concept described herein. Therefore, it is intended that claimed subject matter not be limited to the particular embodiments disclosed, but that such claimed subject matter can also include all embodiments falling within the scope of the appended claims, and equivalents thereof.

In the detailed description above, numerous specific details are set forth to provide a thorough understanding of claimed subject matter. However, it will be understood by those skilled in the art that claimed subject matter can be practiced without these specific details. In other instances, methods, devices, or systems that would be known by one of ordinary skill have not been described in detail so as not to obscure claimed subject matter.

Reference throughout this specification to "one embodiment" or "an embodiment" can mean that a particular feature, structure, or characteristic described in connection with a particular embodiment can be included in at least one embodiment of claimed subject matter. Thus, appearances of the phrase "in one embodiment" or "an embodiment" in various places throughout this specification are not necessarily intended to refer to the same embodiment or to any one particular embodiment described. Furthermore, it is to be understood that particular features, structures, or characteristics described can be combined in various ways in one or more embodiments. In general, of course, these and other issues can vary with the particular context of usage. Therefore, the particular context of the description or the usage of these terms can provide helpful guidance regarding inferences to be drawn for that context.

Various implementations have been specifically described. However, many other implementations are also possible.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

What is claimed is:

1. A computer-implemented method for providing educational guidance for peripheral IV therapy, the method comprising:
    displaying, on a display of a machine, a main menu including a plurality of person profiles;
    prompting, by the machine, the user to select a person profile of the plurality of person profiles, wherein the selected person profile identifies a person;
    prompting, by the machine, the user to select an insertion site from a plurality of insertion sites on the person's appendage, based at least in part on the selected person profile;
    prompting, by the machine, the user to select one or more appropriate products for properly inserting an IV catheter in the person's appendage at the selected insertion site, based at least in part on the selected person profile;
    presenting, by the machine, to the user, a line access process menu including a plurality of line access process steps associated with the one or more appropriate products;
    prompting, by the machine, the user to place the plurality of line access process steps in a most appropriate sequential order within a plurality of line access process step locations displayed on the display;
    once the user places the plurality of line access process steps in the most appropriate sequential order, instructing, by the machine, the user to position a sticker at the selected insertion site;
    in response to one or more selections of the one or more appropriate products or one or more placements of the plurality of line access process steps in the most appropriate sequential order being incorrect:
    displaying, by the machine, a selection review screen indicating that at least one of the user's selections or placements is considered a sub-optimal selection or placement and displaying an information icon providing access to more information on why the at least one user's selection or placement is considered the sub-optimal selection or placement;
    rendering, by a processing device of the machine, a first graphical image of the selected insertion site;
    displaying, on the display, the first graphical image indicating placement of the sticker at the selected insertion site;
    displaying, on the display, one or more complications associated with the selected insertion site;
    prompting the user to select a complication of the one or more complications for further information regarding the selected complication;
    rendering, by the processing device of the machine, a second graphical image of the person's arm indicating the selected complication; and
    displaying on the display, the second graphical image,
    wherein the second graphical image is rendered with at least one data item corresponding to the selected insertion site, and wherein the at least one data item includes a time-lapse image of the selected complication arising and progressing as an actuator of the machine is manipulated by the user.

2. The computer-implemented method of claim 1, further comprising:
    prompting, by the machine, the user to initiate a review of the user's selection of the most appropriate sequential order.

3. The computer-implemented method of claim 1, wherein the second graphic image is rendered with informational text indicating a definition of the at least one complication and an indication of risks associated with the at least one complication.

4. The computer-implemented method of claim 1, wherein the second graphic image is rendered with an additional graphical image illustrating one or more effects of the at least one complication.

5. The computer-implemented method of claim 1, further comprising querying the user whether the user would like to achieve a better outcome for the person identified in the person profile.

6. The computer-implemented method of claim 1, further comprising displaying, by the machine, on the display a selection review screen including optimal selections to properly gain IV access for the person identified in the select person profile, wherein the selection review screen includes a plurality of most appropriate selections.

7. A method for initiating an educational guidance mode on a machine, the method comprising:
    receiving, by the machine, a request from a user to initiate a consequence-based learning program;
    presenting to the user, via a display of the machine, a plurality of patient profiles;
    querying the user, by the machine, to select a patient profile of the plurality of patient profiles presented on the display, wherein the selected patient profile identifies a patient;
    upon selection of the patient profile by the user, prompting the user, by the machine, to select an insertion site from a plurality of potential insertion sites on the patient's appendage for inserting an IV catheter;
    instructing the user, by the machine, to select one or more appropriate products required for properly inserting the IV catheter in the patient's appendage at the selected insertion site, based at least in part on the first patient profile;
    prompting, by the machine, the user to continue with a line access process, wherein, during the line access process, the machine prompts the user to place a plurality of line access process steps associated with the one or more appropriate products in a numbered process step location;
    in response to one or more selections of the one or more appropriate products or one or more placements of the plurality of line access process steps in the numbered process step location being incorrect:

instructing, by the machine, the user to position a sticker at the selected insertion site;

displaying, by the machine, a selection review screen indicating that at least one of the user's selections or placements is considered a sub-optimal selection or placement and displaying an information icon providing access to more information on why the at least one user's selection or placement is considered the sub-optimal selection or placement;

rendering, by a processing device of the machine, a first graphical image of the selected insertion site;

displaying, on the display, the first graphical image indicating placement of the sticker at the selected insertion site;

displaying, on the display, one or more complications associated with the selected insertion site;

prompting the user to select a complication of the one or more complications for further information regarding the selected complication;

rendering, by the processing device of the machine, a second graphical image of the patient's arm indicating the selected complication; and displaying on the display, the second graphical image, wherein the second graphical image is rendered with at least one data item corresponding to the selected insertion site, and wherein the at least one data item includes a time-lapse image of the selected complication arising and progressing as an actuator of the machine is manipulated by the user.

8. The method of claim 7, wherein instructing the user, by the machine, to select the one or more appropriate products required for properly inserting the IV catheter in the patient's appendage at the selected insertion site further comprises:

displaying, on the display, available products; and instructing the user to select the one or more appropriate products of the available products to be used in a correct sequence.

9. The method of claim 8, wherein instructing the user to select the one or more appropriate products of the available products to be used in the correct sequence comprises:

prompting the user, by the machine, to select from a plurality of catheters an appropriate catheter for the first patient profile;

prompting the user, by the machine, to select an appropriate process for preparing the first insertion site for insertion of the catheter;

prompting the user, by the machine, to select an appropriate connector from a plurality of connectors;

prompting the user, by the machine, to select an appropriate dressing from a plurality of dressing choices; and prompting the user, by the machine, to determine whether an extension set is required.

10. The method of claim 9, further comprising:

prompting the user, by the machine, to build the catheter with the one or more appropriate products selected, scrub a hub, flush the IV catheter, and administer an example medicine.

11. The method of claim 10, further comprising:

in response to the one or more selections of the one or more appropriate products or the one or more placements of the plurality of line access process steps in the numbered process step location being correct, displaying on the display a congratulatory response for positive reinforcement.

12. The method of claim 10, further in response to the one or more selections of the one or more appropriate products or the one or more placements of the plurality of line access process steps in the numbered process step location being incorrect:

prompting the user, by the machine, to re-select at least one of the following: a product incorrectly selected or a position of a non-sequential step of the line access process;

determining, by the machine, that the user selected correct products and correctly positioned the line access process steps sequentially;

determining, by the machine, that the user is interested in learning more about peripheral IV therapy; and providing the user, by the machine, with a link to a site to learn more about peripheral IV therapy.

* * * * *